(12) United States Patent (10) Patent No.: US 9,297,800 B2
Isojima et al. (45) Date of Patent: Mar. 29, 2016

(54) BIOMATERIAL CONSTRUCT, ITS PRODUCING METHOD, BIOMATERIAL SUPPORT, TARGET MATERIAL PURIFYING METHOD, AFFINITY CHROMATOGRAPHY CONTAINER, SEPARATION CHIP, ANALYZING METHOD AND ANALYZING SEPARATOR FOR TARGET MATERIAL, BIOMATERIAL COMPLEX, AND ITS SUPPORT, SENSOR CHIP, SOLID SUPPORT WITH BIOMATERIAL FIXED THEREON

(75) Inventors: Tatsushi Isojima, Yokohama (JP);
Hiroyuki Tanaka, Yokohama (JP);
Toshifumi Shiroya, Yokohama (JP);
Hisao Takeuchi, Yokohama (JP);
Minako Hanasaki, Yokohama (JP);
Yasuo Ifuku, Shinjuku-ku (JP)

(73) Assignees: Mitsubishi Chemical Corporation, Tokyo (JP); LSI Medience Corporation, Tokyo (JP)

( * ) Notice: Subject to any disclaimer, the term of this patent is extended or adjusted under 35 U.S.C. 154(b) by 1144 days.

(21) Appl. No.: 13/239,985

(22) Filed: Sep. 22, 2011

(65) Prior Publication Data
US 2012/0053078 A1 Mar. 1, 2012

Related U.S. Application Data

(63) Continuation of application No. 11/575,259, filed as application No. PCT/JP2005/017330 on Sep. 14, 2005, now Pat. No. 8,183,057.

(30) Foreign Application Priority Data

Sep. 14, 2004 (JP) ................ 2004-267272
Jul. 11, 2005 (JP) ................ 2005-201134
Jul. 27, 2005 (JP) ................ 2005-217572

(51) Int. Cl.
*G01N 33/543* (2006.01)
(52) U.S. Cl.
CPC .................... *G01N 33/54346* (2013.01)
(58) Field of Classification Search
None
See application file for complete search history.

(56) References Cited

U.S. PATENT DOCUMENTS

| 4,418,152 | A | 11/1983 | Hosaka et al. | |
| 5,017,696 | A | 5/1991 | Farmar et al. | |
| 5,242,828 | A | 9/1993 | Bergstrom et al. | |
| 6,174,683 | B1 | 1/2001 | Hahn et al. | |
| 6,214,560 | B1 | 4/2001 | Yguerabide et al. | |
| 7,615,340 | B2 * | 11/2009 | Bamdad | 435/6.11 |
| 8,183,057 | B2 * | 5/2012 | Isojima et al. | 436/518 |
| 2002/0098526 | A1 | 7/2002 | Bamdad | |
| 2002/0127741 | A1 | 9/2002 | Sales Amill et al. | |
| 2002/0132371 | A1 | 9/2002 | Kreimer et al. | |
| 2003/0170392 | A1 | 9/2003 | Chari et al. | |
| 2003/0171666 | A1 | 9/2003 | Loeb et al. | |
| 2004/0146500 | A1 * | 7/2004 | Miyata et al. | 424/130.1 |
| 2005/0158723 | A1 | 7/2005 | Viovy et al. | |
| 2005/0239155 | A1 * | 10/2005 | Alarcon et al. | 435/14 |

FOREIGN PATENT DOCUMENTS

| JP | 3-53167 | 3/1991 |
| JP | 7 318561 | 12/1995 |
| JP | 8-509064 | 9/1996 |
| JP | 10 195099 | 7/1998 |
| JP | 2002 102338 | 4/2002 |
| JP | 2002-543398 | 12/2002 |
| JP | 2003 327784 | 11/2003 |
| JP | 2004 45120 | 2/2004 |
| JP | 2004-531688 | 10/2004 |
| WO | 02 056021 | 7/2002 |
| WO | WO 03/071276 A1 | 8/2003 |

OTHER PUBLICATIONS

Extended Search Report issued Oct. 31, 2011 in Europe Application No. 11162983.8.
Interchim: "Uptibeads", Online—Internet Archive, Jun. 21, 2004, URL <http://web.archive.org/web/20040621032633/http://www.interchim.com/interchim/bio/produits_uptima/product_line/uptibeads.htm>, Retrieved on Oct. 11, 2011, XP002661191, 2 pages.
Office Action issued Mar. 1, 2011, in Japan Patent Application No. 2006-068318 (with English Translation).
Masanori Abe, et al., " Novel Techniques for Fabricating Magnetic Nanobeads", Bio Industry, vol. 21, No. 8, pp. 7-13, 2004. (with partial English translation).
Brady J. Cheek, et al., " Chemiluminescence Detection for Hybridization Assays on the Flow-Thru Chip, A Three-Dimensional Microchannel Biochip", Analytical Chemistry, vol. 73, No. 24, pp. 5777-5783, 2001.
Amy L. Hiddessen, et al., "Assembly of Binary Colloidal Structures Via Specific Biological Adhesion", Lungmuir 2000, vol. 16, No. 25, pp. 9744-9753, XP002507138.
Claire Minard-Basquin, et al., "Oligonucleotide-Polymer Conjugates: Effect of the Method of Synthesis on Their Structure and Performance in Diagnostic Assays", Bioconjugate Chemistry, Nov. 2000, pp. 795-804.
Marie-Noëlle Erout, et al., "Preparation of Conjugates between Oligonucleotides and N-Vinylpyrrolidone/N-Acryloxysuccinimide Copolymers and Application in Nucleic Acid Assays to Improve Sensitivity", Bioconjugate Chemistry, XP 000616696, Sep. 1, 1996, pp. 568-575.
Paul T. Charles, at al., "Fabrication and characterization of 3D hydrogel microarrays to measure antigenicity and antibody functionality for biosensor applications", Biosensors and Bioelecronics, vol. 20, No. 4, XP004633823, Nov. 1, 2004, pp. 753-764.

* cited by examiner

*Primary Examiner* — Ann Lam
(74) *Attorney, Agent, or Firm* — Oblon, McClelland, Maier & Neustadt, L.L.P.

(57) ABSTRACT

A biomaterial structure containing a larger amount of biomaterial than the conventional art with maintaining the reactivity of the biomaterial is provided by linking particulate lumps in which the biomaterial is bound with a compound capable of binding to the biomaterial, wherein the particle diameter of the particulate lumps is 10 μm or smaller.

23 Claims, 35 Drawing Sheets

PARTICULATE LUMP

PARTICULATE LUMP

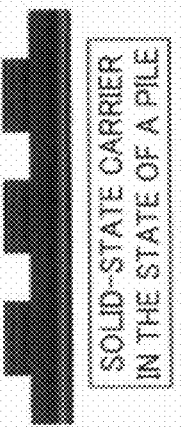
FIG. 9(a) SOLID-STATE CARRIER IN THE STATE OF A WELL
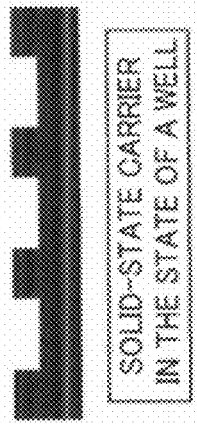
FIG. 9(b) SOLID-STATE CARRIER IN THE STATE OF A PILE

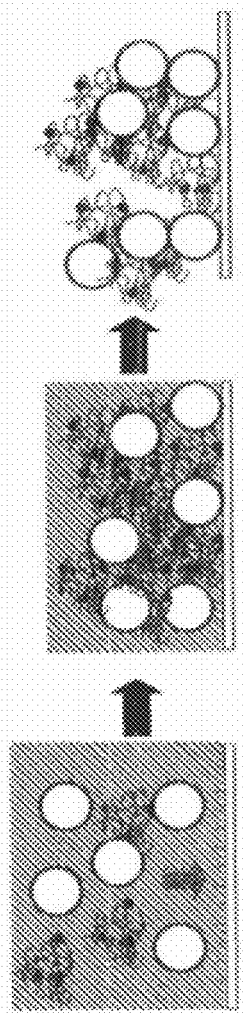

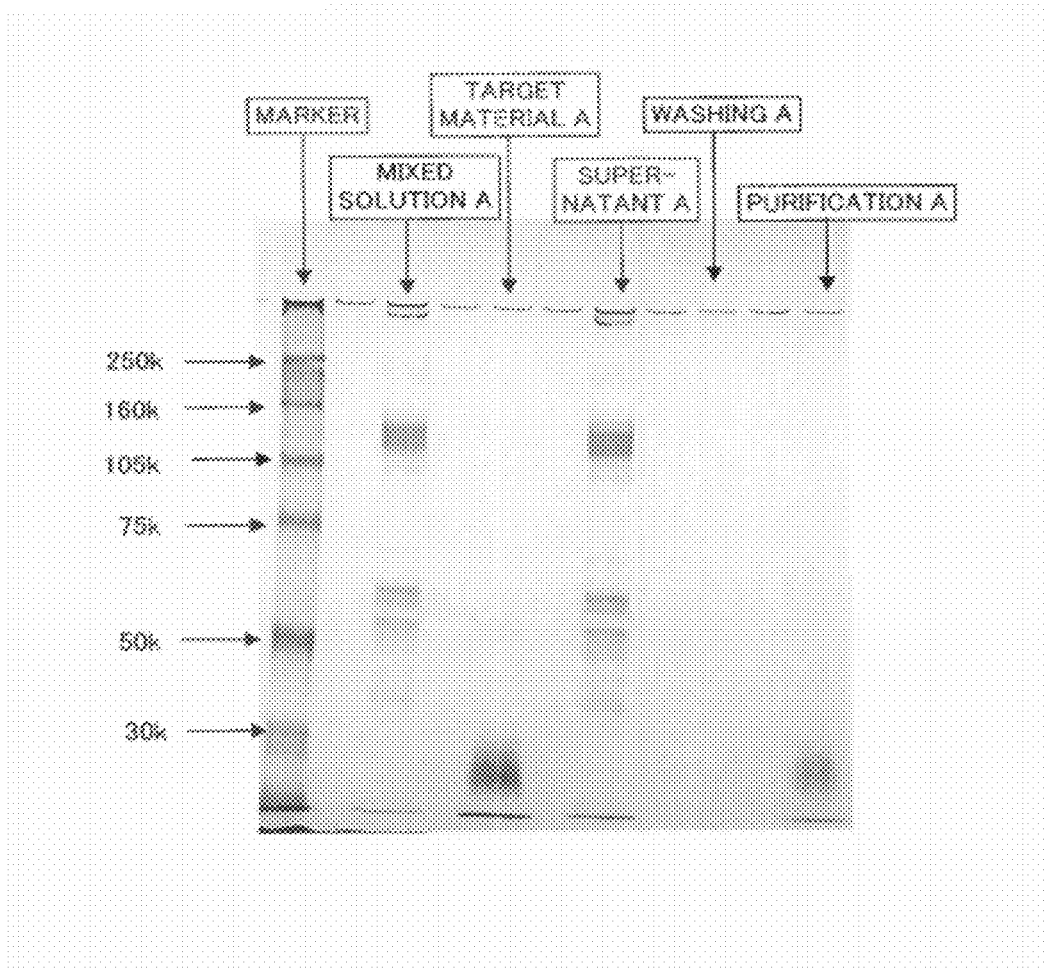

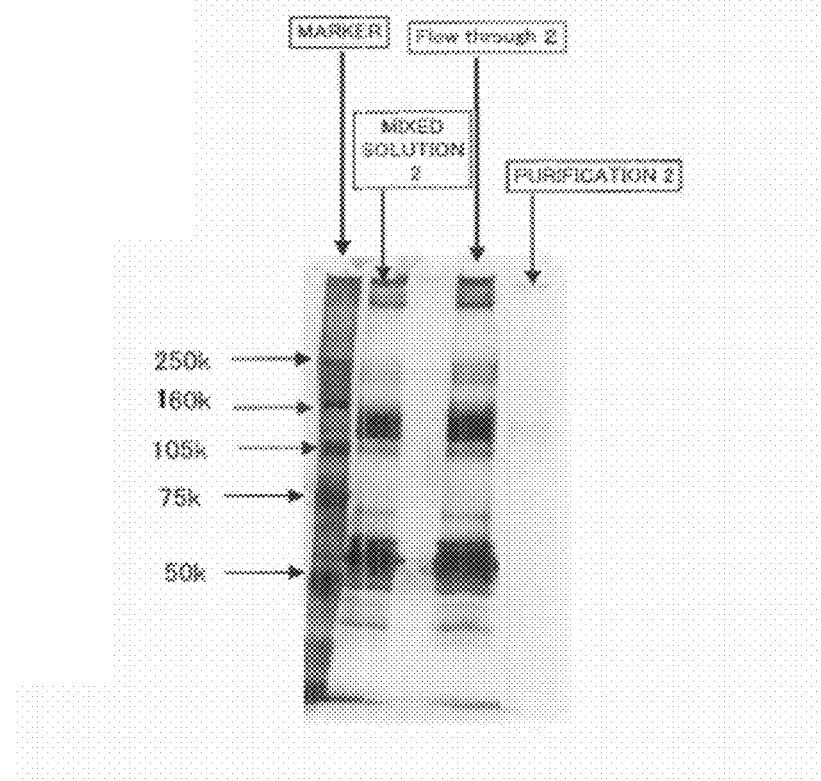

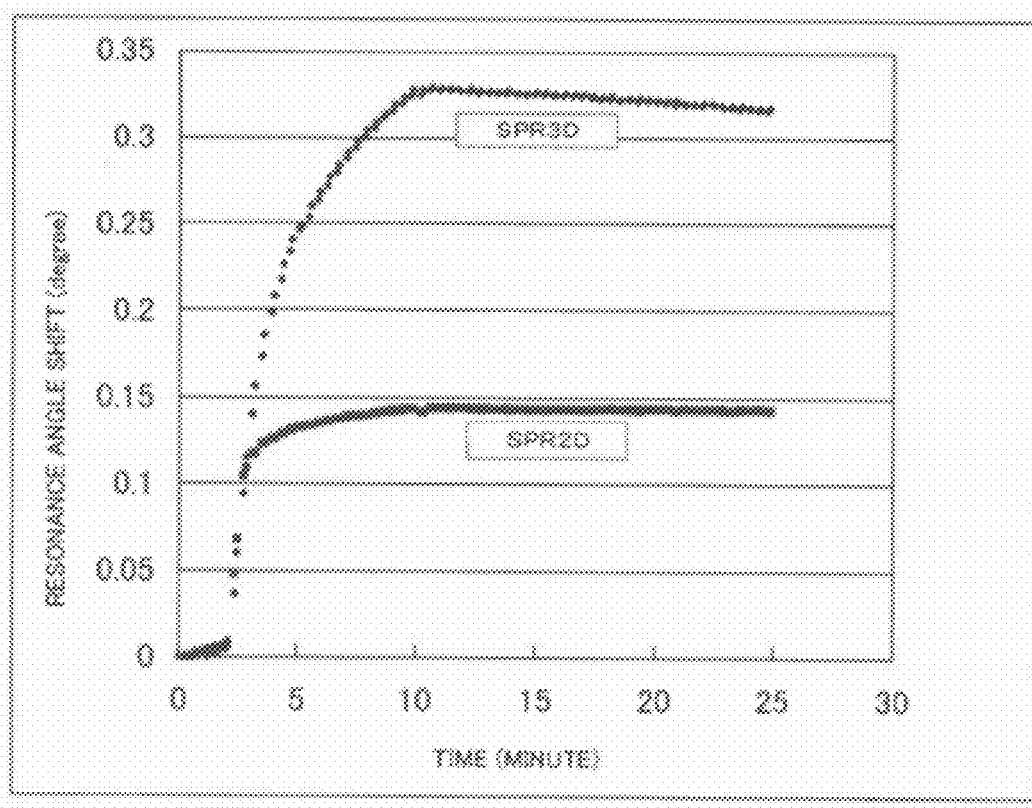

BIOMATERIAL CONSTRUCT, ITS PRODUCING METHOD, BIOMATERIAL SUPPORT, TARGET MATERIAL PURIFYING METHOD, AFFINITY CHROMATOGRAPHY CONTAINER, SEPARATION CHIP, ANALYZING METHOD AND ANALYZING SEPARATOR FOR TARGET MATERIAL, BIOMATERIAL COMPLEX, AND ITS SUPPORT, SENSOR CHIP, SOLID SUPPORT WITH BIOMATERIAL FIXED THEREON

TECHNICAL FIELD

The invention relates to a biomaterial structure and a method of its production, a biomaterial-carrying object, a method of purifying a target material, a container for affinity chromatography, a separation chip, a method of analyzing a target material, a separation apparatus for analysis of a target material, a biomaterial complex, a biomaterial-complex-carrying object, a sensor chip, a solid-state carrier with an immobilized biomaterial and a method of its production, a biomaterial immobilization kit, a novel solid-state carrier and a method of its production, and their uses.

BACKGROUND ART

Biomaterial structures can be used in fields including medical treatment and diagnosis, gene analysis, and proteomics, being especially suitable for tools such as affinity purification tools and analysis tools of pharmacological actions. Some reports have been made as to structures used for such tools as affinity purification tools and analysis tools of pharmacological actions.

Examples of the carriers conventionally used for affinity chromatography are: inorganic materials such as porous silica gel particles; particles made of natural macromolecules such as polysaccharides including agarose, dextran, and cellulose; and particles made of synthetic polymer such as polystyrene and polyacrylamide.

However, the use of these conventional affinity chromatography carriers for affinity purification often causes difficulty in inhibiting non-specific adsorption into the carriers for affinity chromatography; an increase in purity through purification involves a decrease in the efficiency of recovery.

To address these problems, methods of affinity purification using latex microparticles have been reported recently, as described in Patent Document 1. Since the method employs Brownian motion of the latex particles, a target object for purification can specifically be adsorbed to the surface of the latex microparticles with efficiency. In addition, the method has the advantage of requiring a small amount of sample, because the latex to which the target object is adsorbed can be recovered through centrifugation.

On the other hand, technologies are suggested which carryout separation magnetically without centrifugation. To attain the object, the lattices containing magnetic materials are developed (Patent Document 2, Non-Patent Document 1).

Patent Document 3 discloses biochemical microparticles composed of agglomerate lumps in which albumin insolubilized with glutaraldehyde is combined with antibodies or antigens.

In addition, solid-state carriers with immobilized biomaterials are known, and their applications are examined to fields including medical treatment and diagnosis, genes analysis, proteomics, microelectronics, and membrane separation, especially to the fields of biochips and biosensor chips such as DNA chips and protein chips.

Some reports have also been made as to methods of producing such solid-state carriers with immobilized biomaterials as described above, namely, methods of immobilizing biomaterials onto solid-state carrier surfaces.

To immobilize a biomaterial to a solid-state carrier, an example of the methods includes coating the surface of the solid-state carrier with hydrophilic polymer compound to form a polymer film on the solid-state carrier surface, after which the polymer chains composing the polymer film are bound to a biomaterial such as a ligand. Compared to the case where the solid-state carrier surface is not coated with a hydrophilic polymer compound, the method can advantageously improve the introduction amount (immobilization amount) of the biomaterial per unit area, and is therefore applied to a variety of fields as mentioned above.

Patent Document 4 discloses a method of forming a coating film of a hydrophilic polymer provided with an electrically-charged functional group. In accordance with the aforementioned method, in which a biomaterial such as a ligand is immobilized in a polymer film on a solid-state carrier, it is difficult to immobilize the biomaterial with high density due to its penetration into the polymer film. By contrast, the method disclosed in Patent Document 4 has an advantage in that if the pH of the solution is adjusted such that the surface charge of the biomaterial the polymer film is opposite to the charge of the electrically-charged functional group, the biomaterial to the polymer film can be acceleratedly immobilized through electrostatic interaction, resulting in high-density immobilization.

Commercially available products made through the method described in Patent Document 4 include a glass plate covered with gold and surface treated with a CM-dextran film (Sensor Chip CM5 manufactured by BIACORE).

Another commercially available product is a slide glass, which serves as a solid-state carrier, covered with a polyacrylamide film (HydroGel Coated Slide manufactured by PerkinElmer, Inc.). Since the product is prepared with polyacrylamide gel swelling due to water content, it is suitable for the purpose of dropping a sample in the order of nanoliters, which is easy to dry. Also advantageously, the product is in no need of activation because the biomaterial is adsorbed to the polyacrylamide.

Patent Document 5 discloses a method that includes mixing a polyurethane polymer with a biomaterial in an organic solvent and adding a condensing agent to the mixture so that the polymer is polymerized and bound to the surface of a basal plate. Different from the conventional complicated methods, the method can yield a film containing the biomaterial on the solid-state carrier surface through simple operations; the biomaterial is easily immobilized onto the solid-state carrier.

Patent Document 6 discloses a method in which monomers having activated ester groups are polymerized on a solid-state carrier to extend the polymer chains, and the resultant brush-like polymer chains formed on the solid-state carrier is coupled with a biomaterial. The method allows the immobilization of a biomaterial such as a ligand, and is in no need of activating the polymer chains for introduction (immobilization) onto the solid-state carrier.

As explained above, the conventional techniques for forming a hydrophilic polymer film on a solid-state carrier have their respective advantages.

On the other hand, Non-Patent Document 2, for example, discloses a method of immobilizing a biomaterial onto a solid-state carrier (microchannel wafer) on which a porous structure is formed in advance for increasing the surface area and allowing a larger amount of the biomaterial to be bound to the surface. Compared to the case where the solid-state carrier has a flat surface, the method can advantageously improve the introduction amount (immobilization amount) of the biomaterial per unit area, and is therefore applied to a variety of fields as mentioned above.

[Patent Document 1] Japanese Unexamined Patent Laid-Open Application Publication No. HEI 10-195099
[Patent Document 2] Japanese Unexamined Patent Laid-Open Application Publication No. 2003-327784
[Patent Document 3] Japanese Patent No. 2836009
[Patent Document 4] Specification of U.S. Pat. No. 5,242,828
[Patent Document 5] Specification of U.S. Pat. No. 6,174,683
[Patent Document 6] Pamphlet of WO 02/056021
[Non-Patent Document 1] Masanori ABE, Hiroshi HANDA, BIO INDUSTRY, Vol. 21, No. 8, p. 7.
[Non-Patent Document 2] Brandy J. Cheek, et al., Anal. Chem., 2001, 73, 5777-5783

DISCLOSURE OF THE INVENTION

Problem to be Solved by the Invention

However, the method described in Patent Document 1 is difficult to automate and to carry out unattended because it requires complicated operation such as centrifugation; it lacks enough efficiency to be applied to the field of recent drug design, which requires high throughput.

The method described in Patent Document 2 and Non-Patent Document 1 requires fully encapsulating a magnetic material to inhibit non-specific adsorption of a protein. When, for example, iron oxide is used as the magnetic material, the method also requires reducing elution of iron ions. In addition, the latex particles containing the magnetic material are difficult to maintain dispersing stability because of their large specific surface areas. Both the latex particles and the magnetic material containing latex particles are difficult to manufacture, having difficulties in mass production and quality control in view of industrialization.

In accordance with the method described in Patent Document 3, the use of a low-molecular-weight compound such as glutaraldehyde may bring about: denaturation of proteins; non-specific adsorption to the denatured proteins; a decline in reactivity with decreasing internal space due to closely bound structure; and non-specific adsorption to a hydrophobic compound such as glutaraldehyde.

As for the cases where a biomaterial or a specific material is immobilized onto a solid-state carrier, the methods described in Patent Documents 4-6 and Non-Patent Document 2 mentioned above may not allow the biomaterial to be immobilized on the solid-state carrier in sufficient amount, or may bring about unevenness in immobilization and prevent accurate and uniform immobilization, failing to provide enough performance when applied to such uses as a biosensor. The methods also require an expensive and special solid-state carrier, or any special device or method for immobilization.

When either a combination of an antigen and an antibody or a combination of a protein and a ligand, in particular, is used as the biomaterial and the target material to be detected, such a combination has only a weak biological reaction such as antigen-antibody reaction. Such a case requires not only that a sufficient amount of the biomaterial is immobilized but also that the immobilized material retains its biological activity and is exposed at the surface so that it can participate in the reaction. However, in accordance with conventionally used solid-state carriers, even though a large amount of biomaterial can be immobilized to provide a sufficient film thickness, the biomaterial is enclosed in the film. These carriers therefore fail to retain enough reactivity and are not applicable to such uses as a biosensor or a diagnostic device, with which detection of a weak reaction such as antigen-antibody reaction is required.

Consequently, in the fields of medical treatment and diagnostic, genes analysis, and proteomics, especially in the fields of affinity purification tools or analysis tools of pharmacological actions, there has been a demand for the development of tools involving low non-specific adsorption, offering high efficiency, allowing operations within a short time, and being suitably used as a carrier for affinity chromatography.

As for the cases where a biomaterial or a specific material is immobilized onto any solid-state carrier, there has been a demand for a technique that can increase the amount of the biomaterial or the specific material introduced onto the solid-state carrier without impairing the reactivity (activity) of the biomaterial or the specific material. There has also been a demand for a technique to produce a solid-state carrier accurately at a low cost.

The present invention has been made in view of the problems mentioned above.

A first objective of the present invention is to provide a biomaterial structure that can both have a larger amount of biomaterial than the conventional art and maintain the reactivity of the biomaterial, a method of producing the biomaterial structure, and a biomaterial-carrying object including the biomaterial structure, and to thereby provide a method of purifying a target material and a method of analyzing a target material, which methods can suppress non-specific adsorption and carry out separation easily with high efficiency, and a container for affinity chromatography, a separation chip, a separation apparatus for analyzing a target material, and a sensor chip, each used for either of the methods.

A second objective of the present invention is to provide a solid-state carrier with an immobilized biomaterial that can both have a larger amount of biomaterial immobilized on the solid-state carrier than the conventional art and maintain the reactivity of the biomaterial, and a method of producing a solid-state carrier with an immobilized biomaterial both immobilize a larger amount of biomaterial on the solid-state carrier than the conventional art and maintain the reactivity of the biomaterial, a biomaterial immobilization kit for making the solid-state carrier with an immobilized biomaterial, and a sensor chip having the solid-state carrier with an immobilized biomaterial.

A third objective of the present invention is to provide a biomaterial complex that can contain a desired specific material in a larger amount than the conventional art, and a bio-material-complex carrying object having the biomaterial complex, and to thereby provide a method of purifying a target material, a container for affinity chromatography, a separation chip, a method of analyzing a target material, a separation apparatus for analyzing a target material, and a sensor chip, that can suppress non-specific adsorption and separate or analyze a target material easily with high efficiency.

A fourth objective of the present invention is to provide a solid-state carrier that can both have a larger amount of bio-related material immobilized on the solid-state carrier with high precision and maintain the reactivity of the bio-related material, to provide a method of producing the solid-state carrier, and to provide a biosensor, a diagnostic device, a bio-related-material immobilization kit including the solid-state carrier, and a method of measurement such as immunoassay using the solid-state carrier.

Means for Solving the Problem

The inventors of the present invention carried out an earnest study in order to solve the objectives and, as the result, have found that the problems can be solved by a biomaterial structure in which a biomaterial is bound to a compound that can bind to the biomaterial, and have attained the present invention.

Specifically, the inventors of the present invention carried out an earnest study in order to achieve the first objective and, as the result, have found that a biomaterial structure composed of mutually-linked particulate lumps, each of which includes a biomaterial combined with a compound capable of binding to the biomaterial and has a particle diameter of 10 µm or smaller, makes it possible to suppress non-specific adsorption without denaturing the biomaterial, and that the biomaterial structure allows affinity separation easily with high efficiency.

Also, the inventors of the present invention carried out an earnest study in order to achieve the second objective and, as the result, have found that if a mixture of a solution containing a biomaterial and a solution containing a compound having a functional group capable of binding to the biomaterial is introduced onto a solid-state carrier, the biomaterial and the compound combine to form a matrix in a chain and/or reticular structure linked to the solid-state carrier surface, thereby producing a solid-state carrier on which a larger amount of biomaterial is immobilized than the conventional art with maintaining the reactivity of the biomaterial.

In addition, the inventors of the present invention carried out an earnest study in order to achieve the third objective and, as the result, have found that if a biomaterial structure composed of mutually-linked particulate lumps, each of which includes a biomaterial combined with a compound capable of binding the biomaterial, is combined with a desired specific material capable of interacting a sample, non-specific adsorption can be suppressed to increase reactivity and to carry out affinity separation with high efficiency.

Moreover, the inventors of the present invention carried out an earnest study in order to achieve the fourth objective and, as the result, have found that a support material, a bio-related material, and a compound capable of binding to the bio-related material and/or support material are mixed in the presence of a solvent to form a mixture, which is introduced onto a solid-state carrier surface and from which the solvent is removed to form a matrix, thereby producing a solid-state carrier on which a larger amount of bio-related material than the conventional art is immobilized precisely with maintaining the reactivity of the bio-related material.

In accordance with an aspect of the present invention that can achieve the first objective, there is provided a biomaterial structure comprising mutually-linked particulate lumps, each of which includes at least one biomaterial and at least one compound capable of binding to the biomaterial, wherein the particle diameter of the particulate lumps is 10 µm or smaller. The biomaterial structure can contain a larger amount of biomaterial than the conventional art with maintaining the reactivity of the biomaterial. It also allows efficient affinity purification in a medium such as a solvent or a dispersion medium.

Preferably, spaces may be defined between the particulate lumps. The spaces increase the specific surface area of the biomaterial structure, and also function as a reaction field in which the biomaterial can work efficiently.

The weight ratio of the biomaterial to the biomaterial structure may preferably be 0.1 or higher. The feature means an increased content of the biomaterial in the biomaterial structure, allowing efficient separation of the biomaterial from a material that is specifically adsorbed, or interacts with, the biomaterial (e.g. a target material), within a limited area.

The biomaterial structure may preferably have a diameter of 30 nm or larger in a dry state. The biomaterial structure within the size range allows a larger amount of target material to be separated.

The compound may preferably include at least one compound having two or more functional groups capable of binding to the biomaterial. The feature facilitates the manufacture of the biomaterial structure.

The compound may also preferably be electrically uncharged. The feature can suppress possible non-specific interaction of the biomaterial structure with a material such as a target material. The term non-specific interaction means an undesired adsorption or interaction that occurs when the biomaterial structure is aimed at a desired adsorption or interaction between the biomaterial and a material such as a target material.

Preferably, the compound can be mixed with water and also can be mixed with at least one organic solvent. The feature extends the range of choices for the solvent used in the production of the biomaterial structure, and increases flexibility in designing the biomaterial structure. In addition, when the biomaterial structure is used together with any medium such as a solvent or a dispersion medium, the feature may also extend the range of choices for the medium and widen the range of potential uses for the biomaterial structure.

The molecular weight of the compound may preferably be 1000 or higher. The feature prevents internal cross-linking to the biomaterial during the manufacture of the biomaterial structure, allowing efficient production of the biomaterial structure.

The compound may preferably have a diameter of 1 nm or larger in a state of being mixed with a liquid. The feature also prevents internal cross-linking to the biomaterial during the manufacture of the biomaterial structure, allowing efficient production of the biomaterial structure.

In accordance with another aspect of the present invention that can achieve the first objective, there is provided a method of producing a biomaterial structure as defined above, comprising the step of mixing the biomaterial with the compound. The method ensures the production of the biomaterial structure.

In accordance with still another aspect of the present invention that can achieve the first objective, there is provided a biomaterial-carrying object, comprising: a solid-state carrier; and a biomaterial structure as defined above, immobilized at the solid-state carrier. The biomaterial-carrying object widens the range of applications of the biomaterial structure to, e.g., chips (basal plates), beads, and separation membranes.

In the biomaterial-carrying object, the biomaterial structure may preferably have a thickness of 5 nm or larger. The biomaterial structure within the size range allows a larger amount of target material to be separated when the biomaterial-carrying carrier is used for separation.

In accordance with still another aspect of the present invention that can achieve the first objective, there is provided a method of purifying a target material, comprising the steps of: contacting a biomaterial structure as defined above, with a sample liquid containing a target material that can be specifically adsorbed to the biomaterial; separating the biomaterial structure from the sample liquid; and liberating the target material caught in the biomaterial structure. The method suppresses non-specific adsorption and allows separation easily with high efficiency, providing tools for affinity purification or analysis of pharmacological actions with suppressing non-specific adsorption.

In accordance with still another aspect of the present invention that can achieve the first objective, there is provided a method of purifying a target material, comprising the steps of: passing a sample liquid through a flow channel holding a biomaterial structure as defined above, the sample liquid containing a target material capable of interacting specifically with the biomaterial; and retrieving a fraction containing the target material from an eluate flowing out of the flow channel. The method also suppresses non-specific adsorption and allows separation easily with high efficiency, providing tools for affinity purification or analysis of pharmacological actions with suppressing non-specific adsorption.

In accordance with still another aspect of the present invention that can achieve the first objective, there is provided a container for affinity chromatography, comprising: a container body capable of retaining fluid; and a biomaterial structure as defined above, held in the container body. The container also suppresses non-specific adsorption and allows separation easily with high efficiency, providing tools for affinity purification or analysis of pharmacological actions with suppressing non-specific adsorption.

In accordance with still another aspect of the present invention that can achieve the first objective, there is provided a separation chip, comprising: a basal plate provided with at least one flow channel; and a biomaterial structure as defined above, held by the flow channel. The separation chip also suppresses non-specific adsorption and allows separation easily with high efficiency, providing tools for affinity purification or analysis of pharmacological actions with suppressing non-specific adsorption.

In accordance with still another aspect of the present invention that can achieve the first objective, there is provided a method of analyzing a target material, comprising the steps of: contacting a sample liquid containing a target material with a biomaterial structure as defined above, the biomaterial structure including a biomaterial that can specifically adsorb a material with a specific structure; separating the biomaterial structure from the sample liquid; measuring the amount of the target material adsorbed to the biomaterial; and analyzing the structure of the target material. The method also suppresses non-specific adsorption and allows separation easily with high efficiency, providing tools for affinity purification or analysis of pharmacological actions with suppressing non-specific adsorption.

In accordance with still another aspect of the present invention that can achieve the first objective, there is provided a method of analyzing a target material, comprising the steps of: passing a sample liquid containing target material through a flow channel holding a biomaterial structure as defined above, the biomaterial structure including a biomaterial capable of interacting specifically with a material having a specific structure; measuring the amount of the target material in a fraction obtained from an eluate flowing out of the flow channel; and analyzing the structure of the target material. The method also suppresses non-specific adsorption and allows separation easily with high efficiency, providing tools for affinity purification or analysis of pharmacological actions with suppressing non-specific adsorption.

In accordance with still another aspect of the present invention that can achieve the first objective, there is provided a separation apparatus for analysis of target material, comprising: a separation chip having a basal plate provided with at least one flow channel, and a biomaterial structure as defined above, held by the flow channel, the biomaterial structure including a biomaterial capable of interacting specifically with a material having a specific structure; a sample-liquid providing unit for passing a sample liquid containing a target material through the flow channel of the separation chip; and a measuring unit for measuring the amount of the target material in a fraction obtained from an eluate flowing out of the flow channel. The apparatus also suppresses non-specific adsorption and allows separation easily with high efficiency, providing tools for affinity purification or analysis of pharmacological actions with suppressing non-specific adsorption.

In accordance with still another aspect of the present invention that can achieve the first objective, there is provided a separation apparatus for analysis of target material, comprising: a chip mounting unit to which a separation chip is mounted, the separation chip having a basal plate provided with at least one flow channel, and a biomaterial structure as defined above, held by the flow channel and including a biomaterial capable of interacting specifically with a material having a specific structure; a sample-liquid providing unit for passing a sample liquid containing a target material through the flow channel of the separation chip mounted to the chip mounting unit; and a measuring unit for measuring the amount of the target material in a fraction obtained from an eluate flowing out of the flow channel. The apparatus also suppresses non-specific adsorption and allows separation easily with high efficiency, providing tools for affinity purification or analysis of pharmacological actions with suppressing non-specific adsorption.

In accordance with still another aspect of the present invention that can achieve the first objective, there is provided a sensor chip comprising a biomaterial structure as defined above. The sensor chip can suppress non-specific adsorption and have high sensitivity.

In accordance with an aspect of the present invention that can achieve the second objective, there is provided a biomaterial-immobilized solid-state carrier, comprising: a solid-state carrier; and a matrix formed on the surface of the solid-state carrier, the matrix including principal chains composed of at least one biomaterial and at least one compound capable of binding to the biomaterial (i.e. biomaterial structure). The biomaterial-immobilized solid-state carrier allows a larger amount of biomaterial to be immobilized thereon with maintaining the reactivity of the biomaterial. In addition, the matrix holds the biomaterial, such as a ligand, being immobilized three-dimensionally, thus providing a reaction field in which the biomaterial can work effectively.

The term "principal chains" means chain and/or reticular structure composed of the biomaterial linked with the compound and constituting the skeleton of the matrix; the compound is linked to the biomaterial via linking groups to form the structure. In other words, the matrix (at least partially) has abridged structure in which a piece of biomaterial is positioned among molecules of the compound while a molecule of the compound is positioned among pieces of the biomaterial, thus the biomaterial and the compound composing the principal chains of the matrix.

The matrix may preferably be formed by supplying a mixture containing both the biomaterial and the compound onto the surface of the solid-state carrier in the presence of a solvent. Thus the matrix can be produced with facility.

In accordance with another aspect of the present invention that can achieve the second objective, there is provided a biomaterial-immobilized solid-state carrier, comprising: a solid-state carrier; and a matrix formed on the surface of the solid-state carrier by supplying a mixture containing both the biomaterial and the compound onto the surface of the solid-state carrier in water. The biomaterial-immobilized solid-state carrier also allows a larger amount of biomaterial to be immobilized than the conventional art. In addition, the matrix holds the biomaterial, such as a ligand, being immobilized three-dimensionally, thus providing a reaction field in which the biomaterial can work effectively.

The compound may preferably include at least one compound having two or more functional groups capable of binding to the biomaterial. The feature facilitates the formation of the matrix.

The weight ratio of "the biomaterial/(the compound and the biomaterial)" in the mixture may preferably be 0.1 or higher. The feature allows a larger amount of biomaterial to be immobilized.

Also the weight ratio of the biomaterial to the matrix may preferably be 0.1 or higher. The feature helps suppress non-specific adsorption to the compound.

The matrix may preferably have a film thickness of 5 nm or larger in a dry state. The matrix with a film thickness within the range allows a larger amount of biomaterial immobilized on the solid-state carrier.

The compound may preferably be electrically uncharged. The feature helps prevent the biomaterial from being involved in non-specific interaction. The term non-specific interaction means an interaction that occurs when the biomaterial structure is aimed at a desired adsorption or interaction between the biomaterial and a material such as a target material, but which is not the desired adsorption or interaction.

Preferably, the compound can be mixed with water and also can be mixed with at least one organic solvent. The feature widens the range of choices for the solvent used in the production of the solid-state carrier in accordance with the present invention, and increases flexibility in designing the structure of the matrix. In addition, when the biomaterial-immobilized solid-state carrier in accordance with the present invention is used together with any solvent, the feature may also extend the range of choices for the solvent and widen the range of potential uses.

When the matrix is contacted with a solution containing an interacting substance capable of specifically interacting with the biomaterial, the ratio of the amount of the interacting substance that interacts with the biomaterial to the amount of the biomaterial in the matrix may preferably be 0.5 or higher. The feature means that the matrix can induce the interaction between the biomaterial and the interacting substance more efficiently than the conventional art.

In accordance with still another aspect of the present invention that can achieve the second objective, there is provided a biomaterial-immobilized solid-state carrier, comprising: a solid-state carrier; and a matrix formed on the surface of the solid-state carrier, the matrix including at least one biomaterial and at least one compound capable of binding to the biomaterial; wherein the matrix has a film thickness of 5 nm or larger in a dry state, and when the matrix is contacted with a solution containing an interacting substance capable of specifically interacting with the biomaterial, the ratio of the amount of the interacting substance that interacts with the biomaterial to the amount of the biomaterial in the matrix is 0.5 or higher. The biomaterial-immobilized solid-state carrier allows a larger amount of biomaterial to be immobilized onto the solid-state carrier with maintaining the reactivity of the biomaterial. In addition, the biomaterial-immobilized solid-state carrier can bring about the interaction between the biomaterial and the interacting substance more efficiently than the conventional art.

This feature also enables the biomaterial-immobilized solid-state carrier to be applied to a sensor chip: in accordance with still another aspect of the present invention that can achieve the second objective, there is provided a sensor chip comprising a biomaterial-immobilized solid-state carrier as defined above.

In accordance with still another aspect of the present invention that can achieve the second objective, there is provided a method of producing a biomaterial-immobilized solid-state carrier, comprising: supplying a mixture containing both at least one biomaterial and at least one compound capable of binding to the biomaterial onto a solid-state carrier in the presence of a solvent, thereby forming a matrix having principal chains composed of the biomaterial and the compound on the surface of the solid-state carrier. The method can produce a solid-state carrier on which a larger amount of biomaterial is immobilized than the conventional art with maintaining the reactivity of the biomaterial. The method of production is a quite simple and easy method in the point that a solid-state carrier coated with the matrix having the above effect can be obtained simply by mixing the target biomaterial, which is to be immobilized, with the compound and bringing the mixture into contact with a solid-state carrier.

The solvent may preferably be water.

In accordance with still another aspect of the present invention that can achieve the second objective, there is provided a biomaterial immobilization kit for producing a biomaterial-immobilized solid-state carrier as defined above, comprising: at least one compound capable of binding the biomaterial; and a solvent that can be mixed with both the biomaterial and the compound. The kit facilitates the production of the solid-state carrier with an immobilized biomaterial.

In accordance with an aspect of the present invention that can achieve the third objective, there is provided a biomaterial complex comprising: a biomaterial structure as defined above; and a specific material bound to the biomaterial structure, the specific material being a material other than either the biomaterial or the compound. Namely, the biomaterial complex comprises: a biomaterial structure having mutually-linked particulate lumps, each of which includes at least one biomaterial and at least one compound capable of binding to the biomaterial, the particle diameter of the particulate lumps being 10 µm or smaller; and a specific material bound to the biomaterial structure, the specific material being a material other than either the biomaterial or the compound. The complex can carry a larger amount of specific material than the conventional art with maintaining the properties of the specific material. The complex also has an increased specific surface area and offers reactivity with high efficiency.

Preferably, spaces may be defined between the particulate lumps. The spaces can function as a reaction field in which the biomaterial can work efficiently.

The weight ratio of the biomaterial to the biomaterial structure may preferably be 0.1 or higher. The feature means an increased content of the biomaterial in the biomaterial complex accompanied by an increased content of the specific material, allowing full use of the characteristics of the specific material.

The biomaterial complex in accordance with the present invention may preferably have a diameter of 30 nm or larger in a dry state. The biomaterial complex with a size in the range allows interaction and separation of a larger amount of target material.

The compound may preferably include at least one compound having two or more functional groups capable of binding to the biomaterial. The feature facilitates the formation of the biomaterial complex.

The compound may also preferably be electrically uncharged. The feature can suppress possible non-specific interaction of the biomaterial complex with a material such as a target material. The term non-specific interaction means an interaction that occurs when the biomaterial complex is aimed at a desired adsorption or interaction between the biomaterial and a material such as a target material, but which is not the desired adsorption or interaction.

Preferably, the compound can be mixed with water and also can be mixed with at least one organic solvent. The feature extends the range of choices for the solvent used in the production of the biomaterial complex, and increases flexibility in designing the biomaterial complex. In addition, when the biomaterial complex is used together with any medium such as a solvent or a dispersion medium, the feature may also extend the range of choices for the medium and widen the range of potential uses for the biomaterial complex.

The molecular weight of the compound may preferably be 1000 or higher. The feature prevents internal cross-linking to the biomaterial during the manufacture of the biomaterial complex, allowing efficient production of the biomaterial complex.

The compound may preferably have a diameter of 1 nm or larger in a state of being mixed with a liquid. The feature also prevents internal cross-linking to the biomaterial during the manufacture of the biomaterial complex, allowing efficient production of the biomaterial complex.

The biomaterial may preferably be biomolecules, and more preferably be a protein. The feature enables the biomaterial complex in accordance with the present invention to employ the characteristics of the protein. Specifically, the use of, for example, albumin as the biomaterial can suppress non-specific adsorption. As another example, the use of avidin as the biomaterial allows a large amount of biotinylated specific material to be immobilized easily. As another example, the use of protein A as the biomaterial, when combined with the use of an antibody as the specific material, allows a large amount of antibody to be immobilized easily.

The specific material may preferably be at least one selected from the group consisting of metal chelates, vitamins, saccharides, glutathione, boronic acid, proteins, antigens, nucleic acids, physiologically active substances, lipids, hormones, environmental hormones, and chelate-forming groups. More preferably, the specific material may be at least one selected from the group consisting of a metal chelate, biotin, a saccharide, glutathione, boronic acid, an antibody, an antigen, a receptor, a physiologically active substance, and a chelate forming group. The use of a metal chelate, glutathione, or a saccharide as the specific material enables effective interaction for purification and separation in purifying a protein fused with an affinity tag selected from polyhistidine (His-tag), glutathione-s-transferase (GST), and maltose-binding protein. The use of a saccharide as the specific material enables specific interaction of a virus. The use of boronic acid as the specific material enables purification or interaction of a sugar chain or a compound having a saccharide, such as a glycosylated protein. The use of an enzyme as the specific material enables interaction of a substrate, offering an effective immobilized enzyme. The use of a lipid as the specific material enables screening or separation/purification of a lipid binding protein. The use of a hormone or environmental hormone as the specific material enables screening of a biomaterial binding to the hormone or environmental hormone. The use of a vitamin, e.g. biotin, as the specific material, when combined with the use of avidin, streptavidin, or an avidin derivative as an interacting substance, enables effective purification or interaction through biotin-avidin binding.

The use of an antibody or an antigen as the specific material enables effective purification or interaction of an antigen or an antibody, respectively. The use of a nucleic acid (e.g. a nucleic acid such as DNA or RNA, or a peptide nucleic acid such as PNA) as the specific material allows the biomaterial complex in accordance with the present invention to be applied to analysis of gene interaction. The use of a physiologically active substance, or a protein such as a receptor involved in a disease, as the specific material allows the biomaterial complex in accordance with the present invention to be applied to a tool for screening candidate compounds for medicines or elucidating the action mechanisms of medicines. The use of a chelate forming group as the specific material enables separation of metal ions.

The specific material may preferably be coupled to the biomaterial via hydrophilic molecules. The hydrophilic molecules may preferably include ethylene oxide. The feature can induce interaction between the sample and the specific material with effectively, when the biomaterial complex in accordance with the present invention is used for affinity separation.

In accordance with still another aspect of the present invention that can achieve the third objective, there is provided a biomaterial-complex carrying object comprising: a solid-state carrier; and a biomaterial complex as defined above, immobilized at the solid-state carrier. The biomaterial-complex carrying object widens the range of applications of the biomaterial complex to, e.g., chips (basal plates), beads, and separation membranes.

In the biomaterial complex carrying object, the biomaterial complex may preferably have a thickness of 5 nm or larger. The biomaterial complex with a size in the range allows a larger amount of target material to be separated when the biomaterial complex carrying object is used for separation.

In accordance with still another aspect of the present invention that can achieve the third objective, there is provided a method of purifying a target material, comprising the steps of: contacting a sample liquid with a biomaterial complex as defined above, the sample liquid containing a target material that can be specifically adsorbed to the specific material; separating the biomaterial complex from the sample liquid; and liberating the target material caught by the specific material. The method suppresses non-specific adsorption and allows separation easily with high efficiency, providing tools for affinity purification or analysis of pharmacological actions with suppressing non-specific adsorption.

In accordance with still another aspect of the present invention that can achieve the third objective, there is provided a method of purifying a target material, comprising the steps of: passing a sample liquid through a flow channel holding a biomaterial complex as defined above, the sample liquid containing a target material capable of specifically interacting with the specific material; and retrieving a fraction containing the target material from an eluate flowing out of the flow channel. The method also suppresses non-specific adsorption and allows separation easily with high efficiency, providing tools for affinity purification or analysis of pharmacological actions with suppressing non-specific adsorption.

In accordance with still another aspect of the present invention that can achieve the third objective, there is provided a container for affinity chromatography, comprising: a container body capable of retaining fluid; and a biomaterial complex as defined above, held in the container body. The container also suppresses non-specific adsorption and allows separation easily with high efficiency, providing tools for affinity purification or analysis of pharmacological actions with suppressing non-specific adsorption.

In accordance with still another aspect of the present invention that can achieve the third objective, there is provided a separation chip, comprising: a basal plate provided with at least one flow channel; and a biomaterial complex as defined above, held by the flow channel. The separation chip also suppresses non-specific adsorption and allows separation easily with high efficiency, providing tools for affinity purification or analysis of pharmacological actions with suppressing non-specific adsorption.

In accordance with still another aspect of the present invention that can achieve the third objective, there is provided a method of analyzing a target material, comprising the steps of: contacting a biomaterial complex as defined above, with a sample liquid containing a target material, the biomaterial complex including a specific material capable of specifically adsorbing a material having a specific structure; separating the biomaterial complex from the sample liquid; measuring the amount of the target material adsorbed to the specific material; and analyzing the structure of the target material. The method also suppresses non-specific adsorption and allows separation easily with high efficiency, providing tools for affinity purification or analysis of pharmacological actions with suppressing non-specific adsorption.

In accordance with still another aspect of the present invention that can achieve the third objective, there is provided a method of analyzing a target material, comprising the steps of: passing a sample liquid containing a target material through a flow channel holding a biomaterial complex as defined above, the biomaterial complex including a specific material capable of specifically interacting with a material having a specific structure; measuring the amount of the target material in a fraction obtained from an eluate flowing out of the flow channel; and analyzing the structure of the target material. The method also suppresses non-specific adsorption and allows separation easily with high efficiency, providing tools for affinity purification or analysis of pharmacological actions with suppressing non-specific adsorption.

In accordance with still another aspect of the present invention that can achieve the third objective, there is provided a separation apparatus for analyzing a target material, comprising: a separation chip having a basal plate provided with at least one flow channel and a biomaterial complex as defined above, the biomaterial complex being held by the flow channel and including a specific material capable of specifically interacting with a material having a specific structure; a sample-liquid providing unit for passing a sample liquid containing a target material through the flow channel of the separation chip; and a measuring unit for measuring the amount of the target material in a fraction obtained from an eluate flowing out of the flow channel. The separation apparatus also suppresses non-specific adsorption and allows separation easily with high efficiency, providing tools for affinity purification or analysis of pharmacological actions with suppressing non-specific adsorption.

In accordance with still another aspect of the present invention that can achieve the third objective, there is provided a separation apparatus for analyzing a target material, comprising: a chip mounting unit to which a separation chip is mounted, the separation chip having a basal plate provided with at least one flow channel and a biomaterial complex as defined above, the biomaterial complex being held by the flow channel and including a specific material capable of specifically interacting with a material having a specific structure; a sample-liquid providing unit for passing a sample liquid containing a target material through the flow channel of the separation chip mounted to the chip mounting unit; and a measuring unit for measuring the amount of the target material in a fraction obtained from an eluate flowing out of the flow channel. The separation apparatus also suppresses non-specific adsorption and allows separation easily with high efficiency, providing tools for affinity purification or analysis of pharmacological actions with suppressing non-specific adsorption.

In accordance with still another aspect of the present invention that can achieve the third objective, there is provided a sensor chip comprising a biomaterial complex as defined above. The use of the biomaterial complex for a sensor chip, such as a DNA chip or a protein chip, allows the sensor chip to suppress non-specific adsorption and increase reactivity.

An aspect of the present invention that can achieve the fourth objective provides (1) a biomaterial-immobilized solid-state carrier, comprising: a solid-state carrier; and a matrix formed on a surface of the carrier, the matrix including a support material, a bio-related material, and a compound capable of binding to the bio-related material and/or the support material.

Preferred features of the aspect of the present invention that can achieve the fourth objective include:

(2) a biomaterial-immobilized solid-state carrier as defined in (1), wherein the bio-related material is cross-linked via a compound capable of binding to the bio-related material;

(3) a biomaterial-immobilized solid-state carrier as defined in (1) or (2), wherein the matrix has voids;

(4) a biomaterial-immobilized solid-state carrier as defined in any one of (1) to (3), wherein the matrix is formed by supplying a mixture containing a support material, a bio-related material, and a compound capable of binding the bio-related material and/or the support material, onto an surface of the solid-state carrier in the presence of a solvent, and then removing the solvent;

(5) a biomaterial-immobilized solid-state carrier as defined in (4), wherein the solvent is water;

(6) a biomaterial-immobilized solid-state carrier as defined in any one of (1) to (5), wherein the matrix has a void ratio of 5% or higher;

(7) a biomaterial-immobilized solid-state carrier as defined in any one of (1) to (6), wherein the matrix has a film thickness of 20 nm or larger in a dry state;

(8) a biomaterial-immobilized solid-state carrier as defined in any one of (1) to (7), wherein the compound has two or more bonding functional groups in each molecule;

(9) a biomaterial-immobilized solid-state carrier as defined in any one of (1) to (8), wherein the compound is a polymer compound;

(10) a biomaterial-immobilized solid-state carrier as defined in any one of (1) to (9), wherein the compound can be mixed with water and also can be mixed with at least one organic solvent; and

(11) a biomaterial-immobilized solid-state carrier as defined in any one of (1) to (10), wherein the support material is in the form of particles having an average diameter of about 10 nm-100 μm.

Another aspect of the present invention provides (12) a method of producing a biomaterial-immobilized solid-state carrier as defined in any one of (1) to (11), comprising the steps of: supplying a mixture containing the support material, the bio-related material, and the compound capable of binding to the bio-related material and/or the support material, onto the surface of the solid-state carrier in the presence of a solvent; and removing the solvent to form the matrix.

Still other aspects of the present invention provide:

(13) a bio-related-material immobilization kit for producing a biomaterial-immobilized solid-state carrier as defined in any one of (1) to (11), comprising at least the support material and the compound capable of binding to the bio-related material and/or the support material;

(14) an array of a bio-related material, comprising a solid-state carrier and at least two matrices arranged in different areas on the solid-state carrier, each of the matrices including the bio-related material, a support material, and a compound capable of binding to the bio-related material and/or the support material;

(15) a biosensor comprising a biomaterial-immobilized solid-state carrier as defined in any one of (1) to (11) and/or an array as defined in claim (14); and

(16) a diagnostic device comprising a biomaterial-immobilized solid-state carrier as defined in any one of (1) to (11) and/or an array as defined in claim (14).

Still other aspects of the present invention provide:

(17) a method of assaying at least one assay target in a sample, comprising the steps of (a) delivering the sample to a biomaterial-immobilized solid-state carrier as defined in any one of (1) to (11) and/or an array as defined in claim (14), the carrier and/or the array including at least one bio-related material that can react with the assay target, and (b) detecting an interaction between the bio-related material and the assay target or a reaction caused by adding a labeling material capable of reacting with the assay target, to thereby detect the presence or the amount of the assay target;

(18) a method as defined in (17), wherein at least the sample is fluid, and the delivery of the sample is carried out by means of flow;

(19) a method as defined in (17) or (18), further comprising the step of detecting a reaction in a reference area defined on the biomaterial-immobilized solid-state carrier as defined in any one of (1) to (11) and/or the array as defined in (14), to determine whether or not the assay is successful or to correct the detection results of the presence of, or the amount of, the assay target; and

(20) a method as defined in any one of (17) to (19), further comprising the step of (c) associating the presences or the amounts of two or more assay targets with specific symptoms in order to assay the two or more assay targets simultaneously.

Advantageous Effects of the Invention

The biomaterial structure, the method of producing the biomaterial structure and the biomaterial-carrying object in accordance with the present invention can provide a structure that contains a large amount of biomaterial with maintaining its reactivity. The method of purifying a target material, the container for affinity chromatography, the separation chip, the method of analyzing a target material, and the separation apparatus for analyzing a target material in accordance with the present invention can suppress non-specific adsorption and facilitates efficient separation, allowing purification and analysis easily with high precision. The sensor chip having the biomaterial structure in accordance with the present invention has high sensitivity.

The biomaterial-immobilized solid-state carrier, the method of producing the biomaterial-immobilized solid-state carrier, and the biomaterial immobilization kit in accordance with the present invention can markedly increase the amount of the biomaterial introduced onto the solid-state carrier with maintaining the reactivity of the biomaterial, compared to the conventional art.

The biomaterial-immobilized solid-state carrier in accordance with the present invention also can provide a sensor chip with high sensitivity.

The biomaterial complex and the biomaterial-complex-carrying object in accordance with the present invention can provide a structure that contains a large amount of specific material with maintaining its reactivity. The method of purifying a target material, the container for affinity chromatography, the separation chip, the method of analyzing a target material, and the separation apparatus for analyzing a target material in accordance with the present invention can suppress non-specific adsorption and facilitates efficient separation, allowing purification and analysis easily with high precision. The sensor chip in accordance with the present invention can suppress non-specific adsorption and enables analysis with high sensitivity.

The solid-state carrier and the method of producing the solid-state carrier in accordance with the present invention can provide a solid-state carrier on which a bio-related material is precisely immobilized in a larger amount than the conventional art with maintaining the reactivity of the bio-related material, which can be produced easily at a low cost, and which is also excellent in its storage stability. The solid-state carrier can be used for producing a device such as a diagnostic device or a biosensor that has higher precision and sensitivity than the conventional art and can be used in the fields such as medical treatment and diagnosis, gene analysis, and proteomics.

BRIEF DESCRIPTION OF THE DRAWINGS

Each of FIG. 1(a)

Each of FIG. 2(a)

Figure 3A:
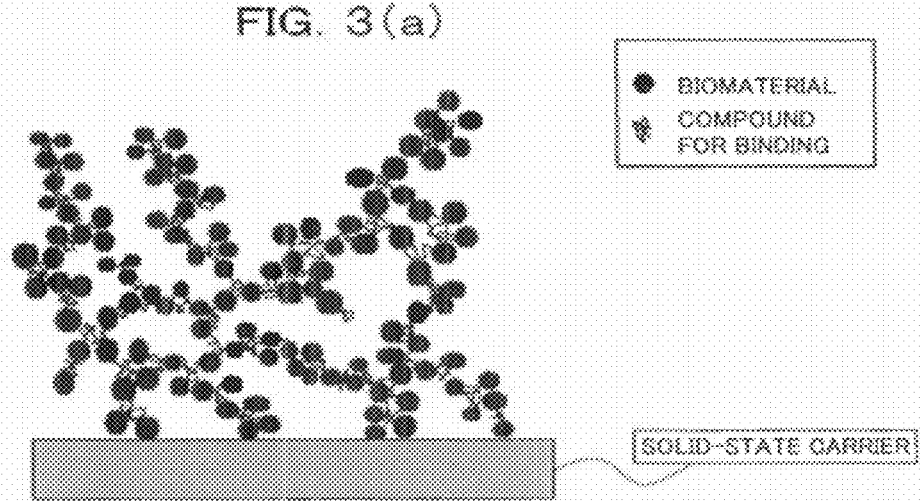
Figure 3B:
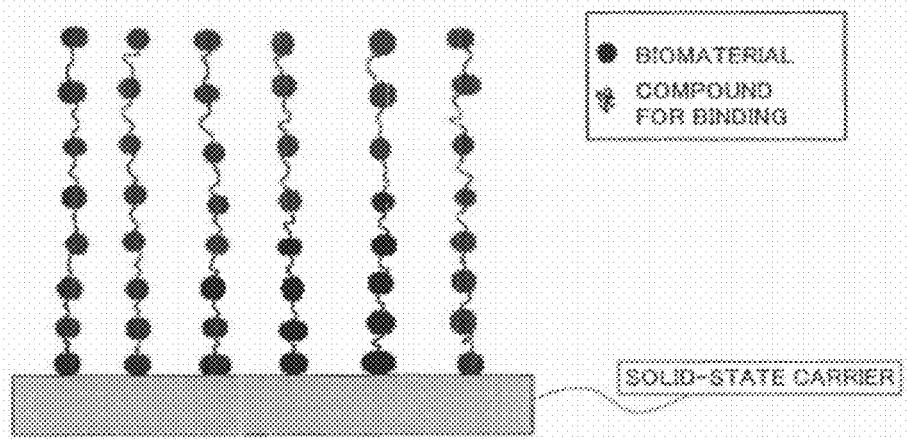
Figure 3C:
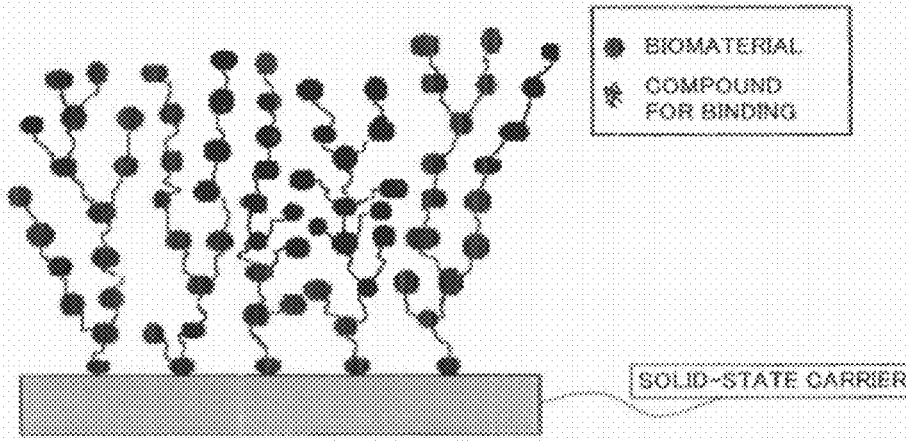
Figure 4:
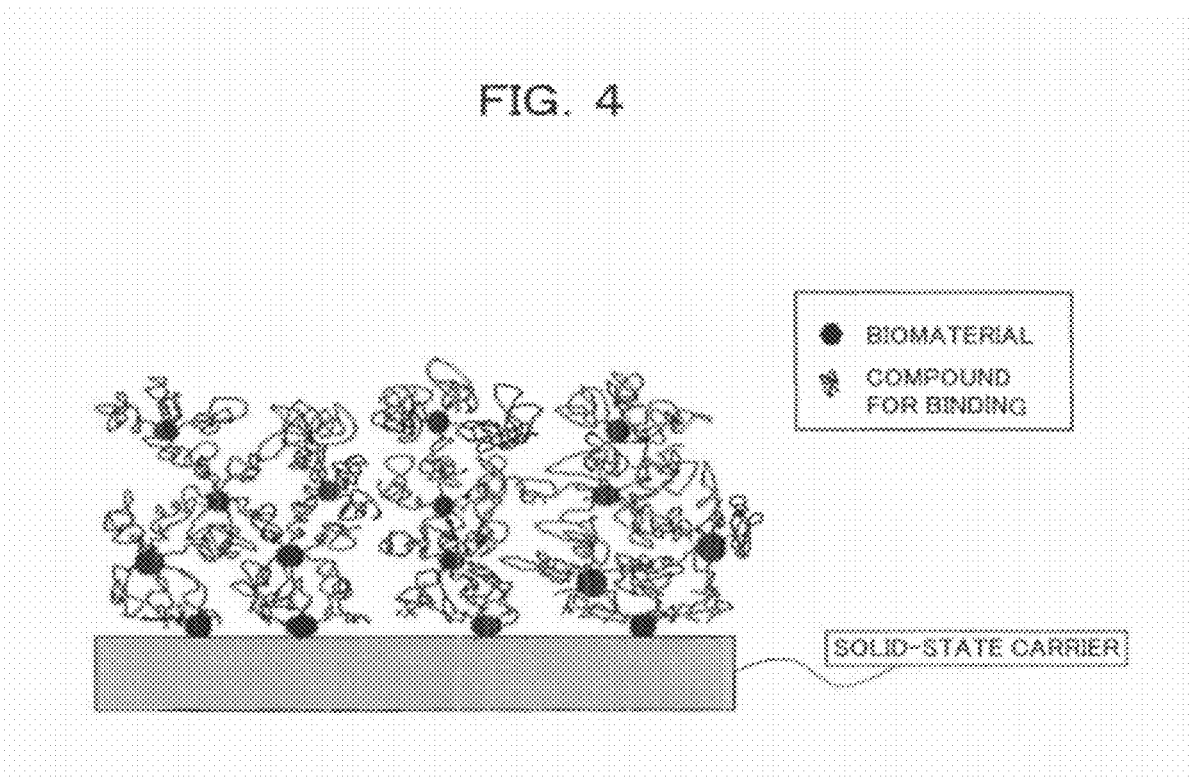
Figure 5:
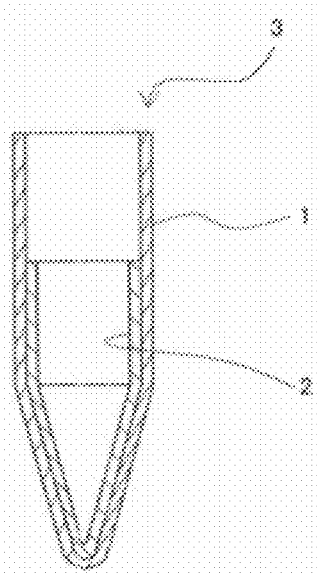
Figure 6:
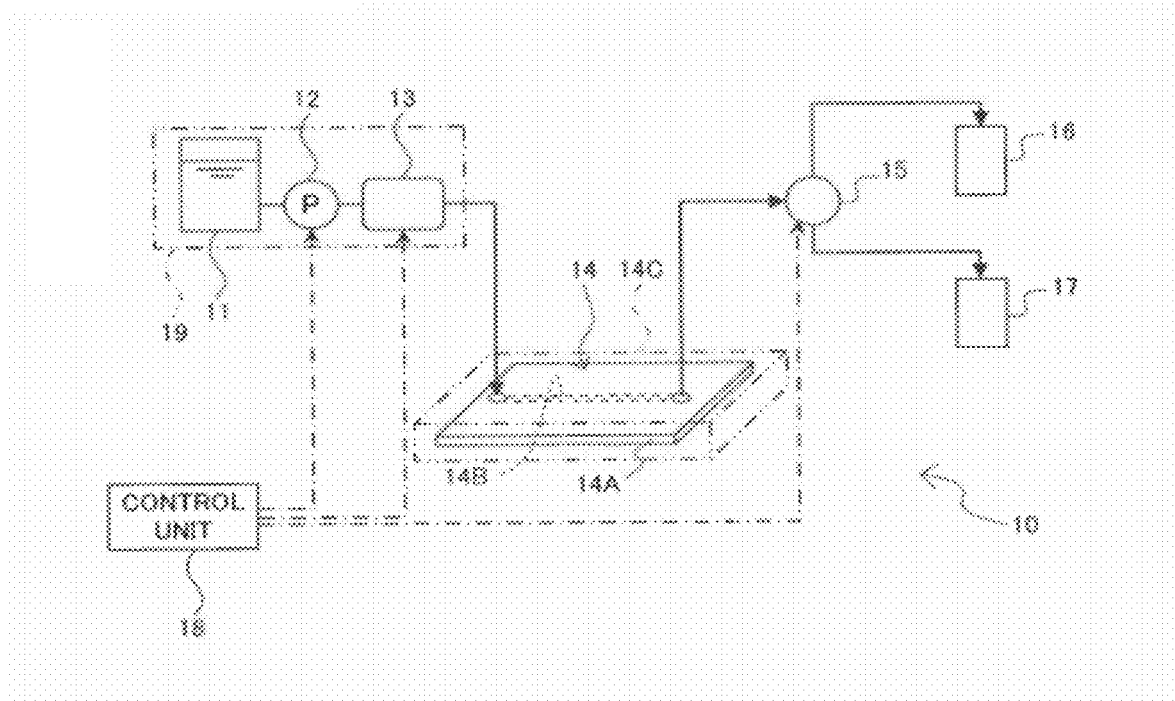
Figure 7:
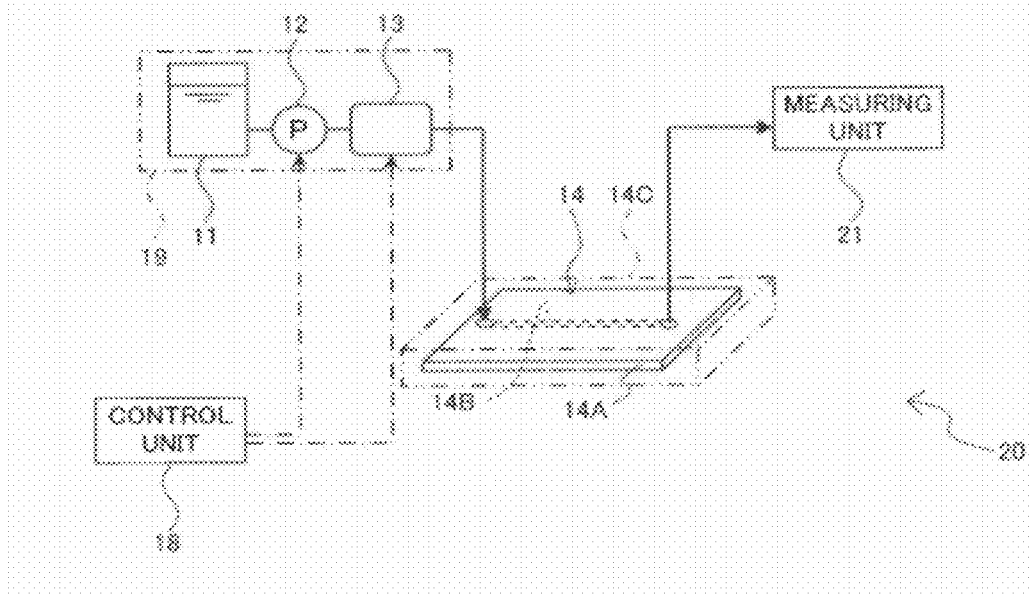
Figure 8:
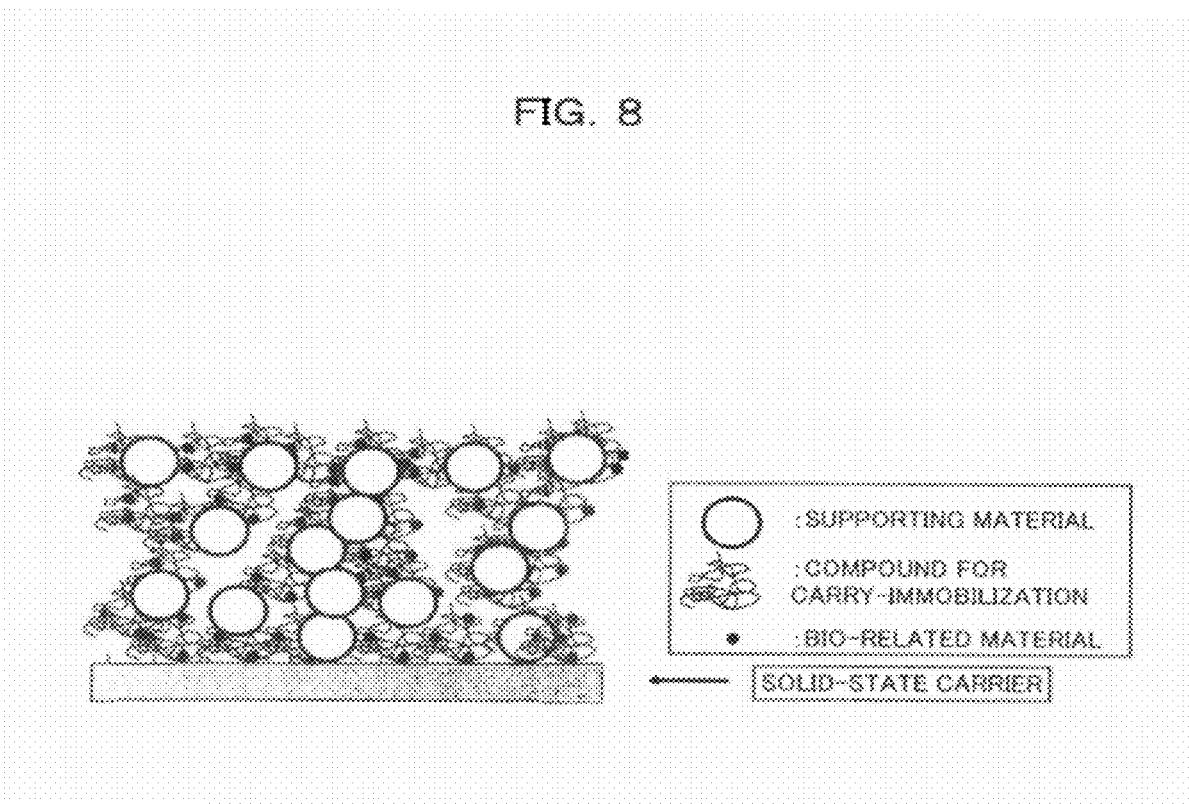
Figure 12:
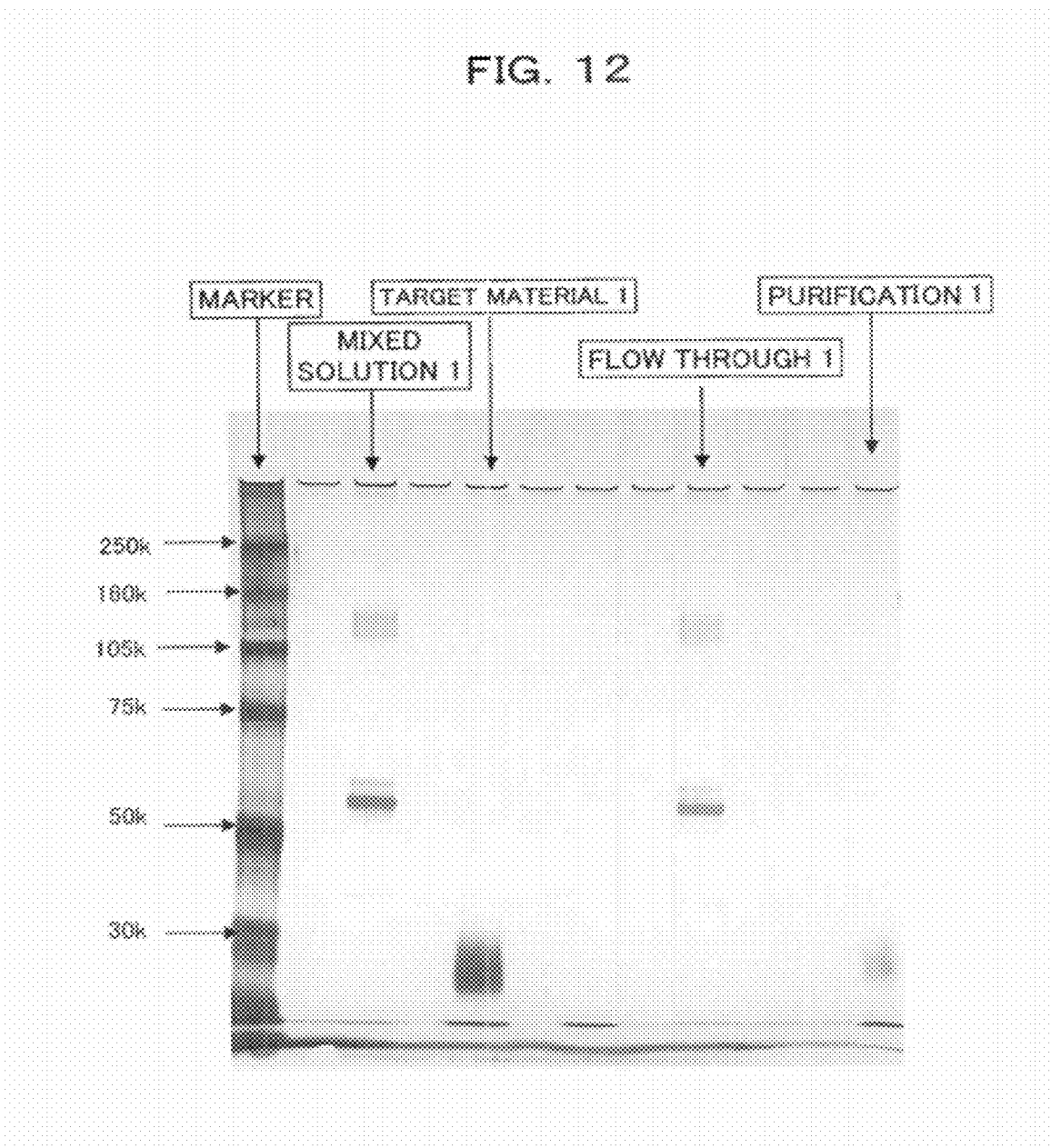
Figure 13:
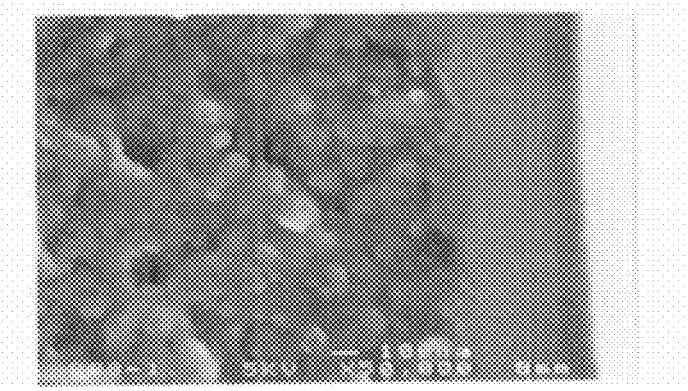
Figure 14:
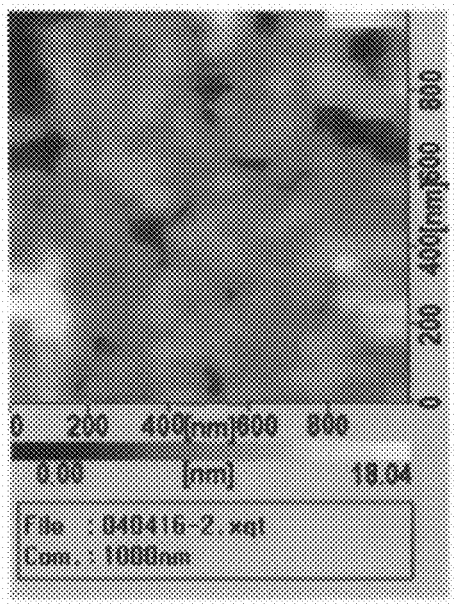
Figure 16A:
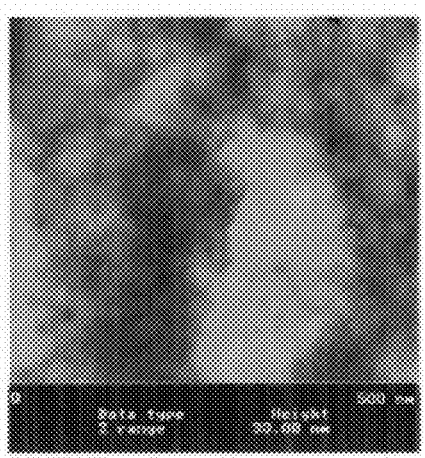
Figure 16B:
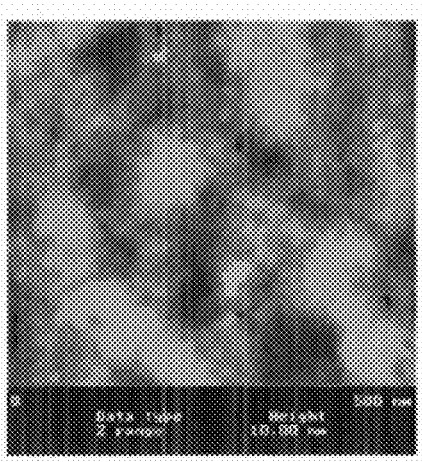
Figure 16C:
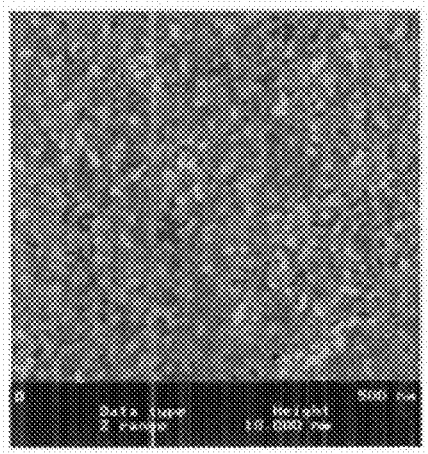
Figure 17A:
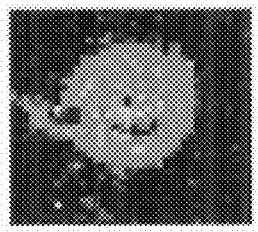
Figure 17B:
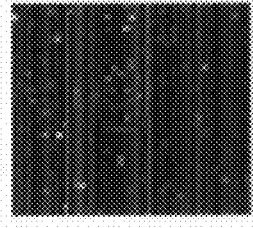
Figure 18:
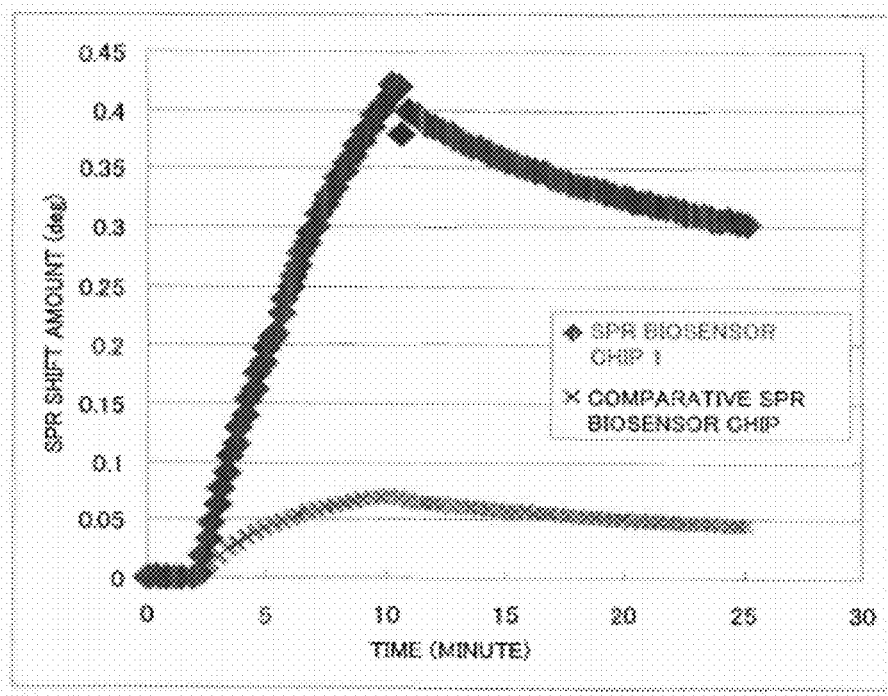
Figure 19:
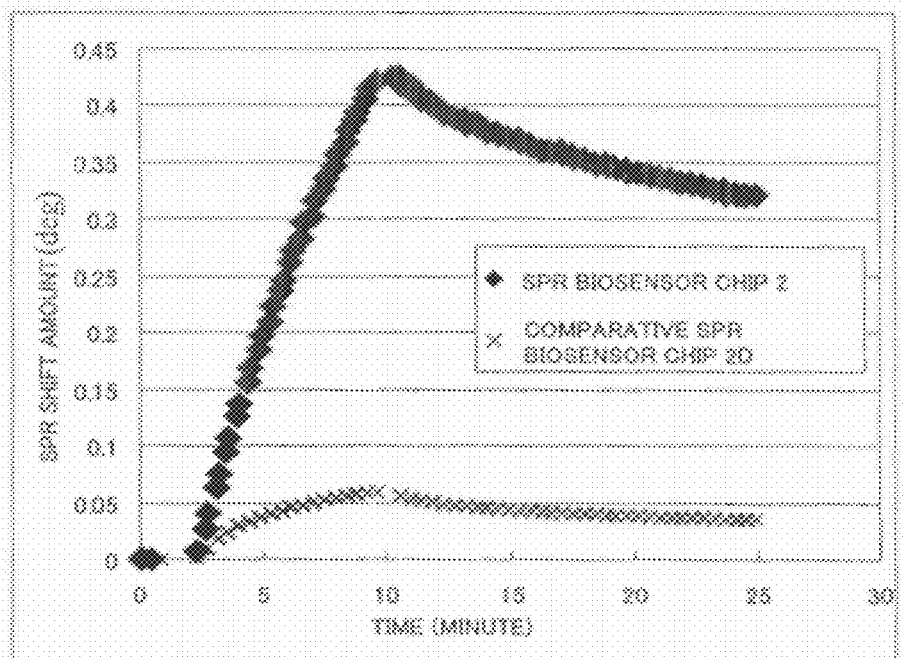
Figure 20:
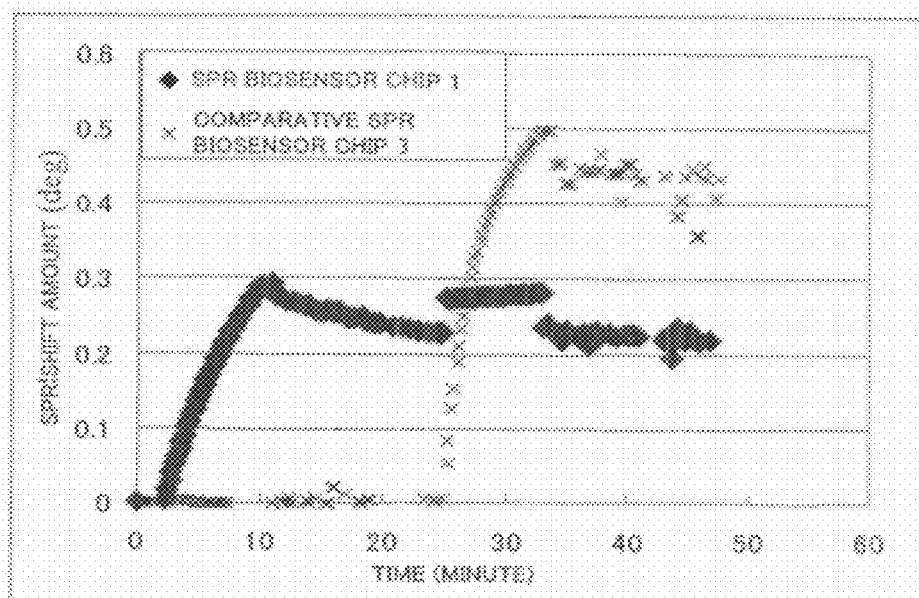
Figure 21:
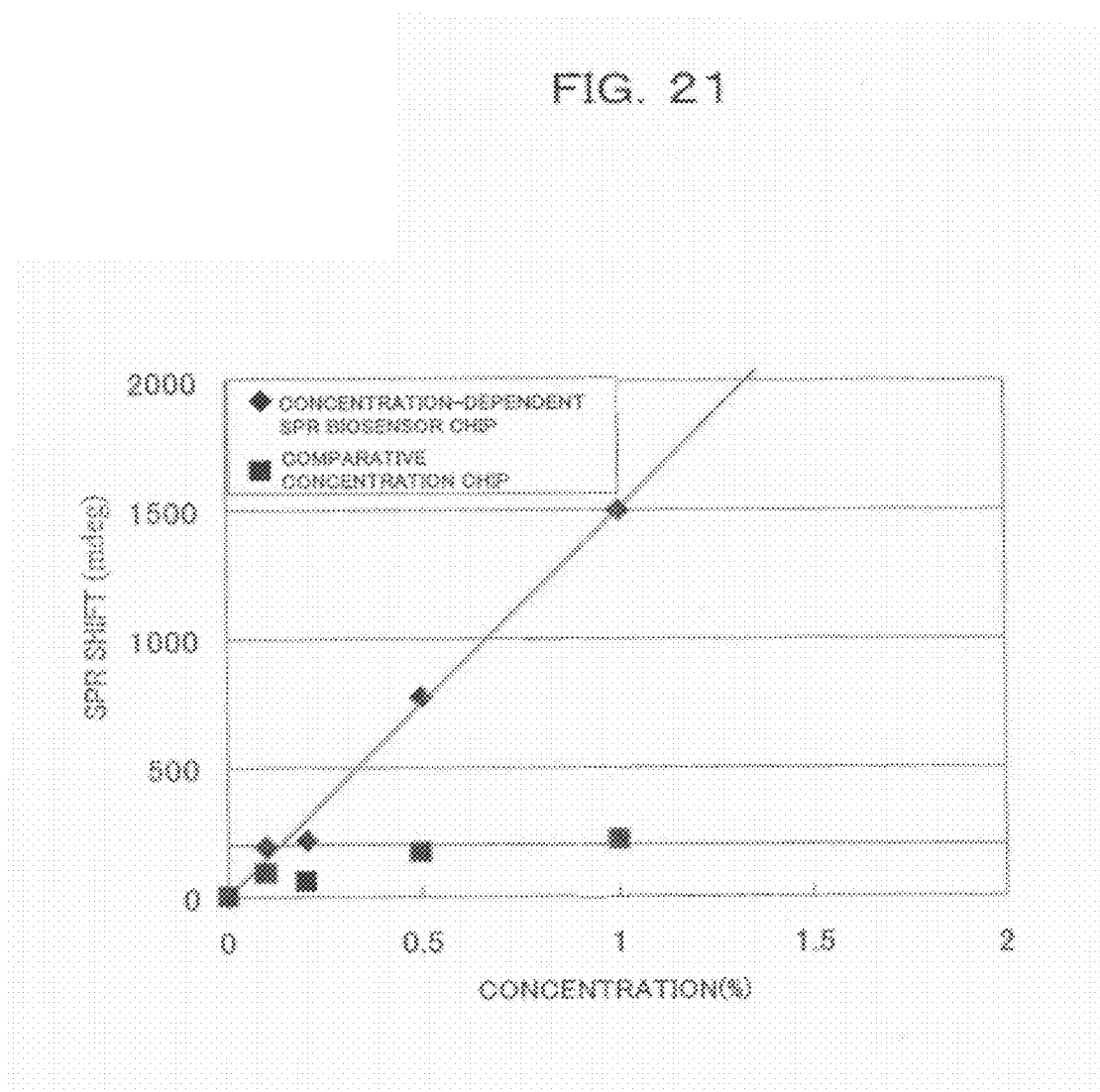
Figure 22:
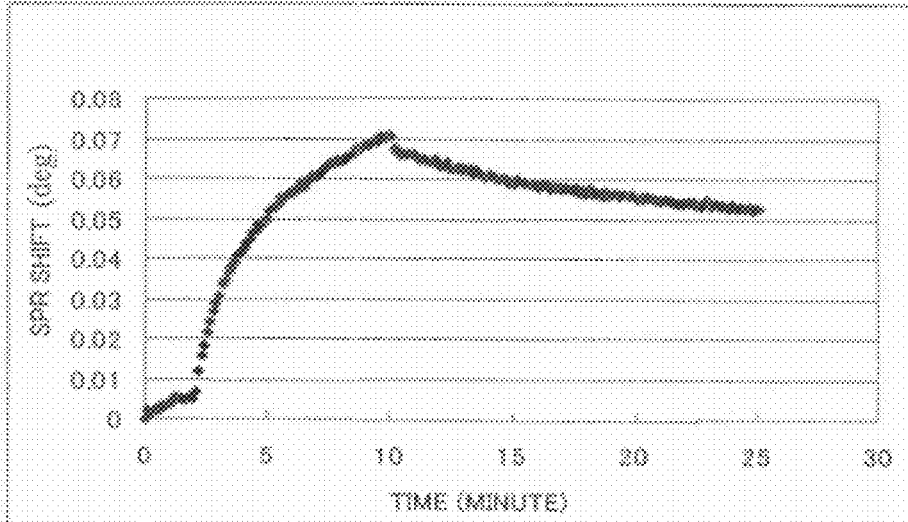
Figure 23:
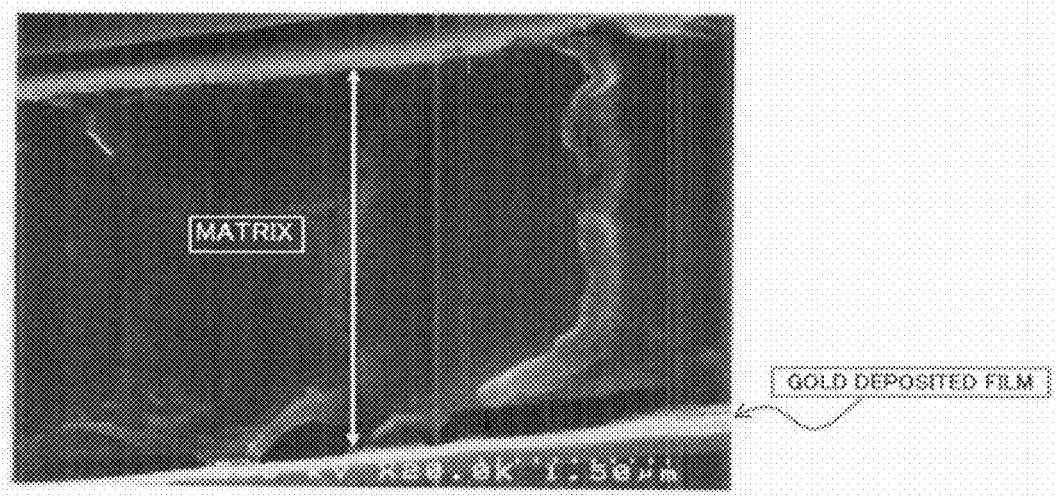
Figure 24:
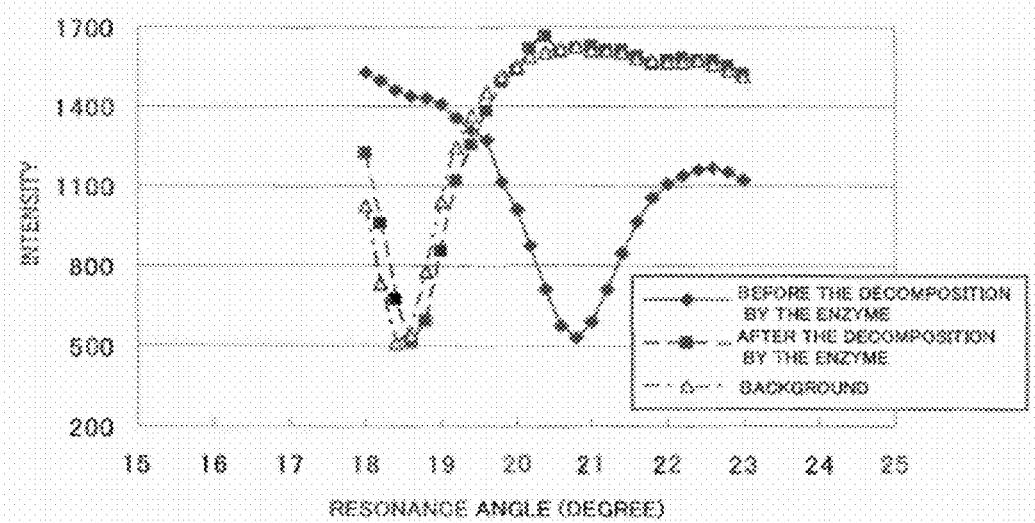
Figure 25:
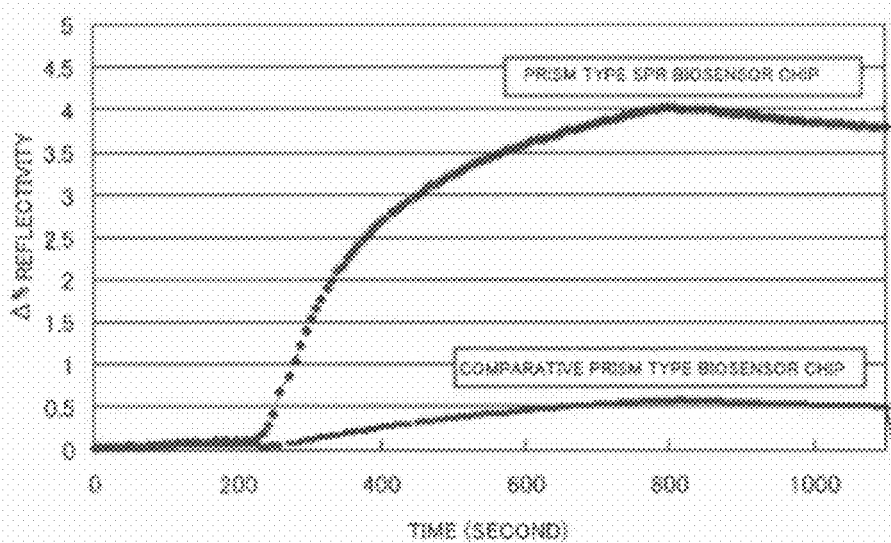
Figure 26A:
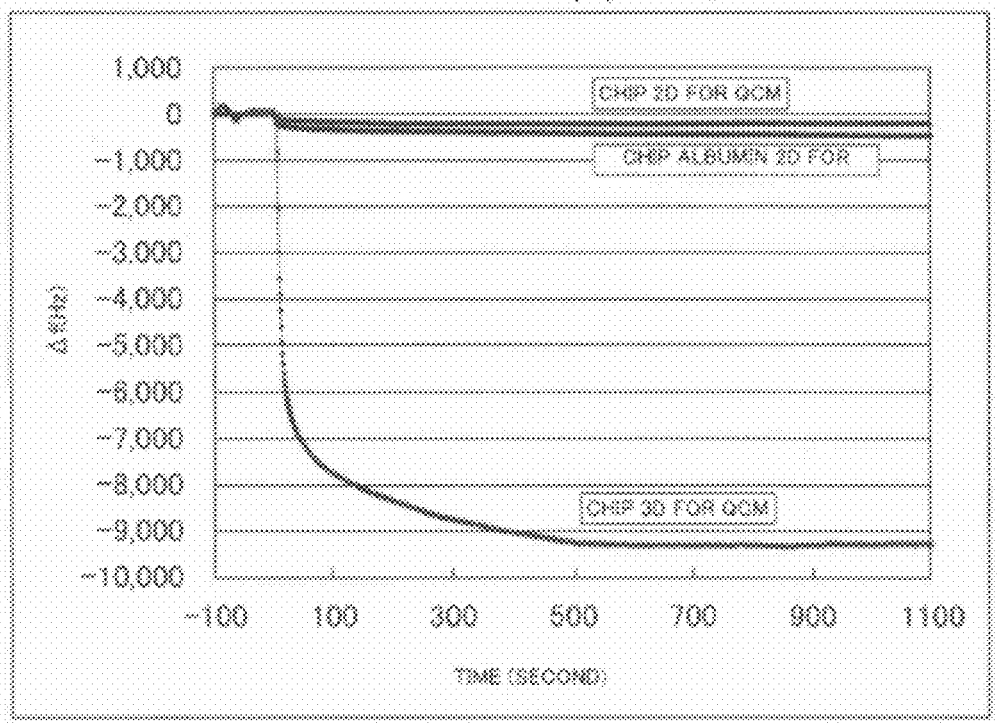
Figure 26B:
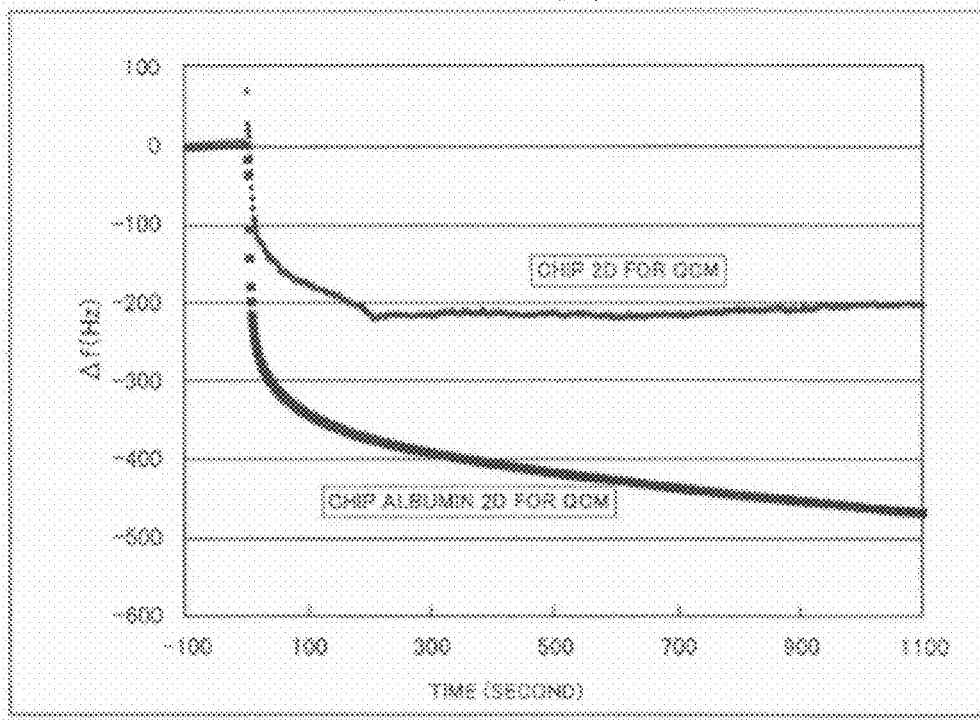
Figure 28:
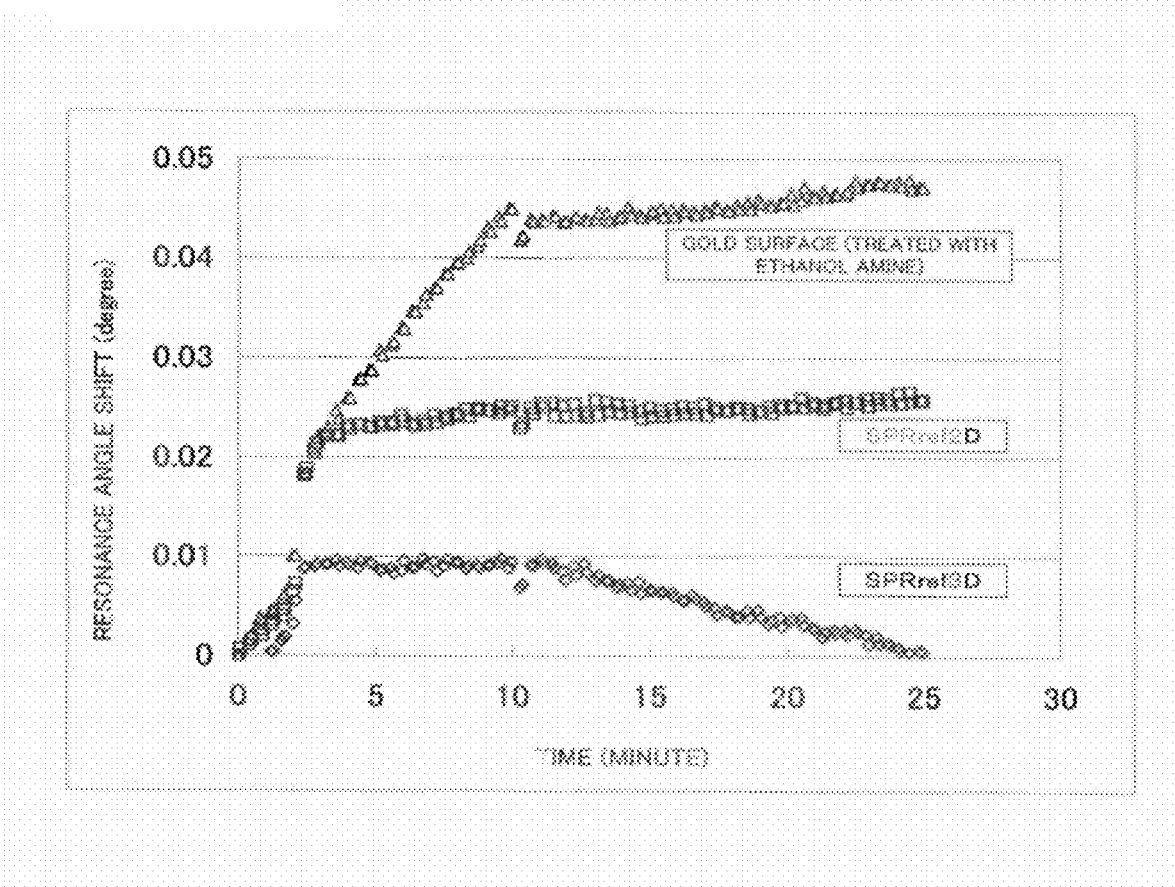
Figure 29:
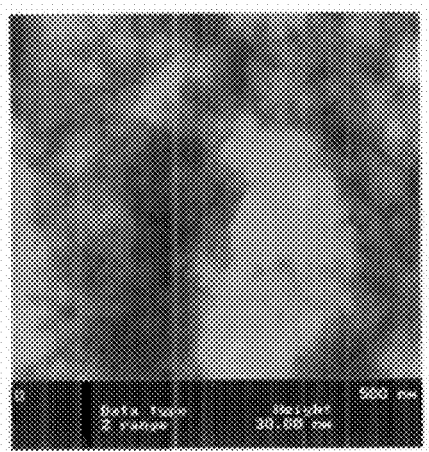
Figure 30A:
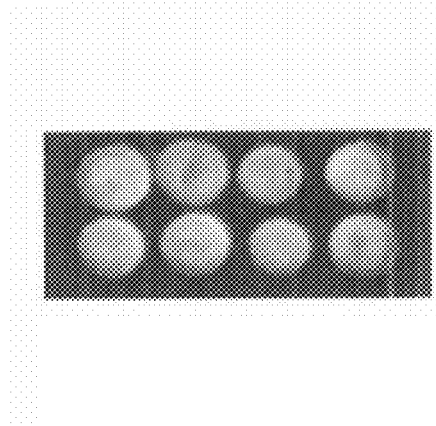
Figure 30B:
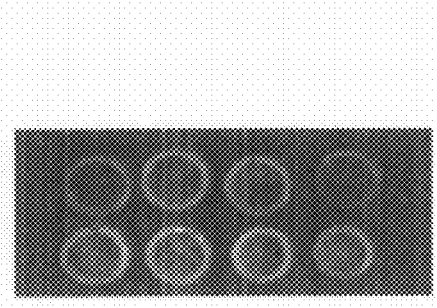
Figure 31A:
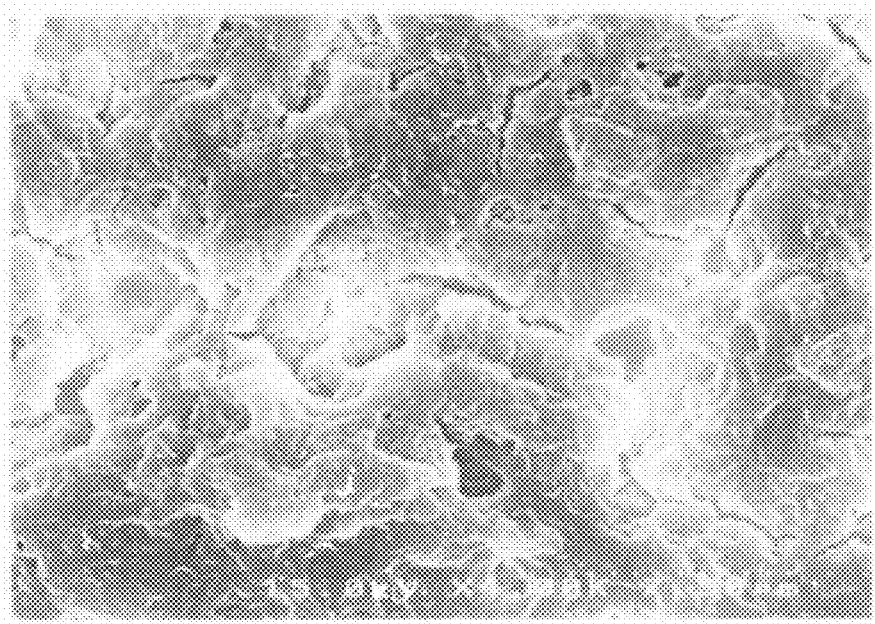
Figure 31B:
Figure 32:
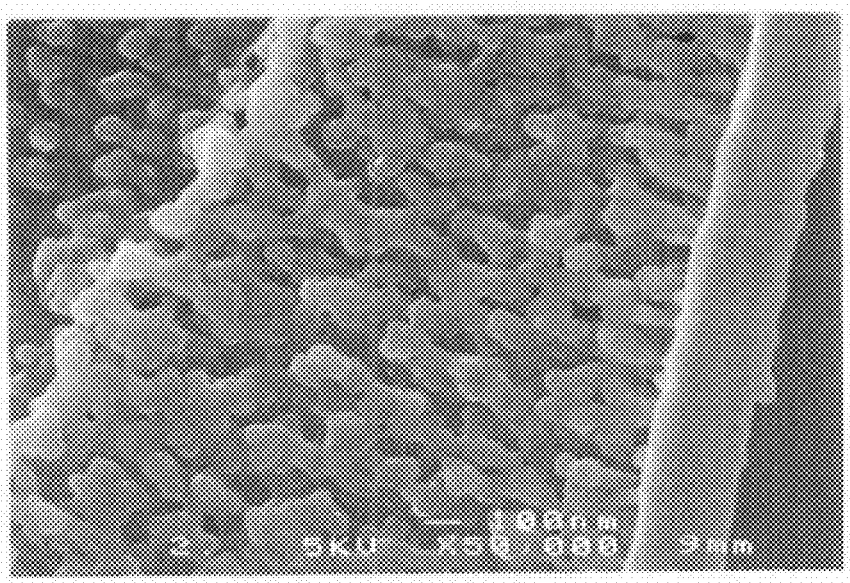
Figure 33:
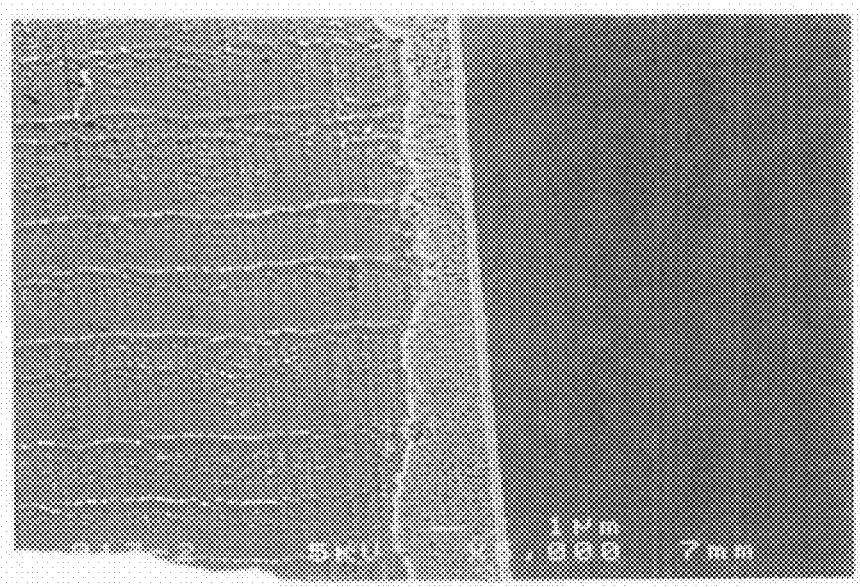
Figure 34:
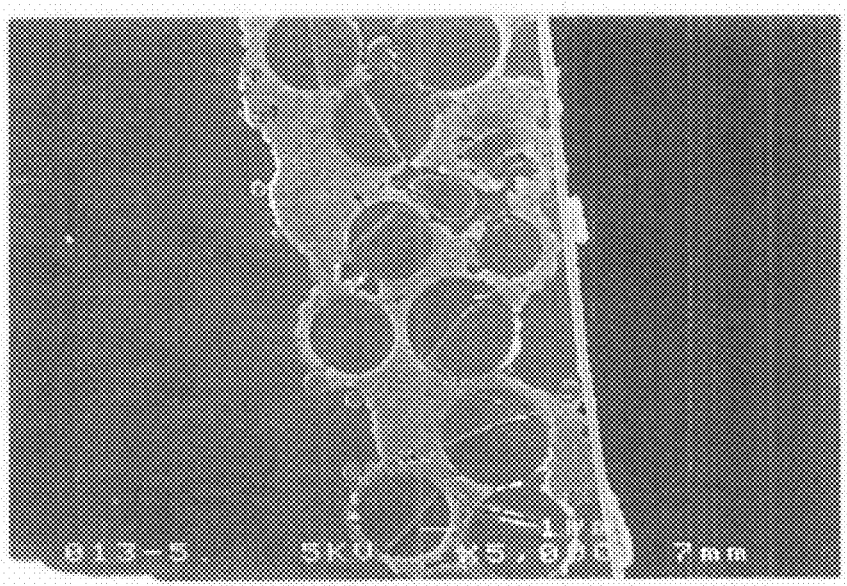
Figure 35:
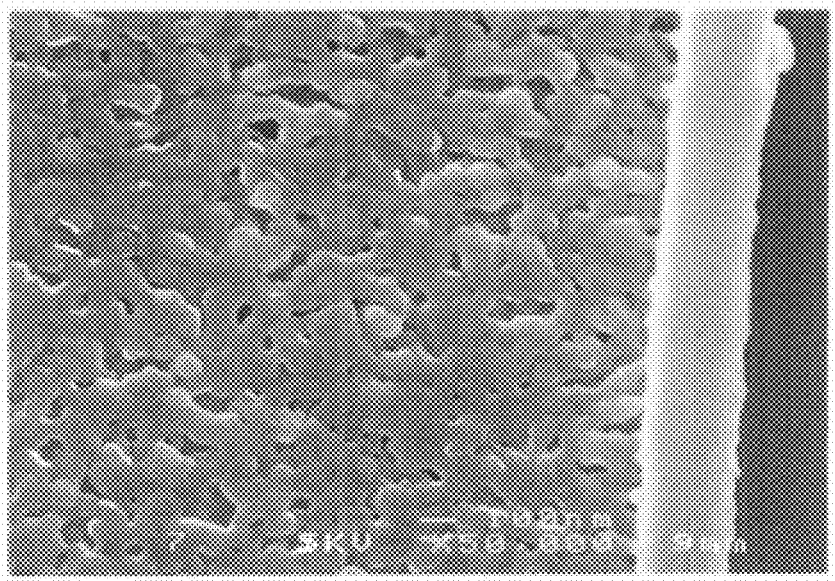

Each of FIG. 3(a) to FIG. 3(c) is an enlarged view of a partial area including the surface of a biomaterial-carrying object in accordance with the present invention, by way of explanation of a matrix structure in accordance with the present invention;

FIG. 4 is an enlarged view of a partial area including the surface of a biomaterial-carrying object in accordance with the present invention, by way of explanation of a matrix structure in accordance with the present invention;

FIG. 5 is a schematic cross-sectional view of a container for affinity chromatography in accordance with an embodiment of the present invention;

FIG. 6 is a diagram showing an apparatus for affinity chromatography in accordance with an embodiment of the present invention;

FIG. 7 is a diagram showing an apparatus for affinity chromatography in accordance with an embodiment of the present invention;

FIG. 8 is an enlarged cross-sectional view of a part of a matrix structure in accordance with the present invention;

FIG. 9(a) is a diagram showing a well-type carrier, whose solid-state carrier has a concaved surface, and FIG. 9(b) is a diagram showing a pile-type carrier, whose solid-state carrier has a convexed surface;

Each of FIGS. 10(a) to 10(c) is a diagram illustrating a process of forming a matrix structure in accordance with the present invention;

FIG. 11 is a diagram showing SDS electrophoresis patterns of the fractions obtained through operation (3) in Example 1-1 of the present invention, in which operation the mixture of a rabbit serum and a rabbit serum anti-mouse-Fab' was subjected to affinity purification to obtain the anti-mouse Fab' using a biomaterial structure with mouse IgG as the biomaterial;

FIG. 12 is a diagram showing SDS electrophoresis patterns of the fractions obtained through operation (5) in Example 1-2 of the present invention, in which operation the mixture of a rabbit serum and a rabbit serum anti-mouse-Fab' was subjected to affinity purification to obtain the anti-mouse Fab' using a biomaterial structure basal plate 1 with mouse IgG as the biomaterial;

FIG. 13 is a cross-sectional SEM photograph of a biomaterial structure basal plate 1 produced through operation (6) in Example 1-2 of the present invention using mouse IgG as the biomaterial;

FIG. 14 is an AFM image of the surface of a biomaterial structure basal plate 1 produced through operation (6) in Example 1-2 of the present invention using mouse IgG as the biomaterial;

FIG. 15 is a diagram showing SDS electrophoresis patterns of the fractions obtained through operation (9) in Example 1-3 of the present invention, in which operation a rabbit serum was subjected to affinity purification to obtain rabbit IgG using a biomaterial structure basal plate 2 with protein A as the biomaterial;

Each of FIG. 16(a) to FIG. 16(c) is an AFM image taken through operation (14) in Example 1-5 of the present invention, FIG. 16(a) showing the surface of a biomaterial structure basal plate 3, FIG. 16(b) showing the surface of a biomaterial structure basal plate 4, FIG. 16(c) showing the surface of a reference basal plate;

Each of FIG. 17(a) and FIG. 17(b) is a photograph taken in fluorescence observation in Example 2-1 of the present invention, FIG. 17(a) showing a biosensor chip A for fluorescence measurement, FIG. 17(b) showing a biosensor chip B for fluorescence measurement;

FIG. 18 is a graph showing the results of SPR measurement of an SPR biosensor chip 1 and a comparative biosensor chip 2D in Example 2-3 of the present invention;

FIG. 19 is a graph showing the results of SPR measurement of an SPR biosensor chip 2 and a comparative biosensor chip 2D in Example 2-3 of the present invention;

FIG. 20 is a graph showing the results of SPR measurement of SPR biosensor chips 1, 3 in Example 2-4 of the present invention;

FIG. 21 is a graph showing a relation between the amount of SPR shift and the concentrations of mixture liquids used for producing a concentration-dependent SPR biosensor chip and a relation between the amount of SPR shift and the concentrations of mouse IgG aqueous solutions used for producing a comparative SPR biosensor chip in Example 2-5 of the present invention;

FIG. 22 is a graph showing the results of SPR measurement of a polyacrylic-acid SPR biosensor chip in Comparative Example 2-1;

FIG. 23 is a cross-sectional SEM photograph taken in Example 2-7 of the present invention;

FIG. 24 is a graph showing the results of SPR measurement of a chip for confirming a matrix structure before and after enzyme digestion together with a background in Example 2-8 of the present invention;

FIG. 25 is a graph showing the results of SPR measurement of antibody-antigen reaction in Example 2-10 of the present invention;

Each of FIG. 26(a) and FIG. 26(b) is a graph showing the results of QCM measurement in Example 3-1 and Comparative Examples 3-1, 3-2 of the present invention, FIG. 26(b) being an enlarged view of a main part of FIG. 26(a);

FIG. 27 is a graph showing the results of SPR measurement in Example 3-2 and Comparative Example 3-3 of the present invention;

FIG. 28 is a graph showing the results of SPR measurement in Referential Examples 3-1, 3-2;

FIG. 29 is a photograph taken in observation of a biomaterial complex in Example 3-3 of the present invention;

Each of FIG. 30(a) and FIG. 30(b) is an image taken by CCD camera in chemiluminescence measurement through the chemiluminescence measurement results 1, FIG. 30(a) showing a biosensor chip 1, FIG. 30(b) showing a comparative biosensor chip 2;

Each of FIG. 31(a) and FIG. 31(b) is an SEM photograph of a matrix surface of a biosensor chip 1 produced in Production Example 4-5 of the present invention, FIG. 31(a) being a photograph under a magnification of 4000 times, FIG. 31(b) being a photograph under a magnification of 60000 times;

FIG. 32 is a cross-sectional SEM photograph of a matrix of a biosensor chip 1 produced in Production Example 4-5 of the present invention, under a magnification of 50000 times;

FIG. 33 is a cross-sectional SEM photograph of a matrix of a biosensor chip 1 produced in Production Example 4-5 of the present invention, under a magnification of 5000 times;

FIG. 34 is a cross-sectional SEM photograph of a matrix of a biosensor chip 4 produced in Production Example 4-8 of the present invention, under a magnification of 5000 times; and FIG. 35 is a cross-sectional SEM photograph of a matrix of a biosensor chip 3(b) produced in Production Example 4-7 of the present invention, under a magnification of 50000 times.

EXPLANATIONS OF REFERENCE NUMERALS 1 container body
2 biomaterial structure (biomaterial complex)
3 container for affinity chromatography
10, 20 apparatus for affinity chromatography
11 tank
12 pump
13 auto-injector
14 affinity separation chip
14A basal plate
14B flow channel
14C chip mounting unit
15 flow channel selector valve
16, 17 recovery bottle
18 control unit
19 sample liquid providing unit
21 measuring unit

BEST MODE OF CARRYING OUT THE INVENTION

Now, the present invention will be described in detail, but the invention is not limited to the following embodiments and examples and any modification can be carried out in the invention without departing from the scope thereof.

A biomaterial structure (matrix) of the present invention includes structures comprising a biomaterial and a compound capable of binding to the biomaterial ("compound for immobilizing"; hereinafter, sometimes, referred to as a "compound for binding"). The biomaterial structure can be used as a biomaterial-carrying object (a solid-state carrier on which the biomaterial is immobilized) by immobilizing it on some solid-state carrier; as a biomaterial complex or a biomaterial-complex-carrying object, by binding a specific material to a biomaterial and/or a compound for binding; or as a carrier on which a bio-related material is immobilized by binding the biomaterial on some supporting material.

I. Biomaterial Structure

The biomaterial structure of the invention is a structure comprising a biomaterial, and a compound for binding. The biomaterial structure usually comprises mutually-linked particulate lumps, each of which includes the biomaterial and the compound for binding. When the biomaterial structure is observed microscopically, a matrix having a principal chain comprising the biomaterial and the compound for binding can be found.

I-1. Biomaterial

The biomaterial is a constituting element of the biomaterial structure of the present invention, and any substances can be used as the biomaterial according to the object unless the effects of the invention are not remarkably impaired.

Of these, when the biomaterial structure of the invention is used for purification or analysis of a target material, a substance capable of interacting with a given substance (hereinafter, a substance interacting with a biomaterial is sometimes referred to as "interacting substance") is usually used as the biomaterial.

For example, when the biomaterial structure of the present invention is used for purification of a target material, and the like, a substance capable of interacting with an interacting substance is used as the biomaterial, and the interacting substance (namely, the compound capable of interacting with the biomaterial) is used as the target material. Then, the separation/purification of the target material is carried out by utilizing their interaction.

Alternatively, when the biomaterial structure of the present invention is used for analyzing a target material, the substance capable of interacting with the interacting substance is also used as the biomaterial. First, whether the target material and the biomaterial can interact or not is examined, and if the interaction occurs between the target material and the biomaterial, the above-mentioned target material is one kind of the interacting substances. Namely, it can be analyzed that the target material has a specific structure capable of interacting with the biomaterial. Structures of the target materials and interacting substances can be analyzed by utilizing this mechanism.

Here, the "interaction" between the biomaterial and the interacting substance is not particularly limited, but usually refers to an action due to a force between substances caused from at least one of covalent binding, ionic binding, chelate binding, coordinate bond, hydrophobic binding, hydrogen binding, van der Waals binding and binding by electrostatic force. However, the "interaction" used herein should be most broadly interpreted, and it must not be interpreted imitatively. In addition, the binding by electrostatic force includes electrical repulsive as well as electrostatic binding. Further, the interaction includes binding reaction, synthesis reaction and decomposition reaction which are caused by the above-mentioned actions.

In addition, when the biomaterial structure of the present invention is used for purification or analysis, the above-mentioned interaction is arbitrary so long as the purification and the analysis can be performed. In such a case, specific examples of the interaction include binding and dissociation between an antigen and an antibody, binding and dissociation between a protein receptor and a ligand, binding and dissociation between an adhesive molecule and a counter-molecule, binding and dissociation between an enzyme and a substrate, binding and dissociation between an apoenzyme and a coenzyme, binding and dissociation between a nucleic acid and a nucleic acid or protein binding thereto, binding and dissociation between proteins in a signal transduction system, binding and dissociation between a glycoprotein and a protein, binding and dissociation between a sugar chain and a protein, and the like.

There are cases where the interaction in which the biomaterial can adsorb to the target material is used depending on the method for purifying or analyzing.

Examples of the biomaterial include enzymes, antibodies, lectins, receptors, protein A, protein G, protein A/G, avidin, streptavidin, neutravidin, glutathione-S-transferase, proteins such as glycoprotein, peptide, amino acids, cytokines, hormones, nucleotides, oligonucleotides, nucleic acids (DNA, RNA, PNA), oligosaccharides, polysaccharides, sialic acid derivatives, sugar chains such as sialylated sugar chains, lipids, polymer organic substances, low molecular compounds, inorganic substances or fusions thereof which are derived from biomaterial other than the above-mentioned substances, viruses, and biological molecules such as molecules constituting a cell, and the like.

In addition, substances other than the biological molecule such as the cell can be used as the biomaterial.

Further, examples of the biomaterial also include immunoglobulin and its derivatives such as $F(ab')_2$, Fab', and Fab, receptors or enzymes and their derivatives, nucleic acid, natural or artificial peptides, synthetic polymers, saccharide, lipid, inorganic substances or organic ligands, virus and cells.

Examples of the protein among the above-mentioned the biomaterials may include the entire length of the protein, partial peptides including a binding active moiety. Further, proteins whose amino acid sequence and its function are either known or unknown are included. Still further, synthesized peptide chains, proteins obtained by purification of a living body, or proteins obtained by translation from a cDNA library with a suitable translation system and purification of it can also be used as the mark material explained below. The synthesized peptide chain may be glycoprotein to which a sugar chain is bound. Preferable proteins are purified ones.

The biomaterial complex of the present invention can utilize the characteristic features of the protein by using the protein. Specifically, for example, when albumin is used as the biomaterial, non-specific adsorption can be inhibited. In another aspect, when avidin is used as the biomaterial, a large amount of a specific biotinylated material can be easily immobilized. In another aspect, when protein A is used as the biomaterial, and an antibody is used as the specific material, a large amount of the antibody can be easily immobilized.

Further, the nucleic acid in examples of the above-mentioned biomaterials is not particularly limited, and includes nucleic acid bases such as aptamer, and peptide nucleic acids such as PNA, as well as DNA and RNA. Also, nucleic acids whose base sequence or function is either known or unknown may be used. Of these, nucleic acids capable of binding a protein, whose functions and base sequence as the nucleic acid are known, and nucleic acids obtained by cutting and separating from a genome library and the like using a restriction enzyme can be preferably used.

As the sugar chain in the examples of the above-mentioned biomaterials, sugar chains whose saccharide sequence or function is either known or unknown may be used. Preferably, the sugar chains whose saccharide sequence or function is known by separation analysis are used.

Further, the low molecular compounds in the above-mentioned biomaterials are not particularly limited so long as they satisfy conditions required for the biomaterials (for example, ability of interacting as mentioned above). Both low molecular compounds whose functions are unknown and compounds whose ability of binding to a protein is known can be used. Pharmaceutical candidate compounds are suitably used.

When the biomaterial structure of the present invention is used in separation/purification utilizing an affinity separation technique such as affinity purification or analysis, the above-mentioned biomaterial is a mark material of a target material which is to be separated/purified. When the biomaterial of the invention is used in analysis, these biomaterials are mark materials when the interaction (binding and the like) between a detection target material and a biomaterial in a sample is measured.

The biomaterials may be used alone or in combination thereof in any kinds and in any ratio.

I-2. Compound for Binding (Compound for Immobilizing)

As the compound for binding, any compounds can be used so long as they can bind with the above-mentioned biomaterial. As the compound for binding, accordingly, compounds having a functional group capable of binding to the biomaterial (hereinafter, sometimes, referred to as "binding functional group") can be arbitrarily used.

Here, binding usually means at least one of covalent binding, ionic binding, chelate binding, coordinate bond, hydrophobic binding, hydrogen binding, van der Waals binding, and binding by electrostatic force. The covalent binding is preferable.

As the binding functional group, any functional groups can be used without any limitation so long as they can bind to the above-mentioned biomaterial. Usually, a suitable functional group is preferably selected depending on the kind of the biomaterial and the use of the biomaterial structure of the invention.

The binding functional groups may be used alone or as a mixture thereof in any ratio.

The binding functional groups are usually classified into two groups, that is, groups binding to a biomaterial through covalent binding as a reactive group, and groups binding to a biomaterial through non-covalent binding.

In case of the binding through the covalent binding, the binding functional group includes succinimide group, epoxy group, aldehyde group, maleimide group, and the like.

In such a case, examples of the biomaterial binding to the binding functional group through the covalent binding include, for example, protein, nucleic acid, saccharide, and the like.

When the biomaterial is a protein, usually, amino group, hydroxyl group, thiol group, or the like on the surface layer of the protein binds to the binding functional group of the compound for binding. In such a case, for example, when the amino group binds to the binding functional group, examples of the binding functional group include succinimide group, epoxy group, aldehyde group, and the like. Also, when the hydroxyl group binds to the binding functional group, examples of the binding functional group include epoxy group, and the like. Further, when the thiol group binds to the binding functional group, examples of the binding functional group include maleimide group, and the like.

When the biomaterial is nucleic acid, usually, amino group, hydroxyl group, thiol group, or the like which is introduced into the terminal of the nucleic acid, binds to a binding functional group of the compound for binding. In such a case, for example, when the amino group binds to the binding functional group, examples of the binding functional group include succinimide group, epoxy group, aldehyde group, and the like. When, for example, the hydroxyl group binds to the binding functional group, examples of the binding functional group include epoxy group, and the like. When, for example, the thiol group binds to the binding functional group, examples of the binding functional group include maleimide group, and the like.

When the biomaterial is saccharide, usually, amino group, hydroxyl group, thiol group, or the like on a side chain of the saccharide binds to a binding functional group of the compound for binding. In such a case, for example, when the amino group binds to the binding functional group, examples of the binding functional group include succinimide group, epoxy group, aldehyde group, and the like. When, for example the hydroxyl group binds to the binding functional group, examples of the binding functional group include epoxy group, and the like. When, for example, the thiol group binds to the binding functional group, examples of the binding functional group include maleimide group, and the like.

On the other hand, when the biomaterial binds to the compound for binding through non-covalent binding, for example, they can bind to each other through coordination compound formation, interaction between the biomaterials or the like.

When binding between the biomaterial and the compound for binding is caused by forming the complex, examples of the binding functional group include boronic acid group, and the like.

Also, when, for example, binding is caused by through avidin-biotin interaction in the interactions between the biomaterials, examples of the binding functional group include biotin group, and the like.

[Chemical formula]

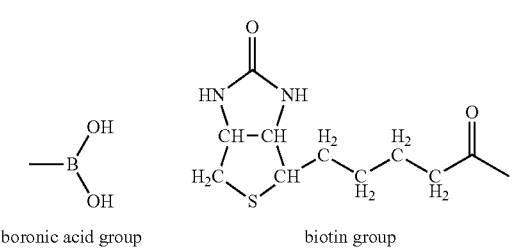

Further, when, for example, as the biomaterial, virus is used, examples of the binding functional group include saccharide, and polysaccharide.

When, for example, the biomaterial has a hydrophobic region, the binding may be caused by physical adsorption due to the hydrophobic interaction.

When the compound for binding has the binding functional group, it is preferable that the compound for binding comprises at least one compound having usually two or more, preferably three or more binding functional groups in one molecule, for easier formation of the structure of the present invention. Specifically, if the compound has two or more binding functional groups in one molecule, then a particulate lump in which the biomaterial and the compound for binding bind to each other can be easily formed, and the particulate lumps are bind to each other to form the biomaterial structure which is a higher order structure. Further, if the compound has two or more binding functional groups in one molecule, then the biomaterial structure can be easily formed by concentration, and the like.

In order to easily form particulate lump mentioned below from the biomaterial structure of the invention, it is preferable that the compounds for binding do not bind to each other, and binding between the biomaterial and the compound for binding is main. When the compounds for binding bind to each other, the agglomeration of the compounds for binding is easily formed, and it tends to produce a particulate lump having a larger particle size, and it is difficult to control the particle size of the particulate lumps. Also, when the compounds for binding bind to each other, the biomaterials cannot be bound efficiently. Further, when a sample is reacted with the biomaterial structure of the invention, desirable reaction efficiency may not be obtained.

Furthermore, in case where the compounds for binding bind to each other, when a polymer compound is used as the compound for binding, internal cross-lining is caused in the compound for binding, and it is difficult to immobilize the biomaterial. Here, binding between compounds for binding exclude intermolecular attraction, hydrophobic interaction, and electric interaction.

In order to form a biomaterial structure with no compounds for binding which bind to each other, it is desirable that a binding functional group which does not bind to each other is selected, and conditions where the compounds for binding bind to each other are eliminated. Examples of the functional group include, as mentioned above, succinimide group, epoxy group, aldehyde group, maleimide group, boronic acid group, biotin group, and the like. The conditions where the functional groups for binding bind to each other include a condition where excessive heat is applied, and a condition where strong ultra violet rays are irradiated.

For examining the binding between the compounds for binding in the biomaterial structure, it can be determined by the formation of an insoluble matter when the biomaterial in the biomaterial structure is decomposed in a method mentioned below. Alternatively, it can be determined by analyzing the biomaterial structure with heat decomposal gas chromatography and detecting a compound suggesting the binding between the compounds for binding. Specifically, for example, in a step in which the biomaterial and a compound for binding having a photo-reactive group are bound by irradiating ultra violet rays, if the compounds for binding bind to each other due to the photo-reactive group in the compound for binding (for example, azide group), the binding between the compounds for binding can be presumed by the presence of the binding involving the photo-reactive group or the presence of the remaining photo-reactive groups (see Affinity Chromatography: Tokyo Kagaku Dojin, written by Ken-ichi Kasai Isatake Matsumoto and Masatoshi Beppu, page 238).

Further, in order to maintain the activity of the biomaterial for utilizing its characteristic, it is preferable that the above-mentioned functional groups of the biomaterial and the compound for binding are selected so that the biomaterial does not lose its activity. For example, when the protein has thiol group in its active moiety in immobilization of the protein, groups other than the thiol group such as amino group is selected as the binding functional group of the biomaterial, and succinimide group or epoxy group is selected as the binding functional group of the compound for binding, in order to bind to the amino group.

Further, the compounds for binding are, usually, compounds which can be mixed with water desirably, because, though any mediums can be used on preparation of the biomaterial structure, water is usually used as a medium such as a solvent or a dispersion medium. Specifically, when the biomaterial structure is prepared, usually, the compound for binding is mixed with the biomaterial in the presence of water, and the compound for binding is bound to the biomaterial to prepare particulate lumps. In such a step, if the compounds which can be mixed with water are used, the biomaterial and the compound for binding are uniformly mixed and the binding reaction is performed smoothly. The state of the mixing herein may be solution or dispersion.

The compounds for binding which can be mixed with at least one organic solvent are preferable. Such compounds can expand the range of choice of solvent used in synthesis of the compound for binding, and a variety of the structures of the biomaterial structure can be designed. For example, when the compound for binding can be mixed with an organic solvent, the synthesis can be carried out in the organic solvent in order to protect the binding functional group on preparation of the compound for binding.

Further, compounds for binding which can be mixed with both of water and an organic solvent are preferable. That is, the compounds which can be mixed with at least one organic solvent as well as mixed with water are more preferable. If the compound for binding can be mixed with water and the organic solvent, then the number of the kinds of the solvent, which can be used in the application of the biomaterial structure, can be increased, thus resulting in expansion of its application.

Further, compounds for binding are electrically uncharged desirably. When the compound for binding has the same charge as the biomaterial (the same sign in charge), the binding between the compound for binding and the biomaterial may be interrupted due to the electrostatic repulsive power. On the other hand, when the compound for binding has an opposite charge to that of the biomaterial (opposite sign in charge), the biomaterial and the electrically charged moiety in the compound for binding are bound due to the electrostatic attraction, and the effective binding of the binding functional group in the compound for binding to the biomaterial may be interrupted. Also, the binding between the compound for binding and the biomaterial due to the electrostatic attraction is not preferable, because when the biomaterial structure of the invention is used in separation/purification, the binding can be easily broken by pH and/or additives such as salt of a solution used in the application and additives.

Further, when a target material has the same charge as the compound for binding in the separation of the target material using the biomaterial structure of the present invention, the specific interaction with the biomaterial included in the biomaterial structure may be interrupted; and when the target material has an opposite charge to that of the compound for binding, the non-specific interaction such as non-specific adsorption can be caused between the target material and the compound for binding due to the electric attraction.

Similarly, when an analyte, or an interacting substance, has the same charge as the compound for binding on detection of the selective interaction between the biomaterials using the biomaterial-carrying object of the present invention, a specific interaction with a ligand, or the biomaterial, may be interrupted; and when the analyte has an opposite charge to that of the compound for binding, a non-specific interaction such as non-specific adsorption may be caused between the analyte and the compound for binding.

If the compound for binding has, at least, a nonionic structure formula, such a compound is an electrically uncharged compound for binding. However, even if the above-mentioned compound for binding is electrically charged by hydrolysis of the binding functional group, and the like, during the preparation procedure of the biomaterial complex of the invention, such a compound for binding can be suitably used so long as the effects of the invention are not impaired.

Other examples of the compound for binding include, for example, organic compounds, inorganic compounds, organic-inorganic hybrid materials, and the like.

The compounds for binding may be used alone or as a mixture thereof in any ratios.

Although the organic compounds used as the compound for binding may be either low molecular compounds or polymer compounds, the polymer compounds are preferable.

Examples of the low molecular compound used as the compound for binding include glutaraldehyde, diepoxybutane, diepoxyhexane, diepoxyoctane, bismaleimide hexane, bis(sulfosuccinimidyl) suberate, disuccinimidyl glutarate, ethylene glycolbis(succinimidyl) succinate, sulfoethylene glycol bis(succinimidyl)succinate, sulfosuccinimidyl-4-(N-maleimidemethyl)-cyclohexane-1-carboxylate, succinimidyl-4-(N-maleimidemethyl)-cyclohexane-1-carboxylate, sulfosuccinimidyl-4-(p-maleimidephenyl)-butyrate, succinimidyl-4-(p-maleimidephenyl)-butyrate, sulfo-m-maleimidebenzoyl-N-hydroxysuflosuccinimide ester, and the like.

On the other hand, when the polymer compounds are used as the compound for binding, they may be synthetic polymer compounds and natural polymer compounds.

When the synthetic polymer compounds are used as the compound for binding, any synthetic polymer compounds can be used so long as they satisfy the above-mentioned conditions. In general, however, compounds having a monomer capable of binding a biomaterial are desirable. Further, usually, in order to make the synthetic polymer compound capable of mixing with water, compounds having a hydrophilic monomer are preferable. Furthermore, it is more preferable to use synthetic polymer compounds which are obtained by copolymerizing the monomer capable of binding the biomaterial with the hydrophilic monomer.

That is, in the synthesis of the synthetic polymer compounds used as the compound for binding, it is preferable to use a monomer capable of forming a particulate lump by binding to the biomaterial as at least one monomer species (which is a kind (a part) of a monomer capable of forming a conjugate by reacting with the biomaterial), and a monomer having a binding functional group forming a structure in which the particulate lumps bind to each other in a state of a chain and/or a network state (namely, the structure of the biomaterial structure) (which is a kind (a part) of a monomer having a binding functional group for forming the chain and/or reticular structure between the bound conjugates), and further, it is more preferable to use a monomer having hydrophilic or amphipathic functional group. In addition, for controlling a structure such as a micelle and its spread of the synthetic polymer compound formed in a solution, it is also preferable to contain a hydrophobic monomer. The monomers herein may be different monomers and a single monomer having two or more functions mentioned above.

Examples of the monomer used in radical polymerization, among examples of the monomer constituting the synthetic polymer compound which can be used as the compound for binding, include polymerizable unsaturated aromatic compounds such as styrene, chlorostyrene, α-methyl styrene, divinyl benzene and vinyl toluene; polymerizable unsaturated carboxylic acids such as (meth)acrylic acid, itaconic acid, maleic acid, and phthalic acid; polymerizable unsaturated sulfonic acid such as styrene sulfonic acid, and styrene sulfonic acid sodium salt; polymerizable carboxylic acid esters such as methyl (meth)acrylate, ethyl (meth)acrylate, n-butyl (meth)acrylate, 2-hydroxyethyl (meth)acrylate, hydroxypropyl(meth)acrylate, glycidyl(meth)acrylate, N-(meth)acryloyloxysuccinimide, ethylene glycol di(meth)acrylic acid ester, tribromophenyl(meth)acrylate, glycosyloxyethyl (meth)acrylate, and 2-methacryloyloxyethylphosphorylcholine; unsaturated carboxylic acid amides such as (meth)acrylonitrile, (meth)acrolein, (meth)acrylamide, N,N-dimethylacrylamide, N-isopropyl(meth)acrylamide, N-vinyl formamide, 3-acrylamidephenyl boronic acid, N-acryloyl-N'-biotinyl-3,6-dioxaoctane-1,9-diamine, butadiene, isoprene, vinyl acetate, vinyl pyridine, N-vinylpyrrolidone, N-(meth)acryloylmorpholine, vinyl chloride, vinylidene chloride and vinyl bromide; polymerizable unsaturated nitriles; halogenated vinyl compounds; conjugated dienes; macromonomers such as polyethylene glycol mono(meth)acrylate and polypropylene glycol mono(meth)acrylate, and the like.

Examples of the monomer of the synthetic polymer compound which can be used as the compound for binding may include, for example, monomers used in addition polymerization. Examples of the monomer used in the addition polymerization include aliphatic or aromatic isocyanates, ketenes, epoxy group-containing compounds and vinyl group-containing compounds, such as diphenyl methane diisocyanate, naphthalene diisocyanate, tolylene diisocyanate, tetramethyl xylene diisocyanate, xylene diisocyanate, dicyclohexanediisocyanate, dicyclohexylmethane diisocyanate, hexamethylene diisocyanate, and isophorone diisocyanate.

The above-mentioned compounds can be reacted with a monomer having a functional group with active hydrogen. Examples thereof are compounds having hydroxyl group or amino group such as polyols such as ethylene glycol, diethylene glycol, propylene glycol, 1,4-butanediol, 1,6-hexanediol, glycerin, trimethylolpropane, pentaerythritol, sorbitol, methylene glycoside, saccharose, and bis(hydroxyethyl) benzene; polyamines such as ethylenediamine, hexamethylenediamine, N,N'-diisopropyl methylenediamine, N,N'-di-sec-butyl-p-phenylene diamine, and 1,3,5-triaminobenzene; and oximes.

Further, the synthetic polymer compound which can be used as the compound for binding may be used together with a polyfunctional compound which will be a cross-lining agent, in addition to the above-mentioned monomers. Examples of the functional compound include, for example, N-methylolacrylamide, N-ethanol acrylamide, N-propanol acrylamide, N-methylol maleimide, N-ethylol maleimide, N-methylol maleic amide acid, N-methylol maleic amide acid ester, vinyl aromatic acids such as N-alkylolamide (for example, N-methylol-p-vinyl benzamide, and the like), N-(isobutoxymethyl)acrylamide, and the like.

Of the above-mentioned monomers, polyfunctional monomers such as divinyl benzene, divinyl naphthalene, divinyl chlorohexane, 1,3-dipropyl benzene, ethylene glycol di(meth)acrylate, diethylene glycol di(meth)acrylate, diethylene glycol di(meth)acrylate, butylene glycol, trimethylolethane tri(meth)acrylate, and pentaerythritol tetra(meth)acrylate can be used as a cross-linking agent.

The spread in a medium and hardness of the compound for binding can be controlled by using the polyfunctional compound which will be a cross-linking agent as the monomer.

Examples of the monomer having succinimide group, epoxy group, aldehyde group, maleimide group or the like, among the monomer having the binding functional group capable of binding the above-mentioned biomaterial include N-(meth)acryloyloxysuccinimide, (meth)acrylic acid glycidyl, acrolein, maleimide acrylate, and the like.

Examples of the monomer having boronic acid group as the binding functional group include 3-acrylamide phenylboronic acid, and the like.

Examples of the monomer having biotin group as the binding functional group include N-acryloyl-N'-biotinyl-3,6-dioxaoctane-1,9-diamine, and the like.

Examples of the monomer having saccharide or polysaccharide as the binding functional group include glycosyloxyethyl 2-(meth)acrylate, and the like.

Further, examples of the hydrophilic monomer include (meth)acrylic acid, itaconic acid, 2-hydroxyethyl(meth)acrylate, 2-hydroxypropyl(meth)acrylate, maleic acid, sulfonic acid, sodium sulfonate, (meth)acrylamide, N,N-dimethyl (meth)acrylamide, N-isopropyl acrylamide, N-vinyl formamide, (meth)acrylonitrile, N-(meth)acryloylmorpholine, N-vinyl pyrrolidone, N-vinyl acetamide, N-vinyl-N-acetamide, polyethylene glycol mono(meth)acrylate, glycidyl (meth)acrylate, 2-methacryloxyethyl phosphoryl choline, and the like.

As the compound for binding, as mentioned above, electrically uncharged compounds are preferable. When monomers used for forming the synthetic polymer compounds, which are used as the compound for binding, are electrically uncharged, the obtained synthetic polymer compounds are also electrically uncharged, and accordingly such electrically uncharged monomers can be used without particular limitations. Examples thereof include 2-hydroxyethyl (meth)acrylate, 2-hydroxypropyl(meth)acrylate, (meth)acrylamide, N,N-dimethyl(meth)acrylamide, N-isopropyl acrylamide, N-vinyl formamide, (meth)acrylonitrile, N-(meth)acryloylmorpholine, N-vinylpyrrolidone, N-vinyl acetamide, N-vinyl-N-acetamide, polyethylene glycol mono(meth)acrylate, glycidyl(meth)acrylate, and the like.

When the radical polymerization of the monomers is performed to obtain the synthetic polymer compounds, the polymerization is initiated by mixing the monomers with a radical polymerization initiator. In such a case, any radical polymerization initiators can be used so long as the effects of the present invention are not remarkably impaired. Examples of the radical polymerization initiators used herein include azo (azobisnitrile) type initiators such as 2,2'-azobisisobutyronitrile, 2,2'-azobis(2-methylpropanenitrile), 2,2'-azobis(2,4-dimethylpentanenitrile), 2,2'-azobis(2-methylbutanenitrile), 1,1'-azobis(cyclohexanecarbonitrile), 2,2'-azobis(2,4-dimethyl-4-methoxyvaleronitrile), 2,2'-azobis(2,4-dimethylvaleronitrile), and 2,2'-azobis(2-amidinopropane)hydrochloride; peroxide type initiators such as benzoyl peroxide, cumene hydroperoxide, hydrogen peroxide, acetyl peroxide, lauroyl peroxide, persulfates (for example, ammonium persulfate), and peracid esters (for example, t-butylperoctate, α-cumylperoxy pivalate, and t-butyl peroctate), and the like.

Further, the polymerization may be initiated by mixing the monomer with a redox initiator. Any redox initiators may be used so long as the effects of the invention are not impaired. Examples thereof include ascorbic acid/iron sulfate (II)/sodium peroxydisulfate, tert-bytylhydroperoxide/sodium disulfite, tert-butylhydroperoxide/Na hydroxymethanesulfinic acid, and the like. Individual components such as reduction components may be mixtures such as a mixture of sodium salt of hydroxymethanesulfinic acid, and sodium disulfite.

When the synthetic polymer compounds are used as the compound for binding, polymer compounds which are synthesized by ring-opening polymerization, and the like may be used. Examples thereof include polyethylene glycol, and the like.

As the above-mentioned synthetic polymer compounds, polymer compounds which are synthesized by hydrolysis and the like may be used. Examples thereof include polyvinyl alcohol which is obtained by hydrolysis of the polyvinyl acetate, and the like.

The synthetic polymer compounds may be synthesized by chemical modification with a functional group capable of binding to the biomaterial.

In addition, as the compound for binding, commercially available, synthetic polymer compounds may be used. Examples thereof include SUNBRIGHT series, DE-030AS, DE-030CS, DE-030GS, PTE-100GS, PTE-200GS, HGEO-100GS, and HGEO-200GS, which are made by NOF Corporation, and the like.

On the other hand, when the natural polymer compounds are used as the compound for binding, examples thereof include polysaccharides such as dextran, carboxymethyl dextran, starch, and cellulose; proteins such as albumin, collagen and gelatin; nucleic acids such as DNA, RNA, and the like. These natural compounds may be used as they are, or modified ones may also be used.

When the polymer compounds such as the synthetic polymer compounds and the natural polymer compounds are used as the compound for binding, the polymer compounds can be used in any state. For example, aqueous solution containing the dissolved compound may be used, and microparticles, such as an aggregate such as micelle or emulsion and polymer latex may be used.

Examples of the inorganic compounds used as the compound for binding include, for example, metal particles such as Au colloid, inorganic microparticles such as silica, and the like. Further, compounds for binding which have a functional group capable of binding to the biomaterial, which are obtained by chemically modifying these inorganic compounds, may be used.

Examples of the organic-inorganic hybrid used as the compound for binding include, for example, colloidal silica on which a polymer is coated; metal colloid on which a polymer is coated (such as gold, silver or platinum particles on which a protective colloid is coated); porous substrate such as clay in which a polymer is adsorbed, and the like. The organic-inorganic hybrid can be synthesized in a known method (see Polymer Nanocomposite, Kogyo Chosakai Publishing, Inc., written by Susumu Nakajyo).

By modifying the organic-inorganic hybrid with the binding functional group, the obtained compound can also be used as the compound for binding.

The molecular weight and the structure of the compound for binding are not particularly limited, and any compounds can be used. As the compound for binding, accordingly, low molecular compounds may be used. In such a case, however, there is a case where the cross-linking is caused in one biomaterial to be immobilized, and therefore a principal chain cannot be efficiently formed and the biomaterial structure cannot be formed. Also, when the cross-linking is caused in the biomaterial, the activity of the biomaterial may not be maintained. For preventing these, the compound for binding has a molecular weight of usually 1000 or higher, preferably 10,000 or higher, and it is usually 1,000,000 or smaller, preferably 500,000 or smaller. When the synthetic or natural polymer compounds are used as the compound for binding, it is preferable that weight average molecular weights are within the above-mentioned range, because if the molecular weight is lower than the above-mentioned range, biomaterial structures in which particulate lumps are effectively aggregated may not be formed.

The molecular weight can be measured by using various methods, and general methods such as GPC (gel permeation chromatography) SEC (size exclusion chromatography), static light scattering measurement, and viscosity measurement may be used to determine.

The diameter of the compound for binding is not particularly limited, and any diameter can be used so long as the effects of the invention are not remarkably impaired. In order to effectively bind the biomaterial to the compound for binding, however, the particle diameter of the compound for binding in the state in which the compound is mixed with liquid (medium, in this case) such as solvent or dispersion medium is usually 1 nm or larger, preferably 2 nm or larger, more preferably 3 nm or larger. For satisfying this condition, it is desirable that in a stage where the compound for binding is prepared prior to the production of the biomaterial structure of the invention, a compound for binding having a particle diameter within the above-mentioned range is prepared, and using the same, the biomaterial structure of the invention is produced. The compound has no upper limit, and usually it is 5 μm or smaller.

The diameter of the compound for binding can be measured by various methods. When the metal colloid in which metal particles are dispersed in liquid, inorganic particles, or polymer microparticles are used as the compound for binding, the diameter can be determined by using a general method such as static light scattering measurement, dynamic light scattering measurement, or optical diffraction method. When the residue obtained by separating a medium and the like from a dispersion liquid in which Au colloid, inorganic particles, polymer microparticles are dispersed is observed by using an electron microscope such as SEM (scanning electron microscope) or TEM (transmission electron microscope), the obtained values may be regarded as the diameter of the compound for binding in the liquid.

On the other hand, when the polymer in a solution or an aggregate such as micelle is used as the compound for binding, the diameter can be examined by using a general method such as static light scattering measurement, dynamic light scattering measurement, or optical diffraction method. In general, the particle diameter of the polymer in a solution or micelle varies depending on the measurement method or analysis method, but the particle diameter can be evaluated based on the measured values obtained by either method.

When the diameter of the compound for binding in liquid is measured by using an optical method, it is desirable that the average particle diameter of the compound for binding is within the above-mentioned range for effectively binding the biomaterial to the compound for binding.

The content of the binding functional groups in the compound for binding is not particularly limited. Although the content depends on the kind of the compound for binding and cannot be universally defined, for example, when the polymer is used as the compound for binding, the content is usually 0.1% by mole or higher based on the compound for binding, preferably 0.5% by mole or higher, more preferably 1% by mole or higher, still more preferably 5% by mole or higher, and it is usually 90% by mole or lower, preferably 80% by mole or lower, more preferably 70% by mole or lower. When the content is lower than the above-mentioned range, the compound for binding cannot efficiently bind to the biomaterial, and when the content is higher than the above-mentioned range, the compound may not be mixed with the solvent or dispersion medium.

I-3. Structure of Biomaterial Structure

The biomaterial structure of the invention is a structure in which particulate lumps are mutually-linked, the lumps being formed by binding the biomaterial and the compound capable of binding the biomaterial to each other. Further, in the biomaterial structure of the invention, the particle diameter of the particulate lumps is 10 μm or smaller.

Figure 1A:
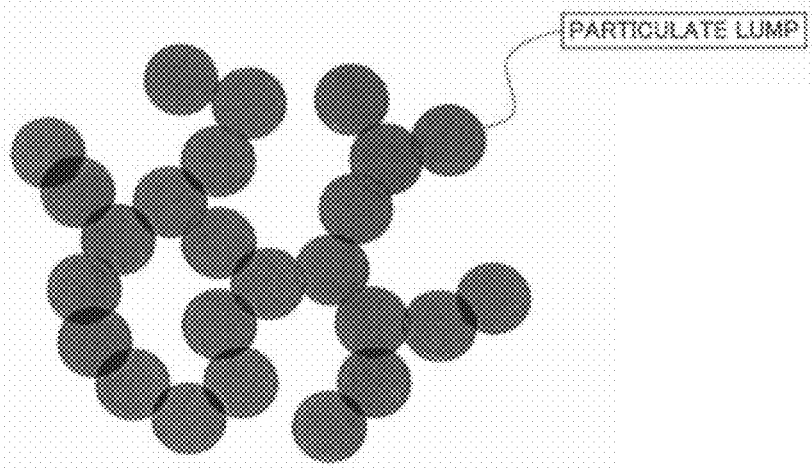
FIG. 1(b) is a diagram illustrating a biomaterial structure in accordance with an embodiment of the present invention.
Figure 1B:
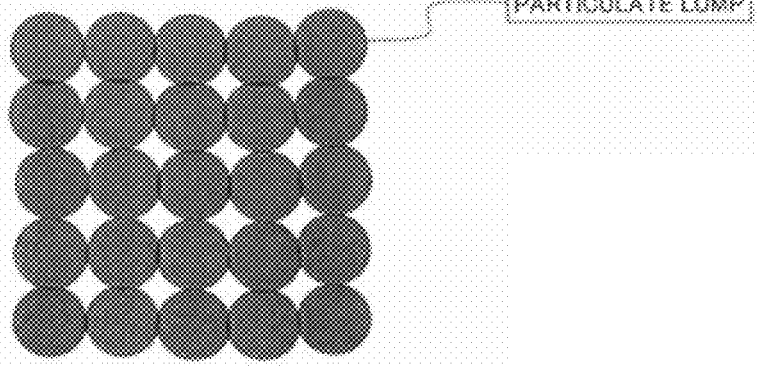
Figure 2A:
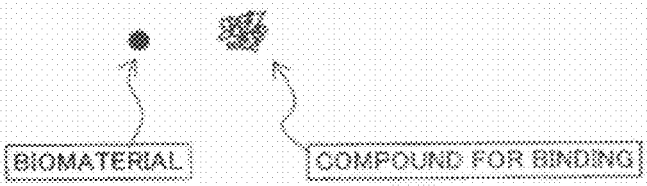
FIG. 2(b) is a diagram for explaining an embodiment of the present invention, FIG. 2(a) illustrating a biomaterial and a compound for binding, FIG. 2(b) illustrating particulate lumps.
Figure 2B:
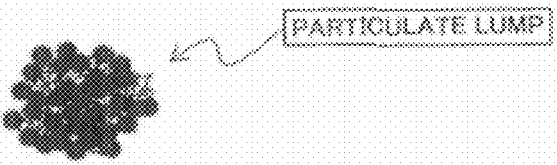

Specifically, the biomaterial structure of the invention is a structure in which, as shown schematically in FIG. 2(a) and FIG. 2(b), the biomaterial and the compound for binding are bound to form a particulate lump as a single unit, having a particle diameter of 10 μm or smaller, and, as shown schematically in FIG. 1(a) and FIG. 1(b), the lumps bind to each other to form a chain and/or reticular structure. This particulate lump is usually the one in which the biomaterial and the compound for binding, as shown in FIG. 2(a), are mutually-linked to form a particulate, as shown in FIG. 2(b). The lumps do not necessary have a complete circular form, and in FIG. 1(a) and FIG. 1(b) the particulate lump is schematically described in a circular form.

The biomaterial structure of the invention has a structure in which the particulate lumps formed from both of the biomaterial and the compound for binding are aggregated and/or bound to form, as mentioned above. Consequently, the percentage of the biomaterial can be increased, and thus the biomaterial structure of the invention can hold the biomaterial in a larger amount than the conventional ones. According to the conventional technique for immobilizing the biomaterial on the solid-state carrier, when it is used in affinity purification, the amount of the biomaterial immobilized is limited until the pre-determined upper limit (usually, the single layer adsorption of the protein is at most 0.3 to 1.0 μg/cm$^2$), since the biomaterial is bound to the surface of the solid-state carrier such as resin microparticle, and accordingly a large amount of the biomaterial cannot be held.

According to the biomaterial structure of the present invention, because it can hold a large amount of the biomaterial, the advantage that the non-specific interaction caused by the compound for binding (and a solid-state carrier, mentioned below) can be inhibited, can be obtained. That is, if as the biomaterial, a compound which does not generate the non-specific interaction is used, a compound for binding which can generate the non-specific interaction can be covered with a large amount of the biomaterial. In such a case, since the biomaterial structure has the biomaterial in a large amount, it is possible to effectively inhibit the non-specific interaction. Consequently, while the influence due to the non-specific interaction is excluded, the analysis or the affinity separation can be carried out by using the interaction between the biomaterial and the interacting substance.

The particulate lumps forming the biomaterial structure are aggregated to contact with each other due to the attraction force between the particulate lumps or the carbon chains are entangled with each other, to bind to each other, thereby forming the biomaterial structure. For example, the biomaterial structure is formed by binding the particulate lumps due to only the intermolecular attraction; the biomaterial structure is formed by binding the particulate lumps through the binding between the functional group of the compound for binding and the biomaterial; or the biomaterial structure is formed by combining the two factors mentioned above to bind the particulate lumps. Here, the binding include at least one of, usually, covalent binding, ionic binding, chelate binding, coordinate bond, hydrophobic binding, hydrogen binding, van der Waals binding, and binding by electrostatic force. Of these, the covalent binding is preferable. In such a case, only a part of the particulate lumps may bind to each other, but it is preferable that the number of the particulate lumps is larger, and more preferably, all of the particulate lumps bind to each other to form the biomaterial structure.

It can be considered that the particulate lumps are aggregated due to a multiple factors such as entangling and binding to form the biomaterial structure.

The particulate lump forming the biomaterial structure has usually a particle diameter of 10 μm or smaller, preferably 5 μm or smaller, more preferably 1 μm or smaller. When the particle diameter of the particulate lump is too large, sufficient specific surface area cannot be obtained in case of using the structure in separation/purification, and highly efficient separation/purification results may not be obtained in case of using the structure in affinity separation. The lower limit is not particularly limited, and usually it is 1.5 nm or higher.

When the particle diameters of the particulate lumps are individually measured, it is sufficient so long as at least a part of the particulate lumps contained in the biomaterial structure has a particle diameter within the above-mentioned range. It is preferable that the most possible particulate lumps have the particle diameter within the above-mentioned range, and more preferably all of the particulate lumps have the particle diameter within the above-mentioned range.

Here, the particle diameter of the particulate lump can be measured by observing with a microscope such as an optical microscope, an electron microscope such as SEM and TEM, AFM (atomic force microscope). When the lumps are observed with the microscope, the shape of the particulate lump is sometimes observed as a tufted state extending from the biomaterial structure, in addition to the particulate state. Since it can be considered that the lump part of the tufted state (tufted lump) is formed by extending the particulate lump from the biomaterial structure, if a diameter (usually, a minor axis) of the tufted lump is within the above-mentioned range, such a lump can be used.

The particle diameter of the particulate lump can be determined by using a spectroscopic method such as optical scattering, X-rays, or neutron scattering. In such a case, the average particle diameter to be measured may be within the above-mentioned range. When the average particle diameter of the particulate lumps is within the above-mentioned range, the similar advantages obtained in the case that the particular diameter is within the above-mentioned range can be obtained.

In the biomaterial structure of the invention, the particulate lumps are not completely packed usually, and spaces (voids) are formed between the particulate lumps. When an affinity separation is carried out using the biomaterial structure, a target material, which interacts with the biomaterial, can enter into the spaces. Usually, in the spaces, the interaction between the biomaterial and the target material is performed. Accordingly even if the biomaterial structure of the invention has a three dimensional structure, the biomaterial contained therein can be interacted with the target material and the like. That is, the biomaterial structure of the invention can three-dimensionally have many biomaterials therein, and further does not lose the activity of the biomaterial, and it is possible to conduct the interaction. Therefore, the biomaterial structure of the invention can retain the activity of the biomaterial, and can contain a larger amount of the biomaterial than the conventional ones.

A method for examining whether the biomaterial structure of the present invention has spaces among the particulate lumps is not particularly limited, and it can be determined by using, for example an optical microscope, an electron microscope such as SEM or TEM, a microscope such as AFM, and the like. In addition, it can be determined by using a light scattering, X-rays, a spectroscopic method such as neutron scattering, and the like.

Further, when the volume of the biomaterial structure of the invention in dry state is compared with the volume of the structure dipped in liquid, and the volume is increased, it can be considered that the liquid enters into the spaces to increase the volume, and can be evaluated that the biomaterial structure of the invention has spaces. The change in volume may be confirmed by any methods. For example, when the biomaterial structure is a film, it can be determined by measuring the film thickness in dry state and the thickness of the film dipped in liquid with AFM, and the like, and comparing the obtained values.

The size of the biomaterial structure of the invention is not particularly limited, and any size can be used. When the structure does not bind to any solid-state carrier, the diameter in dry state is usually 30 nm or higher, preferably 40 nm or higher, more preferably 50 nm or higher. The upper limit is not particularly limited, but it is usually 10 cm or smaller. The diameter of the biomaterial structure can be measured by using an electron microscope such as SEM or TEM, a microscope such as AFM, and the like. When the size of the biomaterial structure is too small, it may be difficult to retrieve the biomaterial structure with a centrifugation separation operation, in the purification/separation, in case of using the structure in affinity separation, and the like.

Further, the biomaterial structure of the invention can be immobilized on a solid-state carrier, which can be used in affinity purification, or as a pharmaceutical function analysis tool or a sensor chip, and further used for surface treatment of drugs for DDS (drug delivery system), surface treatment of regeneration medicine carriers, surface treatment of artificial organs, surface treatment of catheters, and the like. When the biomaterial structure of the invention is applied to the surface treatment and the like, the biomaterial structure of the invention is immobilized on the desired solid-state carrier in any manner to form the biomaterial-carrying object of the invention, which is to be used.

When the biomaterial structure of the invention is microscopically observed, it is found that the structure is a matrix structure having a principal chain comprising the biomaterial and the compound for binding. That is, the biomaterial structure of the invention is a matrix comprising, as schematically shown in FIG. 3(a) to FIG. 3(c), the biomaterial and the compound for binding, the skeleton of the matrix being formed by binding the biomaterial to the compound for binding to form a chain and/or reticular structure. Usually, the matrix forms a particulate lump, as shown in FIG. 2(a).

FIG. 3(a) to FIG. 3(c) are schematic diagrams showing the enlarged surface vicinity of one example of the biomaterial structure of the invention immobilized on a solid-state carrier, for explaining the biomaterial structure of the invention. In FIG. 3(a) to FIG. 3(c), circular parts show the biomaterials and linear parts show the compounds for binding. In order to explain the structure of the principal chain comprising the biomaterial and the compound for binding, however, in FIG. 3(a) to FIG. 3(c), the structure of the principal chain is described in two dimensions regardless of whether they form the particulate lumps or not. Accordingly, it should be considered that when the biomaterial structure has particulate lumps, the diagrams of FIG. 3(a) to FIG. 3(c) show the principal chains of the particulate lumps of the biomaterial structure, which are spread in two dimensions.

Also, the biomaterial structure of the invention comprises mutually-linked many conjugates in which the biomaterial and the compound for binding are bound, and usually is a gel structure in which the biomaterial and the compound for binding are bound in the state of chain and/or network (see FIG. 3(a) to FIG. 3(c), and FIG. 4). This conjugate is formed by binding the biomaterial to the compound for binding, and can be made by only mixing the biomaterial and the compound for binding in a solvent or a dispersion medium to contact the molecules to each other.

The biomaterial structure of the invention is a structure having a principal chain comprising the above-mentioned biomaterial and compound for binding. Here, the principal chain of the biomaterial structure of the invention forms the skeleton of the matrix structure. Specifically, it is formed by binding the biomaterial and the compound for binding to each other. More specifically, the compound for binding binds to the biomaterial through a binding functional group, and such a structure is formed repeatedly to form a chain and/or reticular structure.

Therefore, the biomaterial structure of the invention has usually two or more partial structures having the following formula (A):

$$R^1\text{-}R^2 \qquad \text{Formula (A)}$$

(in Formula (A), $R^1$ is a biomaterial and $R^2$ is a compound for binding. When the biomaterial structure binds to some solid-state carrier, $R^2$ is a compound for binding which is not bound directly to the solid-state carrier, and each of $R^1$ and $R^2$ may be the same or different.)

That is, the biomaterial structure of the invention is a structure in which partial structures in which the biomaterial binds to the compound for binding bind in the state of a linear chain and/or network as shown in Formula (A). Specifically, in the above-mentioned Formula (A), $R^1$ binds independently to one or more $R^2$s, and $R^2$ binds independently binds to one or more $R^1$s. The biomaterial structure of the invention may include, for example, a partial structure in which the biomaterials $R^1$ bind to each other, or the compounds $R^2$ for binding bind to each other. Here, the binding between the $R^1$s or $R^2$s includes binding caused by physical interactions such as intermolecular attraction, hydrophobic interaction, and electric interaction.

Consequently, the biomaterial structure of the invention at least partially contains a cross-linked structure in which there is the biomaterial between the compounds for binding and there is the compound for binding between the biomaterials, and the principal chain of the matrix structure is formed by both of the biomaterial and the compound. Therefore, the biomaterial structure of the invention is produced in the presence of both of the biomaterial and the compound for binding in the production system.

As mentioned above, since the biomaterial structure of the invention has the matrix skeleton formed from both of the biomaterial and the compound, it is possible to increase the percentage of the biomaterial.

It can be confirmed that the biomaterial structure has the principal chain comprising the biomaterial and the compound for binding by the following method:

Since the biomaterial structure of the invention, as mentioned above, has the principal chain comprising the biomaterial and the compound for binding, the structure is decomposed by breaking the linkage of the biomaterial, which is the constituent element thereof. Utilizing this mechanism, the principal chain comprising the biomaterial and the compound for binding can be confirmed by decomposing the biomaterial of the biomaterial structure alone. For example, when the biomaterial structure is immobilized on some solid-state carrier, at least a part of the compound for binding is immobilized on the solid-state carrier through the biomaterial, and accordingly, when the biomaterial is decomposed while the compound for binding is not decomposed, in the biomaterial structure of the invention, parts in which the compound for binding is immobilized on the solid-state carrier through the biomaterial are removed from the solid-state carrier.

Specifically, compounds forming the biomaterial structure other than the biomaterial constituent element can be specified by decomposing the biomaterial with an enzyme or other chemical which does not decompose the compound for binding but decomposes only the biomaterial, and examining substances eliminated from the solid-state carrier; or by examining substances remaining on the surface of the solid-state carrier. If the biomaterial structure has the principal chain comprising the biomaterial and the compound for binding, then the compound for binding can be detected in the substances eliminated. Also, the compound for binding is not detected on the solid-state carrier surface, or even if it is detected, the amount is reduced.

On the other hand, when the biomaterial structure utilizes a polymer film according to the conventional method, and the biomaterial is decomposed, all of the polymer film (namely the polymer chain) remains in the solid-state carrier, and the biomaterial constituent elements are detected but polymer chains corresponding to the compound for binding are not detected in substances eliminated, because the principal chain is a polymer chain. The presence of the principal chain comprising the biomaterial and the compound for binding can be determined by utilizing this difference, and it can be specified that a compound is the biomaterial structure of the invention or not.

The enzyme and chemical used for decomposing the biomaterial in the above-mentioned method are suitably selected in accordance with the kind of the biomaterial or compound for binding used. Examples thereof include, in case where the biomaterial is the nucleic acid, for example, nucleic acid degrading enzymes such as ribonuclease, and deoxyribonuclease.

In case where the biomaterial is a protein, examples of the enzyme and chemical include, for example, protein degrading enzymes such as microbial protease, trypsin, chymotrypsin, papain, rennet, and V8 protease, chemical substances having proteolytic ability such as cyanogen bromide, 2-nitro-5-thiocyanobenzoic acid, hydrochloric acid, sulfuric acid, and sodium hydroxide, and the like.

When the biomaterial is a lipid, examples of the enzyme and chemical include, for example, lipid degrading enzymes such as lipase and phospholipase A2, and the like.

When the biomaterial is a saccharide, examples of the enzyme and chemical include, for example, saccharide degrading enzymes such as α-amylase, β-amylase, glucoamylase, pullulanase, and cellulase, and the like.

The enzymes and chemicals for decomposing the biomaterial may be used alone or as a mixture thereof in any ratio.

Of the above-mentioned examples, however, the enzymes and chemicals which perhaps decompose not only the biomaterial but also the compound for binding should not be used, because the accurate determination of the principal chain cannot be performed.

When decomposition of the biomaterial, and substance remaining on the solid-state carrier after the decomposition are determined, any determination methods can be used. For example, they can be determined by using, for example, surface plasmon resonance (SPR), crystal oscillator microbalance (QCM), electron microscope, ellipsometry, or the like.

When substances which are removed from the solid-state carrier after decomposition of the biomaterial are determined, any analysis methods can be used, and examples of the determination method include, for example, liquid chromatography, gas chromatography, mass spectroscopy (MS), infrared spectroscopy, nuclear magnetic resonance (NMR), high performance liquid chromatography (HPLC), gel electrophoresis, capillary electrophoresis, absorbance measurement, fluorometry, elemental analysis, amino acid determination, and the like. The determination methods may be used alone or in combination thereof in the analysis.

I-4. Composition of Biomaterial Structure

I-4-1. Content Ratio of Biomaterial

In the biomaterial structure of the invention, the content ratio of the biomaterial is not limited, but it is desirable that a larger amount of the biomaterial is contained. Specifically, the weight ratio of the biomaterial to the biomaterial structure, "(the weight of the biomaterial)/(the weight of the biomaterial structure)" is usually 0.1 or higher, preferably 0.3 or higher, more preferably 0.5 or higher, still more preferably 0.7 or higher, particularly preferably 0.9 or higher. The content does not particularly have an upper limit, and it is usually 0.999 or lower. When the ratio of the biomaterial is lower than the above-mentioned range, the compound for binding in the formed biomaterial structure cannot be sufficiently covered with the biomaterial, and therefore, the non-specific adsorption to the compound for binding can occur. When separation/purification is performed by using such a biomaterial structure, the efficiency of the separation/purification can be lowered.

I-4-2. Measurement of Biomaterial Content Ratio

Methods for measuring the above-mentioned ratio of the biomaterial are not particularly limited. For example, the biomaterial contained in the biomaterial structure of the invention may be decomposed with an enzyme or a chemical, and each substance derived from the biomaterial and the compound for binding may be quantified in various methods.

Now, based on the above-mentioned method, a method for measuring the content ratio of the biomaterial will be described.
(1) Decomposition Method of Biomaterial When the ratio of the biomaterial is measured by the above-mentioned method, an enzyme and a chemical for decomposing the biomaterial, and the like may be suitably used depending on the kind of the biomaterial and the compound for binding used. Examples thereof include the same enzymes and chemicals as those for decomposing the biomaterial used in the determination method of the principal chain comprising the biomaterial and the compound for binding.

The above-mentioned enzymes and chemicals for decomposing the biomaterial may be used alone or as a mixture thereof in any ratio.
(2) Quantification Method of Substances Derived from Biomaterial and Compound for Binding Methods for quantifying the substances derived from the biomaterial and the compound for binding after the decomposition of the biomaterial structure are not limited, and any methods can be used. Examples thereof include, for example, liquid chromatography, gas chromatography, mass spectroscopy (MS), infrared spectroscopy, nuclear magnetic resonance ($^1$H-NMR, $^{13}$C-NMR, $^{29}$Si-NMR), high performance liquid chromatography (HPLC), gel electrophoresis, capillary electrophoresis, absorbance measurement, fluorometry, elemental analysis, amino acid determination, and the like. These methods may be used alone or as a mixture thereof in the analysis.

I-4-3. Response Ratio of Biomaterial

In the biomaterial structure of the invention, a major part of the biomaterial in the biomaterial structure does not lose the activity. Specifically, when the biomaterial structure is contacted with a solution containing an interacting substance, which can be specifically interacted with the biomaterial, the ratio of the number of the interacting substances which are interacted with the biomaterials to the number of the biomaterials in the biomaterial structure (hereinafter, sometimes, referred to as "response ratio") is usually 0.5 or higher, preferably 0.6 or higher, more preferably 0.7 or higher. The upper limit thereof is not particularly limited, but it is usually 1.0 or less. As mentioned above, since the biomaterial structure of the invention has many spaces as well as contains many biomaterials, the response ratio can be made high, whereby the biomaterial can be efficiently used. When the biomaterial and the interacting substance are the biological molecule and the molecule such as an interacting molecule, respectively, this response ratio can be found as a ratio of the number of each molecule. The response ratio can also be measured by using, for example, SPR (surface plasmon resonance) or QCM (quartz crystal microbalance), and the like.

This advantage can be also obtained in the case where the biomaterial structure is immobilized on the solid-state carrier, and a biomaterial-carrying object is formed.

I-5. Production Method of Biomaterial Structure

The biomaterial structure of the invention is usually produced through a step in which the biomaterial and the compound for binding are mixed (hereinafter, sometimes, referred to as "mixing step"). In this mixing step, the biomaterial and the compound for binding are mixed in a medium such as a solvent or a dispersion medium, and the biomaterial and the compound for binding are bound in the same system to form the biomaterial structure of the invention.

In order to efficiently obtain the biomaterial structure, a concentration step for removing the medium and a drying step may be performed after the mixing step.

In some steps in the production steps of the biomaterial structure, additives may be suitably added to the system.

I-5-1. Mixing Step

In the mixing step, the biomaterial and the compound for binding are mixed.

I-5-1-1. Biomaterial Used in Production of Biomaterial Structure

The biomaterial is as described above. The biomaterial is usually prepared in the state of a solution or a dispersion in which the biomaterial is dissolved or dispersed in some medium. In this case, preferably the solvent or the dispersion medium for diluting the biomaterial is prepared in consideration of the activity and structure stability of the biomaterial.

I-5-1-2. Compound for Binding Used in Production of Biomaterial Structure

The compound for binding is as described above.

I-5-1-3. Medium Used in Production of Biomaterial Structure

When the biomaterial and the compound for binding are mixed, it is preferable that the biomaterial and the compound for binding are bound in the presence of the medium (reaction medium) such as the solvent or the dispersion medium. As mentioned above, the biomaterial and the compound for binding are not necessarily bound through a chemical reaction, but in the present description, a substance forming a place where the biomaterial and the compound for binding are bound is referred to as "medium."

Any media can be used so long as the biomaterial structure of the invention can be produced, and usually it is desirable to use media which can be mixed with the biomaterial, the compound for binding and optionally used additives. In such a case, the biomaterial, the compound for binding and the additives may be mixed in any state, such as in the state of a solution and dispersion. In order to stably bind the biomaterial and the compound for binding, however, a solution in which the biomaterial and the compound for binding are dissolved in the medium is preferable.

Liquid is usually used as the medium. In this case, the medium forms a place where the biomaterial and the compound for binding are bound, and the medium influences on the activity and the structure stability of the biomaterial and the compound for binding, and accordingly, it is preferable that the medium is selected in consideration of the influences. Usually, water is used as the medium.

Liquid other than water may be used as the medium, for example, organic solvents may be used. Of the organic solvents, amphipathic solvents, namely organic solvents which can be mixed with water are preferable. Examples of the medium other than water include THF (tetrahydrofuran), DMF (N,N-dimethylformamide), NMP (N-methyl pyrrolidone), DMSO (dimethyl sulfoxide), dioxane, acetonitrile, pyridine, acetone, glycerin, and the like, in addition to alcohol solvents such as methanol, ethanol, and 1-butanol.

When liquid is used as the medium, a salt may be added to the medium. Any salts may be used so long as the effects of the invention are not impaired. Examples of the salt include NaCl, KCl, sodium phosphate, sodium acetate, calcium chloride, sodium hydrogenecarbonate, ammonium carbonate, and the like. The amount of the salt used is not limited and any amount can be used according to the use.

When water is used as the medium, the water is not limited to purified water but may be solutions in which a solute other than the biomaterial and the compound for binding is dissolved in water. Examples thereof include various buffers such as carbonate buffer, phosphate buffer, acetate buffer, HEPES buffer, and TRIS buffer.

The media may be used alone or as a mixture thereof in any ratio.

I-5-1-4. Additive Used in Production of Biomaterial Structure

In any step in the preparation steps of the biomaterial structure, any additives may be added to the biomaterial, the compound for binding, the medium and the mixture thereof, so long as the effects of the invention are not remarkably impaired. Examples of the additives include acids, bases, buffers, moisturizing agents such as glycerin, stabilizers for the biomaterial such as metal ions, e.g. zinc, antifoaming agents, modifiers, and the like, in addition to the above-mentioned salts.

The additives may be used alone, or as a mixture thereof in any ratio.

I-5-1-5. Mixing Operation in Production of Biomaterial Structure

When the biomaterial structure of the invention is produced, the above-mentioned biomaterial and compound for binding are mixed in the presence of the medium to obtain a mixture containing at least the biomaterial and the compound for binding in the medium. The resulting mixture contains both of the biomaterial and the compound for binding, which can bind to the biomaterial, in the medium, and in the mixture, the biomaterial and the compound for binding are bound to prepare the biomaterial structure. It is preferable that the biomaterial and the compound for binding are mixed with the medium in the mixture.

Any forms of the biomaterial, the compound for binding, the medium, the additive and the like may be used in mixing, so long as the biomaterial structure of the invention can be produced. The biomaterial, however, is usually prepared in the state of a solution or dispersion in which the biomaterial is dissolved or dispersed in some solvent or dispersion medium. In this case, preferably, the solvent or dispersion medium diluting the biomaterial is prepared in consideration of the activity or structure of the biomaterial, and for example the same medium as used in the mixing step can be used as the solvent or dispersion medium.

The biomaterial, the compound for binding, the medium, the additive and the like may be arbitrarily mixed. For example, a solution such as aqueous solution or a dispersion of the biomaterial and a solution such as an aqueous solution or a dispersion of the compound for binding may be mixed; a solution or dispersion of the biomaterial and the solid compound for binding may be mixed; the solid biomaterial and a solution or a dispersion of the compound for binding may be mixed; and the solid biomaterial, the solid compound for binding and the solvent may be mixed. Also, it is possible to prepare a mixture on a solid-state carrier, for immobilizing the biomaterial structure of the invention on a solid-state carrier mentioned below.

I-5-1-6. Composition in Mixing for Production of Biomaterial Structure

Any mixing ratios of the biomaterial, the compound for binding, the medium, the additive and the like may be used in mixing, so long as the biomaterial structure of the invention can be obtained. However, the mixing ratio "(the weight of the biomaterial)/{(the weight of the biomaterial)+(the weight of the compound for binding)}" is usually 0.1 or higher, preferably 0.3 or higher, more preferably 0.5 or higher, still more preferably 0.7 or higher, particularly preferably 0.9 or higher. Although the upper limit is not particularly limited, it is usually 0.999 or lower. When the mixing ratio is lower than the above-mentioned range, the content of the biomaterial in the formed biomaterial structure is lowered, and therefore the compound for binding cannot be sufficiently covered with the biomaterial, and the non-specific adsorption can occur.

When the mixing ratio of the biomaterial is higher, a biomaterial structure comprising a principal chain having a binding point of the compound for binding, as shown in FIG. 3(a), is formed. On the other hand, when the mixing ratio of the compound for binding is higher, a biomaterial structure comprising a principal chain having a binding point of the biomaterial for binding, as shown in FIG. 4, is formed. It is possible, therefore, to inhibit the non-specific adsorption to the compound for binding by increasing the ratio of the biomaterial, as the above-mentioned range. FIG. 4 is a schematic view showing the enlarged surface vicinity of one example of the biomaterial structure of the invention immobilized on a solid-state carrier, for explaining the biomaterial structure of the invention. In FIG. 4, circular parts show the biomaterials and linear parts show the compounds for binding. In order to explain the structure of the principal chain comprising the biomaterial and the compound for binding, however, in FIG.

4, the structure of the principal chain is described in two dimensions regardless of whether they form the particulate lumps or not. Accordingly, it should be considered that when the biomaterial structure has particulate lumps, FIG. 4 shows the principal chain of the particulate lump of the biomaterial structure, which are spread in two dimensions.

Any percentages (concentrations) of the biomaterial and the compound for binding in the medium may be used so long as the biomaterial structure of the invention can be obtained. The total concentration of the biomaterial and the compound for binding is usually 0.1 g/L or higher, preferably 1 g/L or higher, more preferably 10 g/L or higher. When the concentration is lower than the above-mentioned range, it is difficult to generate the particulate lumps and the biomaterial structure.

I-5-1-7. Formation Mechanism of Biomaterial Structure

The biomaterial and the compound for binding are mixed to form the particulate lumps, and the particulate lumps are aggregated to form the biomaterial structure of the invention.

Although the formation process of the biomaterial structure of the invention is not clear, the process can be considered as follows: That is, when the mixture containing the biomaterial and the compound for binding is prepared, the biomaterial and the compound for binding bind to each other (see FIG. 2($a$)) in the mixture to generate the particulate lumps as shown in FIG. 2($b$). The particulate lumps are aggregated to form the biomaterial structure having a structure in which the particulate lumps are aggregated in the state of a chain and/or a network, as shown in FIGS. 1($a$) and ($b$).

It can be also considered that the biomaterial and the compound for binding contained in each particulate lump are bound, thereby generating the particulate lumps to form the biomaterial structure of the invention. In this case, since the obtained biomaterial structure is more stable, it can be applied to wider environments or uses.

When the mixture containing the biomaterial and the compound for binding is prepared, usually the biomaterial and the compound for binding are bound to generate a conjugate in the mixture. This conjugate is one in which the biomaterial and the compound for binding are bound. The particulate lump is one form of such conjugates.

Further, the conjugates (usually particulate lumps) are aggregated and the biomaterial and the compound for binding, which are contained in each conjugate, bind to each other to form a biomaterial structure having a larger matrix structure, in which the conjugates are bound in the state of a chain and/or a network structure. In this case, in the biomaterial structure of the invention, a matrix in which the particulate lumps are bound is usually formed.

I-5-2. Concentration Step and Drying Step

A concentration step or a drying step, in which the medium is removed from the above-mentioned mixture, may be suitably performed during or after the mixing step.

When the amount of the solvent in the above-mentioned mixture is large, there are cases where it is difficult to generate the conjugates (usually particulate lumps) or the biomaterial structure in the mixture, or cases where they are not generated. In such a case, the conjugates (usually particulate lumps) can be efficiently formed and the biomaterial structure can be efficiently produced by concentrating the mixture.

When the mixture contains fragments of the conjugate (usually particulate lumps) or the biomaterial structure, the concentration can form additional conjugates (usually particulate lumps) and biomaterial structure. In order to grow such conjugates (usually particulate lumps) or such a biomaterial structure, the concentration may be performed.

In order to form a uniform biomaterial structure, it is preferable to uniformly mix the biomaterial and the compound for binding in the medium in an initial stage of the preparation of the mixture. It is preferable, therefore, that the biomaterial and the compound for binding are contained in a relatively large amount of a medium, and then the mixture is concentrated to generate particulate lumps, and thereafter the biomaterial structure is produced using such lumps.

After the biomaterial structure is formed, the mixture may be dried to remove the medium. Since the mixture is usually concentrated during the drying step of the mixture, the concentration and drying can be carried out in a series of operation.

Any method for drying and concentrating may be used, and examples thereof include, for example, ultrafiltration, drying under reduced pressure, and the like. In addition, evaporation under normal pressure may be carried out to dry or concentrate.

The temperature conditions, when the mixture is dried and concentrated, are arbitrary, and the temperature is usually 25° C. or lower, preferably 10° C. or lower, in order to avoid the denaturation of the biomaterial.

The pressure conditions when the mixture is dried and concentrated are arbitrary, and the operation is preferably carried out under normal pressure or reduced pressure.

Further, the concentration of the mixture is performed for the purpose of easily forming the conjugates (usually particulate lumps) by increasing the probability to contact the biomaterial and the compound for binding, or the purpose of easily forming the biomaterial structure of the invention by increasing the probability to contact the conjugates or the particulate lumps. For this purpose, the mixture may be precipitated with centrifugation separation, or the conjugates (usually particulate lumps) and the biomaterial structure may be precipitated by adding a poor solvent or additives such as ammonium sulfate before, during or after the concentration.

I-5-3. Other Steps

In the production process of the biomaterial structure of the invention, steps other than the above-mentioned steps may be performed.

For example, after producing the biomaterial structure, the biomaterial in the biomaterial structure may be modified with desired functional groups.

Also, for example, the biomaterial structure of the invention may be immobilized on some solid-state carrier to make a biomaterial-carrying object (the biomaterial immobilized on the solid-state carrier).

I-6. Explanation of Affinity Separation Using Biomaterial Structure

The biomaterial structure of the invention is suitably used in affinity separation. The biomaterial structure of the invention, therefore, can be used, for example, in affinity purification or as a pharmaceutical function analysis tool.

Specifically, when a bioactive substance is used as the biomaterial in affinity purification or a pharmaceutical effect and mechanism analysis tool, a trace amount of a biomaterial such as a protein contained in serum is a target material to be purified, and the target material can be obtained from a crude product by interaction between the biomaterial and the target material. When the effect and mechanism of a pharmaceutical candidate compound to the biomaterial contained in the biomaterial structure is analyzed, a protein contributing to a disease such as a receptor is used as the biomaterial, multiple pharmaceutical candidate compounds are used as target materials, and they are contacted with the biomaterial structure, followed by analysis of pharmaceutical candidate compounds which specifically bind, and the pharmaceutical candidate compounds can be selected or the effect and mechanism thereof can be unraveled.

When the affinity separation is performed as mentioned above, the separation/purification and the analysis of structures or functions are performed by utilizing the above-mentioned specific interaction between the biomaterial contained in the biomaterial structure and the target material. In this case, first, a sample liquid (specimen) containing the target material is contacted with the biomaterial structure, and the target material in the sample liquid is separated from other substances.

I-6-1 Target Material which is a Target in Separation/Purification

The target in the separation/purification, namely the target material is an interacting substance which specifically interacts with (affinity binding takes place) the biomaterial. Examples of the target material include the biomaterials contained in the above-mentioned biomaterial structure.

Specifically, when a substance which can be a pharmaceutical (pharmaceutical candidate substance) is separated, a substance which can make the pharmaceutical candidate substance to generate a desired interaction is used as the biomaterial, a compound which can be the pharmaceutical candidate substance is used as the target material, and the target material can be separated from a sample which may contain pharmaceutical candidate substances.

I-6-2. Sample Liquid Containing the Target Material

The target material is usually contained in a specimen together with other substances. Although the specimen may be gas, it is usually liquid. In many cases, the specimen is a solution or a dispersion in which the target material is contained in some solvent. The liquid specimen in the state of a solution or dispersion is hereinafter referred to as "sample liquid," for convenience.

Any solvents or dispersion mediums for the sample liquid can be used so long as the effects of the invention are not impaired. For example, as the medium used in production of the biomaterial structure, the above-mentioned mediums can be used.

Any concentrations of the target material in the sample liquid can be used. The concentration is usually 1 µg/L or higher, preferably 5 µg/L or higher, more preferably 10 µg/L or higher. When the concentration is lower than the above-mentioned range, the efficiency of purification is reduced, and the advantage of the invention cannot show sufficiently.

The concentration of substances other than the target material is usually 50% by weight or lower in the sample liquid, preferably 40% by weight or lower, more preferably 30% by weight. When the concentration is higher than the above-mentioned range, the viscosity of the sample liquid is too high, the target material may not completely enter into the inside of the biomaterial structure, and cannot be contacted with the biomaterial.

I-6-3. Method for Contacting Biomaterial Structure with Sample Liquid

Methods for contacting the sample liquid containing the target material with the biomaterial structure of the invention are not particularly limited. For example, a method in which the sample liquid containing the target material is passed through a column filled with the biomaterial structure together with a mobile phase to contact them. In this case, the biomaterial structure can be used in dry state, but it is preferable to wet the biomaterial structure with the mobile phase liquid before contacting with the sample liquid.

Alternatively, for example, it is possible that the sample liquid containing the target material is contained in a container such as micro tube, through which the biomaterial structure is passed to contact, or that the sample liquid containing the target material is added to a container containing the biomaterial structure to contact.

It is possible that the efficiency of the separation/purification can be further increased by immobilizing the biomaterial structure of the invention on the solid-state carrier. For example, the biomaterial structure of the invention is immobilized on a surface of a micro channel, and the sample liquid containing the target material is fed into the channel, whereby a small separation/purification apparatus with high efficiency can be formed.

When the sample liquid containing the target material is contacted with the biomaterial structure, any conditions can be adopted, but the temperature is preferably 25° C. or lower, more preferably 10° C. or lower.

The sample liquid can be dried or concentrated before, while or after contacting. Any pressure conditions can be adopted, but the pressure is desirably normal pressure or lower.

I-6-4. Separation of Target Material

How to separate the target material from the mixture after contacting the biomaterial structure of the invention with the sample liquid is arbitrary and can be decided according to the kind of the biomaterial or the target material.

For example, when there is a difference in the retention time between the target material and other substances due to the specific interaction between the biomaterial and the target material, fraction purification is performed by utilizing the difference in retention time whereby the target material can be separated from the other substances (affinity chromatography).

When the target material adsorbs to the biomaterial by a specific interaction, the target material is adsorbed to the biomaterial, the sample liquid is separated from the biomaterial structure, while the target material is adsorbed to the biomaterial, and the target material is released and retrieved from the biomaterial, whereby the target material can be separated from the other substances. Methods for releasing the target material from the biomaterial are not particularly limited. For example, the target material can be released and retrieved from the biomaterial structure by adding a salt, controlling the pH, elevating the temperature, adding a known chemical substance which has a stronger adsorptivity than that of the target of separation/purification, or adding a high concentration of a chemical substance which has a equal or weaker adsorptivity than that of the target to the biomaterial structure, and the like.

The separated target material can be diluted or concentrated according to the purpose. For example, when the target material is diluted, a solvent suitable for the purpose may be added, and when the target material is concentrated, the solvent may be evaporated under reduced pressure, by heating it or combination thereof, or the solvent may be completely removed by using an ultrafiltration filter or by freeze drying.

When the target material separated through the biomaterial structure of the invention is analyzed, though the analysis methods are not limited, in general, examples thereof, for example, include liquid chromatography, gas chromatography, mass spectroscopy (MS), infrared spectroscopy, nuclear magnetic resonance ($^1$H-NMR, $^{13}$C-NMR, $^{29}$Si-NMR), high performance liquid chromatography (HPLC), gel electrophoresis, capillary electrophoresis, absorbance measurement, fluorometry, and the like. In the analysis, the analysis methods may be used alone or in combination thereof. In the second embodiment mentioned below, wherein the amount of the target material, which adsorbs to the biomaterial, is measured, and in the fourth embodiment wherein the amount of the target material in the fraction in a measuring unit 21 is measured, measuring apparatus using the example methods can be used.

I-6-5. Advantage of Affinity Separation Using Biomaterial Structure

According to the conventional affinity separation, the amount of the biomaterial introduced is limited (single layer adsorption of a protein is usually 0.3 to 1.0 µg/cm$^2$), because the biomaterial is immobilized on the surface of a carrier for affinity chromatography used in the separation. According to the conventional carrier for affinity chromatography, therefore, when the interaction between the biomaterial and the target material is carried out, an amount of the target material which can interact per unit volume is small.

Further, according to the conventional technique, the carrier for the affinity chromatography cannot be completely covered with the biomaterial, and therefore, non-specific interaction to the carrier for affinity chromatography easily occurs, and the efficiency of the separation/purification is low. Consequently, in order to increase the purity of the purification, multiple purification operations are necessary, which leads to a large amount of time and labor for the separation/purification.

On the contrary, the biomaterial structure of the invention can maintain the reactivity of the biomaterial introduced into the biomaterial structure. In addition, the amounts of the biomaterial per unit volume of the biomaterial structure and the target material which specifically interacts can be increased by increasing the percentage of the biomaterial in the biomaterial structure. Further, the percentage of the compound for binding can be reduced in a low value by increasing the percentage of the biomaterial contained in the biomaterial structure, whereby the non-specific adsorption based on the compound for binding can be inhibited. As a result, the non-specific adsorption can be further inhibited compared with the conventional technique, and the necessary time for the separation/purification can be shortened.

The biomaterial structure of the invention can be formed on a surface of any solid-state carrier, and can be applied to micro chips, micro channels and the like, which have been vigorously studied in recent years. That is, application to wide range of use is one advantage obtained by using the biomaterial structure of the invention.

I-6-6. Embodiment

Now, embodiments wherein the target material is separated from the sample liquid using the biomaterial structure will be described. However the present invention is not limited to the embodiments.

I-6-6-1. The First Embodiment

In this embodiment, a target material is separated/purified from a sample liquid in which the target material (separation target material) and other substances are contained in liquid.

FIG. 5 is a cross-sectional view schematically showing a container for affinity chromatography used in this embodiment.

In this embodiment, a container 3 for affinity chromatography (hereinafter, sometimes, referred to as "container for affinity") in which a biomaterial structure 2 is contained in a container body 1, as shown in FIG. 5, is used. Here, the shape of the container body 1 is not limited and any shapes can be used so long as it can contain the sample liquid and the like therein.

In the container 3 for affinity used in this embodiment, the biomaterial structure 2 is immobilized on the inner surface of the container body 1, whereby the biomaterial structure 2 is kept in the container body 1, so the structure 2 does not run out from the container body 1. The biomaterial structure 2 may be contained in the container body 1 and is not necessarily immobilized on the container body 1.

The biomaterial of the biomaterial structure 2 and the target material which is the target in the purification, which are used in this embodiment, are specifically interacted, whereby the target material can specifically adsorb to the biomaterial.

When the target material is separated from the sample liquid by using this container 3 for affinity, the sample liquid is first injected into the container 3 for affinity, whereby the biomaterial structure 2 is contacted with the sample liquid and the target material adsorbs to the biomaterial.

Next, in order to separate the sample liquid from the biomaterial structure 2, the sample liquid is ejected from the container 3 for affinity, whereby components other than the target material contained in the sample liquid is ejected. On the other hand, the target material adsorbs to the biomaterial of the biomaterial structure 2 and it is held in the container 3 for affinity.

Then the target material is released from the biomaterial structure 2 by, for example, pouring a solution for retrieval, whose pH is controlled to a pre-determined value with which the interaction between the target material and the biomaterial is weakened, into the container 3 for affinity, and the released target material is retrieved together with the solution for retrieval.

The target material in the sample liquid can be separated/purified by the above-mentioned procedure. In this case, the substance specifically interacting with the target material is used as the biomaterial, and moreover, the biomaterial structure of the invention contains a large amount of biomaterial with activity, and therefore the non-specific adsorption is inhibited and highly efficient separation/purification can be easily performed.

Further, in case where an interacting substance which causes certain pre-determined interaction with the above-mentioned biomaterial is unknown, in screening to find what substance is interacted with the biomaterial, the technique of this embodiment can be applied. That is, for example, in the above-mentioned embodiment, if a sample liquid containing a substance causing some interaction is used, a substance (target material) obtained by separating/purifying from other substances in the sample liquid is the interacting substance causing the interaction, and accordingly the screening can be suitably performed.

In this embodiment, when the biomaterial structure 2 is not immobilized on the container body 1, it is preferable to collect the biomaterial structure 2 by using a centrifugation separator prior to ejecting the sample liquid, because the operation efficiency and the retrieval efficiency are improved.

I-6-6-2, The Second Embodiment

In this embodiment, a target material (analysis target material) contained in a sample liquid is separated/purified, and analyzed.

This embodiment is explained by using FIG. 5, similar to the first embodiment. In this embodiment, the same numerals as in the first embodiment show the same parts as in the first embodiment.

The container 3 for affinity used in this embodiment has a material which specifically interacts with a substance (interacting substance) having a specific structure (molecular structure) to specifically adsorbs to the substance as the biomaterial contained in the biomaterial structure 2.

Other elements are the same as in the first embodiment.

When the target material in the sample liquid is analyzed using the container 3 for affinity, as in the first embodiment, the sample liquid is injected into the container 3 for affinity to contact the biomaterial structure with the sample liquid, and then, the sample liquid is ejected from the container 3 for affinity for separating the biomaterial structure 2 from the sample liquid. When the target material has a specific structure capable of specifically interacting with the biomaterial, the target material adsorbs to the biomaterial in the biomaterial structure 2 to be held in the container 3 for affinity. On the contrary, if the target material does not have the above-mentioned specific structure, the target material is ejected from the container 3 for affinity together with the sample liquid.

Therefore, whether the target material has the specific structure or not can be determined by checking whether the target material adsorbs to the biomaterial or not, in other words, by checking whether the target material remains in the container 3 for affinity or not.

For checking whether the target material adsorbs to the biomaterial or not, specifically, the amount of the target material adsorbing to the biomaterial may be measured. For example, as in the first embodiment, a solution for retrieval, whose pH is controlled to a pre-determined value with which the interaction between the target material and the biomaterial is weakened, may be injected into the container 3 for affinity to release the target material from the biomaterial structure 2, the solution for retrieval may be retrieved, and the amount of the target material contained in the solution for retrieval may be measured by using the above-mentioned measuring method.

It is possible to analyze whether the target material in the sample liquid has a specific structure corresponding at least to the biomaterial or not by using the above-mentioned procedure.

Further, by utilizing this, the technique of this embodiment can be applied to a case where a molecular structure which the interacting substance should have for interacting with the biomaterial is examined. That is, for example, in case where a group of substances (target materials) are separated from another group of substances by interacting with the biomaterial, if the former group of the substances have the common molecular structure, it can be considered that such a molecular structure is a molecular structure that the interacting substance should have for interacting with the biomaterial.

By using the biomaterial structure of the invention, as in the first embodiment, the non-specific adsorption is inhibited and highly efficient separation/purification can be easily performed, and therefore, it is possible to accurately analyze the target material with high sensitivity.

In this embodiment, modification can be conducted as in the first embodiment.

I-6-6-3. The Third Embodiment

In this embodiment, a target material is separated/purified from a sample liquid containing the target material (purification target material) and other substances.

FIG. 6 is a diagram schematically showing a general outline of an affinity chromatography apparatus used in this embodiment.

In this embodiment, the apparatus for affinity chromatography (hereinafter, sometimes, referred to as "affinity chromato apparatus") 10, as shown in FIG. 6, is used. The affinity chromato apparatus 10 has a tank 11, a pump 12, an auto-injector 13, an affinity separation chip 14, a flow channel selector valve 15, retrieval bottles 16 and 17, and a control unit 18.

The tank 11 stores carrier liquid which forms a mobile phase.

The pump 12 runs the carrier liquid stored in the tank 11 at a pre-determined flow rate according to the control by the control unit 18.

The auto-injector 13 injects the sample liquid into the flow of the carrier liquid according to the control by the control unit 18.

Accordingly, the carrier liquid stored in the tank 11 is supplied to the affinity separation chip 14 through the auto-injector 13 by the pump 12 at a pre-determined rate, and the sample liquid is injected into the carrier liquid by the auto-injector 13, whereby a sample liquid supplying unit 19 in which the sample liquid is passed through a flow channel 14B of the affinity separation chip 14 by the tank 11, the pump 12 and the auto-injector 13 is formed.

On the affinity separation chip 14, a basal plate 14A and a flow channel 14B are formed, and the channel 14B is filled with the biomaterial structure (not shown in FIG. 6). Here, the biomaterial of the biomaterial structure used in this embodiment and the target material which is the target in the purification are specifically interacted to change the retention time of the target material passing through the channel 14B. A filter (not shown in FIG. 6) is formed at the downstream end part of the channel 14B, for preventing the biomaterial structure outflow, which ensures that the biomaterial structure is held in the channel 14B.

As a result, the supplied carrier liquid (including one into which the sample liquid is injected) passes through the channel 14B filled with the biomaterial structure. The carrier liquid which elutes from the channel 14B (hereinafter, the liquid eluting from the channel 14B is sometimes referred to as "eluate") is sent to the downstream flow channel selector valve 15.

In this embodiment, the affinity separation chip 14 is detachable from the affinity chromato apparatus 10. Specifically, the affinity chromato apparatus 10 has a chip mounting unit 14C by which the affinity separation chip 14 is mounted, and the affinity separation chip 14 is mounted on the chip mounting unit 14C and the separation is carried out in use.

The flow channel selector valve 15 switches the channel according to the control by the control unit 18, to retrieve the eluate sent from the chip 14 for affinity-separation into either the retrieval bottle 16 or the retrieval bottle 17. That is, the eluate sent from the channel 14B of the affinity separation chip 14 is fractionated by the flow channel selector valve 15 and retrieved into either of the retrieval bottles 16 and 17.

In this embodiment, the carrier liquid containing the target material is retrieved into the retrieval bottle 16, and the carrier liquid containing no target material is retrieved into the retrieval bottle 17.

The control unit 18 controls the pump 12, the auto-injector 13 and the flow channel selector valve 15, and, in this embodiment, is embodied with a computer loading a program for control.

In this control unit 18, retention time information in the interaction between the biomaterial of the biomaterial structure and the target material, which are used in this embodiment, is recorded, and the switching time of the channel selector valve 15 is controlled according to the amount of the supplied carrier liquid after the sample liquid is poured from the auto-injector 13, and the elapsed time based on the information.

In FIG. 6, the dashed arrows show the control by the control unit 18.

When the target material is separated from the sample liquid using this affinity chromato apparatus 10, first, the affinity separation chip 14 is mounted on the chip mounting unit 14C, and then the control unit 18 makes the pump 12 work. Initially, the flow channel selector valve 15 is set so that the eluate is retrieved into the retrieval bottle 17. In this case, the carrier liquid in the tank 11 flows downstream, and passes through the auto-injector 13, the channel 14B of the affinity separation chip 14, and the flow channel selector valve 15, and is retrieved into the retrieval bottle 17.

After that, the control unit 18 controls the auto-injector 13 so that the sample liquid is injected into the carrier liquid. The control unit 18 starts time count at the time when the injection starts.

The injected sample liquid flows to the channel 14B and passes through the channel 14B. At this time, the sample liquid contacts with the biomaterial structure in the channel 14B, and the biomaterial and the target material are interacted and the flow rate of the target material lowers. As a result, the components other than the target material in the sample liquid pass through the channel 14B together with the carrier liquid, but the speed of the target material delays by the retention time caused by the interaction and so the target material passes through the channel 14B. Consequently, in the eluate running from the channel 14B, a fraction obtained after the time when the components other then the target material pass through the flow channel selector valve 15, which corresponds to the retention time of the target material, contains the carrier liquid and the target material, but does not contain other components which are not targets in the separation.

Then, the control unit 18 switches the flow channel selector valve 15 the retention time caused by the interaction after the time when the components other than the target material pass through the flow channel selector valve 15 based on the count time, and the fraction containing the target material is retrieved into the retrieval bottle 16.

After that, when the separation/purification is carried out continuously, the control unit 18 switches the flow channel selector valve 15 again so that the fraction of the eluate containing no target material is retrieved into the retrieval bottle 17, and the above-mentioned operation is repeated. When the separation/purification is stopped, the control unit 18 makes the pump 12 stop, and the supply of the carrier liquid is stopped.

The separation/purification of the target material in the sample liquid can be performed by the above-mentioned operation. In this case, the substance which specifically interacts with the target material is used as the biomaterial, and the biomaterial structure of the invention has a large amount of the biomaterial with the activity. Therefore, highly efficient separation/purification can be easily performed, inhibiting the non-specific interaction.

Further, as in the first embodiment, in case where an interacting substance which causes certain pre-determined interaction with the above-mentioned biomaterial is unknown, what kind of substance interacts with the above-mentioned biomaterial can be screened.

In the configuration of this embodiment, as in the first embodiment, the biomaterial structure may be immobilized on the affinity separation chip 14.

In addition, as to the above-mentioned affinity chromato apparatus 10, the affinity separation chip 14 is arbitrarily mounted or demounted on the affinity chromato apparatus 10, but the affinity separation chip 14 and the affinity chromato apparatus 10 may be integrated.

I-6-6-4. The Fourth Embodiment

In this embodiment, a target material (analysis target material) is analyzed by separation/purification of the target material in a sample liquid containing the target material.

FIG. 7 is a diagram schematically showing a general outline of an affinity chromatography apparatus used in this embodiment in which the same numerals used in FIG. 6 show the same parts in FIG. 6.

In this embodiment, an affinity chromato apparatus 20, as shown in FIG. 7, is used. The affinity chromato apparatus 20 has a tank 11, a pump 12, an auto-injector 13, an affinity separation chip 14, a control unit 18, and a measuring unit 21.

A sample liquid supplying unit 19, namely, the tank 11, the pump 12 and the auto-injector 13 are the same as in the third embodiment.

The affinity separation chip 14 is the same as in the third embodiment except that a material which changes the retention time of the target material passing through the channel 14B by specifically interacting with a substance having a specific structure (molecular structure) (interacting substance) is used as the biomaterial in the biomaterial structure.

The control unit 18 is the same as in the third embodiment except that it does not control a selector valve because the affinity chromato apparatus 20 used in this embodiment does not have the selector valve.

The affinity chromato apparatus 20 has the measuring unit 21 which measures the amount of a detection target material in a fraction of the eluate sent from the channel 14B downstream of the chip 14 for affinity separation. Specifically, the measuring unit 21 measures the amounts of the target material in the eluate over time, thereby measuring an amount of the target material contained in each fraction, the fraction being an eluate which flows into the measuring unit 21 at each time. Examples of the measuring unit 21 include the above-mentioned examples.

When the target material in the sample liquid is analyzed using the affinity chromato apparatus 20, as in the third embodiment, the affinity separation chip 14 is mounted on the chip mounting unit 14C, and the control unit 18 makes the pump 12 work to flow the carrier liquid in the tank 11, whereupon the measuring unit 21 starts to measure the target material in the eluate.

After that, the control unit 18, as in the third embodiment, controls the auto-injector 13 whereby the sample liquid is injected into the carrier liquid. The injected sample liquid flows into and passes through the channel 14B together with the carrier liquid. At this time, the sample liquid contacts with the biomaterial structure in the channel 14B.

The eluate running out from the channel 14B flows into the measuring unit 21. Then, in the measuring unit 21, the amount of the target material contained in the fraction of the eluate measured at each time.

Here, in case where the biomaterial structure contacts with the sample liquid, if the target material has the above-mentioned specific structure, then the retention time of the target material changes in the channel 14B, and the time at which the target material runs out from the channel 14B delays accordingly. On the other hand, if the target material does not have the above-mentioned specific structure, then the retention time of the target material does not change.

Accordingly, whether the target material has the specific structure or not, and how many structures are contained can be analyzed by examining which fraction has the target material among the fractions of the eluate, and how much is detected.

That is, when the target material is detected in the fraction obtained at the time when the retention time does not change, it can be considered that the target material does not have the specific structure.

When the target material is detected in the fraction obtained after the time when the retention time does not change, it can be considered that the target material has the specific structure. Further, the degree of the interaction is detected by measuring how big the retention time change is (that is, how long it takes until the target material is measured), whereby the number of the specific structures in the target material can be analyzed. In addition, when the target material comprises two or more kinds of substances, it can be evaluated which target material has the specific structure and how many specific structures are contained in the target material by measuring an amount of the target material contained in each fraction.

As mentioned above, according to the affinity chromato apparatus 20 of this embodiment, it is possible to analyze that the target material in the sample liquid has the specific structure corresponding to the biomaterial or not. The biomaterial structure of the invention, as in the third embodiment, can inhibit the non-specific interaction, and highly efficient separation/purification can be easily performed, and therefore it is possible to accurately perform the analysis of the target material with high sensitivity.

Furthermore, as in the second embodiment, a molecular structure for the interaction with the biomaterial contained in the interacting substance can be examined by utilizing this mechanism.

The measurement results in the measuring unit 21 can be output to an analysis part in which the above-mentioned analysis is performed, and in the analysis part, the target material can be analyzed. For example, it is possible that the analysis part reads the measurement results output from the measuring unit 21, and in the analysis part, whether the target material has the specific structure or not is evaluated by detecting or not detecting the target material in the fraction obtained at the time when the retention time does not change. In this case, however, it is preferable to provide a storage part in which the kinds of the biomaterial structure, the specific structures corresponding to the biomaterial structure, and retention time information used for evaluation are recorded, in the analysis part. The hardware of the analysis part can be, for instance, a computer in which a program that makes the computer functions as the analysis parts is loaded.

In this embodiment, as in the third embodiment, the modification may be performed.

II. Biomaterial-Carrying Object

The biomaterial-carrying object (referred, sometimes, to as "solid-state carrier on which the biomaterial is immobilized" or "biomaterial immobilized carrier") is a solid-state carrier on which the biomaterial structure of the invention is immobilized. That is, it has the biomaterial structure of the invention on the surface of the solid-state carrier. The containers for affinity and chips for the affinity separation used in the first to fourth embodiments are examples of the biomaterial-carrying objects.

When the biomaterial structure of the invention is used as a tool for affinity purification or pharmaceutical function mechanism analysis, it is desirable to use the biomaterial-carrying object in which the biomaterial structure is immobilized on the solid-state carrier, depending on the condition.

II-1. Biomaterial Structure Contained in Biomaterial-Carrying Object

The biomaterial structure of the invention contained in the biomaterial-carrying object and its constituent element, the biomaterial and the compound for binding are as stated above.

As mentioned above, the biomaterial structure of the invention has the matrix skeleton comprising the biomaterial and the compound for binding, whereby the percentage of the biomaterial can be increased. For this reason, the biomaterial-carrying object of the invention also can immobilize a larger amount of the biomaterial than the conventional ones. That is, the biomaterial can be immobilized in a high concentration to the solid-state carrier (an amount per unit surface of the solid-state carrier; surface concentration). According to the conventional polymer film, the principal chain is formed from a polymer chain which is previously formed on the solid-state carrier, and the biomaterial binds to the principal chain in the sate of a branch (graft). Consequently, according to the conventional technique, the amount of the biomaterial immobilized is limited at a pre-determined upper limit, and a large amount of the biomaterial cannot be immobilized.

Although the thickness of the biomaterial structure (film thickness) is arbitrary, it is usually 5 nm or more, preferably 10 nm or more, more preferably 15 nm or more, still more preferably 20 nm or more in the dry biomaterial structure. Although the upper limit is not limited, it is usually 10 cm or less. When the film thickness is too thin, the biomaterial structure may easily peel off, and it is difficult to obtain a uniform film thickness of the biomaterial structure. Furthermore, there is a case where it is difficult to immobilize the biomaterial with higher reproducibility, and the film may not be formed sufficiently. The film thickness can be measured by using SEM, TEM, AFM, and the like.

II-2. Solid-State Carrier Contained in Biomaterial-Carrying Object

The solid-state carrier is a basal plate having the biomaterial structure of the invention formed on its surface, and the biomaterial-carrying object of the invention is the biomaterial structure formed on the surface of the solid-state carrier. The solid-state carrier used in the invention is not limited, and any materials, shapes and sizes can be used, so long as they are targets to form the biomaterial structure of the invention.

Examples of the material of the solid-state carrier include various resin materials such as polyolefin, polystyrene, polyethylene, polycarbonate, polyamide, and acrylic resins; inorganic materials such as glass, alumina, carbon, and metals, and the like. The materials of the solid-state carrier may be used alone or as a mixture thereof in any ratio.

Examples of the shape of the solid-state carrier include a plate, particle, fiber, film, sheet, and the like. Specifically, chips (basal plate) in which a number of biomaterials can be arranged; beads used as a chromatography carrier or a latex diagnostic agent; hollow fiber and porous film utilized as a separation film can be listed. When a chip having a channel, as used in the third and fourth embodiments, is used as the solid-state carrier, the shape and the size of the channel can be variously changed according to the use. When the biomaterial structure is only filled and held in the channel 14B, in order to prevent the biomaterial structure from outflowing from the channel 14B, it is preferable to provide means for preventing the outflow such as a filter at the channel 14B, though it is not necessary in the case where the biomaterial structure is immobilized on the basal plate, and the like.

Further, the solid-state carrier may be used as it is, or after subjecting its surface to surface treatment, the biomaterial structure may be formed on the treated surface. For example, after the surface is coated with a coating material such as metals and metal oxides, the biomaterial structure may be formed on the surface.

Examples of the solid-state carrier, which may be subjected to such a coating treatment, include metal-coated chips, glass slides, fiber slides, sheets, pins, microtiter plates, capillary tubes, beads, and the like.

In order to bind the solid-state carrier to the biomaterial structure, for example, functional groups may be introduced into the solid-state carrier by surface treatment. Any functional groups can be used, and examples thereof include groups which bind the solid-state carrier to the biomaterial structure by chemical binding, such as hydroxyl group, carboxyl group, thiol group, aldehyde group, hydrazide group, carbonyl group, epoxy group, vinyl group, amino group, and succinimide group.

When the water is used as a medium such as a solvent or a dispersion medium in the production of the biomaterial-carrying object, functional groups which bind the solid-state carrier to the biomaterial structure by physical adsorption due to hydrophobic interaction, such as alkyl groups and phenyl group, can be used.

The functional groups introduced may be used alone, or as a mixture thereof in any ratio.

In case where the surface of the solid-state carrier is coated with gold, examples of the surface treatment include, for example, a treatment in which the following compound is immobilized on the surface of the gold:

[Chemical formula]

wherein each of $n_1$ and $n_2$ is independently an integer of 2 or more.

II-3. Production of Biomaterial-Carrying Object

The production method of the biomaterial-carrying object of the invention is arbitrary. For example, the biomaterial structure is previously prepared, and it may be bound to the solid-state carrier, but usually, the biomaterial-carrying object of the invention is produced by supplying a mixture containing the biomaterial and the compound for binding to the solid-state carrier in the presence of a medium (usually, a solvent), and in this step, the biomaterial structure having a principal chain comprising the biomaterial and the compound for binding is formed on the surface of the solid-state carrier. Now, this method will be described in detailed.

II-3-1. Biomaterial, Compound for Binding, and Other Components Used in Production of Biomaterial-Carrying Object The biomaterial and the compound for binding are the same as in the description of the production of the biomaterial structure. In the production of the biomaterial-carrying object of the invention, additives may be suitably used in addition to the biomaterial and the compound for binding.

II-3-2. Medium Used in Production of Biomaterial-Carrying Object

The medium used in production of the biomaterial-carrying object of the invention is the same medium used in the production of the biomaterial structure. It is preferable, accordingly, to select the medium in consideration of the activity and structure stability of the biomaterial and the compound for binding.

As in the production of the biomaterial structure, in the production of the biomaterial-carrying object of the invention, water is also used usually as the medium. Here, the fact that water can be used as the medium, that is, a mixture in which the biomaterial and the compound for binding are contained in water is supplied to the solid-state carrier to produce the biomaterial-carrying object is one advantage of the advantages of the invention. That is, according to the conventional technique, the biomaterial is immobilized in an organic solvent (see Patent Document 5), but the immobilization cannot be performed using water as the medium (solvent). According to the present invention, the immobilization can be performed in the presence of water. As a result, it is possible to maintain the activity of the biomaterial, as well as the range of choice of the biomaterial and the compound for binding can be expanded, and therefore, the expansion of the application range can be expected.

II-3-3. Mixture Used in Production of Biomaterial-Carrying Object

The mixture used in the preparation of the biomaterial-carrying object is a mixture in which at least the biomaterial and the compound for binding are contained in the presence of the medium. This mixture is the same mixture as prepared in production of the biomaterial structure.

II-3-4. Supply of Mixture to Solid-State Carrier

When the biomaterial-carrying object of the invention is produced, the above-mentioned mixture is supplied to the solid-state carrier. That is, the above-mentioned mixture is contacted with the solid-state carrier. Any concrete operations may be used. For example, the mixture is previously prepared and the mixture may be contacted with the solid-state carrier, or each component of the mixture is prepared separately and mixture may be prepared in the presence of the solid-state carrier to contact the mixture with the solid-state carrier. Specifically, for example, a solution (an aqueous solution or the like) containing the biomaterial and a solution (an aqueous solution or the like) containing the compound for binding are supplied to the solid-state carrier separately, and then the two solutions are stirred in the presence of the solid-state carrier. Alternatively, when the mixture is previously prepared, the above-mentioned conjugates (including the particulate lumps which is one form of the conjugate) or the biomaterial structure may be produced in the mixture before supply, and then the mixture may be supplied to the solid-state carrier.

II-3-5. Formation of Biomaterial Structure on Solid-State Carrier Surface

Next, the biomaterial structure having the principal chain comprising the biomaterial and the compound for binding is formed on the surface of the solid-state carrier. Since the mixture contains the conjugates (including the particulate lumps which is one form of the conjugate) or the biomaterial structure, as mentioned above, the mixture is contacted with the solid-state carrier, for example, and the conjugates (including the particulate lumps which is one form of the conjugate) or the biomaterial structures in the mixture are integrated on the surface of the solid-state carrier; the biomaterial structures produced by binding the conjugates (including the particulate lumps which is one form of the conjugate) to each other in the medium are bound to the solid-state carrier; or the biomaterial and the compound for binding in the mixture are bound to the surface of the solid-state carrier, whereby the biomaterial structure can be formed on the surface of the solid-state carrier.

The concentration step and drying step may be suitably performed, as in the production of the biomaterial structure.

Further, any condition can be used when the biomaterial structure is bound to the solid-state carrier. For avoiding the denaturation of the biomaterial and the like, the temperature is usually 25° C. or lower, preferably 10° C. or lower.

When the mixture is dried or concentrated after it is immobilized to the solid-state carrier, any pressure conditions can be used. Usually, the pressure is preferably normal pressure or less.

Further, when the biomaterial structure is immobilized to the solid-state carrier, it is desirable that the solid-state carrier is allowed to stand for a pre-determined period of time after supplying the mixture. Although the period of time is arbitrary, it is usually 24 hours or shorter, preferably 12 hours or shorter.

II-3-6. Other Steps in Production of Biomaterial-Carrying Object

As mentioned above, according to the above-mentioned method, the biomaterial structure can be formed on the surface of the solid-state carrier by only contacting the mixture containing the biomaterial and the compound for binding in the medium (usually the solvent) with the solid-state carrier, whereby the biomaterial-carrying object of the invention can be produced or, in other words, the biomaterial can be immobilized on the solid-state carrier. That is, the method is a very easy method.

The biomaterial-carrying object of the invention may be produced with steps other than the above-mentioned steps.

For example, a different biomaterial may be bound to the biomaterial in the biomaterial structure. If this technique is utilized, after the production of the biomaterial-carrying object, a different biomaterial which is modified so that it specifically binds to the biomaterial in the biomaterial structure is bound later, and, as a result, the different biomaterial can be immobilized on the solid-state carrier in a high density. Specifically, avidin is used as the biomaterial, and this avidin and the compound for binding are bound to form the biomaterial structure, thereby producing the biomaterial-carrying object. After that, a different biomaterial which is modified with biotin can be immobilized by avidin-biotin interaction. Similarly, the biomaterial can be immobilized through a histidine tag or a glutathione-S-transferase.

II-4. Comparison with Prior Art

The biomaterial can be immobilized in a larger amount than that in the conventional technique by using the biomaterial-carrying object of the invention. For example, according to the prior art described in Patent Documents 4 to 6, the biomaterial is bound to a polymer film formed on the surface of the solid-state carrier. In this case, however, the biomaterial is bound to the solid-state carrier in such a manner that the biomaterial is bound to the polymer chain terminal of the principal chain of the polymer chain, or bound to the polymer chain in the state of a graft, and therefore, it is necessary to form the polymer chain as the principal chain and it is necessary to use the polymers in a certain amount with respect to the biomaterial to be immobilized, which limits the amount of the biomaterial immobilized.

On the contrary, according to the present invention, the biomaterial structure having a biomaterial structure skeleton (corresponding to the above-mentioned principal chain) comprising the biomaterial and a polymer (corresponding to the compound for binding) is formed, and the biomaterial can be immobilized on the solid-state carrier, utilizing the biomaterial structure, whereby the percentage of the biomaterial in the biomaterial structure can be increased (in other words, the percentage of the compound for binding can be decreased). As a result, when the biomaterial is immobilized, there is no limitation as caused in the conventional technique, and it is possible to immobilize the biomaterial on the surface of the solid-state carrier in a larger amount, or in a higher density than that in the conventional technique.

One of the advantages of the biomaterial-carrying object of the invention is that the production is easy. According to the conventional methods, many labors are required to immobilize the biomaterial in high densities. Specifically, in the conventional methods, a polymer film is previously formed on the solid-state carrier, the biomaterial is immobilized on the polymer film, and the biomaterial structure containing a ligand is formed on the solid-state carrier. According to the methods, however, when the polymer is formed on the solid phase, it is necessary to suitably control the molecular weight of the polymer and the introduction density to the solid-state carrier, which are very troublesome, and it is difficult to perform the immobilization with high reproducibilities. In particular, according to the method described in Patent Document 6, it is technically difficult to form a polymer chain in the state of a brush from the surface of the solid-state carrier, which is not suitable for mass production.

On the contrary, the biomaterial-carrying object of the invention can be very easily produced by only contacting the mixture containing the biomaterial and the compound for binding in the medium (usually, the solvent) with the solid-state carrier to form the biomaterial structure, in other words, to immobilize the biomaterial, on the solid-state carrier. Further, since the solvents used in the production of the biomaterial-carrying object are not limited to organic solvents, and the biomaterials which can be used are not limited to the solvents, as the technique described in Patent Document 5, it is possible to expand the range of choice of the biomaterial to be immobilized.

Further, the biomaterial structure which is formed into the biomaterial-carrying object of the invention can immobilize the biomaterial almost uniformly and three-dimensionally on the solid-state carrier. Consequently, the biomaterial structure can give optimal reaction sites for the interaction between the biomaterial and the interacting substance which specifically interact with the biomaterial, whereby, for example, when the biomaterial-carrying object of the invention is used in a sensor which utilizes the interaction, the detection sensitivity of the sensor can be increased.

The present inventors assume the reason why the optimal reaction sites as follows: That is, according to the conventional method in which the biomaterial is immobilized on the solid-state carrier whose surface is treated with the polymer film, the biomaterial is placed on the surface of the film, and there are no voids through which the interacting substance can enter into the inside of the polymer film. Further, according to the conventional technique in which the principal chain is formed from only the hydrophilic polymer, it can be considered that the access of the interacting substance to the biomaterial is prevented by the excluded volume effect of the hydrophilic polymer chain and the movement of the polymer chain (see Real Time Analysis Experimental Method for Biomaterial Interaction—focused on BIA CORE, edited by Kazuhiro Nagata, and Hiroshi Handa, published by Springer-Verlag Tokyo Kabushiki Kaisha, page 258; Development and Application of Polymer Material for Pharmaceutical polymer, CMC, page 19). In the biomaterial structure formed in the biomaterial-carrying object of the invention, however, the biomaterial can be immobilized almost uniformly and three-dimensionally on the solid-state carrier. Further, it can be considered that the structure of the biomaterial structure has spaces in which interacting substances can sufficiently react within the polymer film by using the technique of the present invention, whereby the optimal reaction sites can be obtained.

The biomaterial structure formed in the biomaterial-carrying object of the invention can arbitrarily control the film thickness. According to the conventional technique, it is difficult to arbitrarily control the film thickness of the biomaterial structure from submicron to several microns. According to the present invention, however, it is possible to control the film thickness of the biomaterial structure at the precise level, and therefore, the degree of freedom of the design of the biomaterial structure can be increased.

For example, when the interaction observation by SPR is performed, it is considered that a thickness of a film which is used for immobilizing an observation target is optimally from about 200 nm to 300 nm. Alternatively, for example, when medical instruments and carriers for regenerative medicine are surface-treated, the film thickness is required to be an order of micron for film used in the surface-treatment, in order to realize sufficient strength and coating film. Further, for example, when the surface-treatment of drugs used in DDS (drug delivery system) is performed, it is required to arbitrarily control the thickness of the film used for the surface-treatment, for controlling the drug release. As mentioned above, when the immobilization of the biomaterial is performed utilizing some film, the control of the film thickness is one of the important points, and the control is difficult in the conventional technique. According to the present invention, however, the film thickness can be arbitrarily controlled by controlling a concentration and an amount of the mixture and reaction conditions (temperatures, times and the like), according to the use.

Further, when the biomaterial-carrying object of the invention is used in order to interact the biomaterial with the interacting substance, the non-specific interaction caused by the biomaterial structure constituent elements other than the biomaterial can be inhibited. That is, the percentage of the biomaterial in the biomaterial structure is increased, whereby the percentage of the substances other than the biomaterial, which cause the non-specific interaction, can be decreased.

When an electrically uncharged substance is used as the compound for binding, the non-specific interaction caused by charge can be further reduced. That is, for example, in the method described in Patent Document 4, since a polymer film is electrically charged, the pH and the ionic strength of a buffer solution used exert great influence to the reaction of the biomaterial, and the electrically charged protein cannot avoid the non-specific adsorption caused by electrostatic interaction (see Nanotechnology Basic Series, Bionanotechnology, edited by Yasuhiro Horiike and Kazunori Kataoka, page 186). However, if the electrically uncharged substance is used as the compound for binding, then the above-mentioned trouble does not occur, and a specific interaction can be caused selectively.

II-5. Biomaterial-Immobilization Kit

In order to produce the above-mentioned biomaterial-carrying object, a product used for immobilizing the biomaterial on the solid-state carrier, namely a biomaterial-immobilization kit in which the above-mentioned compound for binding, and the medium such as the solvent or dispersion medium, which can mix the biomaterial and the compound for binding are contained, may be used. That is, in order to produce the biomaterial-carrying object, the biomaterial-immobilization kit comprising the compound for binding, and the medium capable of mixing the biomaterial and the compound for binding may be prepared. When the biomaterial-immobilization kit is used, the biomaterial-carrying object can be easily produced, or the above-mentioned biomaterial structure can be easily formed on the solid-state carrier, and therefore, a large amount of the biomaterial can be easily immobilized on the solid-state carrier.

The compounds for binding contained in the biomaterial-immobilization kit are as stated above. The compound for binding can be contained in the biomaterial-immobilization kit in any state. For example, the compounds may be in any state such as a solution in which it is dissolved in any solvent, a dispersion in which it is dispersed in any dispersion medium, a solid such as powder or lump.

The media contained in the biomaterial-immobilization kit are the same media used in the production of the biomaterial-carrying object. Further, the medium in the biomaterial-immobilization kit may be contained in a container different from that for the compound for binding, or may be contained in a container together with the compound for binding as the solvent or the dispersion medium for the compound for binding.

Further, the biomaterial-immobilization kit may contain other elements as necessary.

For example, it may contain a reagent which facilitates the production of the biomaterial structure. Specifically, when polyacrylic acid is used as the compound for binding, 1-ethyl-3-(3-dimethylaminopropyl) carbodiimidehydrochloride (abbreviation: EDC) may be contained as a drug, in order to activate carboxyl group in the polyacrylic acid.

II-6. Use of Biomaterial-Carrying Object

The biomaterial-carrying object of the invention can be used in a wide range of industrial fields. The uses are not limited, and it can be used in any use. Usually, it is suitably used in a use utilizing an "interaction" between the biomaterial and the interacting substance which specifically interacts with the biomaterial.

For example, the biomaterial-carrying object of the invention can be suitably used as a biosensor which detects an interacting substance which interacts with the biomaterial. The above-mentioned biosensor analyzes the interaction for example using a sensor chip immobilized with DNA or a protein, which is referred to as a DNA array or DNA chip, or a protein array or protein chip. The biomaterial-carrying object of the invention can be applied to the sensor chip. That is, when the biomaterial is immobilized on the sensor chip, the biomaterial structure is formed on the sensor chip body by the above-mentioned method, and the sensor chip can be used as the biomaterial-carrying object of the invention.

Examples of the biosensor to which the biomaterial-carrying object of the invention can be applied, include fluorescence method, chemiluminescence method, RI method, SPR (surface plasmon resonance) method, QCM (quartz crystal microbalance) method, piezo type canti-lever method, laser type canti-lever method, mass spectroscopy, a sensor by electrochemical method, electrode method, field effect transistor (FET) method, FET and/or single electron transistor method using a carbon nanotubes, and the like. Of these, the detections by the SPR method and the QCM method are suitably used, because a label-free sample can be easily analyzed by these methods.

As to the SPR method, since surface plasmon waves are induced, it is preferable that the surface of the sensor chip is coated with a metal. Any metal can be used so long as it can induce the surface plasmon wave, and examples thereof include gold, silver, copper, aluminum, and alloys thereof, and the like. Of these, silver is preferable in terms of the sensitivity and inexpensive cost, and gold is also preferable in terms of stability. A metal layer is formed by deposition, sputtering, plating or other coating methods. The thickness of the metal is usually about 20 nm or more, preferably about 30 nm or more, and usually about 300 nm or less, preferably about 160 nm or less.

When the biomaterial-carrying object of the present invention is applied to the SPR method or the QCM method, in order to firmly bind the biomaterial structure to the sensor chip body, it is preferable that the sensor chip body has functional groups on its surface. In this case, any functional groups can be used, and examples thereof include hydroxyl group, carboxyl group, thiol group, aldehyde group, hydrazide group, carbonyl group, epoxy group, vinyl group, amino group, succinimide group, and the like.

Further, the biomaterial-carrying object of the invention can be applied to surface treatment of drugs for DDS (drug delivery system), surface treatment of carriers for regenerative medicine, surface treatment of artificial organs, surface treatment of catheters, and the like.

II-7. Biomaterial-Carrying Object which May not have Particulate Lumps

In the biomaterial-carrying object, the biomaterial structure immobilized on the solid-state carrier can be used as the biomaterial structure (matrix), even it does not have the above-mentioned particulate lumps, so long as it has a principal chain comprising the biomaterial and the compound for binding. Now, such a biomaterial-carrying object will be described in detail. The biomaterial-carrying objects, which will be explained below, have the same structure as the biomaterial structure except that the biomaterial structure may not have the particulate lumps. Thus, in the following explanation, the substantially same structures will appear, but such structures will be explained again.

The biomaterial-carrying object (the solid-state carrier on which the biomaterial is immobilized) has a matrix (a biomaterial structure; hereinafter, sometimes, referred to as "matrix of the invention") on the surface of the solid-state carrier. Here, the matrix of the invention is a matrix having a principal chain comprising the biomaterial and the compound for binding capable of binding to the biomaterial (compound for immobilization). The biomaterial structure explained in [I. Biomaterial structure] is one form of the matrix of the invention here. The biomaterial structure in this column is different from the biomaterial structure of the invention described in [I. Biomaterial structure], and the matrix of the invention contained in the biomaterial-carrying object described in this column may not have the particulate lumps. That is, the matrix of the invention contains the biomaterial and the compound for binding, as schematically shown in FIG. 3(a) to FIG. 3(c), and its skeleton is a matrix structure having a structure in which the biomaterial and the compound for binding are bound to form the chain and/or reticular structure. FIG. 3(a) to FIG. 3(c) are schematic views showing the enlarged surface vicinity of one example of the biomaterial-carrying object of the invention, for explaining the structure of the matrix of the invention. In FIG. 3(a) to FIG. 3(c), circular parts show the biomaterials and linear parts show the compounds for immobilization. In order to explain the structure of the principal chain comprising the biomaterial and the compound for binding, however, in FIG. 3(a) to FIG. 3(c), the structure of the principal chain is described in two dimensions regardless of whether they form the particulate lumps or not.

II-7-1. Solid-State Carrier

The solid-state carrier contained in the biomaterial-carrying object having the matrix of the invention is substantially the same as the solid-state carrier described in [II-2. Solid-state carrier contained in biomaterial-carrying object]. That is, the solid-state carrier is a basal plate for forming the matrix of the invention on its surface, and the matrix of the invention formed on the surface of the solid-state carrier is the biomaterial-carrying object of the invention. The solid-state carrier used in the present invention is not limited, and any material, shape and size can be used, so long as it is a target to form the matrix of the invention.

Examples of the material of the solid-state carrier include various resin materials such as polyolefin, polystyrene, polyethylene, polycarbonate, polyamide, and acrylic resins; inorganic materials such as glass, alumina, carbon, and metals, and the like. The materials of the solid-state carrier may be used alone or as a mixture thereof in any ratio.

Examples of the shape of the solid-state carrier include a plate, particle, fiber, film, sheet, and the like. Specifically, chips (basal plate) in which a number of biomaterials can be arranged; beads used as a chromatography carrier or a latex diagnostic agent; hollow fiber and porous film utilized as a separation film can be listed.

Further, the solid-state carrier may be used as it is, and after subjecting its surface to surface treatment, the matrix may be formed on the treated surface. For example, after the surface is coated with a coating material such as metals and metal oxides, the matrix may be formed on the surface. Further, in order to bind the solid-state carrier to the matrix, functional groups may be introduced into the solid-state carrier. Any functional groups can be used, and examples thereof include functional groups which bind the solid-state carrier to the matrix by chemical binding, such as hydroxyl group, carboxyl group, thiol group, aldehyde group, hydrazide group, carbonyl group, epoxy group, vinyl group, amino group, and succinimide group. When the water is used as a solvent in the production of the biomaterial molecule substance solid-state carrier, functional groups which bind the solid-state carrier to the biomaterial structure by physical adsorption due to hydrophobic interaction, such as alkyl groups and phenyl group can be used.

In case where the surface of the solid-state carrier is coated with gold, examples of the surface treatment include, for example, a treatment in which the following compounds are immobilized on the surface of the gold:

[Chemical formula]

wherein each of $n_1$ and $n_2$ is independently integers of 2 or more.

Examples of the solid-state carrier, which may be subjected to the coating treatment, include chips coated with a metal, glass slides, fiber slides, sheets, pins, microtiter plates, capillary tubes, beads, and the like.

II-7-2. Biomaterial

The biomaterial contained in the biomaterial-carrying object containing the matrix of the invention is substantially the same as the biomaterial described in [I-1. Biomaterial]. That is, the biomaterial is a substance which is immobilized on the solid-state carrier, and any substance can be used according to the object. Examples thereof include enzymes, antibodies, lectins, receptors, protein A, protein G, protein A/G, avidin, streptavidin, neutravidin, glutathione-S-transferase, proteins such as glycoprotein, peptides, amino acids, hormones, nucleic acids, saccharides, oligosaccharides, polysaccharides, sialic acids and their derivatives, sugar chains such as sialylated sugar chains, lipids, low molecular compounds, polymer organic substances other than the above-mentioned polymers, inorganic substances, fusions thereof, viruses, biological molecules such as molecules constituting a cell, and the like. In addition, substances other than the biological molecule such as the cell can be used as the biomaterial. In case where the biomaterial-carrying object of the invention is used in an analysis, these biomaterials act as a mark material, when the interaction (binding property and the like) between a detection target material and the biomaterial in the sample is measured.

The above-mentioned detection target material is usually an interacting substance which specifically interacts with the biomaterial. Here, "interaction" between the biomaterial and the interacting substance is not particularly limited, but usually refers to an action due to a force between substances caused from at least one of covalent binding, ionic binding, chelate binding, coordinate bond, hydrophobic binding, hydrogen binding, van der Waals binding and binding by electrostatic force. However, the "interaction" used herein should be most broadly understood, and it must not be understood limitatively in any meanings. The covalent binding includes coordinate bond. The binding by electrostatic force includes electrical repulsive as well as electrostatic binding. Further, the interaction includes binding reaction, synthesis reaction and decomposition reaction which are caused by the above-mentioned actions.

Examples of the interaction include, but are not limited to, binding and dissociation between an antigen and an antibody, binding and dissociation between a protein receptor and a ligand, binding and dissociation between an adhesive molecule and a counter-molecule, binding and dissociation between an enzyme and a substrate, binding and dissociation between an apoenzyme and a coenzyme, binding and dissociation between a nucleic acid and a nucleic acid or protein reacting therewith, binding and dissociation between proteins in a signal transduction system, binding and dissociation between a glycoprotein and a protein, binding and dissociation between a sugar chain and a protein, and the like. Further, for example, immunoglobulin and its derivatives such as $F(ab')_2$, Fab', and Fab, receptors or enzymes and their derivatives, nucleic acid, natural or artificial peptides, synthetic polymers, saccharide, lipid, inorganic substances or organic ligand, virus, cells, and drugs are also included.

Examples of the protein among the above-mentioned biomaterials may include the entire length of the protein, partial peptides including a binding active moiety. Also, examples thereof include amino-acid sequence, and protein whose function is known or unknown. Further, synthesized peptide chains, proteins obtained by purification of a living body, or proteins obtained by translation from, e.g., a cDNA library with a suitable translation system and purification of it can also be used as the mark material. The synthesized peptide chain may be glycoprotein to which a sugar chain is bound. Preferable proteins are purified proteins.

Further, the nucleic acid is not particularly limited, and nucleic acid bases such as aptamer, and peptide nucleic acids such as PNA, as well as DNA and RNA can be used. Also, nucleic acids whose base sequence or function is either known or unknown may be used. Of these, nucleic acids capable of binding a protein, whose functions and base sequence as the nucleic acid are known, and nucleic acids obtained by cutting and separating from a genome library and the like using a restriction enzyme can be preferably used.

As the sugar chain, sugar chains whose saccharide sequence or function is either known or unknown may be used. Preferably, the sugar chains whose saccharide sequence or function is known by separation analysis are used.

Further, the low molecular compounds are not particularly limited so long as they have an ability of interacting. Both low molecular compounds whose functions are unknown and compounds whose ability of binding to a protein is known can be used. Pharmaceutical candidate compounds are suitably used.

The biomaterials may be used alone, or as a mixture thereof in any ratio.

II-7-3. Compound for Binding

The compound for binding contained in the biomaterial-carrying object having the matrix of the invention is substantially the same as the compound for binding described in [I-2. Compound for binding (compound for immobilizing)]. That is, as the compound for binding, any compounds can be used so long as they can bind with the above-mentioned biomaterial. As the compound for binding, accordingly, compounds having a functional group capable of binding to the biomaterial (namely, "binding functional group") can be arbitrarily used. Here, as the binding functional group, any functional groups can be used without any limitation so long as they can bind to the above-mentioned biomaterial. Usually, a suitable functional group is preferably selected depending on the kind of the biomaterial and the use of biomaterial-carrying object of the invention. The binding functional group may be used alone or as a mixture thereof in any ratio.

In order to form the above-mentioned principal chain by the matrix contained in the biomaterial-carrying object of the invention, it is preferable that there is no binding between the compounds for binding, and the binding between the biomaterial and the compound for binding is mainly formed. If there is the binding between the compounds for binding, then aggregated lumps composed of the compounds for binding are formed, and therefore the biomaterials cannot efficiency be bound, and further, desirable reaction efficiency may not be obtained when the sample is reacted with the biomaterial-carrying object of the invention.

When a polymer is used as the compound for binding in the presence of the binding between the compounds for binding, internal cross-linking occurs in the compound for binding, and further, it is difficult to immobilize the biomaterial. Here, binding between compounds for binding exclude intermolecular attraction, hydrophobic interaction, and electric interaction.

In order to form a matrix with no compounds for binding which bind to each other, it is desirable that a binding functional group which does not bind to each other is selected, and conditions where the compounds for binding bind to each other are excluded. Examples of the functional group include, as mentioned below, succinimide group, epoxy group, aldehyde group, maleimide group, boronic acid group, biotin group, and the like. The conditions where the functional groups for binding bind to each other are, for example, a condition where excessive heat is applied, and a condition where strong ultra violet rays are irradiated.

For examining the binding between the compounds for binding in the matrix, it can be determined by the formation of an insoluble matter when the biomaterial in the matrix is decomposed in a method mentioned below, or the remaining agglomeration lumps of the compound for binding in the solid-state carrier such as a basal plate. Alternatively, it can be determined by analyzing the matrix with heat decomposal gas chromatography and detecting a compound suggesting the binding between the compounds for binding. For example, a compound suggesting a urethane binding can be listed as such a compound.

Further, in order to maintain the activity of the biomaterial, it is preferable to select functional groups of the biomaterial and the compound for binding, mentioned below. For example, when the protein has thiol group in its active moiety in immobilization of the protein, groups other than the thiol group such as amino group is selected as the binding functional group of the biomaterial, and succinimide group or epoxy group is selected as the binding functional group of the compound for binding, in order to bind to the amino group.

The binding functional groups are usually classified into two groups, that is, groups binding to a biomaterial through covalent binding as a reactive group, and groups binding to a biomaterial through non-covalent binding. When binding through the covalent binding, the binding functional group includes succinimide group, epoxy group, aldehyde group, maleimide group, and the like.

Now, the binding with the biomaterial will be specifically described. Examples of the biomaterial binding to the binding functional group include, for example, protein, nucleic acid, saccharide, and the like.

When the biomaterial is a protein, amino group, hydroxyl group, or thiol group on the surface layer of the protein binds to the binding functional group of the compound for binding. In such a case, when the amino group binds to the binding functional group, examples of the binding functional group include succinimide group, epoxy group, aldehyde group, and the like. Also, when the hydroxyl group binds to the binding functional group, examples of the binding functional group include epoxy group, and the like. Further, when the thiol group binds to the binding functional group, examples of the binding functional group include maleimide group, and the like.

When the biomaterial is nucleic acid, amino group, hydroxyl group, or thiol group, which is introduced into the terminal of the nucleic acid, binds to a binding functional group of the compound for binding. In such a case, when the amino group binds to the binding functional group, examples of the binding functional group include succinimide group, epoxy group, aldehyde group, and the like. When the hydroxyl group binds to the binding functional group, examples of the binding functional group include epoxy group, and the like. When the thiol group binds to the binding functional group, examples of the binding functional group include maleimide group, and the like.

Further, when the biomaterial is saccharide, amino group, hydroxyl group, or thiol group on a side chain of the saccharide binds to a binding functional group of the compound for binding. In such a case, when the amino group binds to the binding functional group, examples of the binding functional group include succinimide group, epoxy group, aldehyde group, and the like. When the hydroxyl group binds to the binding functional group, examples of the binding functional group include epoxy group, and the like. When the thiol group binds to the binding functional group, examples of the binding functional group include maleimide group, and the like.

On the other hand, when the biomaterial binds to the compound for binding through non-covalent binding such as coordination compound formation, examples of the binding functional group include boronic acid group, and the like. For example, when binding is caused by interaction between the biomaterials, avidin-biotin interaction can be utilized, and examples of the binding functional group used in this interaction include biotin group, and the like. For example, when virus is bound as the biomaterial, examples of the binding functional group include saccharide and polysaccharide. When the biomaterial has a hydrophobic region, binding may be caused by physical adsorption due to hydrophobic interaction.

[Chemical formula]

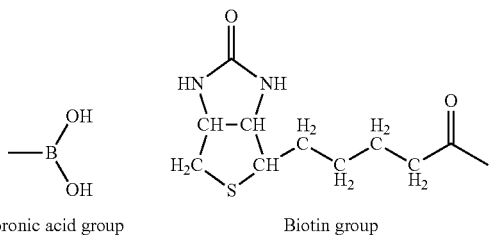

Boronic acid group          Biotin group

When the compound for binding has the binding functional group, it is preferable that the compound for binding comprises at least one compound having usually two or more, preferably three or more binding functional groups in one molecule, for easier formation of the structure of the matrix of the invention. Specifically, if the compound has two or more binding functional groups in one molecule, then the matrix can be easily formed when concentration or the like is performed.

In general, it is desirable to use compounds which can be mixed with water as the compound for binding. Although any solvents may be used in the preparation of the matrix, water is usually used as the solvent. When the compound for binding is mixed with the biomaterial in the presence of water, then the compound for binding binds to the biomaterial. In this case, if the above-mentioned compound is used, the biomaterial and the compound for binding are uniformly mixed and the binding reaction proceeds smoothly. The state of mixing used in the present description may include solutions and dispersions.

The compounds for binding which can be mixed with at least one organic solvent are preferable. Such compounds can expand the range of choice of solvent used in synthesis of the compound for binding, and a variety of the structures of the biomaterial structure can be designed. For example, if the compound for binding can be mixed with an organic solvent, then the synthesis can be carried out in the organic solvent, in order to protect the binding functional group in synthesis of the compound for binding.

Further, if the compounds for binding can be mixed with both of water and an organic solvent, then the number of the kinds of the solvent, which can be used in the application of the biomaterial-carrying object of the invention, can be increased, thus resulting in expansion of its application.

Further, compounds for binding which are electrically uncharged are preferable. When the compound for binding has the same charge as the biomaterial (the same sign in charge), the binding between the compound for binding and the biomaterial may be interrupted due to the electrostatic repulsive power. On the other hand, when the compound for binding has an opposite charge to that of the biomaterial (opposite sign in charge), the biomaterial and the electrically charged moiety in the compound for binding are bound due to the electrostatic attraction, and the effective binding of the binding functional group in the compound for binding to the biomaterial can be interrupted. The binding between the compound for binding and the biomaterial due to the electrostatic attraction is not preferable, because when the biomaterial-carrying object of the invention is used, the binding can be easily broken by pH of a solution used in the application and additives. When an analyte, or an interacting substance, has the same charge as the compound for binding in detection of the selective interaction between the biomaterials using the biomaterial-carrying object of the present invention, a specific interaction with a ligand, or the biomaterial, may be interrupted; and when the analyte has an opposite charge to that of the compound for binding, a non-specific interaction such as non-specific adsorption can be caused between the analyte and the compound for binding.

If the compound for binding has, at least, a nonionic structure formula, such a compound is an electrically uncharged compound for binding. However, even if the above-mentioned compound for binding is electrically charged by hydrolysis of the binding functional group, and the like, during the preparation procedure of the biomaterial complex of the invention, such a compound for binding can be preferably used so long as the effects of the invention are not impaired.

Examples of the compound for binding include, for example, organic compounds, inorganic compounds, organic-inorganic hybrid materials, and the like. The compounds for binding may be used alone or as a mixture thereof in any ratios.

Although the organic compounds used as the compound for binding may be low molecular compounds or polymer compounds, the polymer compounds are preferable. Examples of the low molecular compound used as the compound for binding include glutaraldehyde, diepoxybutane, diepoxyhexane, diepoxyoctane, bismaleimide hexane, bis(sulfosuccinimidyl) suberate, disuccinimidyl glutarate, ethylene glycolbis(succinimidyl) succinate, ethylene glycol bis (sulfosuccinimidyl) succinate, sulfosuccinimidyl 4-(N-maleimide methyl)cyclohexane-1-carboxylate, succinimidyl-4-N-maleimide methyl cyclohexane-1-carboxylate, sulfosuccinimidyl 4-(p-maleimide phenyl)-butyrate, succinimidyl 4-(p-maleimidephenyl)-butyrate, sulfo-m-maleimidebenzoyl-N-hydroxysuflosuccinimide ester, and the like.

On the other hand, when the polymer compounds are used as the compound for binding, they may be synthetic polymer compounds or natural polymer compounds.

When the synthetic polymer compounds are used as the compound for binding, any synthetic polymer compounds can be used so long as they satisfy the above-mentioned conditions. In general, however, compounds having a monomer capable of binding a biomaterial are desirable. Further, usually, in order to make the synthetic polymer compound capable of mixing with water, the compounds having a hydrophilic monomer are preferable. Furthermore, it is preferable to use synthetic polymer compounds which are obtained by copolymerizing the monomer capable of binding the biomaterial with the hydrophilic monomer. That is, in the synthesis of the synthetic polymer compounds, it is preferable to use, at least, a monomer having a binding functional group capable of forming conjugates by reacting with the biomaterial, the conjugates forming a structure in which they are bound to each other in the sate of a chain and/or reticular structure, and a monomer having a hydrophilic or amphipathic functional group, as monomer species, and to copolymerize them. In addition, for controlling a structure such as a micelle and its spread of the synthetic polymer compound formed in a solution, it is also preferable to copolymerize a hydrophobic monomer.

Examples of the monomer used in radical polymerization, among examples of the monomer constituting the synthetic polymer compound include polymerizable unsaturated aromatic compounds such as styrene, chlorostyrene, α-methyl styrene, divinyl benzene and vinyl toluene; polymerizable unsaturated carboxylic acids such as (meth)acrylic acid, itaconic acid, maleic acid, and phthalic acid; polymerizable unsaturated sulfonic acids such as styrene sulfonic acid, and styrene sulfonic acid sodium salt; polymerizable carboxylic acid esters such as methyl (meth)acrylate, ethyl (meth)acrylate, n-butyl (meth)acrylate, 2-hydroxyethyl (meth)acrylate, hydroxypropyl(meth)acrylate, glycidyl(meth)acrylate, N-(meth)acryloyloxysuccinimide, ethylene glycol di(meth) acrylic acid ester, tribromophenyl(meth)acrylate, glycosyloxyethyl(meth)acrylate, and 2-methacryloyloxyethylphosphorylcholine; unsaturated carboxylic acid amides such as (meth)acrylonitrile, (meth)acrolein, (meth)acrylamide, N,N-dimethylacrylamide, N-isopropyl(meth)acrylamide, N-vinyl formamide, 3-acrylamidephenyl boronic acid, N-acryloyl-N'-biotinyl-3,6-dioxaoctane-1,9-diamine, butadiene, isoprene, vinyl acetate, vinyl pyridine, N-vinylpyrrolidone, N-(meth)acryloylmorpholine, vinyl chloride, vinylidene chloride and vinyl bromide; polymerizable unsaturated nitriles; halogenated vinyl compounds; conjugated dienes; macromonomers such as polyethylene glycol mono(meth)acrylate and polypropylene glycol mono(meth)acrylate, and the like.

As the monomer of the synthetic polymer compound, monomers used in addition polymerization can be used. Examples of the monomer used in the addition polymerization include aliphatic or aromatic isocyanates, ketenes, epoxy group-containing compounds and vinyl group-containing compounds, such as diphenyl methane diisocyanate, naphthalene diisocyanate, tolylene diisocyanate, tetramethyl xylene diisocyanate, xylene diisocyanate, dicyclohexanediisocyanate, dicyclohexylmethane diisocyanate, hexamethylene diisocyanate, and isophorone diisocyanate. As a monomer which is reacted with the above-mentioned compounds, compounds having a functional group with active hydrogen, such as hydroxyl group or amino group, can be listed, and examples thereof include polyols such as ethylene glycol, diethylene glycol, propylene glycol, 1,4-butanediol, 1,6-hexanediol, glycerin, trimethylolpropane, pentaerythritol, sorbitol, methylene glycoside, saccharose, and bis(hydroxyethyl) benzene; polyamines such as ethylenediamine, hexamethylenediamine, N,N'-diisopropyl methylenediamine, N,N'-di-sec-butyl-p-phenylene diamine, and 1,3,5-triaminobenzene; and oximes, and the like.

Further, the synthetic polymer compound may be used together with a functional compound which will be a cross-lining agent, in addition to the above-mentioned monomers. Examples of the polyfunctional compound include, for example, N-methylolacrylamide, N-ethanol acrylamide, N-propanol acrylamide, N-methylol maleimide, N-ethylol maleimide, N-methylol maleic amide acid, N-methylol maleic amide acid ester, vinyl aromatic acids such as N-alkylolamide (for example, N-methylol-p-vinyl benzamide, and the like), N-(isobutoxymethyl)acrylamide, and the like. Of the above-mentioned monomers, polyfunctional monomers such as divinyl benzene, divinyl naphthalene, divinyl chlorohexane, 1,3-dipropenyl benzene, ethylene glycol di(meth) acrylate, diethylene glycol di(meth)acrylate, diethylene glycol di(meth)acrylate, butylene glycol, trimethylolethane tri (meth)acrylate, and pentaerythritol tetra(meth)acrylate can be used as a cross-linking agent.

Examples of the monomer having succinimide group, epoxy group, aldehyde group, maleimide group, or the like among the monomer having the binding functional group capable of binding the above-mentioned biomaterial include N-(meth)acryloyloxysuccinimide, (meth)acrylic acid glycidyl, acrolein, maleimide acrylate, and the like. Examples of the monomer having boronic acid group as the binding functional group include 3-acrylamide phenylboronic acid, and the like. Examples of the monomer having biotin group as the binding functional group include N-acryloyl-N'-biotinyl-3,6-dioxaoctane-1,9-diamine, and the like. Examples of the monomer having saccharide or polysaccharide as the binding functional group include glycosyloxyethyl 2-(meth)acrylate, and the like.

Further, examples of the hydrophilic monomer include (meth)acrylic acid, itaconic acid, 2-hydroxyethyl(meth)acrylate, 2-hydroxypropyl(meth)acrylate, maleic acid, sulfonic acid, sodium sulfonate, (meth)acrylamide, N,N-dimethyl (meth)acrylamide, N-isopropyl acrylamide, N-vinyl formamide, (meth)acrylonitrile, N-(meth)acryloylmorpholine, N-vinyl pyrrolidone, N-vinyl acetamide, N-vinyl-N-acetamide, polyethylene glycol mono(meth)acrylate, glycidyl (meth)acrylate, 2-methacryloxyethyl phosphoryl choline, and the like.

As the compound for binding, as mentioned above, electrically uncharged compounds are preferable. When monomers used for forming the synthetic polymer compounds, which are used as the compound for binding, are electrically uncharged, the obtained synthetic polymer compounds are also electrically uncharged, and accordingly such electrically uncharged monomers can be used without particular limitations. Examples thereof include 2-hydroxyethyl (meth)acrylate, 2-hydroxypropyl(meth)acrylate, (meth)acrylamide, N,N-dimethyl(meth)acrylamide, N-isopropyl acrylamide, N-vinyl formamide, (meth)acrylonitrile, N-(meth)acryloylmorpholine, N-vinylpyrrolidone, N-vinyl acetamide, N-vinyl-N-acetamide, polyethylene glycol mono(meth)acrylate, glycidyl(meth)acrylate, and the like.

When the radical polymerization of the monomers is performed to synthesize the synthetic polymer compounds, radical polymerization is initiated by mixing the monomers with a radical polymerization initiator. Examples of the radical polymerization initiators used herein include azo(azobisnitrile) type initiators such as 2,2'-azobisisobutyronitrile, 2,2'-azobis(2-methylpropanenitrile), 2,2'-azobis(2,4-dimethylpentanenitrile), 2,2'-azobis(2-methylbutanenitrile), 1,1'-azobis(cyclohexanecarbonitrile), 2,2'-azobis(2,4-dimethyl-4-methoxyvaleronitrile), 2,2'-azobis(2,4-dimethylvaleronitrile), and 2,2'-azobis(2-amidinopropane) hydrochloride; peroxide type initiators such as benzoyl peroxide, cumene hydroperoxide, hydrogen peroxide, acetyl peroxide, lauroyl peroxide, persulfates (for example, ammonium persulfate), and peracid esters (for example, t-butylperoctate, α-cumylperoxy pivalate, and t-butyl peroctate), and the like.

Further, the polymerization may be initiated by mixing the monomer with a redox initiator. Examples thereof include ascorbic acid/iron sulfate (II)/sodium peroxydisulfate, tert-butylhydroperoxide/sodium disulfite, tort-butylhydroperoxide/Na hydroxymethanesulfinic acid, and the like. Individual components such as reduction components may be mixtures such as a mixture of sodium salt of hydroxymethanesulfinic acid, and sodium disulfite.

As the synthetic polymer compound, polymer compounds which are synthesized by ring-opening polymerization, and the like may be used. Examples thereof include polyethylene glycol and the like.

As the polymer compounds, polymer compounds which are synthesized by hydrolysis and the like may be used. Examples thereof include polyvinyl alcohol which is obtained by hydrolysis of the polyvinyl acetate, and the like.

The synthetic polymer compounds mentioned above may be synthesized by chemical modification with a functional group capable of binding to the biomaterial.

In addition, as the compound for binding, commercially available, synthetic polymer compounds may be used. Examples thereof include SUNBRIGHT series, DE-030AS, DE-030CS, DE-030GS, PTE-100GS, PTE-200GS, HGEO-100GS, and HGEO-200GS, which are made by NOF Corporation, and the like.

On the other hand, when the natural polymer compounds are used as the compound for binding, examples thereof include polysaccharides such as dextran, carboxymethyl dextran, starch, and cellulose; proteins such as albumin, collagen and gelatin; DNA, RNA, nucleic acid, and the like. These natural compounds may be used as they are, or modified ones may also be used.

When the polymer compounds such as the synthetic polymer compounds and the natural polymer compounds are used as the compound for binding, the polymer compounds can be used in any state. For example, aqueous solution containing the dissolved compound may be used, and microparticles, for example, an assembly such as micelle or emulsion and polymer latex may also be used.

Examples of the inorganic compounds used as the compound for binding include, for example, metal particles such as Au colloid, inorganic microparticles such as silica, and the like. Further, compounds for binding which have a functional group capable of binding the biomaterial, which are obtained by chemically modifying these inorganic compounds, may be used.

Examples of the organic-inorganic hybrid used as the compound for binding include, for example, colloidal silica on which a polymer is coated; metal colloid on which a polymer is coated (such as gold, silver or platinum particles on which a protective colloid is coated); clay in which a polymer is adsorbed, and the like. The organic-inorganic hybrid can be synthesized in a known method (see Polymer Nanocomposite, Kogyo Chosakai, written by Susumu Nakajyo).

By modifying the organic-inorganic hybrid with the binding functional group, the obtained compound can also be used as the compound for binding.

The molecular weight and the structure of the compound for binding are not particularly limited, and any compounds can be used, for example low molecular compounds may be used. In such a case, however, there is a case where the cross-linking is caused in one biomaterial to be immobilized, and therefore the matrix cannot be formed. For preventing this, the compound for binding has a molecular weight of usually 1000 or higher, preferably 10,000 or higher, and it is usually 1,000,000 or smaller, preferably 500,000 or smaller. When the synthetic or natural polymer compounds are used as the compound for binding, it is preferable that weight average molecular weights are within the above-mentioned range, because if the molecular weight is lower than the above-mentioned range, matrices may not be formed efficiently.

The content of the binding functional groups in the compound for binding is not particularly limited. Although the content depends on the kind of the compound for binding and cannot be generally defined, for example, when the polymer is used as the compound for binding, the content is usually 0.1% by mole or higher based on the compound for binding, preferably 0.5% by mole or higher, more preferably 1% by mole or higher, still more preferably 5% by mole or higher, and it is usually 90% by mole or lower, preferably 80% by mole or lower, more preferably 70% by mole or lower. When the content is lower than the above-mentioned range, the compound for binding may not efficiently bind to the biomaterial, and when the content is higher than the above-mentioned range, the compound may not be mixed with the solvent.

II-7-4. Structure of Biomaterial-Carrying Object

The biomaterial-carrying object of the invention has, as mentioned above, the solid-state carrier and the matrix of the invention formed on surface of the solid-state carrier. The matrix contained in the biomaterial-carrying object of the invention is formed by binding a number of conjugates, which are formed by binding the biomaterial with the compound for binding, to each other, and usually has a gel structure wherein the biomaterial and the compound for binding are bound in the state of a chain and/or network (see FIG. 3(a) to FIG. 3(c) and FIG. 4).

Further, the matrix of the invention is a structure having a principal chain comprising the above-mentioned biomaterial and compound for binding. Here, the principal chain of matrix of the invention forms the skeleton of the matrix structure. Specifically, it is formed by binding the biomaterial and the compound for binding to each other. More specifically, the compound for binding binds to the biomaterial through a binding functional group, and such a structure is formed repeatedly to form a chain and/or reticular structure.

Therefore, the matrix of the invention has usually two or more partial structures having the following formula (A):

$$R^1\text{-}R^2 \quad \quad \text{Formula (A)}$$

wherein $R^1$ is a biomaterial and $R^2$ is a compound for binding which is not bound directly to the solid-state carrier, and each of $R^1$ and $R^2$ may be the same or different.

That is, the matrix of the invention is a structure in which partial structures in which the biomaterial binds to the compound for binding bind, as shown in the Formula (A), in the state of a linear chain and/or network. Specifically, in the above-mentioned Formula (A), $R^1$ binds independently to one or more $R^2$s, and $R^2$ binds independently binds to one or more $R^1$s. The matrix of the invention may include, for example, a partial structure in which the biomaterials $R^1$ bind to each other, or the compounds $R^2$ for binding bind to each other.

In this manner, the matrix of the invention at least partially contains a cross-linked structure in which there is the biomaterial between the compounds for binding and there is the compound for binding between the biomaterials, and the principal chain of the matrix is formed by both of the biomaterial and the compound for binding. That is, the matrix of the invention is produced in the presence of both of the biomaterial and the compound for binding in the production.

As mentioned above, since the matrix of the invention has the matrix skeleton formed from both of the biomaterial and the compound for binding, it is possible to increase the percentage of the biomaterial, and therefore, in biomaterial-carrying object of the invention, the biomaterial can be immobilized in a larger amount than the conventional one. The conventional polymer film is formed from a polymer chain which is previously formed on the solid-state carrier, and has a structure in which the biomaterial binds to the principal chain in a branched state (grafted state). As a result, the immobilization amount is limited at a pre-determined upper limit, and a large amount of the biomaterial cannot be immobilized.

It can be confirmed that the matrix has the principal chain comprising the biomaterial and the compound for binding by, for example, the following method:

Since the matrix of the invention, as mentioned above, has the principal chain comprising the biomaterial and the compound for binding, the structure is broken by decomposing the linkage of the biomaterial, which is the constituent element thereof. Utilizing this mechanism, the principal chain comprising the biomaterial and the compound for binding can be confirmed by decomposing the biomaterial of the matrix alone. That is, since at least a part of the compound for binding is immobilized on the solid-state carrier through the biomaterial, if the biomaterial is decomposed while the compound for binding is not decomposed, in the matrix of the invention, parts in which the compound for binding is immobilized on the solid-state carrier through the biomaterial are removed from the solid-state carrier.

Specifically, compounds forming the matrix other than the biomaterial constituent element can be specified by decomposing the biomaterial with an enzyme or other chemical which does not decompose the compound for binding but decomposes only the biomaterial, and examining substrates separated from the solid-state carrier by this treatment; or by examining substances remaining on the surface of the solid-state carrier. If the matrix has the principal chain comprising the biomaterial and the compound for binding, then the compound for binding can be detected in the substances separated. Also, the compound for binding is not detected on the solid-state carrier surface, or even if it is detected, the amount is reduced.

On the other hand, when the matrix utilizes a polymer film according to the conventional method and the biomaterial is decomposed, all of the polymer film (namely the polymer chain) remains in the solid-state carrier, and the biomaterial constituent elements are detected but polymer chains corresponding to the compound for binding are not detected in substances separated, because the principal chain is a polymer chain. The presence of the principal chain comprising the biomaterial and the compound for binding can be determined by utilizing this difference, and it can be specified whether a compound is the matrix of the invention or not.

The enzyme and chemical used for decomposing the biomaterial in the above-mentioned method are suitably selected in accordance with the kind of the biomaterial or compound for binding used. Examples thereof include, in case where the biomaterial is the nucleic acid, for example, nucleic acid degrading enzymes such as ribonuclease, and deoxyribonuclease.

In case where the biomaterial is a protein, examples of the enzyme and chemical include, for example, protein degrading enzymes such as microbial protease, trypsin, chymotrypsin, papain, rennet, and V8 protease, chemical substances having proteolytic ability such as cyanogen bromide, 2-nitro-5-thiocyanobenzoic acid, hydrochloric acid, sulfuric acid, and sodium hydroxide, and the like.

When the biomaterial is a lipid, examples of the enzyme and chemical include, for example, lipid degrading enzymes such as lipase and phospholipase A2, and the like.

When the biomaterial is a saccharide, examples of the enzyme and chemical include, for example, saccharide degrading enzymes such as $\alpha$-amylase, $\beta$-amylase, glucoamylase, pullulanase, and cellulase, and the like.

The enzymes and chemicals for decomposing the biomaterial may be used alone or as a mixture thereof in any ratio.

Of the above-mentioned examples, however, the enzymes and chemicals which may decompose not only the biomaterial but also the compound for binding should not be used, because the accurate determination of the principal chain cannot be performed.

When decomposition of the biomaterial, and substances remaining on the solid-state carrier after the decomposition are determined, any determination methods can be used. For example, they can be determined by using surface plasmon resonance (SPR), quartz crystal microbalance (QCM), electron microscope, ellipsometry, or the like.

When substances which are separated from the solid-state carrier after decomposition of the biomaterial are analyzed, any analysis methods can be used, and examples of the analysis method include, for example, liquid chromatography, gas chromatography, mass spectroscopy (MS), infrared spectroscopy, nuclear magnetic resonance (NMR), high performance liquid chromatography (HPLC), gel electrophoresis, capillary electrophoresis, absorbance measurement, fluorometry, and the like. The analysis methods may be used alone or in combination thereof in the analysis.

Although the film thickness of the matrix is arbitrary, it is usually 5 nm or more, preferably 10 nm or more, more preferably 20 nm or more when the matrix is dry and measured by SEM or TEM. When the film thickness is too thin, the matrix may easily peel off, and it is difficult to obtain a uniform film thickness of the matrix. Furthermore, there is a case where it is difficult to immobilize the biomaterial with higher reproducibility. The upper limit is not limited, and it is usually 10 cm or less.

In the matrix, the content ratio of the biomaterial is not limited, but it is desirable that a larger amount of the biomaterial is contained. Specifically, the weight ratio of the biomaterial to the matrix, "(the weight of the biomaterial)/(the weight of the matrix)" is usually 0.1 or higher, preferably 0.3 or higher, more preferably 0.5 or higher, still more preferably 0.7 or higher, particularly preferably 0.9 or higher. The content does not particularly have an upper limit, and it is usually 0.999 or lower. When the ratio of the biomaterial is lower than the above-mentioned range, the compound for binding in the matrix formed cannot be sufficiently covered with the biomaterial, and therefore, the non-specific adsorption to the compound for binding can occur.

Methods for measuring the above-mentioned ratio of the biomaterial are not particularly limited. For example, the biomaterial contained in the matrix may be decomposed with an enzyme or a chemical, and each substance derived from the biomaterial and the compound for binding may be quantified by various methods. The method for analysis and measurement of the biomaterial may be in the same method mentioned above.

Usually, it is desirable that the immobilized biomaterial does not lose the activity. Specifically, when the matrix is contacted with a solution including an interacting substance, which can be specifically interacted with the biomaterial, the ratio of the number of the interacting substances which are interacted with the biomaterials to the number of the biomaterials in the matrix (namely "response ratio") is usually 0.5 or higher, preferably 0.6 or higher, more preferably 0.7 or higher. The upper limit thereof is not particularly limited, but it is usually 1.0 or less. As mentioned above, when the matrix of the invention is used, the biomaterial can be immobilized in a larger concentration (an amount per unit surface of the solid-state carrier; surface concentration) to the solid-state carrier, and the immobilized biomaterial can be efficiently used by increasing the response ratio to the above-mentioned range. When the biomaterial and the interacting substance are molecules such as a biological molecule and an interacting molecule, the response ratio can be found as a ratio of the numbers of these molecules. The response ratio can also be measured by using, for example, SPR (surface plasmon resonance) or QCM (quartz crystal microbalance), and the like.

II-7-5. Production Method of Biomaterial-Carrying Object

The production method of the biomaterial-carrying object having the matrix of the invention is substantially the same method as described in [II-3. Production of biomaterial-carrying object]. That is, the production method of the biomaterial structure of the invention is not limited, and can be produced in any method, so long as the biomaterial structure of the invention can be obtained. Usually, the biomaterial-carrying object of the invention is produced through a step in which a mixture containing the biomaterial and the compound for binding is supplied to the solid-state carrier in the presence of a solvent, and a matrix having a principal chain comprising the above-mentioned biomaterial and the above-mentioned compound for binding is formed on the surface of the solid-state carrier.

(1. Biomaterial)

The biomaterial used in the production of the biomaterial-carrying object is the same as mentioned above. However, when the biomaterial is prepared in the production of the biomaterial-carrying object, it is preferable that the solvent or the dispersion medium, with which the biomaterial is diluted, is prepared in consideration of the activity and the structure stability of the biomaterial, although, usually, the biomaterial is prepared in the state of a solution or a dispersion in which the biomaterial is dissolved or dispersed in some solvent.

(2. Compound for Binding)

The compound for binding used in the production of the biomaterial-carrying object is the same as mentioned above.

(3. Solvent)

As mentioned above, usually, when the biomaterial-carrying object of the invention is produced, the mixture containing the above-mentioned biomaterial and compound for binding is supplied to the solid-state carrier in the presence of the solvent. In this case, the mixture which is supplied to the solid-state carrier contains at least the biomaterial and the compound for binding in the solvent.

The biomaterial and the compound for binding are mixed with the solvent in any state, and therefore, they may be dissolved or dispersed in the solvent. In order to stably bind the biomaterial to the compound for binding, it is preferable to dissolve the biomaterial and the compound for binding.

Any solvents may be used without limitations, so long as they can be a reaction medium in which the biomaterial and the compound for binding can be bound, and they can be mixed with the biomaterial and the compound for binding. Although it is selected in consideration of the activity and the structure stability of the biomaterial and the compound for binding, water is usually used as the solvent. Here, the fact that water can be used as the medium, that is, a mixture in which the biomaterial and the compound for binding are contained in water is supplied to the solid-state carrier to produce the biomaterial-carrying object is one advantage of the invention. That is, according to the conventional technique, the biomaterial is immobilized in an organic solvent (see Patent Document 5) but the immobilization cannot be performed using water as the medium (solvent). According to the present invention, the immobilization can be performed in the presence of water. As a result, it is possible to maintain the activity of the biomaterial, as well as the range of choice of the biomaterial and the compound for binding can be expanded, and therefore, the expansion of the application range can be expected.

Solvents other than water may be used as the solvent, and for example, organic solvents can be used. Among the organic solvents, amphipathic organic solvents, or organic solvents which can be mixed with water, are preferable.

Examples of the solvent other than water include THF (tetrahydrofuran), DMF (N,N-dimethyl formamide), NMP (N-methyl pyrrolidone), DMSO (dimethyl sulfoxide), dioxane, acetonitrile, pyridine, acetone, glycerin, and the like, in addition to alcohol solvents such as methanol, ethanol, and 1-butanol.

A salt may be added to the solvent. Any salts may be used, and examples thereof include NaCl, KCl, sodium phosphate, sodium acetate, calcium chloride, sodium hydrogenecarbonate, ammonium carbonate, and the like. The amount of the salt used is not limited and any amount of the salt can be used according to the use.

When water is used as the solvent, solutions in which a solute other than the biomaterial and the compound for binding is dissolved in water can be used in addition to purified water. Examples thereof include various buffers such as carbonate buffer, phosphate buffer, acetate buffer, and HEPES buffer.

The solvents may be used alone or as a mixture thereof in any ratio.

(4. Mixture)

The mixture contains the biomaterial, and the compound having a functional group capable of binding the biomaterial in a solvent. Specifically, it is a mixture containing the biomaterial and the compound for binding in the above-mentioned solvent. It is preferable that in the mixture, the biomaterial and the compound for binding are mixed with the solvent.

Any mixing ratios of the biomaterial and the compound for binding may be used in the mixture. However, the mixing ratio, "the weight of the biomaterial/(the weight of the compound for binding+the weight of the biomaterial)," is usually 0.1 or higher, preferably 0.3 or higher, more preferably 0.5 or higher, still more preferably 0.7 or higher, particularly preferably 0.9 or higher. Although the upper limit is not particularly limited, it is usually 0.999 or lower. When the mixing ratio of the biomaterial is higher, a matrix comprising a principal chain having a binding point of the compound for binding, as shown in FIG. 3($a$), is formed. On the other hand, when the mixing ratio of the compound for binding is higher, a matrix comprising a principal chain having a binding point of the biomaterial, as shown in FIG. 4, is formed. In this case, it is possible to inhibit the non-specific adsorption to the compound for binding by increasing the ratio of the biomaterial to the above-mentioned range. FIGS. 3($a$) to 3($c$) and FIG. 4 are a schematic view showing the enlarged surface vicinity of one example of the biomaterial-carrying object of the invention, for explaining the matrix of the invention. FIGS. 3($a$) to 3($c$) and FIG. 4, circular parts show the biomaterials and linear parts show the compounds for binding. In order to explain the structure of the principal chain comprising the biomaterial and the compound for binding, however, in FIGS. 3($a$) to 3($c$) and FIG. 4, the structure of the principal chain is described in two dimensions regardless of whether they form the particulate lumps or not.

Any percentages (concentrations) of the biomaterial and the compound for binding in the solvent may be used. It is usually 0.1 g/L or higher, preferably 1 g/L or higher, more preferably 10 g/L or higher. When the concentration is lower than the above-mentioned range, it is difficult to generate the conjugates and the matrix. Although the upper limit is not particularly limited, it is usually 950 g/L or lower.

Further, methods for preparing the mixture are not limited, and any methods can be used. For example, a solution (aqueous solution) or a dispersion of the biomaterial and a solution (aqueous solution) or a dispersion of the compound for binding may be mixed; a solution or a dispersion of the biomaterial and the solid compound for binding may be mixed; the solid biomaterial and a solution or a dispersion of the compound for binding may be mixed; and the solid biomaterial, the solid compound for binding, and a solvent may be mixed.

Any additives may be added to the above-mentioned mixture, in addition to the biomaterial, the compound for binding, and the solvent. Examples of the additive include salts, acids, bases, buffers, moisturizing agents such as glycerin, stabilizers for the biomaterial such as metal ions, e.g. zinc, antifoaming agents, modifiers, and the like.

(5. Supply)

When the biomaterial-carrying object of the invention is produced, the mixture is supplied to the solid-state carrier. That is, the mixture is contacted with the solid-state carrier. Any concrete operations may be used. For example, the mixture is previously prepared and the mixture may be contacted with the solid-state carrier, or each component of the mixture is prepared separately and mixture may be prepared in the presence of the solid-state carrier to contact the mixture with the solid-state carrier. Specifically, for example, a solution (an aqueous solution or the like) containing the biomaterial and a solution (an aqueous solution or the like) containing the compound for binding are supplied to the solid-state carrier separately, and then the two solution are stirred in the presence of the solid-state carrier. Alternatively, when the mixture is previously prepared, conjugates and/or a matrix mentioned below may be produced in the mixture before supply, and then the mixture may be supplied to the solid-state carrier.

(6. Formation of Matrix)

Next, the matrix comprising the principal chain having the biomaterial and the compound are formed on the surface of the solid-state carrier. When the mixture is prepared, then the biomaterial and the compound for binding are bound in the mixture to form the conjugates. The conjugate has a structure in which the biomaterial and the compound for binding are bound to each other, which can be produced only by mixing the biomaterial and the compound for binding in the solvent to contact their molecules. Accordingly, there are usually conjugates in the mixture which is supplied to the solid-state carrier.

The conjugates are aggregated and bind to each other through the biomaterial and compound for binding contained therein to form a matrix having a structure in which the conjugates are bound in the state of a chain and/or a network. Thus, by contacting the mixture, which is supplied to the solid-state carrier, with the solid-state carrier, for example, the conjugates in the mixture are aggregated on the solid-state carrier; the matrix, which is produced by binding the conjugates in the mixture, binds to the solid-state carrier; the biomaterial and the compound for binding in the mixture bind to the solid-state carrier surface to produce the conjugate and/or matrix, whereby the matrix is formed on the surface of the solid-state carrier.

When there is a large amount of the solvent in the mixture, there is a case where it is difficult to generate conjugates or a matrix in the mixture or they may not be generated. In such a case, by concentrating the mixture, the conjugates can be formed efficiently. When the mixture, which is supplied to the solid-state carrier, as mentioned above, has the conjugates and/or a matrix, of course, the concentration may be performed, whereby the conjugates and/or the matrix is further produced.

In order to form a uniform matrix, it is preferable to uniformly mix the biomaterial and the compound for binding in the solvent in an initial stage of the preparation of the mixture. It is preferable, therefore, that the biomaterial and the compound for binding are contained in a relatively large amount of a solvent, and then the mixture is concentrated to generate conjugates.

After the matrix is formed, the mixture may be dried to remove the solvent. Since the mixture is usually concentrated during the drying step of the mixture, the concentration and drying can be carried out in a series of operation.

Any method for drying and concentrating the mixture may be used, and examples thereof include, for example, ultrafiltration, drying under reduced pressure, and the like. In addition, evaporation under normal pressure may be carried out to dry or concentrate.

The temperature conditions, when the mixture is dried and concentrated, are arbitrary, and the temperature is usually 25° C. or lower, preferably 10° C. or lower, in order to avoid the denaturation of the biomaterial.

The pressure conditions, when the mixture is dried and concentrated, are arbitrary, and the operation is preferably carried out under normal pressure or reduced pressure.

Further, when the matrix is immobilized on the solid-state carrier, it is desirable that the solid-state carrier is allowed to stand for a pre-determined period of time after supplying the mixture. Although the period of time is arbitrary, it is usually 24 hours or shorter, preferably 12 hours or shorter.

(7. Other Steps)

As mentioned above, according to the above-mentioned method, the matrix can be formed on the surface of the solid-state carrier by only contacting the mixture containing the biomaterial and the compound for binding in the solvent with the solid-state carrier, whereby the biomaterial-carrying object of the invention can be produced or, in other words, the biomaterial can be immobilized on the solid-state carrier. That is, the method is a very easy method.

The biomaterial-carrying object of the invention may be produced in steps other than the above-mentioned steps.

For example, a different biomaterial or other specific material mentioned below may be bound to the biomaterial in the matrix. If this technique is utilized, after the production of the biomaterial-carrying object, a different biomaterial which is modified so that it specifically binds to the biomaterial in the matrix is bound later; as a result, the different biomaterial can be immobilized on the solid-state carrier in a high density. Specifically, avidin is used as the biomaterial, and this avidin and the compound for binding are bound to form the matrix, thereby producing the biomaterial-carrying object. After that, a different biomaterial which is modified with biotin can be immobilized by avidin-biotin interaction. Similarly, the biomaterial can be immobilized through a histidine tag or a glutathione-S-transferase.

I-7-6. Effects

The biomaterial can be immobilized in larger amount than that in the conventional technique by using the biomaterial-carrying object having the matrix of the invention. For example, according to the prior art described in Patent Documents 4 to 6, the biomaterial is bound to a polymer film formed on the surface of the solid-state carrier. In this case, however, the biomaterial is bound to the solid-state carrier in such a manner that the biomaterial is bound to the polymer chain terminal in the principal chain of the polymer chain, or bound to the polymer chain in the state of a graft, and therefore, it is necessary to form the polymer chain as the principal chain and it is necessary to use the polymers in a certain amount or more with respect to the biomaterial to be immobilized, which limits the amount of the biomaterial immobilized.

On the contrary, according to the present invention, the matrix having a matrix skeleton (corresponding to the above-mentioned principal chain) comprising the biomaterial and a polymer is formed, and the biomaterial can be immobilized on the solid-state carrier, utilizing the matrix, whereby the percentage of the biomaterial in the biomaterial structure can be increased (in other words, the percentage of the compound for binding can be decreased). As a result, when the biomaterial is immobilized, there is no limitation as caused in the conventional technique, and it is possible to immobilize the biomaterial on the surface of the solid-state carrier in a larger amount, or higher density than that in the conventional technique.

One of the advantages of the biomaterial-carrying object of the invention is that the production is easy. According to the conventional methods, many workloads are required to immobilize the biomaterial in high densities. Specifically, in the conventional methods, a polymer film is previously formed on the solid-state carrier, the biomaterial is immobilized on the polymer film, and the matrix containing a ligand is formed on the solid-state carrier. According to the methods, however, when the polymer is formed on the solid phase, it is necessary to appropriately control the molecular weight of the polymer and the introduction density to the solid-state carrier, which are very troublesome, and it is difficult to perform the immobilization in high reproducibilities. In particular, according to the method described in Patent Document 6, it is technically difficult to form a polymer chain in the state of a brush from the surface of the solid-state carrier, which is not suitable for mass production.

On the contrary, the biomaterial-carrying object of the invention can be very easily produced by only contacting the mixture containing the biomaterial and the compound for binding in the solvent with the solid-state carrier to form the matrix, in other words, to immobilize the biomaterial, on the solid-state carrier. Further, since the solvents used in the production of the biomaterial-carrying object are not limited to organic solvents, and the biomaterials which can be used are not limited to the solvents, unlike the technique described in Patent Document 5, it is possible to expand the range of choice of the biomaterial to be immobilized.

Further, the matrix which is formed into the biomaterial-carrying object of the invention can immobilize the biomaterial almost uniformly and three-dimensionally on the solid-state carrier. Consequently, the biomaterial structure can give optimal reaction sites for the interaction between the biomaterial and the interacting substance which specifically interact with the biomaterial, whereby, for example, when the biomaterial-carrying object of the invention is used in a sensor which utilizes the interaction, the detection sensitivity of the sensor can be increased.

The inventors of the present invention presume the reason why the optimal reaction sites can be formed as follows: That is, according to the conventional method in which the biomaterial is immobilized on the solid-state carrier whose surface is treated with the polymer film, the biomaterial is placed on the surface of the film, and there are no voids through which the interacting substance can enter into the inside of the polymer film. Further, according to the conventional technique in which the principal chain is formed from only the hydrophilic polymer, it can be considered that the access of the interacting substance to the biomaterial is prevented by the excluded volume effect of the hydrophilic polymer chain and the movement of the polymer chain (see Real Time Analysis Experimental Method for Biomaterial Interaction—focused on BIA CORE, edited by Kazuhiro Nagata, and Hiroshi Handa, published by Springer-Verlag Tokyo Kabushiki Kaisha, page 258; Development and Application of Polymer Material for Pharmaceutical polymer, CMC, page 19). In the matrix formed in the biomaterial-carrying object of the invention, however, the biomaterial can be immobilized almost uniformly and three-dimensionally on the solid-state carrier. Further, it can be considered that the structure of the matrix has spaces in which interacting substances can sufficiently react within the polymer film by using the technique of the present invention, whereby the optimal reaction sites can be obtained.

The matrix formed in the biomaterial-carrying object of the invention can arbitrarily control the film thickness. According to the conventional technique, it is difficult to arbitrarily control the film thickness of the biomaterial structure from sub-micron to several microns. According to the present invention, however, it is possible to control the film thickness of the matrix at such a precise level, and therefore, the degree of freedom of the design of the matrix can be increased.

For example, when the interaction observation by SPR is performed, it is considered that a thickness of a film which is used for immobilizing an observation target is optimally from about 200 nm to 300 nm. Alternatively, for example, when medical instruments and carriers for regenerative medicine are surface-treated, the film thickness is required to be an order of micron for film used in the surface-treatment, in order to realize sufficient strength and coating film. Further, for example, when the surface-treatment of drugs used in DDS (drug delivery system) is performed, it is required to arbitrarily control the thickness of the film used for the surface-treatment, for controlling the drug release. As mentioned above, when the immobilization of the biomaterial is performed utilizing some film, the control of the film thickness is one of the important points, and the control is difficult in the conventional technique. According to the present invention, however, the film thickness can be arbitrarily controlled by controlling a concentration and an amount of the mixture and reaction conditions (temperatures and times), according to the use.

Further, when the biomaterial-carrying object of the invention is used in order to interact the biomaterial with the interacting substance, the non-specific interaction caused by the matrix constituent elements other than the biomaterial can be inhibited. That is, the percentage of the biomaterial in the matrix is increased, whereby the percentage of the substances other than the biomaterial, which cause the non-specific interaction, can be decreased.

When an electrically uncharged substance is used as the compound for binding, the non-specific interaction caused by charge can further reduced. That is, for example, in the method described in Patent Document 4, since a polymer film is electrically charged, the pH and the ionic strength of a buffer solution used exert great influence to the reaction of the biomaterial, and the electrically charged protein cannot avoid the non-specific adsorption caused by electrostatic interaction (see Nanotechnology Basic Series, Bionanotechnology, edited by Yasuhiro Horiike and Kazunori Kataoka, page 186). However, if the electrically uncharged substance is used as the compound for binding, the above-mentioned trouble does not occur, and a specific interaction can be caused selectively.

II-7-7. Biomaterial-Immobilization Kit

In order to produce the biomaterial-carrying object having the above-mentioned matrix of the invention, a product used for immobilizing the biomaterial on the solid-state carrier, namely a biomaterial-immobilization kit in which the above-mentioned compound for binding, and the solvent, which can mix the biomaterial and the compound for binding are contained, may be used. That is, in order to produce the biomaterial-carrying object, the biomaterial-immobilization kit comprising the compound for binding, and the solvent capable of mixing the biomaterial and the compound for binding may be prepared. When the biomaterial-immobilization kit is used, the biomaterial-carrying object can be easily produced, or the above-mentioned matrix can be easily formed on the solid-state carrier, and therefore, a large amount of the biomaterial can be easily immobilized on the solid-state carrier.

The compounds for binding contained in the biomaterial-immobilization kit are as stated above. The compound for binding can be contained in the biomaterial-immobilization kit in any state. For example, the compounds may be in any state such as a solution in which it is dissolved in any solvent, a dispersion in which it is dispersed in any dispersion medium, a solid such as powder, or lump.

The solvents contained in the biomaterial-immobilization kit are the same solvent used in the production of the biomaterial-carrying object. Further, the solvent in the biomaterial-immobilization kit may be contained in a container different from that for the compound for binding, or may be contained in a container together with the compound for binding as the solvent or the dispersion medium for the compound for binding.

Further, the biomaterial-immobilization kit may contain other elements as necessary.

For example, it may contain a reagent which facilitates the production of the matrix. Specifically, when polyacrylic acid is used as the compound for binding, 1-ethyl-3-(3-dimethylaminopropyl)carbodiimide hydrochloride (abbreviation: EDC) may be contained as a drug, in order to activate carboxyl group in the polyacrylic acid.

II-6-8. Use

The biomaterial-carrying object having the matrix of the invention can be used in a wide industrial range. The uses are not limited, and it can be used in any use. Usually, it is suitably used in a use utilizing an "interaction" between the biomaterial and the interacting substance which specifically interacts with the biomaterial.

For example, the biomaterial-carrying object can be suitably used as a biosensor which detects an interacting substance which interacts with the biomaterial. The above-mentioned biosensor analyzes an interaction using a sensor chip immobilized with DNA or a protein, which is referred to as a DNA array or DNA chip, or a protein array or protein chip. The biomaterial-carrying object of the invention can be applied to the sensor chip. That is, when the biomaterial is immobilized on the sensor chip, the matrix is formed on the sensor chip body by the above-mentioned method, and the sensor chip can be used as the biomaterial-carrying object of the invention.

Examples of the biosensor to which the biomaterial-carrying object of the invention can be applied, include a sensor by fluorescence method, chemiluminescence method, RI method, SPR (surface plasmon resonance) method, QCM (quartz crystal microbalance) method, piezo type canti-lever method, laser type canti-lever method, mass spectroscopy method, a sensor by electrochemical method, electrode method, field effect transistor (FET) method, FET and/or single electron transistor method using a carbon nanotubes, and the like. Of these, the detections by the SPR method and the QCM method are suitably used, because a label-free sample can be easily analyzed by these methods.

As to the SPR method, since surface plasmon waves are induced, it is preferable that the surface of the sensor chip is coated with a metal. Any metal can be used so long as it can induce the surface plasmon wave, and examples thereof include gold, silver, copper, aluminum, and alloys thereof, and the like. Of these, silver is preferable in terms of the sensitivity and inexpensive cost, and gold is also preferable in terms of stability. A metal layer is formed by deposition, sputtering, plating or other coating methods. The thickness of the metal is usually about 20 nm or more, preferably about 30 nm or more, and usually about 300 nm or less, preferably about 160 nm or less.

When the biomaterial-carrying object of the present invention is applied to the SPR method or the QCM method, in order to firmly bind the matrix to the sensor chip body, it is preferable that the sensor chip body has functional groups on its surface. In this case, any functional groups can be used, and examples thereof include hydroxyl group, carboxyl group, thiol group, aldehyde group, hydrazide group, carbonyl group, epoxy group, vinyl group, amino group, succinimide group, and the like.

Further, the biomaterial-carrying object of the invention can be applied to surface treatment of drugs for DDS (drug delivery system), surface treatment of carriers for regenerative medicine, surface treatment of artificial organs, surface treatment of catheters, and the like.

III. Biomaterial Complex

The biomaterial complex of the invention is one in which the specific material binds to the biomaterial structure. The biomaterial complex may be also a biomaterial structure formed by using the biomaterial and/or compound for binding to which the specific material is bound.

As mentioned above, the biomaterial structure is a structure formed from the biomaterial and the compound capable of binding the biomaterial (namely, "compound for binding"). In the biomaterial complex, the specific material binds the biomaterial and/or compound for binding in the biomaterial structure. The specific material may bind to either of the biomaterial and the compound for binding, or may bind to the both of them. In the biomaterial structure, there are usually a larger amount of the biomaterials than the compounds for binding, and therefore, it is preferable that the specific material is bound to at least the biomaterial, from the viewpoint that a larger amount of the specific material are bound to the biomaterial complex.

III-1. Specific Material

The specific material is an element forming the biomaterial complex of the invention, and any substance other than the biomaterial and the compound for binding, which form the biomaterial structure to which the specific substance binds, can be used according to the purpose so long as the effects are not remarkably impaired.

When the biomaterial complex of the invention is used in purification or analysis of a target material, as the specific material, usually, a substance which can interact with a certain substance (interacting substance; in order to distinguish from the "interacting substance" which interacts with the biomaterial, the substance which interacts with the specific material is referred to as "specific interacting substance") is used. Thereby, as in the biomaterial structure of the invention, in which the biomaterial interacts with the corresponding interacting substance, in the biomaterial complex of the invention, the specific material can interact with the specific interacting substance. The specific material, instead of the biomaterial, interacts with the target material.

For example, when the biomaterial complex is used in purification of a target material, as the specific material, a substance which can interact with the specific interacting substance is used, and as the target material, a substance which corresponds to the specific interacting substance (namely a substance which can interact with the specific material) is used. The separation/purification of the target material is performed by utilizing the above-mentioned interaction.

When the biomaterial complex is used in analysis of a target material, a substance which can interact with the specific interacting substance is used as the specific material. Whether the target material and the specific material are interacted or not is examined, if the interaction occurs between the target material and the specific material, then the target material is one of the specific interacting substances. That is, it can be analyzed that the target material has a specific structure which can interact with the specific material. The structures of the target materials or the specific interacting substances can be analyzed by utilizing this mechanism.

Here, the "interaction" between the specific material and the specific interacting substance is not particularly limited, and usually it is the same interaction as that between the biomaterial and the interacting substance.

Examples of the specific material include metal chelates, glutathione, saccharides, vitamins, boronic acid, proteins, antigens, nucleic acids, bioactive substances, lipids, hormones, endocrine disrupters, chelate-forming groups, and the like.

The specific materials may be used alone or as a mixture thereof in any ratio, but when a target material is separated, the specific material is usually used alone.

Of these, the metal chelates, the glutathione, and saccharides are suitably used in, for example, separation of the affinity tag-fused protein.

The expression and purification of the affinity tag fused protein is one method for producing a large amount of a recombinant protein. The example will be briefly described. That is, there can be listed a method in which the protein is modified with an amino acid sequence, which is an affinity tag, and the separation is performed by using the specific material which specifically interacts with the affinity tag, whereby the purification of a desired protein is performed. Examples of such an affinity tag include, for example, polyhistidine (His-tag), glutathione-S-transferase (GST), maltose binding protein, calmodulin, and the like. Of these, preferable affinity tags are His-tag, and GST, and particularly preferable one is His-tag.

Specifically, when a sample having polyhistidine, for example a recombinant protein having His-tag, is purified by using the biomaterial complex of the invention, a metal chelate can be used as the specific material. In this case, affinity interaction between the histidine and the metal chelate is utilized. It is considered that this interaction is caused by coordinating one nitrogen atom at imidazole ring in the polyhistidine to an unsaturated coordination position of a metal.

When the metal chelate is used as the specific material in case where the above-mentioned His-tag is used, any kinds of metal ions can be used as the metal ion contained in the metal chelate, which is the specific material, transition metal ions are usually preferable. Of these, ions of iron, cobalt, nickel, copper and zinc, which are elements in Group IV of the Periodic Table, are preferable in terms of production cost and since they hardly run out in a separation/purification step. Nickel is particularly preferable.

The chelate reagents used for forming a metal chelate are not limited so long as they form a metal chelate. Examples of the chelate reagent include iminodiacetic acid and its derivatives, nitrilotriacetic acid and its derivatives, and the like. Examples of the commercially available reagent include, for example, AB-NTA, Maleimido-C3-NTA, Maleimido-C7-NTA (made by Dojindo Laboratories), and the like. The chelate reagents may be used alone or as a mixture thereof in any ratio.

Further, there is a method in which a functional group contained in the biomaterial is modified without using the chelate reagent. For example, it is possible that amino group contained in the biomaterial is modified with monochloroacetic acid, monobromoacetic acid, monochloropropionic acid, monobromopropionic acid, or a metal salt thereof, to which a metal ion is bound to produce a metal chelate, which is a specific material.

When GST or maltose binding protein is used as the specific material, glutathione or saccharide such as maltose can be used as the specific material.

Further, when an antibody-antigen reaction is caused by using the biomaterial complex of the invention, an antibody or an antigen can be used as the specific material. Any antibodies and antigens can be used in this reaction, and examples thereof include immunoglobulin, derivatives thereof such as $F(ab')_2$, Fab', and Fab, and the like.

The biomaterial complex of the invention can be used in gene analysis. In this case, for example, nucleotide, oligonucleotide, nucleic acids (DNA, RNA and PNA), and the like can be used as the specific material. In this analysis, either of double-stranded nucleic acids and single-stranded nucleic acids can be used.

Further, when the biomaterial complex of the invention is used for clarifying the action mechanism of a medical drug, bioactive substances such as a compound having bioactive property can be used as the specific material.

When the biomaterial complex of the invention is used in case where a bioactive substance is selected as a pharmaceutical candidate agent, a protein such as a receptor contributing to a disease can be used as the specific material.

When the biomaterial complex of the invention is used as a sensor for detecting a virus, a saccharide can be used as the specific material.

When the biomaterial complex of the invention is used in separation/purification of a compound having a saccharide, such as a protein containing a sugar chain, boronic acid can be used as the specific material.

When a protein is used as the specific material, examples of the protein include enzymes, in addition to the above-mentioned antibodies and receptors. Immobilized enzymes with a high efficiency can be provided by using the enzyme as the specific material. In this case, the enzyme can be used repeatedly.

Further, screening or separation/purification of lipid binding protein can be performed by using a lipid as the specific material and the biomaterial complex of the invention.

In order to determine the action mechanism of a hormone or an endocrine disrupter, the hormone or the endocrine disrupter can be used as the specific material. In this case, a biological molecule which binds to the hormone or endocrine disrupter can be screened by using the biomaterial complex of the invention.

Further, when a vitamin is used as the specific material, for example, biotin can be used.

When the biomaterial complex of the invention is used in separation or removal of a metal ion, a chelate-forming group can be used as the specific material. For forming this chelate-forming group, the above-mentioned chelate reagent can be used. Further, as the chelate-forming group, the chemical species listed in the method for modifying the functional group contained in the biomaterial without using the chelate reagent can be used. Examples of the chelate-forming group include iminodicarboxylic acid group, iminopropionic acid group, ethylene diamine triacetic acid group, ethylene diamine tetraacetic acid group, hydroxyethyl iminodiacetic acid group, hydroxyethyl iminotriacetic acid group, and the like.

When the biomaterial complex is used in separation/purification utilizing an affinity separation technique, such as an affinity purification or analysis, the above-mentioned specific material is a mark material of a target material, which is a target of the separation/purification.

Of these, as the specific material, at least one member selected from the group consisting of metal chelates, biotin, saccharides, glutathione, boronic acid, antibodies, antigens, receptors, bioactive substances and chelate-forming groups is more preferable.

III-2. Linker

In the biomaterial complex of the invention, the specific material binds to the biomaterial and/or compound for binding. In this case, the specific material may bind to the biomaterial and/or compound for binding through some linker, as well as they bind directly to each other. It is preferable that the specific material and the biomaterial and/or compound for binding are indirectly bound using a linker, because, usually, the reactivity of the interaction between the specific material and the target material can be increased by using the linker.

Any linkers can be used without limitations, so long as the effects of the invention are not impaired. It is preferable to use a molecule having hydrophilic property (hydrophilic molecule) as the linker. That is, it is preferable that the linker is hydrophilic.

In order to form a hydrophilic linker, it is desirable that a hydrophilic atomic group such as amino group, carboxylic acid group, hydroxyl group, sulfonic acid group, glycidyl group, nitrile group and ethylene oxide is included in the molecule forming the linker. Of these, since it is known that the polyethylene oxide chain inhibits the non-specific adsorption of a protein, when the protein is used as the biomaterial or the target material, it is desirable to use linkers having an ethylene oxide chain.

The linkers may be used alone or as a mixture thereof in any ratio.

III-3. Biomaterial Structure in Biomaterial Complex

The biomaterial structure in the biomaterial complex of the invention is the same as the biomaterial structure of the invention.

III-3-1. Biomaterial in Biomaterial Complex

The same biomaterials in the biomaterial structure of the invention can be used as the biomaterial in the biomaterial complex. The biomaterial is an element forming the biomaterial structure or also an element forming the biomaterial complex.

From the viewpoint that the biomaterial complex is formed by immobilizing the specific material on the biomaterial structure, when the specific material is bound to the biomaterial, a substance capable of binding to the specific material is used as the biomaterial. When the biomaterial binds to the specific material through a linker, a substance capable of binding to the linker is used as the biomaterial.

Any bindings can be adapted when the biomaterial and the specific material or linker are bound, depending on the kinds and uses of the biomaterial complex.

Examples of the binding between the biomaterial and the specific material or linker include covalent binding, ionic binding, chelate binding, coordinate bond, hydrophobic bonding, hydrogen bonding, van der Waals binding, binding by electrostatic force, and the like. Other bindings which are not included in those categories can be used.

On the other hand, when the specific material is bound to the compound for binding so that it is not bound to the biomaterial, any biomaterials can be used according to the use. For example, when a pre-determined interaction is caused between the specific material and some specific interacting substance, it is preferable to use a substance which does not generate any non-specific interaction with the specific interacting substance, as the biomaterial.

III-3-2. Compound for Binding in Biomaterial Complex

As the compound for binding in the biomaterial complex, the same compound for binding in the biomaterial structure of the invention can be used. Thus, similarly to the biomaterial structure of the invention, it is preferable usually that the compound for binding has an appropriate binding functional group according to the kinds of the biomaterial and the use of the biomaterial complex of the invention.

When the specific material is bound to the compound for binding, a substance capable of binding the specific material or the linker is used as the compound for binding. In this case, examples of the binding between the compound for binding and the specific material or linker include covalent binding, ionic binding, chelate binding, coordinate bond, hydrophobic bonding, hydrogen bonding, van der Waals binding, binding by electrostatic force, and the like. Other bindings which are not included in those categories can be used.

In this case, it is desirable to use a substance having a functional group capable of binding to the above-mentioned specific material or the linker is used as the compound for binding, in addition to the above-mentioned binding functional groups. Any functional groups can be used without limitation, and examples thereof include the same groups as the binding functional group. The concrete kind can be selected depending on the kind of the specific material and the use of the biomaterial complex of the invention.

The functional groups capable of binding to the above-mentioned specific material or the linker may be used alone or as a mixture thereof in any ratio.

Also, in the biomaterial complex of the invention, similarly to the biomaterial structure, in order to easily form the above-mentioned particulate lumps, it is preferable that there is no binding between the compounds for binding, and the binding between the biomaterial and the compound for binding is mainly formed. This is because, similarly to the biomaterial structure, if there is the binding between the compounds for binding, then aggregated lumps composed of the compounds for binding are easily formed, and the particle diameter of the particulate lump tends to be larger, which leads to difficult control of the particle diameter of the particulate lump. As in the case of the biomaterial structure, therefore, it is preferable to select a binding functional group which does not cause the binding between the compounds for binding, whereby the binding between the compounds for binding is inhibited. Also, in order to maintain the activity of the biomaterial for utilizing the properties of the biomaterial, it is preferable that functional groups of the biomaterial and the compound for binding are selected so that the biomaterial does not lose its activity.

Further, to use a substance which can be mixed with water as the compound for binding is also preferable, because water is used as the medium such as the solvent or the dispersion medium not only in the production of the biomaterial structure, but also in the production of the biomaterial complex.

To use a substance which can be mixed with at least one organic solvent as the compound for binding is also preferable, because not only the structure of the biomaterial structure but also the structure of the biomaterial complex can be variously designed.

Further, to use a substance which can be mixed with both of water and an organic solvent as the compound for binding is more preferable, because the number of the kinds of the solvents can be increased not only when the biomaterial structure is used but also when the biomaterial complex is used.

Electrically uncharged compounds for binding are preferable when the biomaterial complex as well as biomaterial structure is used in separation of the target material. In case where the target material is separated by using the biomaterial complex, when the target material has the same charge as the compound for binding, the specific interaction with the specific material in the biomaterial complex may be interrupted, and when the target material has an opposite charge to that of the compound for binding, the non-specific adsorption between the target material and the compound for binding can be caused due to electrical attraction force.

When a polymer compound, particularly a synthetic polymer compound is used as the compound for binding, and the specific material binds to the compound for binding, it is desirable that the polymer compound has a monomer capable of binding to the specific material or the linker.

That is, when the specific material and the compound for binding are bound, it is desirable that in addition to the same monomer as the compound for binding of the biomaterial structure of the invention, as the compound for binding of the biomaterial complex, a monomer having a functional group capable of binding the above-mentioned specific material or linker is contained, for binding the specific material to the compound for binding.

Examples of the monomer having the functional group capable of binding the specific material or linker include the monomers having the binding functional group capable of binding the biomaterial, as mentioned above.

III-4 Structure of Biomaterial Complex

The biomaterial complex of the invention is the substance in which the specific material binds to the biomaterial and/or compound for binding of the biomaterial structure of the invention. Further, in the biomaterial complex of the invention, particulate lumps are the same as those of the biomaterial structure of the invention, and the particle diameter of the particulate lumps is usually 10 μm or smaller.

The biomaterial structure, as mentioned above, has a structure in which particulate lumps formed from both of the biomaterial and the compound for binding are aggregated and/or bound, and the biomaterial complex has also a structure in which the particulate lumps are aggregated and/or bound. Accordingly, in the biomaterial complex of the invention in which the specific material binds to the biomaterial structure, the percentage of the biomaterial can be increased, and the percentage of the specific material which binds to the biomaterial can also be increased. Consequently, the biomaterial complex of the invention can hold the specific material in a larger amount than the conventional ones. Further, when the specific material can bind to the compound for binding, in addition to the biomaterial, it can hold a larger amount of the specific material.

Similarly to the biomaterial structure of the invention, according to the biomaterial complex of the invention, because it can hold a large amount of the biomaterial, the advantage that the non-specific interaction caused by the compound for binding (and a solid-state carrier, mentioned below) can be inhibited, is obtained. Consequently, while the influence due to the non-specific interaction is excluded, the analysis or the affinity separation can be carried out by using the interaction between the specific material and the specific interacting substance.

On the other hand, when the specific material binds to the compound for binding, but does not bind to the biomaterial, it can hold a larger amount than the conventional ones, because the biomaterial structure has a three-dimensional structure. The advantage that the non-specific interaction can be inhibited is obtained in case where the compound for binding and the specific material bind.

As mentioned in the explanation of the biomaterial structure of the invention, according to the conventional technique for immobilizing the biomaterial on the solid-state carrier, when it is used in affinity purification, the amount of the biomaterial immobilized is limited at the pre-determined upper limit (usually, the single layer adsorption of the protein is at most 0.3 to 1.0 μg/cm$^2$), since the biomaterial is bound to the surface of the solid-state carrier such as resin microparticle, and accordingly a large amount of the biomaterial cannot be held. Accordingly, even when the specific material is bound to the biomaterial, the amount of the specific material is not sufficient.

Further, in the biomaterial complex of the invention, particle diameter of the particulate lump is the same as in the biomaterial structure of the invention. When the particle diameters of the particulate lumps are individually measured, it is sufficient so long as at least a part of the particulate lumps have a particle diameter with the above-mentioned range, as in the case of the biomaterial structure. It is preferable that the most possible particulate lumps have the particle diameter with the above-mentioned range, and more preferably all of the particulate lumps have the particle diameter with the above-mentioned range.

Methods for measuring the particle diameter of the particulate lumps of the biomaterial complex of the invention are the same as that of the biomaterial structure of the invention.

Further, as mentioned above, spaces (voids) are formed between the particulate lumps in the biomaterial structure, and accordingly in the biomaterial complex of the invention, the particulate lumps usually do not completely bond to each other, and spaces (voids) are formed between the particulate lumps. As in the spaces in the biomaterial structure, when an affinity separation is carried out using the biomaterial complex, a target material, which interacts with the specific material, can enter into the spaces. Usually, in the spaces, the interaction between the specific material and the target material is caused. Accordingly even if the biomaterial complex of the invention has a three dimensional structure, the specific material contained therein can be interacted with the target material and the like. That is, biomaterial complex of the invention can three-dimensionally have many specific materials therein, and further does not lose the activity of the specific material, and it is possible to conduct the interaction. Therefore, the biomaterial complex of the invention can retain the activity of the specific material, and can contain a larger amount of the specific material than the conventional ones.

Methods for examining whether the biomaterial complex of the invention have spaces between the particulate lumps or not are the same as in the case of the biomaterial structure of the invention.

The size of the biomaterial complex of the invention is the same as that of the biomaterial structure of the invention. The measuring methods thereof are the same as in the case of the biomaterial structure of the invention.

Further, similarly to the biomaterial structure, the biomaterial complex of the invention can be immobilized on a solid-state carrier, which can be used in affinity purification, or as a pharmaceutical function analysis tool, and further used for surface treatment of drugs for DDS (drug delivery system), surface treatment of regeneration medicine carriers, surface treatment of artificial organs, surface treatment of catheters, and the like. When the biomaterial complex of the invention is applied to the surface treatment and the like, the biomaterial complex of the invention is immobilized on a desired solid-state carrier in any manner to form the biomaterial-complex-carrying object, which is then used.

III-5. Composition of Biomaterial Complex

III-5-1. Content Ratio of Specific Material

In the biomaterial complex of the invention, the content ratio of the specific material is not limited, but it is usually desirable that a larger amount of the biomaterial is contained. Specifically, the weight ratio of the specific material to the biomaterial complex, "(the weight of the specific material)/(the weight of the biomaterial complex)" is usually 0.001% by weight or higher, preferably 0.003% by weight or higher, more preferably 0.005% by weight or higher. When the ratio of the specific material is lower than the above-mentioned range, in the separation/purification using the biomaterial complex, the efficiency of the separation/purification may be lowered. The content does not particularly have an upper limit, and it is usually 70% by weight or lower.

III-5-2. Measurement of Specific Material Content Ratio

The content of the above-mentioned specific material can be measured by, for example, elemental analysis or amino acid analysis.

III-5-3. Content Ratio of Biomaterial in Biomaterial Complex

In the biomaterial complex of the invention, the content ratio of the biomaterial is not limited, but it is usually desirable that a larger amount of the biomaterial is contained. Specifically, the weight ratio of the biomaterial to the biomaterial structure, "(the weight of the biomaterial)/(the weight of the biomaterial complex)" is usually 0.1 or higher, preferably 0.3 or higher, more preferably 0.5 or higher. The content does not particularly have an upper limit, and it is usually 0.999 or lower. When the ratio of the biomaterial is lower than the above-mentioned range, the compound for binding in the formed biomaterial complex cannot be sufficiently covered with the biomaterial, and therefore, the non-specific adsorption to the compound for binding can occur. Also, when the specific material is bound to the biomaterial alone, a sufficient amount of the specific material cannot be bound. When separation/purification is performed by using such a biomaterial complex, the efficiency of the separation/purification can be lowered.

III-5-4. Measurement of Biomaterial Content Ratio in Biomaterial Complex

Methods for measuring the above-mentioned ratio of the biomaterial in the biomaterial complex are not particularly limited. For example, the biomaterial contained in the biomaterial complex of the invention may be decomposed with an enzyme or a chemical, and each substance derived from the biomaterial, the compound for binding, and the specific material may be quantified in various methods.

The decomposition method of the biomaterial and the quantification method of the substances derived from the biomaterial, the compound for binding and the specific material are the same methods as described in the item [Measurement of biomaterial content ratio in the biomaterial structure].

III-6. Production Method of Biomaterial Complex

The methods for producing the biomaterial complex are not limited, and usually, the specific material is bound to the biomaterial before, during or after at least one step of the production of the biomaterial structure. Therefore, the biomaterial complex may be produced by, for example, previously binding the specific material to the biomaterial and/or compound for binding, and then forming the biomaterial structure; or may be produced by obtaining the biomaterial structure from the biomaterial and the compound for binding, and then binding the specific material to the biomaterial and/or compound for binding in the biomaterial structure.

III-6-1. Method for Producing the Biomaterial Structure in Production of Biomaterial Complex The production method of the biomaterial structure is the same as mentioned above.

As to the mechanism of forming the biomaterial structure, when the biomaterial structure is produced through the above-mentioned method, using the biomaterial and/or compound for binding, to which the specific material is bound, the obtained product is the biomaterial complex of the invention. In this case, the biomaterial complex is caused to be formed in the same mechanism as in the biomaterial structure.

It is preferable that in an initial stage of the preparation of the mixture containing the biomaterial and the compound for binding, the biomaterial and the compound for binding are uniformly mixed in the medium, in order to form the uniform biomaterial structure as well as to obtain the uniform biomaterial complex.

III-6-2. Binding of Specific Material

At least before, during or after each of the production steps of the biomaterial structure, namely, for example, mixing step, concentration step, drying step and other steps, the biomaterial complex of the invention can be obtained by binding the specific material to the biomaterial and/or compound for binding.

Methods for binding the specific material to the biomaterial and/or compound for binding are not limited, and any methods can be used.

Usually, binding can be performed by contacting the specific material to the biomaterial and/or compound for binding. When the linker is used, first, the linker is contacted with the biomaterial and/or compound for binding, and then the specific material is contacted with the biomaterial and/or compound for binding to which the linker is bound; or the linker is contacted with the specific material, and then the specific material with which the linker is contacted is contacted with the biomaterial and/or compound for binding.

As the concrete operation in which the linker or the specific material, and the biomaterial and/or compound for binding are contacted, usually, the biomaterial or compound for binding, and the specific material or optionally used linker are contained in an appropriate medium. In this case, any temperatures, reaction times, and apparatus used can be used so long as the specific material can be bound to the biomaterial. Usually, these conditions are set depending on the kind of the specific material, the biomaterial, the compound for binding, the linker, and the like. It is preferable that the biomaterial does not lose its activity as much as possible.

For example, in general, it is preferable that the binding is conducted at room temperature or lower. Specifically, the binding is conducted at usually 25° C. or lower, preferably 10° C. or lower. When the specific material or the linker cannot bind to the biomaterial and/or compound for binding in the desirable range as mentioned above, however, the binding may be conducted in a temperature range in which the binding easily proceeds.

As the medium in binding, media mainly containing water are preferable in order to inhibit the loss of activity of the biomaterial. When the specific material or linker is hardly dissolved or dispersed in water, and the like, however, water soluble organic solvents may be used as the medium. In such a case, any percentages of the water-soluble organic solvent can be used, and it is usually 80% by weight or less, preferably 70% by weight or less, more preferably 50% by weight or less.

Examples of the water-soluble organic solvent include dimethyll sulfoxide {DMSO) alkyl alcohols having 1 to 5 carbon atoms such as methyl alcohol, ethyl alcohol, n-propyl alcohol, isopropyl alcohol, n-butyl alcohol, sec-butyl alcohol, tert-butyl alcohol, isobutyl alcohol, and n-amyl alcohol; amides such as dimethyl formamide, and dimethyl acetamide; ketones or ketoalcohols such as acetone and diacetonealcohol; ethers such as tetrahydrofuran and dioxane; polyalkylene glycols such as polyethylene glycol, and polypropylene glycol; alkylene glycols in which the alkylene group has 2 to 6 carbon atoms such as ethylene glycol, diethylene glycol, propylene glycol, butylene glycol, triethylene glycol, 1,2,6-hexane triol, thiodiglycol, and hexylene glycol; lower alkyl ethers of polyhydric alcohol such as ethylene glycol monomethyl ether, ethylene glycol monoethyl ether, diethylene glycol monomethyl ether, diethylene glycol monoethyl ether, triethylene glycol monomethyl ether, and triethylene glycol monoethyl ether; lower dialkyl ethers of polyhydric alcohol such as triethylene glycol dimethyl ether, and triethylene glycol diethyl ether; glycerin, sulfolane, N-methyl-2-pyrrolidone, 1,3-dimethyl-2-imidazolidinone, and the like. Of these, dimethyl formamide is preferable. The media in binding may be used alone or as a mixture thereof in any ratio.

After the biomaterial complex is prepared, the medium may be removed.

Now, a specific method will be explained by means of an example in which the metal chelate, which is the specific material, is bound to the biomaterial.

When the metal chelate as the specific material is bound to the biomaterial, for example, first the chelate reagent (chelate-forming group) is bound to the biomaterial, whereby a desired metal ion is bound to the chelate-forming group to bind the specific material to the biomaterial.

Further, the binding of the chelate reagent to the biomaterial, and the binding of the specific material to the biomaterial to which the chelate reagent is bound are usually conducted in a medium. Any media can be used, and examples thereof include, for example, media used in the production of the biomaterial structure, the aqueous organic solvents as listed above, and the like. The solvents used in this case may be used alone or as a mixture thereof in any ratio.

Any reaction conditions can be used in binding so long as the effects of the invention are not remarkably impaired.

III-7. Explanation of Affinity Separation Using Biomaterial Complex

The biomaterial complex of the invention is suitably used in affinity separation. The biomaterial complex of the invention, therefore, can be used, for example, in affinity purification or as a pharmaceutical function analysis tool.

The affinity separation using the biomaterial complex of the invention is performed in the same manner as in the affinity separation using the biomaterial structure of the invention except that the biomaterial complex is used instead of the biomaterial structure, the specific interacting substance is used as the target material instead of the interacting substance, and the specific material is used as a substance which is interacted with the target material instead of the biomaterial.

As to the embodiments using the same, the same embodiments as the affinity separation embodiments using the biomaterial structure of the invention can be listed except that the biomaterial complex is used instead of the biomaterial structure, the specific interacting substance is used as the target material instead of the interacting substance, and the specific material is used as a substance which is interacted with the target material instead of the biomaterial. When the first to the fourth embodiments are understood as the embodiments wherein the biomaterial complex is used, referring to FIG. 5 to FIG. 7, the embodiments are understood in the same manner as in the affinity separation embodiments wherein the biomaterial structure of the invention is used except that the numeral 2 shows the biomaterial complex.

III-8. Sensor Using Biomaterial Complex

In the sensor using the biomaterial complex of the invention the biomaterial complex may be used instead of the biomaterial structure. In this case, the sensor is usually used for detecting the specific interacting substance which interacts with the specific material. Others can be operated in the same manner described in "II-6. Use of biomaterial-carrying object."

IV. Biomaterial-Complex-Carrying Object

The biomaterial complex of the invention is a substance in which the biomaterial complex of the invention is immobilized on the solid-state carrier. The containers for affinity and the chips for the affinity separation used in the first to the fourth embodiments correspond thereto.

When the biomaterial complex of the invention is used as the tools for affinity purification or pharmaceutical effect and mechanism analysis, it is desirable to use the biomaterial-complex-carrying object obtained by immobilizing to the solid-state carrier depending on conditions.

IV-1. Biomaterial Complex Contained in Biomaterial-Complex-Carrying Object

The biomaterial structure contained in the biomaterial-carrying object of the invention and its constituent elements, namely the biomaterial, the compound for binding, and the specific material are as described above.

Although the thickness (film thickness) of the biomaterial complex contained in the biomaterial-complex-carrying object is arbitrary, it is usually 5 nm or more, preferably 10 nm or more, more preferably 15 nm or more, still more preferably 20 nm or more in the dry state. When the film thickness is less than the above range, sufficient film cannot be formed. Although the upper limit is not limited, it is usually 10 cm or less. The thickness can be measured by using SEM, TEM, AFM, and the like.

IV-2. Solid-State Carrier Contained in Biomaterial-Complex-Carrying Object

The solid-state carrier is a basal plate having the biomaterial complex of the invention formed on its surface. The same solid-state carrier contained in the biomaterial-carrying object can be used as the solid-state carrier contained in the biomaterial-complex-carrying object.

When a channel is formed on the chip, as in the third and fourth embodiments, and the biomaterial complex is filled and held in the channel 14B, as in the biomaterial-carrying object, in order to prevent the biomaterial complex outflow from the channel 14B, it is preferable to provide means for preventing the outflow such as a filter.

Further, the solid-state carrier may be used as it is, and after subjecting to surface treatment, the biomaterial complex may be formed on the treated surface, as in the case of the solid-state carrier contained in the biomaterial-carrying object.

IV-3. Production of Biomaterial-Complex-Carrying Object

The production method of the biomaterial-complex-carrying object of the invention is arbitrary, and it can be usually produced in the same manner as in the production of the biomaterial-carrying object. For example, the biomaterial complex is prepared previously, and it may be bound to the solid-state carrier, or each component of the biomaterial complex such as the specific material, the biomaterial, or the compound for binding may be separately prepared, and while they may be mixed on the solid-state carrier to produce the biomaterial complex, the produced complex may be bound to the solid-state carrier. Specifically, for example, a solution (aqueous solution, and the like) containing the specific material, a solution containing the linker, a solution (aqueous solution, and the like) containing the biomaterial, a solution (aqueous solution, and the like) containing the compound for binding are separately supplied to the solid-state carrier, and then the solutions are mixed on the solid-state carrier. Alternatively, when the mixture is previously prepared, before supplying the mixture, the above-mentioned conjugates (including the particulate lumps which are one form of the conjugate) or the biomaterial complex is produced in the mixture, and then such a mixture may be supplied to the solid-state carrier.

The method and condition (temperature condition, pressure condition, standing time, and the like) for binding the biomaterial complex to the solid-state carrier are the same as in the production of the biomaterial-carrying object.

V. Bio-Related Material Immobilized Carrier

The bio-related material immobilized carrier (solid-state carrier on which the bio-related material is immobilized) of the invention is a solid-state carrier on which the bio-related material, a compound which can bind to the bio-related material and/or the supporting material (among the above-mentioned compounds for binding, compounds capable of binding to the supporting material; which is sometimes referred to as "compound for carry-immobilization"), and the matrix containing the supporting material (hereinafter, sometimes, referred to as "pre-determined matrix") are formed. Here, the pre-determined matrix is a supporting material on which the above-mentioned biomaterial structure and/or biomaterial complex are immobilized. Now, it is described in detail.

The bio-related material immobilized carrier of the invention is a solid-state carrier on which the bio-related material is immobilized, and has the pre-determined matrix on its solid-state carrier surface. Here, the pre-determined matrix has the bio-related material, the compound capable of binding to the above-mentioned bio-related material and/or the supporting material (namely "compound for carry-immobilization") and the supporting material. That is, the pre-determined matrix has, as schematically shown in FIG. 8, the bio-related material, the compound for carry-immobilization and the supporting material, and its skeleton is a matrix having a structure in which the bio-related material and the compound for carry-immobilization bind to the supporting material, which is a core, to form a chain, network and/or block shape. FIG. 8 is a schematic view showing the enlarged cross-section of one example of the bio-related material immobilized carrier of the invention, for explaining the structure of the pre-determined matrix. In FIG. 8, painted circular parts show the bio-related materials, linear parts show the compound for carry-immobilization, open circular parts show the supporting material, and blank spaces show the void layers.

The array of the invention is characterized by placing at least two pre-determined matrices on different areas on the solid-state carrier respectively. The array includes an array comprising at least about 10 pre-determined matrices, an array comprising at least about 100 pre-determined matrices, an array comprising at least about $10^3$ pre-determined matrices, an array comprising at least about $10^4$ pre-determined matrices. The integration of these pre-determined matrices is the array which also includes an array in which the area of the bio-related material immobilized carrier which is coated with each of the pre-determined matrices is about 25 mm$^2$ or less, an array in which the area of the bio-related material immobilized carrier which is coated with each of the pre-determined matrices is between about 100 μm$^2$ and about 4 mm$^2$, and an array in which the area of the bio-related material immobilized carrier which is coated with each of the pre-determined matrices is within an area of about 20 cm$^2$ or less.

On the surface of such an array, surface parts around the different areas where the mixed solution is supplied may be hydrophobic (surrounding hydrophobic property). Also, the area may be in the state of a well, which is a recess part of a recess and protrusion structure (FIG. 9(a)), or may be in the state of a pile which is a protrusion part (FIG. 9(b)).

V-1. Production Method

The bio-related material immobilized carrier of the invention is produced through a step in which a mixture containing the supporting material, the bio-related material, and the compound capable of binding to the bio-related material and/or the supporting material in the solvent is supplied to the surface of the solid-state carrier, and then the solvent is removed to form a pre-determined matrix.

V-1-1. Solid-State Carrier

The solid-state carrier is a basal plate on which the pre-determined matrix is formed, and the pre-determined matrix formed on the surface of the solid-state carrier is the bio-related material immobilized carrier of the invention. The solid-state carrier used in the present invention is not limited, and any material, shape and size can be used so long as it is a target for forming the pre-determined matrix.

Examples of the material of the solid-state carrier include various resin materials such as polyolefin, polystyrene, polyethylene, polycarbonate, polyamide, and acrylic resin, and inorganic materials such as glass, alumina, carbon, and metals. The solid-state carrier materials may be used alone, or as a mixture thereof in any ratio. When measurement is performed by using a fluorescence method, the material is suitably selected according to the measurement method or apparatus used, for example a material having a low self-fluorescence is selected, and the like.

Examples of the shape of the solid-state carrier include a plate, beads, fiber, filter, film, sheet, well, and the like. Specifically, chips (basal plate) in which a number of bio-related materials can be arranged; well chips (well basal plate), pile chips (pile basal plate), surrounding hydrophobic chips (surrounding hydrophobic basal plate), beads used as a chromatography carrier or a diagnostic agent, hollow fiber used for increasing the surface area, and porous structure such as nitrocellulose film can be listed.

Further, the solid-state carrier may be used as it is, or after subjecting its surface to some surface treatment, the pre-determined matrix may be formed. For example, after the surface is coated with a coating material such as metals and metal oxides, the pre-determined matrix may be formed. Further, in order to bind the solid-state carrier to the pre-determined matrix, functional groups may be introduced into the solid-state carrier. Any functional groups can be used, and examples thereof include, for example, functional groups binding the solid-state carrier and the pre-determined matrix through chemical binding, such as hydroxyl group, carboxyl group, thiol group, aldehyde group, hydrazide group, carbonyl group, epoxy group, vinyl group, amino group, succinimide group, and maleimide. In the production of the bio-related material solid-state carrier of the invention, when water is used as the solvent, functional groups binding the solid-state carrier and the pre-determined matrix by physical adsorption due to hydrophobic interaction, such as alkyl group and phenyl group can be used.

The surroundings around the different known areas, where the mixed solution is supplied, on the surface of the solid-state carrier may be made hydrophobic (surrounding hydrophobic property).

Specifically, in case where the surface of the solid-state carrier is coated with gold, examples of the surface treatment include, for example, a treatment in which the following compounds are immobilized on the surface of the gold:

[Chemical formula]

wherein each of $n_1$ and $n_2$ is independently an integer of 2 or more.

Examples of the solid-state carrier, which may be subjected to the coating treatment, include chips coated with a metal, glass slides, fiber slides, sheets, pins, microtiter plates, capillary tubes, beads, and the like.

V-1-2. Supporting Material

The supporting material is a core on which the pre-determined matrix is formed, and the pre-determined matrix formed on the surface of the solid-state carrier is the bio-related material immobilized carrier of the invention. The supporting material used in the present invention is not limited, and any material, shape, and size can be used so long as it is a target for forming the pre-determined matrix.

In such a case, the bio-related material, the supporting material and the compound are bound in the sate of a chain, network, or block. The binding may have multiple structures. Examples thereof include for example, the supporting material to which a product formed by binding the compound through the binding moiety to the bio-related material is bound; a product formed by binding the compound to the supporting material and the bio-related material; a product formed by binding the compound to the bio-related material, which is previously bound to the supporting material, and the like. The pre-determined matrix, therefore, is formed by aggregating at least one the supporting material surrounded by the bio-related material cross-linked with the compound.

Examples of the material of the supporting material include various resin materials such as polyolefin, polystyrene, polyethylene, polycarbonate, polyamide and acrylic resin; inorganic materials such as glass, alumina, carbon and metals. The supporting material may include substances which cause fluorescence energy transfer (FRET), conductive materials such as ferrite, graphite, and carbon nanotube, or metals which give electromagnetic resonance such as gold and silver. The supporting materials may be used alone or as a mixture thereof in any ratio.

Examples of the shape of the supporting material include particulate, fiber, and the like. Also, heteromorphic ones may be used so long as they give sufficient spaces and film thickness to the formed pre-determined matrix. Examples thereof include chromatography carriers, latex particles as a latex diagnostic agent, Au colloid, and the like.

Of these, the latex particles are particularly preferably used. The material and particle diameter of the latex particles are arbitrary, and can be suitably selected according to the purpose of the use. Examples thereof include latexes such as polystyrene latex, copolymers of styrene and divinyl benzene, copolymers of acrylic acid and styrene, copolymers of styrene and maleic acid, copolymers of styrene and methacrylic acid, terpolymers of styrene and acrylic acid and alkyl acrylate, or copolymers of vinyl acetate and acrylic acid, and the like. Any particle diameters can be used so long as the pre-determined matrix can be formed, but when the particle diameter is too small, sufficient spaces and film thicknesses cannot be obtained, and when it is too large, sufficient film strength cannot be obtained. The particle diameter, therefore, is suitably selected according to the conditions of use. For example, it is about 10 nm to about 100 μm, preferably 100 nm to 10 μm. Latex particles having different particle diameters may be mixed, and then used. By adjusting the conditions in this manner, the void content, film thickness, and the like of the formed pre-determined matrix can be optimized.

Further, the supporting material may be used as it is, or after subjecting to some surface treatment, it may be used. For example, the surface may be made hydrophilic with a hydrophilic polymer such as polyethylene glycol, a protein such as bovine serum albumin, or the like. When a suitable surface treatment is selected, the degree of binding between the supporting material and the bio-related material and/or compound can be adjusted, and a side-reaction such as reaction a non-specific adsorption reaction to the supporting material can be inhibited.

In order to firmly form the pre-determined matrix, a functional group may be introduced into the surface of the supporting material. Any functional groups can be used, and examples thereof include, for example, functional groups which form the pre-determined matrix through a chemical binding, such as hydroxyl group, carboxyl group, thiol group, aldehyde group, hydrazide group, carbonyl group, epoxy group, vinyl group, amino group, succinimide group, and maleimide group.

Further, as the supporting material, one on which bio-related material and/or compound for carry-immobilization is previously immobilized may be used. For example, when latex particles on which the bio-related material is immobilized are used as the supporting material, carboxyl group, amino group, hydroxyl group, thiol group on the surface of the latex particles may bind to the binding functional group of the bio-related material. When the carboxyl group is bound to the binding functional group, examples of the binding functional group of the bio-related material may include amino group, and the like, and amide binding may be formed by using carbodiimide, and the like. On the other hand, when there is hydrophobic interaction or electrostatic interaction between the latex particles and the bio-related material, the bio-related material can be immobilized on the surface of the latex particles through the physical interaction.

It is desirable that the supporting material is electrically uncharged, because in the detection of the selective interaction between the bio-related materials, using the bio-related material immobilized carrier of the invention, if the detection target material in a sample has the same charge as the supporting material and/or compound for carry-immobilization and the electrostatic repulsion is too strong, the specific interaction with the bio-related material may be interrupted. It can also be considered that when the detection target material and the supporting material and/or compound for carry-immobilization have opposite charges to each other, non-specific interaction such as non-specific adsorption can occur between the detection target material and the supporting material and/or compound for carry-immobilization.

V-1-3. Bio-Related Material

The bio-related material is a substance which is immobilized on the solid-state carrier. Any substances may be used according to the purpose. Examples thereof include biomaterials used in the biomaterial structure, and substances in which the specific material binds to the biomaterial. Examples thereof include enzymes, antibodies, lectins, receptors, protein A, protein G, protein A/G, avidin, streptavidin, neutravidin, glutathione-S-transferase, proteins such as glycoprotein, peptide, amino acid, hormone, nucleic acid, saccharide, oligosaccharide, polysaccharide, sialic acid and their derivatives, sugar chain such as sialylated sugar chain, lipid, low molecular compounds, polymer organic substances other than the above-mentioned polymers, inorganic substance, fusions thereof, virus, biological molecules such as a molecule constituting a cell, and the like. In addition, substances other than the biological molecule such as the cell can be used as the bio-related material.

In case where the bio-related material immobilized carrier of the invention is used in an analysis, these bio-related materials act as a mark material, when the interaction (binding property and the like) between the detection target material (analyte) and the bio-related material in the sample is measured.

The analyte is a substance which specifically interacts with the bio-related material usually (interacting substance; in order to distinguish from the "interacting substance" which interacts with the biomaterial, and "specific interacting substance" which interacts with the specific material, the substance which interacts with the bio-related material is sometimes referred to as "related interacting substance"). Here, the "interaction" between the bio-related material and the related interacting substance is not particularly limited, but usually refers to an action due to a force between substances caused from at least one of covalent binding, hydrophobic bonding, hydrogen bonding, van der Waals binding and binding by electrostatic force. However, the "interaction" used herein should be most broadly understood, and it must not be understood limitatively. The covalent binding includes coordinate bond. The binding by electrostatic force includes electrical repulsive as well as electrostatic binding. Further, the interaction includes binding reaction, synthesis reaction and decomposition reaction which are caused by the above-mentioned actions.

Examples of the interaction include, but do not limited to, binding and dissociation between an antigen and an antibody, binding and dissociation between a protein receptor and a ligand, binding and dissociation between an adhesive molecule and a counter-molecule, binding and dissociation between an enzyme and a substrate, binding and dissociation between an apoenzyme and a coenzyme, binding and dissociation between a nucleic acid and a nucleic acid or protein reacting therewith, binding and dissociation between proteins in a signal transduction system, binding and dissociation between a glycoprotein and a protein, binding and dissociation between a sugar chain and a protein, and the like. Further, examples thereof also include immunoglobulin and its derivatives such as $F(ab')_2$, Fab', and Fab, receptors or enzymes and their derivatives, nucleic acid, natural or artificial peptides, synthetic polymers, saccharide, lipid, inorganic substances or organic ligands, virus, cells, and drugs.

Examples of the protein among the above-mentioned bio-related materials may include the entire length of the protein, partial peptides including a binding active moiety. Further, proteins whose amino acid sequence and its function are either known or unknown are included. Synthesized peptide chains, proteins obtained by purification of a living body, or proteins obtained by translation from a cDNA library with a suitable translation system and purification of it can also be used as the mark material. The synthesized peptide chain may be glycoprotein to which a sugar chain is bound. Preferable proteins are purified ones.

Further, the nucleic acid is not particularly limited, and includes nucleic acid bases such as aptamer, and peptide nucleic acids such as PNA, as well as DNA and RNA. Also, nucleic acids whose base sequence is either known or unknown may be used. Of these, nucleic acids capable of binding a protein, whose functions and base sequence as the nucleic acid is known, and nucleic acids obtained by cutting and separating from a genome library and the like using a restriction enzyme can be preferably used.

As the sugar chain, sugar chains whose saccharide sequence or function is either known or unknown may be used. Preferably, the sugar chains whose saccharide sequence or function is known by separation analysis are used.

The low molecular compounds are not particularly limited so long as they have an ability of interacting. Both low molecular compounds whose functions are unknown and compounds whose ability of binding to a protein is known can be used. Pharmaceutical candidate compounds are preferably used.

When the bio-related material is prepared, it is usually prepared in the state of a solution or dispersion in which the bio-related material is dissolved or dispersed in some solvent. In this case, it is preferable that the solvent or dispersion medium, which dilutes the bio-related material, is selected in consideration of the activity or structure stability of the bio-related material.

The bio-related materials may be used alone or as a mixture thereof in any ratio.

The array of the bio-related material characterized by placing at least two pre-determined matrix comprising the bio-related material, the compound capable of binding the bio-related material and/or the supporting material, and supporting material on different areas on the solid-state carrier respectively, may include arrays of the bio-related material which interacts with the related interacting substance in which all of the bio-related materials placed are functionally associated therewith; arrays of the bio-related material which interacts with the related interacting substance which is structurally associated therewith; and array of the bio-related material which interacts with the related interacting substance which belongs to the same family member.

Examples of the related interacting substance which is functionally associated include disease-based interacting substances such as metabolic functions, medical area diseases, combinations of markers in a digester area, a cardiobascular area, an endocrine area, a tumor area, an infection area, or an allergy area. It is very useful in a "panel test" or a "profile test," which systematically perform the association with the disease, that the interaction with the combination of the related interacting substance associated with the specific disease is assayed in parallel.

Examples of the above-mentioned family include, for example, growth factor receptors, hormone receptors, nerve transmitter substance receptors, catecholamine receptors, amino acid derivative receptors, cytokine receptors, extacellular matrix receptors, antibodies, lecitin, cytokine, serpin, protease, kinase, phosphatase, ras-like GTPase, hydrolase, steroid hormone receptors, transcription factor, heat shock transcription factor, DNA-binding protein, zinc-finger protein, leucin zipper protein, homeo domain protein, intracellular signal transduction modulators and effectors, apoptosis associated factors, DNA synthetic factors, DNA retrieval factors, DNA recombinant factor, cell surface antigens, hepatitis C virus (HCV) protease and HIV protease.

V-1-4. Compound for Carry-Immobilization

As the compound capable of binding the bio-related material and/or the supporting material (namely, the compound for carry-immobilization), any compounds can be used so long as they can bind to the above-mentioned bio-related material and/or the supporting material. Accordingly, as the compound for carry-immobilization, compounds having a functional group capable of binding to the above-mentioned bio-related material and/or the supporting material (hereinafter, sometimes, referred to as "binding functional group") can be arbitrarily used. Here, as the binding functional group, any functional groups can be used so long as they can bind to the bio-related material or the supporting material. Usually, it is preferable to suitably select one according to the kind of the bio-related material and the use of the bio-related material immobilized carrier of the invention. The binding functional groups may be used alone or as a mixture thereof in any ratio.

The binding functional groups are usually classified into two groups, that is, groups binding to the bio-related material and/or the supporting material through covalent binding as a reactive group, and groups binding to the bio-related material and/or the supporting material through non-covalent binding. In case of the binding through the covalent binding, examples of the binding functional group include succinimide group, epoxy group, aldehyde group, maleimide group, and the like.

Now, the binding to the bio-related material will be specifically described. Examples of the bio-related material binding to the binding functional group include, for example, protein, nucleic acid, saccharide, and the like.

When the bio-related material is a protein, usually, amino group, hydroxyl group, or thiol group on the surface layer of the protein binds to the binding functional group of the compound for binding. In such a case, when the amino group binds to the binding functional group, examples of the binding functional group include succinimide group, epoxy group, and the like. Also, when the hydroxyl group binds to the binding functional group, examples of the binding functional group include epoxy group, and the like. Further, when the thiol group binds to the binding functional group, examples of the binding functional group include maleimide group, and the like.

When the bio-related material is nucleic acid, amino group, hydroxyl group, or thiol group, which is introduced into the terminal of the nucleic acid, binds to a binding functional group of the compound for binding. In such a case, when the amino group binds to the binding functional group, examples of the binding functional group include succinimide group, epoxy group, and the like. When the hydroxyl group binds to the binding functional group, examples of the binding functional group include epoxy group, and the like. Further when the thiol group binds to the binding functional group, examples of the binding functional group include maleimide group, and the like.

When the bio-related material is saccharide, amino group, hydroxyl group, or thiol group on a side chain of the saccharide binds to a binding functional group of the compound for carry-immobilization. In such a case, when the amino group binds to the binding functional group, examples of the binding functional group include succinimide group, epoxy group, and the like. When, the hydroxyl group binds to the binding functional group, examples of the binding functional group include epoxy group, and the like. When the thiol group binds to the binding functional group, examples of the binding functional group include maleimide group, and the like.

On the other hand, when the binding is caused through non-covalent binding, for example, through coordination compound formation, examples of the binding functional group include boronic acid group, and the like. When the binding is caused through the interaction between the bio-related materials, the avidin-biotin interaction can be used. Examples of the binding functional groups include biotin group. When, for example, virus is bound as the biomaterial, examples of the binding functional group include saccharide, and polysaccharide. When, for example, the bio-related material has a hydrophobic region, binding through a hydrophobic interaction can be performed.

The binding with the supporting material will be specifically described. When the bio-related material is previously immobilized on the supporting material, the supporting material binds to the compound for carry-immobilization through the bio-related material, as mentioned above.

For example, when the supporting material is a latex particle, amino group, hydroxyl group, or thiol group on the surface of the latex particles binds to the binding functional group of the compound for carry-immobilization. In this case, when the amino group binds to the binding functional group, examples of the binding functional group include succinimide group, epoxy group, and the like. When the hydroxyl group binds to the binding functional group, examples of the binding functional group include epoxy group, and the like. Further, when the thiol group binds to the binding functional group, examples of the binding functional group include maleimide group, and the like.

Further, when there is, for example, hydrophobic interaction or electrostatic interaction between the supporting material and the compound for carry-immobilization, the latex particles can be bound through such an interaction.

When the compound for carry-immobilization has the binding functional group, it is preferable that the compound for carry-immobilization has usually at least two, preferably at least three binding functional groups to the bio-related material and/or the supporting material in one molecule. The compounds may be used as a mixture of multiple kinds thereof, and in such a case, it is preferable to use at least one of the above-mentioned compound having multiple binding sites, for easier formation of the structure of the pre-determined matrix. For example, when the compound having at least two binding functional groups in one molecule, the pre-determined matrix is surely formed when concentration or the like is performed.

Further, as the compound for carry-immobilization, usually, compounds capable of mixing with water are desirably used. Any solvents can be used in production of the pre-determined matrix, but usually, water is used as the solvent. In this case, the compound for carry-immobilization is bound to the supporting material and/or the bio-related material by mixing the compound with the supporting material and/or the bio-related material in the water, and the supporting material and/or the bio-related material and the compound for carry-immobilization are uniformly mixed to conduct the binding reaction smoothly. The state of mixing used in the present description may include solutions and dispersions.

It is preferable that the compound for carry-immobilization can be mixed with at least one solvent. Such compounds can expand the range of choice of solvent used in synthesis of the compound for carry-immobilization, and a variety of the structures of the pre-determined matrix can be designed. For example, if the compound for carry-immobilization can be mixed with an organic solvent, then the synthesis thereof can be carried out in the organic solvent, in order to protect the binding functional group in the synthesis of the compound for carry-immobilization.

Further, if the compound for carry-immobilization can be mixed with both of water and an organic solvent, then the number of the kinds of the solvent, which can be used in the application of the bio-related material immobilized carrier of the invention, can be increased, thus resulting in expansion of its application.

It is desirable that the compound for carry-immobilization is electrically uncharged, because in the detection of the selective interaction between the bio-related materials, using the bio-related material immobilized carrier of the invention, if the detection target material in a sample has the same charge as the supporting material and/or compound for carry-immobilization and the electrostatic repulsion is too strong, the specific interaction with the bio-related material can be interrupted. It can also be considered that when the detection target material and the supporting material and/or compound for carry-immobilization have opposite charges to each other, non-specific interaction such as non-specific adsorption can occur between the detection target material and the supporting material and/or compound for carry-immobilization.

If the compound for carry-immobilization has, at least, a nonionic structure formula, such a compound is an electrically uncharged compound for binding. However, even if the above-mentioned compound for carry-immobilization is electrically charged by hydrolysis of the binding functional group, and the like, during the production procedure of the bio-related material immobilized carrier of the invention, such a compound for carry-immobilization can be suitably used so long as the effects of the invention are not impaired.

Examples of the compound for carry-immobilization include, for example, organic compounds, inorganic compounds, organic-inorganic hybrid materials, and the like. The compound for carry-immobilization may be used alone or as a mixture thereof in any ratios.

The organic compounds used as the compound for carry-immobilization may be either low molecular compounds or polymer compounds. Examples of the low molecular compound used as the compound for binding include glutaraldehyde, diepoxybutane, diepoxyhexane, diepoxyoctane, bismaleimide hexane, bissulfosuccinimidyl suberate, disuccinimidyl glutarate, ethylene glycolbissuccinimidyl succinate, sulfoethylene glycol bissuccinimidyl succinate, succinimidyl-4-N-maleimidemethylcyclohexane-1-carboxylate, succinimidyl-4-N-maleimidemethylcyclohexane-1-carboxylate, sulfosulfosuccinimidyl-4-p-maleimidephenylbutyrate, succinimidyl-4-p-maleimidephenylbutyrate, sulfo-m-maleimidebenzoyl-N-hydroxysuflosuccinimide ester, and the like.

On the other hand, when the polymer compounds are used as the compound for carry-immobilization, they may be synthetic polymer compounds or natural polymer compounds.

When the synthetic polymer compounds are used as compound for carry-immobilization, any synthetic polymer compounds can be used so long as they satisfy the above-mentioned conditions. In general, however, compounds having a monomer capable of binding a bio-related material and/or the supporting material are desirable. Further, usually, in order to make the synthetic polymer compound capable of mixing with water, compounds having a hydrophilic monomer are preferable. Furthermore, it is more preferable to use synthetic polymer compounds which are obtained by copolymerizing the monomer capable of binding the bio-related material and/or the supporting material with the hydrophilic monomer. That is, in the synthesis of the synthetic polymer compounds, it is preferable to use, as at least monomer species, a monomer capable of forming conjugates by reaction with the bio-related material and/or the supporting material, and having a binding functional group for forming a structure in which the conjugates bind to each other in a state of a chain and/or a network or a block state, and a monomer having hydrophilic or amphipathic functional group, and to copolymerize them. In addition, for controlling a structure such as a micelle and its spread of the synthetic polymer compound formed in a solution, a hydrophobic monomer may be copolymerized.

Examples of the monomer used in radical polymerization, among examples of the monomer constituting the synthetic polymer compound, include polymerizable unsaturated aromatic compounds such as styrene, chlorostyrene, α-methyl styrene, divinyl benzene and vinyl toluene; polymerizable unsaturated carboxylic acids such as (meth)acrylic acid, itaconic acid, maleic acid, and phthalic acid; polymerizable unsaturated sulfonic acid such as styrene sulfonic acid, and styrene sulfonic acid; polymerizable carboxylic acid esters such as methyl (meth)acrylate, ethyl (meth)acrylate, n-butyl (meth)acrylate, 2-hydroxyethyl (meth)acrylate, hydroxypropyl(meth)acrylate, glycidyl(meth)acrylate, N-(meth)acryloyloxysuccinimide, ethylene glycol di(meth)acrylic acid ester, tribromophenyl(meth)acrylate, glycosyloxyethyl (meth)acrylate, and 2-methacryloyloxyethylphosphorylcholine; unsaturated carboxylic acid amides such as (meth)acrylonitrile, (meth)acrolein, (meth)acrylamide, N,N-dimethylacrylamide, N-isopropyl(meth)acrylamide, N-vinyl formamide, 3-acrylamidephenyl boronic acid, N-acryloyl-N'-biotinyl-3,6-dioxaoctane-1,9-diamine, butadiene, isoprene, vinyl acetate, vinyl pyridine, N-vinylpyrrolidone, N-(meth)acryloylmorpholine, vinyl chloride, vinylidene chloride and vinyl bromide; polymerizable unsaturated nitriles; halogenated vinyl compounds; conjugated dienes; macromonomers such as polyethylene glycol mono(meth)acrylate and polypropylene glycol mono(meth)acrylate, and the like.

As the monomers of the synthetic polymer compound, monomers used in addition polymerization can be used. Examples of the monomer used in the addition polymerization include aliphatic or aromatic isocyanates, ketenes, epoxy group-containing compounds and vinyl group-containing compounds, such as diphenyl methane diisocyanate, naphthalene diisocyanate, tolylene diisocyanate, tetramethyl xylene diisocyanate, xylene diisocyanate, dicyclohexanediisocyanate, dicyclohexylmethane diisocyanate, hexamethylene diisocyanate, and isophorone diisocyanate. As a monomer to be reacted with the above-mentioned compounds, compounds having a functional group with active hydrogen can be used. Examples thereof are compounds having hydroxyl group or amino group, and specifically polyols such as ethylene glycol, diethylene glycol, propylene glycol, 1,4-butanediol, 1,6-hexanediol, glycerin, trimethylolpropane, pentaerythritol, sorbitol, methylene glycoside, saccharose, and bis(hydroxyethyl)benzene; polyamines such as ethylenediamine, hexamethylenediamine, N,N'-diisopropyl methylenediamine, N,N'-di-sec-butyl-p-phenylene diamine, and 1,3,5-tri aminobenzene; and oximes.

Further, the synthetic polymer compound may be used together with a functional compound which will be a cross-linking agent, in addition to the above-mentioned monomers. Examples of the polyfunctional compound include, for example, N-methylolacrylamide, N-ethanol acrylamide, N-propanol acrylamide, N-methylol maleimide, N-ethylol maleimide, N-methylol maleic amide acid, N-methylol maleic amide acid ester, vinyl aromatic acids such as N-alkylolamide (for example, N-methylol-p-vinyl benzamide, and the like), N-(isobutoxymethyl)acrylamide, and the like. Of the above-mentioned monomers, polyfunctional monomers such as divinyl benzene, divinyl naphthalene, divinyl chlorohexane, 1,3-dipropyl benzene, ethylene glycol di(meth)acrylate, diethylene glycol di(meth)acrylate, diethylene glycol di(meth)acrylate, butylene glycol, trimethylolethane tri (meth)acrylate, and pentaerythritol tetra(meth)acrylate can be used as a cross-linking agent.

Examples of the monomer having succinimide group, epoxy group, aldehyde group, maleimide group or the like, among the monomers having the binding functional group capable of binding the above-mentioned supporting material and/or the bio-related material include N-(meth)acryloyloxysuccinimide, (meth)acrylic acid glycidyl, acrolein, maleimide acrylate, and the like. Examples of the monomer having boronic acid group as the binding functional group include 3-acrylamide phenylboronic acid, and the like. Examples of the monomer having biotin group as the binding functional group include N-acryloyl-N'-biotinyl-3,6-dioxaoctane-1,9-diamine, and the like. Examples of the monomer having saccharide or polysaccharide as the binding functional group include glycosyloxyethyl 2-(meth)acrylate, and the like.

Further, examples of the hydrophilic monomer include (meth)acrylic acid, itaconic acid, 2-hydroxyethyl(meth)acrylate, 2-hydroxypropyl(meth)acrylate, maleic acid, sulfonic acid, sodium sulfonate, (meth)acrylamide, N,N-dimethyl (meth)acrylamide, N-isopropyl acrylamide, N-vinyl formamide, (meth)acrylonitrile, N-(meth)acryloylmorpholine, N-vinyl pyrrolidone, N-vinyl acetamide, N-vinyl-N-acetamide, polyethylene glycol mono(meth)acrylate, glycidyl (meth)acrylate, 2-methacryloxyethyl phosphoryl choline, and the like.

Further, it is preferable that the compound for carry-immobilization is electrically uncharged. When monomers used for forming the synthetic polymer compounds, which are used as the compound for carry-immobilization, are electrically uncharged, the obtained synthetic polymer compounds are also electrically uncharged, and accordingly such electrically uncharged monomers can be used without particular limitations. Examples thereof include 2-hydroxyethyl(meth)acrylate, 2-hydroxypropyl(meth)acrylate, (meth)acrylamide, N,N-dimethyl(meth)acrylamide, N-isopropyl acrylamide, N-vinyl formamide, (meth)acrylonitrile, N-(meth)acryloylmorpholine, N-vinylpyrrolidone, N-vinyl acetamide, N-vinyl-N-acetamide, polyethylene glycol mono(meth)acrylate, glycidyl(meth)acrylate, and the like.

When the radical polymerization of the monomers is performed to obtain the synthetic polymer compounds, the polymerization is initiated by mixing the monomers with a radical polymerization initiator. Examples of the radical polymerization initiators used herein include azo(azobisnitrile) type initiators such as 2,2'-azobisisobutyronitrile, 2,2'-azobis(2-methylpropanenitrile), 2,2'-azobis(2,4-dimethylpentanenitrile), 2,2'-azobis(2-methylbutanenitrile), 1,1'-azobis(cyclohexanecarbonitrile), 2,2'-azobis(2,4-dimethyl-4-methoxyvaleronitrile), 2,2'-azobis(2,4-dimethylvaleronitrile), and 2,2'-azobis (2-amidinopropane)hydrochloride; peroxide type initiators such as benzoyl peroxide, cumene hydroperoxide, hydrogen peroxide, acetyl peroxide, lauroyl peroxide, persulfates (for example, ammonium persulfate), and peracid esters (for example, t-butylperoctate, α-cumylperoxy pivalate, and t-butyl peroctate), and the like.

Further, the polymerization may be initiated by mixing the monomer with a redox initiator. Examples of the redox initiator include ascorbic acid/iron sulfate (II)/sodium peroxydisulfate, tert-bytylhydroperoxide/sodium disulfite, tert-butylhydroperoxide/Na hydroxymethanesulfinic acid, and the like. Individual components such as a reduction component may be mixtures such as a mixture of sodium salt of hydroxymethanesulfinic acid, and sodium disulfite.

As the synthetic polymer compound, polymer compounds which are synthesized by ring-opening polymerization may be used. Examples thereof include polyethylene glycol, and the like.

Further, polymer compounds which are synthesized by hydrolysis and the like may be used. Examples thereof include polyvinyl alcohol which is obtained by hydrolysis of the polyvinyl acetate, and the like.

Also, as the polymer compounds, photoreactive polymer compounds may be use. Examples thereof include, for example, photoreactive polyallyl amine (Bioconj. Chem., 9, 277 (1998) and the like), photoreactive polyacrylic acid (Langmuir, 14, 6610, (1998) and the like), and the like. When they are used, in the formation of the pre-determined matrix of the supporting material and the bio-related material, light such as ultra violet rays are irradiated, thereby forming the pre-determined matrix.

The synthetic polymer compounds may be synthesized by chemical modification with a functional group capable of binding to the bio-related material and/or the supporting material.

In addition, compound for carry-immobilization, commercially available, synthetic polymer compounds may be used. Examples thereof include SUNBRIGHT series, DE-030AS, DE-030CS, DE-030GS, PTE-100GS, PTE-100GS, PTE-200 GS, HGEO-100GS, and HGEO-200GS, which are made by NOF Corporation, and the like.

On the other hand, when the natural polymer compounds are used as the compound for carry-immobilization, examples thereof include polysaccharides such as dextran, carboxymethyl dextran, starch, cellulose, agarose, gum arabic, and alginic acid; proteins such as pectine, albumin, collagen and gelatin; DNA, RNA, nucleic acid, and the like. These natural compounds may be used as they are, or modified ones may also be used.

Of the above-mentioned compounds, in the present invention, it is preferable to use compound which have an ability of cross-linking the bio-related material. Specifically, for example, synthetic polymer compounds which are formed from the combination of a monomer having a cross-linkable functional group at the side chain and an amphipathic monomer are preferably used. Of these, synthetic polymer compounds which are formed from the combination of N-acryloyloxy-succinimide and N-acryloylmorpholine, the combination of N-acryloyloxy-succinimide and dimethyl acrylamide, and the like, are preferably used.

When the polymer compounds such as the synthetic polymer compounds and the natural polymer compounds are used as the compound for carry-immobilization, the polymer compounds can be used in any state. For example, aqueous solution containing the dissolved compound may be used, and an assembly such as micelle or emulsion may be used.

Examples of the organic-inorganic hybrid used as the compound for carry-immobilization include, for example, metal colloid on which a polymer is coated (such as gold, silver or platinum particles on which a protective colloid is coated); porous substrate such as clay in which a polymer is adsorbed, and the like. The organic-inorganic hybrid can be synthesized in a known method (see Polymer Nanocomposite, Kogyo Chosakai, written by Susumu Nakajyo, and the like).

By modifying the organic-inorganic hybrid with the binding functional group of the bio-related material, the obtained compound can also be used as the compound for carry-immobilization.

The molecular weight and the structure of the compound for carry-immobilization are not particularly limited, and any compounds can be used and, therefore, low molecular compounds may be used. In such a case, however, there is a case where the cross-linking is caused in one biomaterial to be immobilized, and therefore the pre-determined matrix structure cannot be formed. For preventing this, the compound for carry-immobilization has a molecular weight of usually 1000 or higher, preferably 10,000 or higher, and it is usually 1,000,000 or smaller, preferably 500,000 or smaller. When the synthetic or natural polymer compounds are used as the compound for carry-immobilization, it is preferable that weight average molecular weights are within the above-mentioned range, because if the molecular weight is lower than the above-mentioned range, the pre-determined matrix may not be effectively formed.

The content of the binding functional groups contained in the binding functional group is usually 0.1% by mole or higher based on the compound for carry-immobilization, preferably 1% by mole or higher, more preferably 5% by mole or higher, and it is usually 90% by mole or lower, preferably 80% by mole or lower, more preferably 70% by mole or lower. When the content is lower than the range, the compound for carry-immobilization may not efficiently bind to the supporting material or the bio-related material, and when the content is higher than the range, the compound may not be mixed with the solvent.

V-1-5. Solvent

When the bio-related material immobilized carrier of the invention is produced, a mixture comprising at least the supporting material, the bio-related material and the compound for carry-immobilization is supplied to the solid-state carrier in a solvent.

In the solvent, the supporting material, the bio-related material, and the compound for carry-immobilization may be mixed in any state, and they may be dissolved or dispersed. In order to stably bind the supporting material, the bio-related material, and the compound for carry-immobilization, however, it is preferable that the bio-related material and the compound for carry-immobilization are dissolved. The supporting material may be sufficiently mixed and dispersed.

The solvent is a reaction medium in which the bio-related material and/or the supporting material and the compound for carry-immobilization are bound. Any solvents may be used without limitations so long as the supporting material, the bio-related material, and the compound for carry-immobilization can be mixed. It is preferable to select the solvent in consideration of the activity, the structure stability, and the functionality of the supporting material, the bio-related material and the compound for carry-immobilization, but usually water is used as the solvent. When the immobilization is performed in the presence of water, it is possible to sufficiently maintain the activity of the bio-related material, and the range of choice of the supporting material, the bio-related material, and the compound for carry-immobilization can be expanded, and therefore, the expansion of the application range can be expected.

Solvents other than water may be used as the solvent, and for example, organic solvents can be used. Among the organic solvents, amphipathic organic solvents, which can be mixed with water, are preferable.

Examples of the solvent other than water include THF, DMF, NMP, DMSO, dioxane, acetonitrile, pyridine, acetone, glycerin, and the like, in addition to alcohol solvents such as methanol, ethanol, and 1-butanol.

A salt may be added to the solvent. Any salts may be used, and examples thereof include NaCl, KCl, sodium phosphate, sodium acetate, calcium chloride, sodium hydrogenecarbonate, ammonium carbonate, and the like. The amount of the salt used is not limited and any amount can be used according to the use.

When water is used as the solvent, solutions in which a solute other than the biomaterial and the compound for carry-immobilization is dissolved in water can be used in addition to purified water. Examples thereof include various buffers such as carbonate buffer, phosphate buffer, acetate buffer, and HEPES buffer.

The solvents may be used alone or as a mixture thereof in any ratio.

V-1-6. Mixture

The mixture contains the supporting material, the bio-related material, and the compound capable of binding to the bio-related material and/or the supporting material in a solvent. Specifically, it is a mixture containing the supporting material, the bio-related material, and the compound for carry-immobilization in the above-mentioned solvent. It is preferable that in the mixture, the supporting material, the bio-related material and the compound for carry-immobilization are mixed with the solvent.

Any mixing ratios of the supporting material, the bio-related material and the compound for carry-immobilization may be used in the mixture, so long as the pre-determined matrix can be formed. As mentioned above, it is preferable that the bio-related material and the compound are dissolved in the solvent, and the supporting material is mixed or dispersed. For example, when the above-mentioned latex particles are used as the supporting material, the concentration of the latex particles suspended in the mixture is about 0.5 to 10% [w/w].

Further, methods for preparing the mixture are not limited, and any methods can be used. For example, a dispersion of the supporting material, a solution (aqueous solution) or a dispersion of the bio-related material, and a solution (aqueous solution) or a dispersion of the compound for carry-immobilization may be mixed; or to a mixture of two of them may be added the other solutions.

Any additives may be added to the above-mentioned mixture, in addition to the supporting material, the bio-related material, the compound for carry-immobilization, and the solvent. Examples of the additive include salts, acids, bases, buffers, moisturizing agents such as glycerin, stabilizers for the bio-related material such as metal ions, e.g. zinc, anti-foaming agents, modifiers, and the like.

V-1-7. Supply

When the bio-related material immobilized carrier of the invention is produced, the above-mentioned mixture is supplied to the solid-state carrier. That is, the mixture is contacted with the solid-state carrier. Any concrete operations may be used. For example, the mixture is previously prepared and the mixture may be contacted with the solid-state carrier, or each component of the mixture is prepared separately and the mixture may be prepared in the presence of the solid-state carrier to contact it with the solid-state carrier. Specifically, for example, a dispersion containing the supporting material, a solution (an aqueous solution or the like) containing the bio-related material, and a solution (an aqueous solution or the like) containing the compound are supplied to the solid-state carrier separately, and then the solutions are stirred in the presence of the solid-state carrier. Alternatively, when the mixture is previously prepared, conjugates and/or pre-determined matrix mentioned below may be produced in the mixture before supply, and then the mixture may be supplied to the solid-state carrier.

V-1-8. Formation of Pre-Determined Matrix

Next, the binding of the supporting material, the bio-related material and the compound are formed such that the compound binds to the bio-related material and/or the supporting material, which is a core, through a binding site to form a pre-determined matrix in the state of a chain, network or block on the surface of the solid-state carrier. When the mixture is prepared, the supporting material, the bio-related material and the compound for carry-immobilization are bound in the mixture, and conjugates comprising the three components in any ratio are formed. The conjugates are ones in which the supporting material, the bio-related material and the compound for carry-immobilization are bound, which can be produced by only stirring the supporting material, the bio-related material and the compound for carry-immobilization in a solvent to contact them. Consequently, in the mixture supplied to the solid-state carrier, there are usually conjugates.

In a step in which a part or all of the solvent is removed by drying, or the like, the conjugates aggregate, the supporting material, the bio-related material, and the compound for carry-immobilization, which are contained in the conjugates, bind to form the pre-determined matrix in the state of a chain, network or block. That is, when the mixture, which is supplied to the solid-state carrier, is contacted with the solid-state carrier, for example, the conjugates in the mixture are aggregated on the surface of the solid-state carrier; the pre-determined matrix in which the conjugates bind to each other in the mixture binds to the solid-state carrier; the supporting material, the bio-related material and the compound for carry-immobilization in the mixture bind to the surface of the solid-state carrier to form the conjugates and/or pre-determined matrix, whereby the pre-determined matrix can be formed on the surface of the solid-state carrier.

When there is a large amount of the solvent in the mixture, there is a case where it is difficult to generate conjugates or a pre-determined matrix in the mixture, or they are not generated. In such a case, by concentrating the mixture, the conjugates can be formed efficiently. When the mixture, which is supplied to the solid-state carrier, as mentioned above, has the conjugates and/or pre-determined matrix, of course, the concentration may be performed, whereby the conjugates and/or pre-determined matrix is further produced. In order to form a uniform pre-determined matrix, it is preferable to uniformly mix the supporting material, the bio-related material and the compound for carry-immobilization in the solvent in an initial stage of the preparation of the mixture. Therefore, it is preferable that the supporting material, the biomaterial and the compound for carry-immobilization are contained in a relatively large amount of a solvent, and then the mixture is concentrated to generate conjugates.

Since the mixture is usually concentrated during the drying step of the mixture, the concentration and drying can be carried out in a series of operation. Any methods for drying and concentrating may be used, and examples thereof include, for example, ultrafiltration, drying under reduced pressure, and the like. In addition, evaporation under normal pressure may be carried out to dry or concentrate.

Preferably, the solid-state carrier of the invention has spaces formed by removing a part or all of the solvent in the pre-determined matrix, as mentioned above. It is preferable that the solvent is removed by drying as mentioned above. The conjugates form the strong pre-determined matrix and the spaces are formed in the pre-determined matrix by this drying step.

For example, the temperature, when the mixture is dried and concentrated, is usually 37° C. or lower, preferably 25° C. or lower, from the viewpoint of avoiding the denaturation of the bio-related material.

Also, the moisture and pressure condition, when the mixture is dried or concentrated, are suitably set, in consideration of the formation state of the pre-determined matrix or the spaces in the pre-determined matrix.

In order to completely immobilize the pre-determined matrix on the solid-state carrier, it is desirable that the solid-state carrier is allowed to stand for a pre-determined period of time after supplying the mixture. Although the period of time is arbitrary, it is usually 24 hours or shorter, preferably 12 hours or shorter. That is, after the above-mentioned mixture is supplied to the solid-state carrier, it is allowed to stand for a pre-determined time to sufficiently promote the formation of the conjugates and the immobilization to the surface of the carrier, and then, the solvent may be removed by drying or the like. When such a step is performed, the solid-state carrier of the invention on which the pre-determined matrix having satisfactory spaces and film thickness is firmly formed can be produced.

One example of the formation steps of the pre-determined matrix is schematically shown in FIG. 10(a) to FIG. 10(c). As shown in FIG. 10(a) to FIG. 10(c), the mixture comprising the bio-related material, the compound for carry-immobilization and the supporting material is supplied to the solid-state carrier (FIG. 10(a)), the conjugate comprising the three components in any ratio is formed (FIG. 10(b)), and then, the solvent is removed to form the pre-determined matrix having a structure in which the bio-related material and the compound for carry-immobilization bind to the supporting material, which is a core, in the state of a chain and/or network and/or block, and having void layers (FIG. 10(c)). FIG. 10(a) to FIG. 10(c)

are schematic views showing enlarged cross-section of one example of the bio-related material immobilized carrier of the invention, for explaining the structure of the pre-determined matrix. In FIG. 10(*a*) to FIG. 10(*c*), painted circular parts show the bio-related materials, linear parts show the compound for carry-immobilization, open circular parts show the supporting material, a hatching part shows the solvent, and blank spaces show the void layers.

V-1-9. Other Steps

As mentioned above, the above-mentioned method is a very easy method in which the mixture comprising the supporting material, the bio-related material and the compound for carry-immobilization in the solvent is only contacted with solid-state carrier to form the pre-determined matrix on the surface of the solid-state carrier, whereby the biomaterial-immobilized carrier of the invention can be produced, in other words, the bio-related material can be immobilized on the solid-state carrier.

In the production of the biomaterial-immobilized carrier, steps other than the above-mentioned steps may be performed.

For example, a different biomaterial may be bound to the biomaterial in the pre-determined matrix. If this technique is utilized, after the production of the biomaterial-immobilized carrier, a different biomaterial which is modified so that it specifically binds to the bio-related material in the pre-determined matrix is bound later; as a result, the different bio-related material can be immobilized on the solid-state carrier in a high density. Specifically, avidin is used as the bio-related material, and this avidin, the supporting material and the compound for carry-immobilization are bound to form the pre-determined matrix, thereby producing the biomaterial-immobilized carrier. After that, a different bio-related material, which is modified with biotin, can be immobilized by avidin-biotin interaction. Similarly, the bio-related material can be immobilized through a histidine tag or a glutathione-S-transferase.

V-2. Bio-Related Material Immobilized Carrier

The bio-related material immobilized carrier of the invention is produced by the above-mentioned method. The pre-determined matrix contained in the bio-related material immobilized carrier of the invention has a structure in which a number of the above-mentioned conjugates bind to the supporting material, which is a core, and is a structure in which the bio-related material and the compound for carry-immobilization are bound in the state of a chain and/or a network, or a block, as shown in FIG. 8.

Further, the pre-determined matrix is a structure having a core of the above-mentioned supporting material, and the principal chain comprising the bio-related material and the compound for carry-immobilization. Here, the principal chain of the pre-determined matrix forms the skeleton of the pre-determined matrix, and specifically, it is formed by surrounding the supporting material with the bio-related material and the compound for carry-immobilization to form a lump, and aggregating at least one of the lump. In detail, the compound for carry-immobilization binds to the supporting material and/or the bio-related material through the binding functional group, or the like to form a cross-linking structure, and such structures are aggregated to form a structure in the state of a chain and/or network, or block.

In this manner, the pre-determined matrix at least partially contains a cross-linked structure in which there is the bio-related material or the supporting material between compounds for carry-immobilization, and the principal chain of the pre-determined matrix is formed by both of the bio-related material and the compound, and the supporting material, which is the core. That is, the pre-determined matrix is produced in the presence of all of the supporting material, the bio-related material and the compound for carry-immobilization in the production system.

Further, the preferable bio-related material immobilized carrier of the invention has, as mentioned above, spaces formed by removing a part or all of the solvent in the pre-determined matrix. The solvent is preferably removed by drying, as mentioned above, by which the above-mentioned conjugates form the strong pre-determined matrix and spaces in the pre-determined matrix.

It is confirmed by the observation using an electron microscope such as a scanning electron microscope (SEM) or a transmission electron microscope (TEM) that the pre-determined matrix has the principal chain comprising the bio-related material and the compound for carry-immobilization, and the supporting material, which is the core. The spaces formed in the pre-determined matrix and the film thickness can also be confirmed in the same manner.

Here, the space is an empty space sterically formed in the pre-determined matrix, and is formed between the chain, network or block shapes contained in the pre-determined matrix. Any spaces can be used so long as sufficient reactivity can be maintained, and preferable ones include crack (fissure or break)-like spaces and micropore-like spaces which porous materials have. The shape of the space can be confirmed by using an electron microscope or the like.

A porosity is a ratio of a space occupying the pre-determined matrix. Examples of the method for measuring the porosity include, for example, a method of analyzing images using an electron microscope, a gas adsorption method, an Hg porosity method, and the like.

Any porosity can be used according to the purpose, and for example, an porosity obtained by analyzing a cross-sectional view of an SEM or TEM image in a dry pre-determined matrix is preferably 5% or higher. Known methods for processing image data can be applied to the image analysis in this case, and there is a method in which an obtained SEM photograph is read with a scanner, noises are removed, a background image is made, shading correction is conducted, particle area is set, the image is formed into a binary phase at the set threshold value, and an area ratio is found.

When the porosity is too low, the diffusion of the related interacting substance into the pre-determined matrix is reduced, or the ratio of the immobilized bio-related material, which exposes on the surface, is lowered, whereby the reaction efficiency between the bio-related material and the related interacting substance can be lowered. Further, the non-specific reaction can be increased due to the lowered washing efficiency. On the contrary, when the porosity is too high, sufficiently strength of the film cannot be maintained. These defects can be controlled by optimizing the formation conditions of the pre-determined matrix, as mentioned above.

Although the film thickness of the pre-determined matrix is arbitrary, it is usually 5 nm or more, preferably 10 nm or more, more preferably 20 nm or more, measured by SEM or TEM in the dry pre-determined matrix. When the film thickness is too thin, it is difficult to obtain a uniform film thickness of the pre-determined matrix, and it is difficult to immobilize a large amount of the bio-related material with a high reproducibility. The film thickness of the pre-determined matrix is a thickness from a contact surface with the solid-state carrier to the immobilized carrier surface in a cross-section of the bio-related material-immobilized carrier of the invention.

In the structure of the pre-determined matrix, the above-mentioned shape of the space, the porosity, and the film thickness can be optimized by selecting the appropriate compound capable of binding to the bio-related material and supporting material according to the purpose, and suitably selecting the structure ratio thereof, immobilization condition, and removal conditions of solvents, and the like.

V-3. Effects

The bio-related material immobilized carrier of the invention immobilizes more inexpensively the bio-related material in a larger amount and a higher degree of precision than conventional ones.

As the method for increasing the immobilization amount, for example, a method in which a solution containing the bio-related material in a high concentration is directly spotted to the solid-state carrier is frequently used. According to this method, however, it is known that, in a step for drying the spotted solution (liquid droplet), steam flux from the liquid droplet is not constant by location, and the flux from outside of the liquid droplet is large. In other words, it is known that flux of the solution from the center of the liquid droplet to the end part occurs in the inside of the liquid droplet, and, with the flux, the solute, which is the bio-related material, flows from the center to the end, and thus, the bio-related material is deposed at the end of the liquid droplet with the evaporation of the solvent, and the bio-related material is locally immobilized in a high concentration at the peripheral part of the spot, thus resulting in the formation of ring spots. The ring spots cause a major problem in measuring steps after the reaction, and one cause of increasing a CV value and lowering the degree of precision of measurement.

According to the conventional technique as described in Patent Documents 1 to 3, the bio-related material is bound to the polymer compound film (polymer film) formed on the surface of the solid-state carrier. In this case, however, the bio-related material is bound to the solid-state carrier in such a manner that the bio-related material is bound to the polymer chain terminal in the principal chain of the polymer chain, or bound to the polymer chain in the state of a graft, and therefore, it is necessary to form the polymer chain as the principal chain and it is necessary to use the polymers in a certain amount or more with respect to the bio-related material to be immobilized, which limits the amount of the bio-related material immobilized.

Also, the bio-related material is disproportionately placed on the film surface, and there is no space where the related interacting substance can enter into the polymer film, thus resulting in a low reactivity. Further, according to the conventional technique in which the principal chain is formed from only the hydrophilic polymer, it can be considered that the access of the interacting substance to the biomaterial is prevented by the excluded volume effect of the hydrophilic polymer chain and the movement of the polymer chain (see Real Time Analysis Experimental Method for Biomaterial Interaction—focused on BIA CORE, edited by Kazuhiro Nagata, and Hiroshi Handa, published by Springer-Verlag Tokyo Kabushiki Kaisha, page 258; Development and Application of Polymer Material for Pharmaceutical Polymer, CMC, page 19).

Further, the conventional technique of Non-Patent Document 2 has a disadvantage that, since the solid-state carrier is porous, the surface area is wide, and therefore a large amount of the bio-related material can be bound, but it is necessary to make the solid-state carrier with a special shape utilizing a porous membrane filter or a special immobilization apparatus, as a result, the solid-state carrier is expensive and limited.

Further, for example, when the pre-determined matrix is formed by using the bio-related material and the compound alone, although the bio-related material can be immobilized in a larger amount compared to a case where only the bio-related material is bound to the carrier, it is usually difficult to form a sufficient film thickness and space, and when the spotting is performed, ring spots are generated, whereby it is difficult to obtain a sufficient degree of precision. Even if a large amount of the bio-related material is immobilized to obtain a sufficient film thickness, if spaces are insufficiently formed, the reaction efficiency can be lowered by impairing the reactivity of the bio-related material in the film, or insufficiently diffusing the related interacting substance to be reacted therewith. In particular, for example, when a combination of an antigen and an antibody or a combination of a protein and a ligand is used as the combination of the bio-related material and the detection target material, the immobilization amount is large, and it is necessary to expose them on the surface in order to maintain the biological activity of the immobilized substance and to contribute the reaction, because the antigen-antibody reaction caused therebetween is a weak biological reaction.

The bio-related material immobilized carrier of the invention can solve these conventional defects. It is very advantageous from the viewpoint that it can form a strong pre-determined matrix with a sufficient film thickness, compared to the conventional technique, by containing three components of the bio-related material, the compound capable of binding to the bio-related material, and the supporting material; that the sufficient immobilization amount is obtained, and that the spaces are formed therein. That is, a large amount of the bio-related material can be immobilized three-dimensionally and almost uniformly on the solid-state carrier. Since the spaces can be a reaction site where the immobilized bio-related material reacts, when the bio-related material immobilized carrier of the invention is utilized in a biosensor or a diagnostic device, sufficient reactivity and sensitivity can be obtained.

The bio-related material immobilized carrier of the invention is advantageous from the point that mixture concentration (mixing ratio of the constituent elements), the temperature, the moisture, and the pressure conditions are optimized during the formation of the pre-determined matrix, whereby the pre-determined matrix having any features can be easily produced in high degree of precision without unevenness. According to the conventional method, many steps are required to immobilize the biomaterial in a high density. Specifically, in the conventional technique, a polymer film is previously formed on the solid-state carrier, and the biomaterial is immobilized on the polymer film, and the pre-determined matrix containing the ligand is immobilized on the solid-state carrier, or a special structure such as a porous carrier is required. According to these methods, however, when the polymer film is formed on the solid phase, it is necessary to suitably control the molecular amount of the polymer or the introduction density to the solid-state carrier, and thus the operation is very troublesome, and it is difficult to perform the immobilization with a high reproducibility; or in case of the porous carrier, the influence by the diffusion of the bio-related material in the porous carrier is generated in immobilization. In particular, according to the method of Patent Document 3, it is technically difficult to form the polymer chain from the solid-state carrier surface in the state of a blush, which is not suitable for mass-production.

On the contrary, the bio-related material immobilized carrier of the invention is very easily produced by only contacting the mixture containing the supporting material, the bio-related material and the compound for carry-immobilization in the solvent with the solid-state carrier, whereby the pre-determined matrix can be formed on the solid-state carrier, in other words, can be immobilized on the bio-related material. Also, it has no disadvantages such that the solvent used in the production of the bio-related material immobilized carrier is limited to an organic solvent, according to which the biomaterial, which can be used, is limited, as in the technique described in Patent Document 2, whereby the range of choice of the bio-related material to be immobilized can be expanded.

Also, the shape, the film thickness or the porosity of the pre-determined matrix formed on the bio-related material immobilized carrier of the invention can be arbitrarily changed by changing the amounts and ratios of the supporting material, the bio-related material, and the immobilized compound and/or the shape of the supporting material under controlled temperature, moisture and pressure conditions. According to the conventional technique, it is usually difficult to arbitrarily control the film thickness of the pre-determined matrix from submicron to several microns. According to the present invention, however, it is possible to control the film thickness of the pre-determined matrix at a precise level, and therefore, the degree of freedom of the design of the pre-determined matrix can be increased.

For example, when an immunoassay is performed, the thickness of the film used for the immobilization is required to immobilize a large amount of the bio-related material and to inhibit the non-specific reaction, and the optimum film thickness depends on the material. Alternatively, for example, when medical instruments and carriers for regenerative medicine are surface-treated, the film thickness is required to be an order of micron for film used in the surface-treatment, in order to realize sufficient strength and coating film. Further, for example, when the surface-treatment of drugs used in DDS (drug delivery system) is performed, it is required to strictly control the thickness of the film used for the surface-treatment, for controlling the drug release. As mentioned above, when the immobilization of the biomaterial is performed utilizing some film, it is known that the control of the film thickness is important, but the control is difficult in the conventional technique. According to the present invention, however, the film thickness can be arbitrarily controlled by controlling a concentration and an amount of the mixture and reaction conditions (temperatures and times), according to the use.

Further, when the bio-related material immobilized carrier of the invention is used in order to interact the bio-related material with the related interacting substance, the non-specific interaction caused by the pre-determined matrix constituent elements other than the bio-related material can be inhibited. This can be attained by increasing the percentage of the bio-related material in the pre-determined matrix, thereby decreasing the percentage of the substances other than the bio-related material, which cause the non-specific interaction.

When an electrically uncharged substance is used as the compound for carry-immobilization, the non-specific interaction caused by charge can further reduced. That is, for example, in the method described in Patent Document 1, since a polymer film is electrically charged, the pH and the ionic strength of a buffer solution used exert great influence to the reaction of the biomaterial, and the electrically charged protein cannot avoid the non-specific adsorption caused by electrostatic interaction (see Nanotechnology Basic Series, Bionanotechnology, edited by Yasuhiro Horiike and Kazunori Kataoka, page 186). However, if the electrically uncharged substance is used as the compound for carry-immobilization, then the above-mentioned trouble can be avoided, and a specific interaction can be caused selectively, which leas to higher sensitivity in measurement.

V-4. Bio-Related Material Immobilization Kit

In order to produce the above-mentioned bio-related material immobilized carrier, a bio-related material immobilization kit in which at least the supporting material and the compound for carry-immobilization are formed into a kit, may be used. When the bio-related material immobilization kit is used, the pre-determined matrix can be easily produced or the bio-related material immobilized carrier of the invention can be easily formed, on the solid-state carrier, and therefore, a large amount of the bio-related material can be easily immobilized on the solid-state carrier.

The supporting material contained in the bio-related material immobilize is as mentioned above. The supporting material can be contained in the biomaterial-immobilization kit in any state. For example, the compounds may be in any state such as a solution in which it is dissolved in any solvent, a dispersion in which it is dispersed in any dispersion medium, a solid such as powder, or lump.

The compound for carry-immobilization contained in the bio-related material immobilize is as mentioned above. The compound for carry-immobilization can be contained in the biomaterial-immobilization kit in any state. For example, the compounds may be in any state such as a solution in which it is dissolved in any solvent, a dispersion in which it is dispersed in any dispersion medium, a solid such as powder, or lump.

Further, the bio-related material immobilization kit may contain other elements as necessary.

For example, a solvent may be further added. The solvents are the same solvents used in the production of the bio-related material immobilized carrier. The solvent in the bio-related material immobilization kit may be provided separately from the supporting material and the compound for carry-immobilization; or may be contained together with the supporting material and the compound for carry-immobilization as the solvent or the dispersion medium of the supporting material or the compound for carry-immobilization.

For example, it may contain a reagent which facilitates the production of the pre-determined matrix. Specifically, when polyacrylic acid is used as the compound for carry-immobilization, 1-ethyl-3-(3-dimethylaminopropyl)carbodiimide hydrochloride (abbreviation: EDC) may be contained as a drug, in order to activate carboxyl group in the polyacrylic acid.

V-5. Use

The bio-related material immobilized carrier of the invention can be used in a wide industrial range. The uses are not limited, and it can be used in any use. Usually, it is suitably used in a use utilizing an "interaction" between the bio-related material and the related interacting substance (analyte) which specifically interacts with the bio-related material.

For example, the bio-related material immobilized carrier of the invention can be suitably used in a biosensor which detects the related interacting substance, which interacts with the bio-related material, as an analyte. The above-mentioned biosensor analyzes the interaction using a sensor chip immobilized with DNA or a protein, which is referred to as a DNA array or DNA chip, or a protein array or protein chip. The bio-related material immobilized carrier of the invention can be applied to the sensor chip. That is, when the bio-related material is immobilized on the sensor chip, the pre-determined matrix is formed on the sensor chip body by the above-mentioned method, and the sensor chip can be used as the bio-related material immobilized carrier of the invention.

Examples of the biosensor to which the bio-related material immobilized carrier of the invention can be applied, include a sensor by fluorescence method, chemiluminescence method, RI method, FRET method, SPR (surface plasmon resonance) method, QCM (quartz crystal microbalance) method, piezo type canti-lever method, laser type canti-lever method, mass spectroscopy, electrode method, field effect transistor (FET) method, FET and/or single electron transistor method using a carbon nanotubes, electrochemical method and the like. Of these, the detections by the chemifluorescence method are suitably used, because a sample can be analyzed with high sensitivity.

For example, the bio-related material immobilized carrier of the invention is applied to the chemiluminescence method, in order to firmly bind the pre-determined matrix to the sensor chip body, it is preferable that the sensor chip body has functional groups on its surface. In this case, any functional groups can be used, and examples thereof include hydroxyl group, carboxyl group, thiol group, aldehyde group, hydrazide group, carbonyl group, epoxy group, vinyl group, amino group, succinimide group, and the like.

For example, when the bio-related material immobilized carrier of the invention is applied to a fluorescence method, it is desirable to use materials having a low self-fluorescence, as the solid-state carrier, the supporting material and the compound for carry-immobilization, and when the self-fluorescence is caused, it is preferable to use a time resolution fluorescence.

For example, the bio-related material immobilized carrier of the invention is suitably used in diagnostic devices, utilizing the characteristics as the biosensor. In the diagnostic device, low molecular compounds such as protein, for example, antibodies, antigens and enzymes, nucleic acids, for example, DNA and RNA, drugs, and antibiotic substance are frequently used as a target to be detected, and preferable measurement methods include chemiluminescence method, fluorescence method, RI method, and the like.

The bio-related material immobilized carrier of the invention is suitably used for assaying an analyte in a sample, as a biosensor, or the like. The method for assaying the analyte of the invention is a method for assaying at least one analyte in the sample, which comprises (a) sending the sample to the immobilized carrier and/or array of the invention, which comprises at least one bio-related material capable of reacting with the analyte; and (b) detecting an interaction between the bio-related material and the analyte or a reaction caused by adding a target substance which reacts with the analyte, whereby the presence, or the amount of the analyte is detected.

Here, any sample can be used so long as it contains an analyte or it may contain an analyte, and the preferable ones are samples derived from a living body such as human. Examples of such a sample, for example, include a body fluid such as blood, serum, plasma, urine, gaeces, nassal discharge, and buccal secretion; cell, composition or organ, and their extracts, and the like. The analytes are as described above.

Now, assays using the bio-related material immobilized carrier of the invention will be described in detail by showing an exemplary case in which antigen antibody reaction is detected using chemiluminescence method.

A bio-related material immobilized carrier on which an antibody (primary antibody) against an antigen, which is an analyte, is immobilized together with a supporting material and a compound for carry-immobilization and the antigen in a sample are reacted for a pre-determined time; next, substances other than unreacted antigen and antigen are removed by washing or the like; then, an antibody (labeled secondary antibody) against the antigen, which is labeled with an enzyme, is reacted for a pre-determined time; and the redundant labeled secondary antibody is removed by washing. In this manner, a sandwich structure made of the primary antibody, the antigen, the enzyme-labeled secondary antibody is formed (sandwich method). The method for assaying the detection label using the antigen-antibody reaction is not limited to the sandwich method, and other methods such as an inhibition method, which are widely known in the immunoassay field, can be used.

After completing the reaction, a chemiluminescence substrate corresponding to the enzyme is added to produce a chemiluminescence based on the presence or amount of the analyte, or the antigen, and light signals emitted from the test area is detected using a detector.

The enzyme used herein includes horseradish peroxidase (HRP), alkaline phosphatase (ALP), and the like. As the substrate, luminol in case of using the HRP, or 1,2-diosetane in case of using the ALP is used.

As the detector, charge coupled device (CCD) camera, photomultiplier tube (PMT), photodiode (PD) and the like are used. In case of an array in which two or more bio-related materials are one-dimensionally or two-dimensionally immobilized, the CCD camera, the photodiode array, and a switching type PMT are preferable as the detector.

In this assay, the sample can be sent to the bio-related material immobilized carrier of the invention or the array in the state of a flow. In such case, it is preferable that at least the sample is fluid, and it is more preferable that other regents are fluid. First, a cell (flow cell) containing an bio-related material immobilized carrier on which an antibody (primary antibody) against an antigen, which is an analyte, is immobilized together with the supporting material and the compound for carry-immobilization is formed, to which the sample is sent with flow to react the antigen in the sample for a pre-determined time. Next, washing liquid is sent to the flow cell with the flow to remove substances other than unreacted antigen and antigen. After that, a solution containing an antibody (labeled secondary antibody) against the antigen, which is labeled with an enzyme, is sent to the flow cell with the flow and the reaction is conducted for a pre-determined time. Washing liquid is sent to the flow cell again to remove the redundant labeled secondary antibody, whereby a sandwich structure made of the primary antibody, the antigen, and the enzyme-labeled secondary antibody is formed (sandwich method). The procedure used, the enzyme and the detector are the same as mentioned above.

In any case, a reference area is previously provided on the bio-related material immobilized carrier of the invention, and the success or failure of the assay is judged, or the judgment of the presence of the analyte and correction of the amount of the detected analyte can be performed by comparing with the reaction detected in the reference area. For example, an analyte, or an antigen, having a certain known concentration is immobilized at a known area (reference area) on a solid-state carrier on which a bio-related material is immobilized, and the assay is conducted in the same manner as mentioned above. Then, the chemiluminescence is generated in the reference area, too. Light signals emitted from the reference area are detected with the above-mentioned detector, and the obtained values are compared with the values obtained from light signals emitted from the reaction by the analyte in the sample, whereby the calculation or correction of the concentration of the analyte can be performed.

Since as to the light signals emitted from the reference area, the emission strength can be previously known, the success or failure of the assay can be judged based on the strength of the light signals.

In the above-mentioned assay method of the invention, a method in which two or more analytes are assayed at the same time, and the presence or amount of the measured analyte is associated with a specific symptom is preferably used. Such a method is very useful as a "panel test" or a "profile test." The panel test is a test in which multiple test markers are combined and more detailed test is conducted as some disease or symptom. For example, in case of a diagnosis of a cancer, it is difficult to specify a place where the cancer is when only one tumor marker shows a high value; but the kind and site of the tumor can be identified by examining multiple tumor markers. The "profile test" is a test in which, in judgment of outcome and treatment effects of the disease treatment, multiple test markers including conventional test markers are measured, different base values for different patients are set using the multifactor analysis of the obtained results, and the variation is analyzed in detailed. Such analysis results are useful as the knowledge for suitably treating without missing a small change in clinical conditions or avoiding a side-effect upon medication.

Specifically, for example, in a test for hierarchization of the degree of risk in a patient with acute coronary syndrome in diagnosis of cardiac infract, all of three kinds of markers, which change independently, that is a B-type natriuretic peptide (BNP), which is a neurohormone marker, troponin T or I, which is an ischemia marker, and a C-reactive protein (CRP), which is an inflammation maker, are measured, and the obtained results are utilized in the judgment of the outcome. Other tests using combinations of various test makers have been proposed, and the bio-related material immobilized carrier, the array and the assay method of the invention are very suitably used in such tests.

Further, the bio-related material immobilized carrier of the invention can be applied to surface treatment of drugs for DDS (drug delivery system); surface treatment of a carrier for regenerative medicine, surface treatment of an artificial organ, surface treatment of a catheter and the like.

Example

Now, the present invention will be described more specifically by means of Examples. The present invention is not limited to the following Examples, and any modification can be made without departing the scope of the invention. In the description of the Examples, "%" is "% by weight" unless noted otherwise 1. Examples with Respect to the Biomaterial Structure and the Biomaterial-Carrying Object (No. 1)

Examples in which a biomaterial structure and a biomaterial-carrying object were studied, focusing on structures of particulate lumps are shown as follows:

Example 1-1

Affinity Purification Using a Biomaterial Structure which was not Immobilized on a Solid-State Carrier (1) Synthesis of Compound for Binding (Polymer A1)

A monomer, N-acryloylmorpholine (NAM made by KOHJIN CO., LTD.) 1.13 parts by weight, N-acryloyloxysuccinimide (NAS made by ACROS ORGANICS) 0.33 parts by weight, and a solvent, dehydrated dioxane (made by Wako Pure Chemical Industries, Ltd.) 18.03 parts by weight were thoroughly mixed, and the mixture was poured into a 50 mL-four necked flask, which was degassed at room temperature for 30 minutes under nitrogen to give a monomer solution.

The temperature of this monomer solution was elevated to 60° C. in an oil bath, to which a solution in which a polymerization initiator azobisisobutyronitrile (AIBN made by Kishida Chemical Co., Ltd.) 0.0016 parts by weight was dissolved in dehydrated dioxane 0.5 g was added to start the polymerization. The polymerization was performed for 8 hours under a nitrogen atmosphere.

After the polymerization, the solution containing the produced polymer was added dropwise to 0.5 L of diethyl ether (made by Kokusan Chemical Co., Ltd.) to precipitate the polymer again, and then the solvent was removed to give a compound for binding polymer A1 as a powder.

As to the obtained polymer A1, SEC (Size Exclusion Chromatography) measurement which was corrected by standard polystyrene was performed. As a result, it was estimated that the polymer A1 had a weight average molecular weight (Mw) of about 150,000.

The molar ratio (NAS/NAM) of NAS and NAM contained in the obtained polymer A1 was estimated to be NAS/NAM=30/70 according to the $^1$H-NMR measurement.

Further, the polymer A1 was diluted with distilled water to adjust the concentrations to 0.2%, 0.4%, and 0.6%, and dynamic optical scattering method was carried out at measured angles of 30°, 40°, 50° and 60°, using a photon correlation measuring device ALV 5000 (made by ALV), and the average hydrodynamic radius of the polymer A1 was estimated to be 6.8 nm.

(2) Production of Biomaterial Structure A

To an eppendorf tube (hereinafter, sometimes, referred to as "eppen tube") was added 500 µL of a liquid containing the biomaterial, a mouse IgG (made by LAMPIREBIOLOGICAL LABORATORIES; Mw=150 kDa) and the compound for binding polymer A1 in a HEPES buffer (10 mM, pH 7.4) in the weight ratio of the mouse IgG:the compound for binding polymer A1=10:1, which was dried at normal temperature under reduced pressure to form a biomaterial structure. The total concentration of the mouse IgG and the compound for binding polymer A1 in the prepared liquid was 10 mg/mL.

After that, the biomaterial structure was concentrated and dried. To this biomaterial structure was added an HEPES buffer 1 mL, and the centrifugation operation (5000 rpm, 10 minutes; hereinafter the centrifugation operation was conducted under these condition, unless noted otherwise), was conducted, whereby the floating biomaterial structure was precipitated and the supernatant was removed.

Further, the HEPES buffer 1 mL was added thereto, the same operation was repeated twice.

Next, in order to block the unreacted succinimide group, 1M of ethanol amine (pH 8.5) 1 mL was added thereto, and the immersion was conducted at room temperature for 15 minutes, and then the supernatant was removed with centrifugation operation.

Further, in order to remove the mouse IgG which was not bound to the polymer A1 through covalent binding, the immersion with a solution containing 1M of KCl in HEPES buffer 1 mL (1M KCl-HEPES) was conducted for 15 minutes, and the supernatant was removed. A glycine buffer (10 mM, pH 1.7) was added thereto, and the supernatant was removed through the centrifugation operation. Finally, the HEPES buffer (pH 7.4) 1 mL was added thereto, and the supernatant was removed through the centrifugation operation to give a biomaterial structure A.

(3) Affinity Purification Using Biomaterial Structure A 1 mL of liquid (mixed solution A) obtained by adding rabbit serum anti-mouse Fab' (purification separation specific target material A which specifically interacts with the mouse IgG) (made by Immuno Probe, Inc., Mw=about 50 kDa) (4.3 mg/mL) to rabbit serum (NRS) (protein concentration: about 70 mg/mL), and having a rabbit serum anti-mouse Fab' concentration of 100 µg/mL, was poured into the eppen tube in which the biomaterial structure A obtained in the above-mentioned step (2), and the immersion was conducted for 30 minutes, and the supernatant was separated through the centrifugation operation (supernatant A).

Further, 1 mL of HEPES buffer was added thereto, the supernatant was removed through the centrifugation operation. This operation was repeated four times.

After that, 1M KCl-HEPES solution 1 mL was added thereto, and the washing was conducted through the centrifugation operation (washing A).

Further, in order to retrieve the specifically bound target material, an aqueous glycine buffer (10 mM, pH 1.7) solution 1 mL was added thereto, the immersion was conducted for 10 minutes. After that, the supernatant (purification A) was retrieved by the centrifugation operation.

After that, with respect to the mixed solution A, the target material A, the supernatant A, the washing A, and the purification A, electrophoresis was conducted by SDS-PAGE, and then, the electrophoretic gel was stained by a silver staining method. As a molecular weight marker, a full range rainbow marker PRN 800 (made by Amersham) was used. The results are shown in FIG. 11.

In the purification A, only the Fab', which was a target material, was observed and, that is, it was confirmed that the separation/purification could be performed without contaminating with non-specific adsorption substances by the above-mentioned purification operation.

Example 1-2

Analysis of Structure and Composition of Biomaterial Structure (4) Production of Biomaterial Structure Basal Plate 1

As a solid-state carrier supporting the biomaterial structure, a flat polycarbonate base plate having a size of length: 2.5 cm×width: 2.5 cm×thickness: 1.2 mm, whose surface was coated with gold deposited in a thickness of about 80 nm, was used. A surface treatment was conducted by immersing this basal plate in an ethanol solution of 10 mM of 16-mercaptohexadecanoic acid (made by ALDRICH), and conducting the reaction at room temperature for 12 hours. After finishing the reaction, the basal plate was washed with ethanol. The surface treatment was conducted for introducing carboxyl group to the basal plate surface through gold-sulfur binding.

Next, a 0.1 M aqueous solution of N-hydroxysuccinimide (NHS, made by Wako Pure Chemical Industries, Ltd.) 1 mL and a 0.4 M aqueous solution of 1-ethyl-3-(3-dimethylaminopropyl) carbodiimide hydrochloride (EDC, made by Dojindo Laboratories,) 1 mL were mixed, which was diluted with desalted water 18 g, the basal plate into which carboxyl groups were introduced was immersed in the obtained solution, and the reaction was conducted for 15 minutes. This treatment was conducted in order to introduce succinimide groups, which can bind the biomaterial structure to the basal plate, to the surface of the basal plate.

20 µL of a mixture of mouse IgG and polymer A1 in the weight ratio of 10:1 (biomaterial:compound for binding) was spotted on the surface of the basal plate, which was allowed to stand under a saturated vapor pressure for 30 minutes, and then was dried at room temperature, and the unreacted active ester group was blocked with ethanol amine.

After that, the basal plate was immersed in the HEPES buffer of 1M-KCl (15 minutes×2), then in the glycine buffer (10 mM, pH 1.7) (15 minutes×1), and unreacted protein was washed off.

After that, the plate was thoroughly washed with desalted water, and dried to give a biomaterial structure basal plate 1.

(5) Affinity Purification Using Biomaterial Structure Basal Plate 1

100 µL of a solution (mixed solution 1) obtained by adding anti-mouse Fab' (target material 1) to NRS and having a concentration of the anti-mouse Fab' (target material 1) of 100 µg/mL was added dropwise to the biomaterial structure basal plate 1. The plate was allowed to stand under a saturated vapor pressure for 30 minutes, and the sample was retrieved (Flow through 1). After that, the biomaterial structure basal plate 1 was washed. The washing was conducted by pre-washing with desalted water and immersing in the HEPES buffer of 1M-KCl (15 minutes×3).

Further, in order to retrieve the anti-mouse Fab' bound by antigen-antibody reaction, the biomaterial structure basal plate 1 was immersed in glycine buffer (10 mM, pH 1.7), the anti-mouse Fab' was retrieved together with the glycine buffer (purification 1). After that, with respect to the mixed solution 1, the target material 1, Flow through 1, and the purification 1, the electrophoresis according to SDS-Page was conducted, and then, the electrophoretic gel was stained by a silver staining method. The results are shown in FIG. 12. In the purification 1, the separation/purification of the separation target material Fab' could be performed without contaminating with non-specific adsorption substances.

(6) Observation of Structure of Biomaterial Structure Basal Plate 1

A cross-section of the biomaterial structure formed on the surface of the biomaterial structure basal plate 1 was observed with SEM (scanning electron microscope), and the surface thereof was observed with AFM (atomic force microscope). As the observation results with SEM, a photograph is shown in FIG. 13 instead of a drawing, and as the observation results with AFM, a photograph is shown in FIG. 14 instead of a drawing.

From FIGS. 13 and 14, it was confirmed that the obtained biomaterial structure had a structure composed of particulate lumps continuously bound to each other, each particle comprising the biomaterial and the compound for binding and having a particle diameter of 100 nm or less.

(7) Component Analysis of Biomaterial Structure Basal Plate 1 Structure

A biomaterial structure basal plate for component analysis was produced in the same manner as in the above-mentioned (4) except that 40 spots (each being 1 µL) of the mixture was spotted on the basal plate.

Then, the biomaterial structure on the biomaterial structure basal plate for component analysis was hydrolyzed with hydrochloric acid, and IgG was quantified from an amount of the generated amino acid. Further, the compound for binding polymer A1 was quantified from an amount of polyacrylic acid in the hydrolysate.

Specifically, the biomaterial structure on the biomaterial structure basal plate for component analysis was hydrolyzed with 6N hydrochloric acid at 150° C. for 1 hour. After that, hydrochloric acid was dried under reduced pressure, and the hydrolysate was dissolved in 1% aqueous ammonia, and insoluble matter was removed through centrifugation separation (10000 rpm, 3 minutes). This hydrolyzed solution was dried under reduced pressure, which was dissolved in 1 mL of 0.1% aqueous ammonia. 100 µL of the solution was used in amino acid analysis and 400 µL of the solution was used in PAA (polyacrylic acid) analysis.

(Sample for Amino Acid Analysis)

The above-mentioned hydrolyzed solution 100 µL was dried under reduced pressure, which was dissolved in 500 µL of 0.02 N hydrochloric acid. This solution was subjected to a centrifugation-type ultrafiltration (MWCO: 10000, Microcon YM-10), and a filtrate 10 µL was subjected to amino acid analysis.

The amino acid analysis was conducted under the conditions described in the following Table 1-1.

TABLE 1-1

| Apparatus | Hitachi High Speed Amino Acid Analyzer L-8500 |
|---|---|
| Analysis conditions | Bio-amino acid separation condition - ninhydrin coloring method (570 nm, 440 nm) |
| Standard | Standard amino acid mixed solution made by Wako Pure Chemical Industries, Ltd. (each containing amino acid 200 uM) |
| Sample | Sample for hydrolysis 10 µL |
| Quantitative calculation | An amino acid content was calculated from a peak area at 440 nm for Pro or at 570 nm for other amino acids, according to the one-point external standard method. |

(Sample for Polyacrylic Acid Analysis)

The above-mentioned hydrolyzed solution 400 µL was concentrated through centrifugation-type ultrafiltration (MWCO: 10000), and was diluted with 400 µL of 1% aqueous ammonia. The dilution-concentration operation through this ultrafiltration was repeated 6 times to remove a low molecular component. A polymer component was retrieved with 1% aqueous ammonia, which was dried under reduced pressure. The resulting product was subjected to a polyacrylic acid (PAA) analysis.

The PAA analysis (reaction thermal decomposition GCMS) was performed in the conditions described in the following Table 1-2.

TABLE 1-2

| Apparatus | HP 5973 MSD made by Agilent |
|---|---|
| Analysis conditions | Thermal decomposition temperature 550° C. |
| Column | DB-1 60 m × 0.25 umφ (film thickness: 1 µm), 50° C. (1 min) – 10° C./min – 260° C. (10 min) |
| Detection | MS (SIM, m/z = 129, 85, 75) |
| Standard | Polyacrylic acid 2000 33 ug/mL × 10 uL |
| Sample | 10 µL |
| Quantitative calculation | A PAA content was calculated from a peak area at m/z = 129, according to the one-point external standard method. |

As a result, the mouse IgG of 390 µg and polymer A1 of 16.9 µg were detected, and the ratio of the biomaterial contained in the biomaterial structure [the weight of the biomaterial/the weight of the biomaterial structure] was 0.958. That is, it was shown that the weight ratio of the biomaterial contained in the biomaterial structure was very high.

Example 1-3

Affinity Purification Using Biomaterial Structure Immobilized on Solid-State Carrier (8) Production of Biomaterial Structure Basal Plate 2

A biomaterial structure basal plate 2 was produced in the same manner as in the above-mentioned (4) except that the mouse IgG was changed to protein A (made by Sigma) and the HEPES buffer was changed to a phosphate buffer (pH 9).

(9) Affinity Purification Using Biomaterial Structure Basal Plate 2

100 µL of NRS (mixed solution 2) was added dropwise to the biomaterial structure basal plate 2, which was allowed to stand under a saturated vapor pressure for 30 minutes, and the sample was retrieved (Flow through 2). After that, the biomaterial structure basal plate 2 was washed. The washing was conducted by pre-washing with desalted water and immersing in the HEPES buffer of 1M-KCl (15 minutes×3). Further, in order to retrieve the IgG binding to the protein A, the biomaterial structure basal plate 2 was immersed in glycine buffer (10 mM pH 1.7), and the anti-mouse IgG was retrieved together with the aqueous HCl solution (purification 2). With respect to the mixed solution 2, Flow through 2, and the purification 2, the electrophoresis was conducted by SDS-Page. After that, the electrophoretic gel was stained by a silver staining method. The results are shown in FIG. 15. It was found that the substance obtained in the purification 2 was IgG, from the result that the molecular weight of the marker was about 150,000 in the purification 2.

From the results, it was confirmed that the separation/purification of IgG, which was the target material, was performed without contamination resulting from the non-specific adsorption.

Example 1-4

Measurement of Amounts of Biomaterial Structure and Target Material which has Interacted with Biomaterial Structure

(10) QCM Measurement

A polymer was synthesized as a compound for binding in the same manner as in the above-mentioned (1) (hereinafter referred to as "polymer B1"), whereupon, 0.564 parts by weight of NAM, 0.169 parts by weight of NAS, 8.75 parts by weight of dioxane, and 0.008 parts by weight of AIBN were used. It was measured that the obtained polymer B1 had a weight average molecular weight (Mw) of about 86,000, and a molar ratio of NAS and NAM of NAS/NAM=30/70.

Sensor chips for QCM (made by Initium Inc.) were prepared by subjecting to surface-treatment in the same manner as in the production of the biomaterial structure basal plate 1 in the above-mentioned (4).

A biomaterial structure having mouse IgG as the biomaterial was immobilized on the sensor chip for QCM in the same manner as in the above-mentioned (4) except that the spot amount was changed from 20 μL to 3 μL, and the polymer B1 was used as the compound for binding.

After that, the sensor chips for QCM were immersed in 10 μg/mL of the HEPES buffer of anti-mouse Fab' (10 mM, pH 7.4) for 1 hour, whereupon the adsorption behavior was measured by using QCM AFFNIX Q (made by Initium Inc.) in each step of the above-mentioned operation. Specifically, after the surface treatment (that is, after conducting the surface treatment and before forming the biomaterial structure); after the biomaterial structure immobilization (that is, before immersing in the aqueous solution of anti-mouse Fab'); or after the reaction with the anti-mouse Fab' (that is, after immersing in the aqueous solution of the anti-mouse Fab'), measurement was conducted. All measurement values were obtained from the products which were dried in air. The results are shown in Table 1-3.

TABLE 1-3

|  | Frequency (Hz) |
| --- | --- |
| After the surface treatment | 26998199 |
| After the immobilization of the biomaterial structure | 26955509 |
| After the anti-mouse Fab' reaction | 26946203 |

A frequency change between values obtained after the immobilization of biomaterial structure and values obtained after the surface treatment was −42690 Hz. Accordingly, an amount of the biomaterial structure was calculated to be about 25.6 μg/cm$^2$ on the QCM sensor chip after the immobilization of the biomaterial structure.

Also, a frequency change between values obtained after the anti-mouse Fab' reaction and values obtained after the immobilization of biomaterial structure was −9306 Hz. Accordingly, an adsorption amount of the anti-mouse Fab' on the QCM sensor chip was calculated to be about 5.6 μg/cm$^2$, after reacting the anti-mouse Fab'.

Example 1-5

Study about Conditions for Forming Biomaterial Structure

(11) Production of Biomaterial Structure Basal Plate 3

A biomaterial structure basal plate 3 was produced in the same manner as in the above-mentioned (8) except that the biomaterial was changed from the mouse IgG to an albumin (PIG ALBUMIN made by Sigma).

(12) Production of Biomaterial Structure Basal Plate 4

A biomaterial structure basal plate 4 was produced in the same manner as in the above-mentioned (8) except that the biomaterial was changed from the mouse IgG to a streptavidin (made by PIERCE).

(13) Reference Example

Production of Basal Plate for Reference, from Glutaraldehyde

A basal plate (basal plate for reference) supporting the biomaterial for reference was produced in the same manner as in the above-mentioned (11) except that glutaraldehyde (made by Tokyo Chemical Industry Co., Ltd., a molecular weight: 100) was used instead of the polymer A1.

(14) Comparison According to AFM Observation

The biomaterial structure basal plates 3 and 4, and the basal plate for reference were respectively observed with AFM, and their structures were confirmed. As the results, photographs are shown in FIG. 16(a) to FIG. 16(c) instead of drawings. FIG. 16(a) shows the observation results of the biomaterial structure basal plate 3; FIG. 16(b) shows the observation results of the biomaterial structure basal plate 4; FIG. 16(c) shows the observation results of the basal plate for reference.

In FIG. 16(a) and FIG. 16(b), it is observed that far greater shadings than those observed in the protein molecule were observed. From these results, it was confirmed that when the compound for binding was used in suitable conditions, as in FIG. 16(a) and FIG. 16(b), the biomaterial structure was formed by binding the particulate lumps.

On the other hand, sizes of the shadings observed in FIG. 16(c) were from about 5 to 10 nm, which is the same as one molecule of the protein. Accordingly, it was known that in the basal plate for reference observed in FIG. 16(c), there were no particulate lumps, and the structure was formed by closely binding the protein molecules through glutaraldehyde. From this result, it was confirmed that when a low molecular weight compound such as glutaraldehyde was used as the compound for binding, if the biomaterial structure was not prepared in suitable conditions which were different from the conditions used for polymer compound such as the polymer A1, it was difficult to form the particulate lumps. Consequently, the biomaterial structure should be prepared in suitable conditions depending on the physical properties of the compound for binding, and the like.

Example 1-6

Confirmation of Spaces Between Particulate Lumps by Swelling

(15) Swelling Confirmation of Biomaterial Structure Basal Plate 1

A biomaterial structure basal plate was produced in the same manner as in the above-mentioned (7) (hereinafter referred to as biomaterial structure basal plate 6), and the film thicknesses of the representative one spot were measured in a dry condition and a wet condition with a solvent according to AFM. As the solvent, HEPES buffer (10 mM, pH 7.4) was used, and the film thickness was measured 30 minutes after the immersion in a solvent.

As a result, the film thickness in a dry condition was 3.7 µm; whereas the thickness after the immersion in the solvent was 5.2 µm. From this result, it was confirmed that the spaces were formed between the particulate lumps in the biomaterial structure on the biomaterial structure basal plate 6.

2. Examples and Comparative Examples with Respect to Biomaterial Structure and Biomaterial-Carrying Object (No. 2)

Examples in which a biomaterial structure and a biomaterial-carrying object were studied, focusing on structures of a matrix principal chain, are shown as follows:

Synthesis of Polymer

Compound for Binding

Production Example 2-1

Synthesis of Polymer A2

A monomer, N-acryloylmorpholine (NAM made by KOHJIN CO., LTD.) 0.564 parts by weight, N-acryloyloxysuccinimide (NAS, made by ACROS ORGANICS) 0.169 parts by weight, and a solvent, dehydrated dioxane (made by Wako Pure Chemical Industries, Ltd.) 8.75 parts by weight were thoroughly mixed, and the mixture was poured into a 50 mL-four necked flask, which was degassed at room temperature for 30 minutes under nitrogen to give a monomer solution. The temperature of this monomer solution was elevated to 60° C. in an oil bath, to which a solution in which a polymerization initiator azobisisobutyronitrile (AIBN made by Kishida Chemical Co., Ltd.) 0.008 parts by weight was dissolved in dehydrated dioxane 0.5 g was added to start the polymerization. The polymerization was performed for 8 hours under a nitrogen atmosphere.

After the polymerization, the solution containing the produced polymer was added dropwise to 0.5 L of diethyl ether (made by Kokusan Chemical Co, Ltd.) to precipitate the polymer again, and then the solvent was removed to give a polymer A2 as a powder.

The SEC measurement, which was corrected by standard polystyrene, of the obtained polymer A2 was performed. As a result, it was estimated that the polymer A2 has a weight average molecular weight (Mw) of about 86,000.

Also, the molar ratio (NAS/NAM) of NAS and NAM contained in the obtained polymer A2 was estimated to be NAS/NAM=30/70 according to the NMR measurement.

Production Example 2-2

Synthesis of Polymer B2

A polymer-B2 was obtained in the same manner as in Production Example 2-1 (synthesis of polymer A2) except that dimethyl acrylamide (DMAA made by KOHJIN CO., LTD.) 0.793 parts by weight and NAS 0.338 parts by weight were used as the monomers, instead of NAM and NAS, and the amount of the dehydrated dioxane used, which was the solvent, was changed to 18.37 parts by weight, and the amount of AIBN used, which was the polymerization initiator, was changed to 0.00164 parts by weight.

The SEC measurement, which was corrected by standard polystyrene, of the obtained polymer B2 was performed. As a result, it was estimated that the polymer B2 has a weight average molecular weight (Mw) of about 26,000.

Also, the molar ratio (NAS/NAM) of NAS and NAM contained in the obtained polymer B2 was estimated to be NAS/NAM=43/57 according to the NMR measurement.

Production Example 2-2'

Synthesis of Polymer C2

A polymer C2 was obtained in the same manner as in Production Example 2-1 (synthesis of polymer A2) except that NAM 1.13 parts by weight and NAS 0.33 parts by weight were used as the monomers, the amount of dehydrated dioxane, which was the solvent, was changed to 18.03 parts by weight, and the amount of AIBN used, which was the polymerization initiator, was changed to 0.0016 parts by weight.

Surface Treatment for Sensor Chip

Production Example 2-3

SPR Sensor Chip A

As a sensor chip for SPR, a polycarbonate basal plate having a size of length: 2.5 cm×width: 2.5 cm×thickness: 1.2 mm, having a diffraction grating with a groove pitch of about 870 nm and a groove depth of about 40 nm on its surface, and having gold deposited on its surface in a thickness of about 80 nm was used.

The sensor chips coated with gold was immersed in a 10 mM ethanol solution of 16-mercaptohexadecanoic acid (made by ALDRICH) and the reaction was conducted at room temperature for 12 hours to treat the surface. After finishing the reaction, the sensor chips coated with gold was washed with ethanol. The surface treatment was conducted for introducing carboxyl group to the surface of the sensor chip coated with gold through gold-sulfur binding.

Next, a 0.1M aqueous solution of N-hydroxysuccinimide (NHS, made by Wako Pure Chemical Industries, Ltd.) 1 mL and a 0.4 M aqueous solution of 1-ethyl-3-(3-dimethylaminopropyl) carbodiimide hydrochloride (EDC, made by Dojindo Laboratories,) 1 mL were mixed, which was diluted with desalted water 18 g, the sensor chips coated with gold, into which carboxyl group was introduced, were immersed in the obtained solution, and the reaction was conducted for 15 minutes to give SPR sensor chips to which carboxyl group is introduced. These sensor chips were used as SPR sensor chips A.

Production Example 2-4

Flat Basal Plate Coated with Gold

A basal plate coated with gold obtained in the same manner as in Production Example 2-3 (surface treatment of SPR sensor chip A) except that the plate did not have a grating was subjected to the same surface treatment as in Production Example 2-3 (surface treatment of SPR sensor chip A) to give a flat basal plate B coated with gold.

Production of Sensor Chip for Measurement

Production Example 2-5

SPR Biosensor Chip 1

10 µL of a 1% aqueous solution of polymer A2 (compound for binding) in 10 mM HEPES buffer (pH 7.4) and 100 µL of an aqueous solution of 1% mouse IgG (made by Lampirebiological Laboratories, Mw=150 kDa; biomaterial) were mixed, and the resulting mixture 1 µL was added dropwise to the SPR sensor chips A, and the immobilization was performed under a saturated vapor pressure for 30 minutes. After that, the solvent was evaporated by air-drying, and then, the chips were immersed in a 1M aqueous solution of ethanol amine hydrochloric acid salt (made by SIGMA, pH 8.5) for 15 minutes to block unreacted succinimide groups, and further, the basal plate was washed with desalted water to give SPR biosensor chips as the biomaterial-carrying object of the invention. These chips were used as SPR biosensor chips 1.

Production Example 2-6

SPR Biosensor Chip 2

SPR biosensor chips were produced in the same manner as in Production Example 2-5 (Production of SPR biosensor chip 1) except that the polymer B2 produced above was used as the compound for binding instead of the polymer A2. The thus produced SPR biosensor chip, which is the biomaterial-carrying object of the invention, was used as an SPR biosensor chip 2.

Production Example 2-7

SPR Biosensor Chip 3

SPR biosensor chips were produced in the same manner as in Production Example 2-5 (Production of SPR biosensor chip 1) except that the concentration of the aqueous polymer A2 solution as the aqueous solution of the compound for binding was changed to 1%, 100 µL of a P-SA aqueous solution having 5% of albumin from pigs (P-SA made by Sigma, Mw=about 60 kDa; biomaterial) in the above-mentioned HEPES buffer was used as the aqueous solution of the biomaterial instead of the aqueous mouse IgG solution. The thus produced SPR biosensor chip, which is the biomaterial-carrying object of the invention, was used as an SPR biosensor chip 3.

Production Example 2-8

Concentration-Dependent SPR Biosensor Chip

The polymer A2 (compound for binding) was diluted with 10 mM HEPES buffer (pH 7.4) to give concentrations of 0.1%, 0.2%, 0.5% and 1.0%, and the mouse IgG (biomaterial) was diluted with 10 mM HEPES buffer (pH7.4) to give concentrations of 0.1%, 0.2%, 0.5%, and 1.0%. 10 µL of the aqueous polymer A2 solution and 100 µL of aqueous mouse IgG solution, both having the same concentration, were mixed, and each of the mixed liquid 1 µL was added dropwise to the above-mentioned SPR sensor chip A, and the immobilization was conducted under a saturated vapor pressure for 30 minutes. After that, the air-drying, blocking and washing were performed in the same manner as in Production Example 2-5 (Production of SPR biosensor chip 1), to produce SPR biosensor chips. The thus produced SPR biosensor chip, which is the biomaterial-carrying object of the invention, was used as a concentration-dependent SPR biosensor chip.

Production Example 2-9

Chip for Electron Microscope Observation

A through-hole having a diameter of 10 mm was formed in a silicon rubber having a length of 15 mm, a width of 15 mm and a thickness of 2 mm, and it was closely attached to the above-mentioned flat basal plate B coated with gold. Separately, 10 µL of a 1% aqueous solution of the polymer A2 in 10 mM of HEPES buffer (pH 7.4) and 100 µL of a 1% aqueous mouse IgG solution were mixed, and the through-hole in the chip B for electron microscope observation to which the silicon rubber was closely attached, was filled with 100 µL of the mixed liquid. After that, the immobilization was performed under a saturated vapor pressure for 30 minutes, and then the solvent was evaporated by air-drying. Then the silicon rubber was removed, and the blocking and the washing were performed in the same manner as in Production Example 2-5 (Production of SPR biosensor chip 1) to produce a basal plate coated with gold. The thus produced basal plate coated with gold, which is the biomaterial-carrying object of the invention, was used as a chip for electron microscope observation.

Production Example 2-10

Biosensor Chip a for Fluorescence Analysis

A basal plate coated with gold was produced in the same manner as in Production Example 2-9 (Production of chip for electron microscope observation) except that the size of the silicon rubber was changed to a length of 2.5 cm, a width of 2.5 cm and a thickness of 0.5 mm, and the diameter of the through-hole was changed to 0.5 mm. The thus produced basal plate coated with gold, which is the biomaterial-carrying object of the invention, was used as a biosensor chip A for fluorescence analysis.

Production Example 2-11

Chip for Confirmation of Matrix Principal Chain

SPR biosensor chips were produced in the same manner as in Production Example 2-5 except that the concentration of the aqueous polymer A2 solution, which is the aqueous solution of the compound for binding, was changed to 0.3%, and the concentration of the aqueous biomaterial solution was changed to 0.3%. The thus produced SPR biosensor chip, which is the biomaterial-carrying object of the invention, was used as a chip for confirmation of matrix principal chain.

Production Example 2-12

Chip for Component Analysis

A chip for component analysis was produced in the same manner as in Production Example 2-5 except that the polymer C2 was used as the compound for immobilization, and 40 spots, each spot having 1 µL, of the mixture were spotted on the above-mentioned flat coated basal plate B.

Production Example 2-13

Prism Type SPR Biosensor Chip

Multi SPR inter Au Chip (made by TOYOBO CO., LTD.) as the basal plate was subjected to the same surface treatment as in Production Example 2-3. The resulting basal plate was used as a prism type SPR sensor chip. A biomaterial-immobilized carrier of the present invention was produced on the flat prism type SPR sensor chip in the same manner as in Production Example 2-5 except that the concentrations of the polymer A2 and mouse IgG were changed to 0.3%. This chip was used as the prism type SPR biosensor chip.

Comparative Production Example 2-1

Comparative SPR Biosensor Chip 2D

An SPR biosensor chip was produced in the same manner as in Production Example 2-5 (production of SPR biosensor chip 1) except that 1 μL of a 1% aqueous mouse IgG solution (aqueous biomaterial solution) was used instead of the mixed liquid of the aqueous polymer A2 solution and the aqueous mouse IgG solution. The thus produced SPR biosensor chip was used as a comparative SPR biosensor chip 2D.

Comparative Production Example 2-2

SPR Biosensor Chip for Concentration Comparison

Mouse IgG (Mw=about 150 kDa; biomaterial) was diluted with 10 mM of HEPES buffer (pH 7.4) to give concentrations of 0.1%, 0.2%, 0.5% and 1.0%. 1 μL of each solution was added dropwise to the SPR sensor chip A, and the immobilization, the air-drying, the blocking and the washing were conduced in the same manner as in Production Example 2-5 (Production of SPR biosensor chip 1) to give an SPR biosensor chip. The thus produced SPR biosensor chip was used as the SPR biosensor chip for concentration comparison.

Comparative Production Example 2-3

Polyacrylic Acid SPR Biosensor Chip

The same sensor chip coated with gold (one before the surface treatment) as used in Production Example 2-3 was immersed in a 10 mM aqueous solution of 2-mercaptoethylamine (made by SIGMA), and the reaction was conducted at room temperature. After finishing the reaction, the sensor chip coated with gold was washed desalted water. This surface treatment was conducted for introducing amino group to the surface of the sensor chip coated with gold through gold-sulfur binding. The thus obtained sensor chip coated with gold to which amino group was introduced was used as the SPR sensor chip B.

Next, the SPR sensor chip B was immersed in a solution in which 1.25 g of polyacrylic acid (average molecular weight: 250000 made by Polysciences Inc.) and 24 mg of EDC were dissolved in 25 mL of desalted water, and the reaction was conducted for 1 hour. After finishing the reaction, the chip was washed with desalted water. This treatment was conducted for immobilizing polyacrylic acid on the gold surface (sensor chip surface) through amide binding obtained by condensation of amino group on the gold surface and carboxyl group of the polyacrylic acid with EDC. The thus obtained sensor chip coated with gold, which was surface-treated with polyacrylic acid, was used as a SPR sensor chip C.

1 μL of a 1% aqueous mouse IgG solution (aqueous biomaterial solution) was added dropwise to the above-mentioned SPR sensor chip C, and the immobilization was conducted under a saturated vapor pressure for 30 minutes. After the immobilization, the blocking and the washing were conducted in the same manner as in Production Example 2-5 (production of SPR biosensor chip 1) to produce an SPR biosensor chip. The thus produced SPR biosensor chip was used as a polyacrylic acid SPR biosensor chip. This method is based on a conventional method in which the solid-state carrier is previously coated with a polymer film, and a biomaterial is immobilized on the polymer film.

Comparative Production Example 2-4

Biosensor Chip B for Fluorescence Analysis

A basal plate coated with gold was produced in the same manner as in Production Example 2-10 (production of biosensor chip A for fluorescence analysis) except that a 1% aqueous mouse IgG solution (aqueous biomaterial solution) was used instead of the mixed liquid of the aqueous polymer A2 solution and the aqueous mouse IgG solution. The thus produced basal plate coated with gold was used as a biosensor chip B for fluorescence analysis.

Comparative Production Example 2-5

Comparative Prism Type SPR Biosensor Chip

A comparative prism type SPR biosensor chip was produced in the same manner as in Production Example 2-13 (production of prism type SPR biosensor chip) except that a 0.3% aqueous mouse IgG solution was used instead of the mixed liquid of the polymer A2 and the aqueous mouse IgG solution.

Example 2-1

Fluorescence Analysis

Using the biosensor chip A for fluorescence analysis produced in Production Example 2-10, and the biosensor chip B for fluorescence analysis produced in Comparative Production Example 2-4, the fluorescence analysis of the antigen-antibody reaction (interaction) was performed.

As a sample (interacting substance), Cy5-labeled rabbit serum anti-mouse Fab' (made by Immuno Probe, Inc., Mw=about 50 kDa) was used. The labeling of this sample was performed as follows: First, to CyDye™ Cy5 monofunctional reactive dye 1 vial (made by Amersham Pharmacia Biotech) was added 1 mL of 1 mg/mL rabbit serum anti-mouse Fab', and the reaction was conducted at normal temperature for 30 minutes. The unreacted labeling regent was removed through gel filtration, using NAP-5 Column (made by Axon Instrument). In this manner, as the sample, a Cy5-labeled rabbit serum anti-mouse Fab' was obtained.

In 2 mL of the 10 μg/mL Cy5 labeled rabbit serum anti-mouse Fab' solution, which was prepared by using the above-mentioned labeled rabbit serum anti-mouse Fab', was immersed the gold basal plate, and the reaction was conducted at normal temperature for 10 minutes. The gold basal plate was washed with MilliQ water and dried. The plate was electrically charged in a GenePix 4000A Microarray scanner (made by Amersham Bioscience), and a fluorescence was measured at a wave length of 650 nm.

As a result, the ratio of the fluorescence intensity (average value) of the biosensor chip A for fluorescence analysis and the fluorescence intensity of the biosensor chip B for fluorescence analysis was 11919:250. From this result, it was confirmed that the fluorescence obtained in case of using the biosensor chip A for fluorescence analysis, which is Example of the present invention, was increased by about 48 times the fluorescence obtained in case of using the conventional biosensor chip B for fluorescence analysis.

In FIG. 17(a) and FIG. 17(b), fluorescence observation photographs at the time of fluorescence analysis are shown instead of drawings. FIG. 17(a) is the photograph of the biosensor chip A for fluorescence analysis, and FIG. 17(b) is the photograph of the biosensor chip B for fluorescence analysis. In FIG. 17(a) and FIG. 17(b), white parts are areas where fluorescence is emitted.

Example 2-2

QCM Measurement

10 μL of a 1% aqueous solution of polymer A2 (compound for binding) synthesized in Production Example 2-1 in 10 mM HEPES buffer (pH7.4), and 100 μL of a 1% aqueous solution of the same mouse IgG (biomaterial) as used in Production Example 2-5 were mixed to prepare a mixed liquid (mixture). Separately, a chip for QCM, which was surface-treated, was prepared in the same manner as in the production of the SPR biosensor chip 1 in Production Example 2-5. 3 μL of the above-mentioned mixed liquid was added dropwise to the surface of this chip for QCM, and the immobilization was conducted for 30 minutes. After that, the solvent was removed by air-drying, and the blocking with 1M ethanol amine was conducted to give a QCM biosensor chip. After that, the QCM biosensor chips were immersed in a 10 mM HEPES solution of 10 μg/mL of a rabbit serum anti-mouse Fab' (Mw=about 50 kDa; interacting substance) for 1 hour. At that time, an adsorption behavior was measured by using a QCM AFFINIX Q (made by Initium) at each stage of the above-mentioned operation. Specifically, after the surface treatment (that is, after conducting the surface treatment and before dripping the mixed liquid dropwise), after the formation of the biomaterial structure (namely, matrix), (that is, after dropping the mixed liquid dropwise and before immersing in the rabbit serum anti-mouse Fab' solution) or after the analyte reaction (that is, after immersing in the rabbit serum anti-mouse Fab' solution), the measurement was conducted. All of the measured values are of those dried in air to remove moisture. The results are shown in Table 2-1.

TABLE 2-1

| | Frequency (Hz) |
|---|---|
| After surface treatment | 26998199 |
| After the formation of the biomaterial structure | 26955509 |
| After the analyte reaction | 26946203 |

A variation of the frequency between the value obtained after the formation of the biomaterial structure and the value obtained after the surface treatment was −42690.3 Hz. From this result, an immobilization amount of the biomaterial (mouse IgG) immobilized on the QCM biosensor chip was calculated to be about 25.6 μg/cm².

Also, a variation of the frequency between the value obtained after the analyte reaction and the value obtained after the formation of the biomaterial structure was −9306.1 Hz. From this result, a reaction amount per unit area of the interacting substance in the QCM biosensor chip was calculated to be about 5.6 μg/cm².

Accordingly, it can be estimated that a response ratio is as follows:

$$\text{Response ratio} = (5.6/50\ \text{kDa})/(25.6/150\ \text{kDa}) = 0.66$$

From this result, it was also confirmed that, in the QCM biosensor chip, a ratio (response ratio) of the number (molecular number) of the interacting substance which interacted with the biomaterial to the number (molecular number) of the biomaterial in the biomaterial structure was 0.5 or higher, when the detection liquid to the biomaterial (a solution containing the interacting substance) was contacted the biomaterial structure.

Example 2-3

SPR Measurement

With respect to the SPR biosensor chip 1 produced in Production Example 2-5, and the SPR biosensor chip 2 produced in Production Example 2-6, a measurement of an antibody-antigen reaction (interaction) was performed according to SPR, using as the analyte (sample) 10 μg/mL rabbit serum anti-mouse Fab' (made by Immuno Probe, Inc., Mw=about 50 kDa), and as the buffer a 10 mM HEPES buffer. In a comparison with the Example 2-3, with respect to the comparative SPR biosensor chip 2D produced in Comparative Production Example 2-1, the measurement of the antibody-antigen reaction was performed in the same manner as mentioned above.

As the measuring apparatus, a grading type SPR measuring apparatus, FLEX CHIPS™ Kinetic Analysis System (HTS Biosystems Inc.) was used. The measurement was performed as follows: 10 mM HEPES buffer (pH 7.4) was sent for 2 minutes after the start of the measurement, then, 10 μg/mL of rabbit serum anti-mouse Fab (analyte) was sent for 8 minutes after that, and finally, 10 mM HEPES buffer (pH7.4) was sent for 15 minutes. The sending speeds were all 500 μL/min.

The measurement results are shown in FIG. 18 and FIG. 19.

As apparent from FIG. 18 and FIG. 19, when the SPR measurement was conducted using the biomaterial-carrying object of the invention, i.e. the SPR biosensor chip 1 or 2, an SPR shift amount was larger, compared with the case where the comparative SPR biosensor chip 2D on which the biomaterial was immobilized in the conventional method was used.

Further, resonance angles before the measurement, and differences between a resonance angle obtained after sending the sample and a resonance angle obtained at the initial stage of the measurement are shown in Table 2-2.

Using the above-mentioned SPR sensor chip A (that is, the sensor chip before immobilizing the biomaterial), the same measurement as above was performed. A difference between the resonance angle of the SPR sensor chip A and each of the SPR biosensor chips 1 and 2 and the comparative biosensor chip 2D was also calculated. These resonance angle differences are shown in Table 2-2. From these results, it is known that a larger amount of the biomaterial was immobilized on the SPR biosensor chip 1 or 2 than the amount of the biomaterial immobilized on the comparative biosensor chip 2D.

TABLE 2-2

|  | Resonance angle before measurement (deg) | Difference from the SPR sensor chip A resonance angle (mdeg) | Difference between the resonance angle after sending the sample and the resonance angle at the initial stage of the measurement (mdeg) |
|---|---|---|---|
| SPR sensor chip A | 18.30 | 0 | — |
| SPR biosensor chip 1 | 19.80 | 1500 | 420 |
| SPR biosensor chip 2 | 19.63 | 1330 | 426 |
| Comparative SPR biosensor chip 2D | 18.56 | 260 | 61 |

Here, if all of the biomaterial structures (matrix) were biomaterial, then a ratio (response ratio) of the number (molecular number) of the interacting substance which interacted with the biomaterial to the number (molecular number) of the biomaterial in the biomaterial structure could be calculated as follows:

$$\text{Response ratio} = (420\ \text{mdeg}/50\ \text{kDa})/(1500\ \text{mdeg}/150\ \text{kDa})$$
$$= 0.84$$

In this calculation, the biomaterial structures are assumed to be formed by biomaterials alone; however, the biomaterial structure actually comprises not only the biomaterials but also the compound for binding, and accordingly it can be considered that the actual response ratios will be larger than the calculated value (0.84). From this fact, it was confirmed that when the biomaterial in the biomaterial structure was contacted with the sample (the solution including the interacting substance), a ratio (response ratio) of the number (molecular number) of the interacting substance which interacted with the biomaterial to the number (molecular number) of the biomaterial in the biomaterial structure was 0.5 or higher.

Similarly, the response ratio of the SPR biosensor chip 2 was calculated to be 0.96. The actual response ratio can be considered to be larger than the calculated value (0.96), as in the case of the SPR biosensor chip 1. From this, it was also confirmed that, in the SPR biosensor chip 2, when the biomaterial in the biomaterial structure was contacted with the biosample (the solution containing the interacting substance), the ratio (response ratio) of the number (molecular number) of the interacting substance which interacted with the biomaterial to the number (molecular number) of the biomaterial in the biomaterial structure is 0.5 or higher.

Example 2-4

Test of Non-Specific Interaction

A sensor chip in which the SPR biosensor chip 1 produced in Production Example 2-5 and the SPR biosensor chip 3 produced in Production Example 2-7 were provided on the same basal plate was produce. The detection of the specific adsorption and the non-specific adsorption to each sample was conducted through SPR, using the sensor chip as the samples, the rabbit serum anti-mouse Fab' and rabbit serum anti pig-SA (made by Immuno Probe, Inc., Mw=about 150 kDa), which were used in Example 2-1, being used.

Specifically, a 10 mM HEPES buffer (pH 7.4) was sent for 2 minutes from the start of the measurement; next, 10 µg/mL of rabbit serum anti-mouse Fab' was sent for 8 minutes as a sample; then, the 10 mM HEPES buffer (pH 7.4) was sent for 15 minutes; after that, 100 µg/mL of rabbit serum anti pig-SA was sent for 8 minutes as the biosample, and finally the 10 mM HEPES buffer (pH 7.4) was sent for 15 minutes. The sending speeds were all 500 µL/min. The same measuring apparatus as in Example 2-3 was used. The results are shown in FIG. 20.

The interaction of the SPR biosensor chip 1 to the anti pig-SA is a non-specific interaction, and the interaction of the SPR biosensor chip 3 to the anti-mouse Fab' is a non-specific interaction. Accordingly, if the non-specific interaction occurs, SPR shift would be measured while the sample is measured while sending it, based on the non-specific interaction. However, according to FIG. 20, SPR shift caused by the non-specific interaction was not measured. From this result, it was confirmed that when the SPR biosensor chip 1 or 3 is used, the non-specific interaction little occurs.

Example 2-5

Test of Film Thickness of Biomaterial Structure

An amount of the biomaterial structure immobilized on each area of the biomaterial structure (matrix), which was produced by using each mixed liquids with different concentrations, on concentration-dependent SPR biosensor chip produced in Production Example 2-8 was measured by SPR. The larger the SPR shift amount measured, the larger the immobilization amount. The same SPR measuring apparatus as used in Example 2-3 was used. The relationship between the SPR shift amount and the concentration of the mixed liquid used in the preparation of the concentration-dependent SPR biosensor chip, measured by SPR measurement, are shown in FIG. 21.

For the comparison, with respect to the SPR biosensor chip for concentration comparison, produced in Comparative Production Example 2-2, the immobilization amount of the mouse IgG immobilized by using an aqueous mouse IgG solution with a different concentration was also measured according to SPR. The larger the SPR shift amount measured, the larger the immobilization amount. The obtained relationship between the SPR shift amount and the concentration of the aqueous mouse IgG solution used in the production of the SPR biosensor chip for concentration comparison is also shown in FIG. 21.

FIG. 21 shows that in case of the SPR biosensor chip for concentration comparison in which the biomaterial (mouse IgG) was immobilized alone, the immobilization amount was saturated at about 200 mdeg in terms of the SPR shift amount.

On the contrary, in the biomaterial-carrying object of the invention, or the concentration-dependent SPR biosensor chip, the SPR shift amount is increased linearly along with increase in the concentration of the mixed liquid used in the formation of the biomaterial structure. From this fact, it was confirmed that the film thickness of the biomaterial structure can be controlled by adjusting the concentration of the mixed liquid (mixture) used in the formation of the biomaterial structure, which means that the film thickness of the biomaterial structure can be accurately controlled according to the use, and can be designed freely.

Comparative Example 2-1

Polyacrylic Acid Coating Film

The antibody-antigen reaction was detected according to the SPR measurement in the same manner as in Example 2-3 except that the polyacrylic acid SPR biosensor chip produced in Comparative Production Example 2-3 was used as the sensor chip.

The measurement results are shown in FIG. 22. FIG. 22 shows that in the SPR measurement of this Comparative Example using the polyacrylic acid SPR biosensor chip, the SPR shift amount was smaller than that obtained in the case where the measurement was conducted using the SPR biosensor chip 1 or 2 in Example 2-3. This shows that a greater interaction occurs in the case where the biomaterial solid-state carrier of the invention is used than in the case where the biomaterial is bound to the polymer chain of the hydrophilic polymer compound coated on the solid-state carrier, as in the conventional methods. From this fact, it is known that a larger amount of the biomaterial was immobilized on the SPR biosensor chip 1 or 2 than on the polyacrylic acid SPR biosensor chip.

Table 2-3 shows the resonance angles before measuring, and the differences between the resonance angle obtained after sending the sample and the resonance angle obtained at the initial stage of the measurement.

Further, using the above-mentioned SPR sensor chip B or C (namely, the sensor chip before the immobilization of the biomaterial), the same measurement as above was performed, and the difference in resonance angle between the SPR sensor chip B and the SPR sensor chip C or polyacrylic acid SPR biosensor chip was calculated. The differences in resonance angle are also shown in Table 2-3.

TABLE 2-3

| | Resonance angle before measurement (deg) | Difference from the SPR sensor chip B resonance angle (mdeg) | Difference between the resonance angle after sending the sample and the resonance angle at the initial stage of the measurement (mdeg) |
|---|---|---|---|
| SPR sensor chip B | 18.30 | 0 | — |
| SPR sensor chip C | 18.56 | 260 | — |
| Polyacrylic acid biosensor chip | 19.04 | 740 | 70.75 |

The response ratio is calculated in the same manner as in Example 2-3, and the response ratio can be estimated as follows:

$$\text{Response ratio} = (70.75 \text{ mdeg}/50 \text{ kDa})/$$

$$\{(740 \text{ mdeg} - 260 \text{ mdeg})/150 \text{ kDa}\}$$

$$= 0.44.$$

This value is far smaller than response ratios (0.84 and 0.96) of the SPR biosensor chips 1 and 2 in Example 2-3, which confirmed that the biomaterial-carrying object of the invention has higher reactivity than the conventional technique, in the reaction between the biomaterial and the interacting substance.

Example 2-7

The cross-section of the chip for electron microscope observation produced in Production Example 2-9 was observed according to SEM. The SEM cross-section photograph observed is shown in FIG. 23.

FIG. 23 shows that the film thickness in a dry condition was about 3 μm.

In FIG. 23, white parts are the matrix skeletons.

Example 2-8

Previously, the SPR measurement of the chip for confirmation of matrix principal chain produced in Production Example 2-11 and the SPR sensor chip A, which is a background of the chip for confirmation of matrix principal chain was performed, using the same measuring apparatus as used in Example 2-3.

An aqueous enzyme solution containing 0.5% of trypsin (made by Wako), 1% of ammonium carbonate, 2M of urea, and 1 mM of calcium chloride, and having a pH of 8.0 was produced as the aqueous enzyme solution which decomposes only the biomaterial. The operation in which the aqueous enzyme solution 5 μL was contacted with the chip for confirmation of matrix principal chain, which was allowed to stand at 37° C. for 12 hours under a saturated vapor pressure, and the chip for confirmation of matrix principal chain was washed with distilled water was repeated twice to decompose the biomaterial. After that, the SPR measurement was performed, using the same measuring apparatus as used in Example 2-3.

The results of the SPR measurement are shown in FIG. 24.

As shown in FIG. 24, the resonance angle was about 20.8 degree before the decomposition of the enzyme, whereas it was about 18.6 degree after the decomposition of the enzyme. From the facts that the resonance angle of the background was about 18.5 degree before forming the biomaterial structure (matrix), and that the measurement results of the background were almost consistent with those after the decomposition of the enzyme, almost all of the biomaterial forming the biomaterial structure and the compound for binding were removed from the solid-state carrier, or the SPR sensor chip A, by the decomposition of the enzyme. Accordingly, it was confirmed that the formed biomaterial structure was the biomaterial structure of the present invention having the principal chain comprising the biomaterial and the compound for binding.

Example 2-9

The matrix on the chip for component analysis produced in Production Example 2-12 was hydrolyzed with hydrochloric acid, and the IgG was quantified from the amount of the generated amino acid. Further, the polymer A2 was quantified from the amount of the polyacrylic acid in the hydrolysate.

Specifically, the biomaterial structure of the chip for component decomposition was hydrolyzed with 6N hydrochloric acid at 150° C. for 1 hour. After that, hydrochloric acid was dried under reduced pressure, the hydrolysate was dissolved in 1% aqueous ammonia, and insoluble matter was removed through centrifugation separation (10,000 rpm, 3 minutes). The hydrolyze solution was dried under reduced pressure, and then dissolved in 0.1% aqueous ammonia 1 mL, and 100 μl, of the solution was used in amino acid analysis, and 400 μL of the solution was used in PAA (polyacrylic acid) analysis.
(Amino Acid Analysis Sample)

The above-mentioned hydrolyze solution 100 μL was dried under reduced pressure and was dissolved in 0.02 N hydrochloric acid 500 μL which was subjected to the centrifugation type ultrafiltration (MWCO:10000, Microcon YM-10). The filtrate 10 μL was used in amino acid analysis.

The amino acid analysis was performed under the conditions stated in the following Table 2-4.

TABLE 2-4

| Apparatus | Hitachi High Speed Amino Acid Analyzer L-8500 |
|---|---|
| Analysis conditions | Separation condition of amino acid from biosample - ninhydrin coloring method (570 nm, 440 nm) |
| Standard | Mixed liquid containing standard amino acid made by Wako Pure Chemical Industries, Ltd. (each containing 200 uM of amino acid) |
| Sample | Hydrolyze sample 10 μL |
| Quantitative calculation | An amino acid content was calculated from a peak area at 440 nm for Pro or at 570 nm for other amino acids, according to the one-point external standard method. |

(Polyacrylic Acid Analysis Sample)

The above-mentioned hydrolyze solution 400 μL was concentrated through centrifugation type ultrafiltration (MWCO: 10000), which was diluted with a 1% aqueous ammonia 400 μL. The dilution-concentration operation through the ultrafiltration was repeated 6 times to remove the low molecular component. The polymer component was retrieved with 1% aqueous ammonia, which was dried under reduced pressure and the resulting component was subjected to the polyacrylic acid (PAA) analysis.

The PAA analysis (reaction thermal decomposition GCMS) was performed under the conditions stated in the following Table 2-5.

TABLE 2-5

| Apparatus | HP 5973 MSD made by Agilent |
|---|---|
| Analysis conditions | Thermal decomposition temperature: 550° C. |
| Column | DB-1 60 m × 0.25 umφ (film thickness: 1 μm), 50° C. (1 min) – 10° C./min – 260° C. (10 min) |
| Detection | MS (SIM, m/z = 129, 85, 75 |
| Standard | Polyacrylic acid 2000 33 ug/mL × 10 uL |
| Sample | 10 μL |
| Quantitative calculation | A PAA content was calculated from a peak area at m/z = 129, according to the one-point external standard method. |

As a result, 390 μg of the mouse IgG and 16.9 μg of polymer C2 were detected, and the ratio of the biomaterial contained in the biomaterial structure, "the weight of the biomaterial/(the weight of the compound for immobilization+the weight of the biomaterial" was 0.958. That is, it was shown that the weight ratio of the biomaterial contained in the matrix was very high.

Example 2-10

The antibody-antigen reaction (interaction) was measured according to SPR, using the 50 μg/mL rabbit serum anti-mouse Fab' as the analyte (sample) of the prism type SPR biosensor chip produced in Production Example 2-13, and using 10 mM HEPES buffer as the buffer. In the comparison with Example 2-10, the antibody-antigen reaction was measured in the same manner as mentioned above, using the comparative prism type biosensor chip produced in Comparative Production Example 2-5.

As the measuring apparatus, the prism type SPR measuring apparatus Multi SPR Inter™ (made by TOYOBO CO., LTD.) was used. The measurement was performed by sending 10 mM HEPES buffer (pH 7.4) for 3 minutes and 30 seconds from the start of the measurement, then sending 50 μg/mL rabbit serum anti-mouse Fab' (analyte) for 10 minutes, and finally sending 10 mM HEPES buffer (pH 7.4) for minutes. The sending speeds were all 100 μL/min.

The measurement results are shown in FIG. 25. As shown in FIG. 25, when the biomaterial-immobilized carrier of the invention, or the prism type SPR biosensor chip was used, in the antibody-antigen reaction, signal seven times larger than that of the case where the comparative prism type SPR biosensor chip in which the biomaterial was immobilized by the conventional method was used, was observed.

3. Examples and Comparative Examples Concerning Biomaterial Complex and Biomaterial-Complex-Carrying Object Now, Examples in which the biomaterial complex and the biomaterial-complex-carrying object were studied are shown.

Example 3-1

Biomaterial Complex Using Albumin (1) Synthesis of Compound for Binding (Polymer A3)

The monomers, N-acryloylmorpholine (NAM made by KOHJIN CO., LTD.) 1.13 parts by weight and N-acryloyloxysuccinimide (NAS made by ACROS ORGANICS) 0.33 parts by weight and the solvent, or dehydrated dioxane (made by Wako Pure Chemical Industries, Ltd.) 18.03 parts by weight were thoroughly mixed, and the mixture was poured into a 50 mL-four necked flask, which was degassed at room temperature for 30 minutes under nitrogen to give a monomer solution.

The temperature of this monomer solution was elevated to 60° C. in an oil bath, to which a solution in which a polymerization initiator azobisisobutyronitrile (AIBN made by Kishida Chemical Co., Ltd.) 0.0016 parts by weight was dissolved in dehydrated dioxane 0.5 g was added to start the polymerization. The polymerization was performed for 8 hours under a nitrogen atmosphere.

After the polymerization, the solution containing the produced polymer was added dropwise to 0.5 L of diethyl ether (made by Kokusan Chemical Co, Ltd.) to precipitate the polymer again, and then the solvent was removed to give a compound for binding polymer A3 as a powder.

As to the obtained polymer A3, SEC (Size Exclusion Chromatography) measurement which was corrected by standard polystyrene was performed. As a result, it was estimated that the polymer A3 had a weight average molecular weight (Mw) of about 150,000.

The molar ratio (NAS/NAM) of NAS and NAM contained in the obtained polymer A3 was estimated to be NAS/NAM=30/70 according to the $^1$H-NMR measurement.

Further, the polymer A3 was diluted with distilled water to adjust the concentrations to 0.2% by weight, 0.4% by weight, and 0.6% by weight, and dynamic optical scattering method was carried out at measured angles of 30°, 40°, 50° and 60°, using a photon correlation measuring device ALV 5000 (made by ALV), and the average hydrodynamic radius of the polymer A3 was estimated to be 6.8 nm.

(2) Formation of Biomaterial Complex on QCM Sensor Chip
(2-1) Surface Treatment of QCM Sensor Chip A sensor chip coated with gold (made by Initium Inc.) for QCM (Quartz Crystal MicroBalance) (AFFINIX Q: made by Initium Inc.) was immersed in an ethanol solution of 10 mM 16-mercaptohexadecanoic acid (made by ALDRICH), and the reaction was conducted at room temperature for 12 hours to complete the surface treatment. After finishing the reaction, the sensor chip was washed with ethanol. This surface treatment was performed for introducing carboxyl group into the surface of the sensor chip through gold-sulfur binding.

Next, a 0.1 M aqueous solution of N-hydroxysuccinimide (NHS, made by Wako Pure Chemical Industries, Ltd.) 1 mL and a 0.4 M aqueous solution of 1-ethyl-3-(3-dimethylaminopropyl)carbodiimide hydrochloride (EDC, made by Dojindo Laboratories,) 1 mL were mixed, which was diluted with desalted water 18 g, the basal plate (sensor chip) into which carboxyl group was introduced was immersed in the obtained solution, and the reaction was conducted for 15 minutes. This treatment was conducted in order to introduce succinimide group, which can bind the biomaterial structure to the basal plate, to the surface of the basal plate.

(2-2) Formation of Biomaterial Structure

Next, 3 μL of a mixture of 10 mg/mL of an aqueous solution of albumin (made by SIGMA) (phosphate buffer 10 mM, pH 9.0) and the polymer A3 in the weight ratio of 10:1 (biomaterial:compound for binding) was spotted on the surface of the sensor chip. After drying at room temperature, the chip was immersed in a 1M aqueous ethanol amine solution (pH 8.5) 8 mL for 15 minutes, in order to block the unreacted active ester group, whereby a biomaterial structure having the albumin as the biomaterial and the polymer A3 as the compound for binding was formed on the surface of the sensor chip.

After that, the sensor chip was thoroughly washed with desalted water, and dried at room temperature to give a chip for biomaterial structure QCM supporting the biomaterial structure on its surface.

(2-3) Chelate Surface Treatment to Biomaterial Structure

300 μL of DMSO (dimethyl sulfoxide made by Kanto Chemical Co., Inc.) solution of 100 mM EGS (ethylene glyco-bis(succinimidylsuccinate) made by PIERCE), and 450 μL of DMSO solution of 100 mM AB-NTA (N-(5-amino-1-carboxypentyl)-iminodiacetic acid made by Dojindo Laboratories) were mixed, and the mixture was allowed to stand at room temperature for 24 hours. Hereinafter, the obtained solution is sometimes referred to as EGS/AB-NTA solution. EGS has succinimide groups at both ends, and by the above-mentioned operation, a compound in which the one end was bound to the amino group of AB-NTA, and EGS was bound to AB-NTA was formed.

With respect to a part of the EGS/AB-NTA solution, NMR measurement was performed and, as a result, it was found that in the EGS/AB-NTA solution, the ratio of the unreacted EGS, the compound obtained by reacting succinimide group at one end of EGS with AB-NTA (EGS/AB-NTA), and the compound obtained by reacting succinimide groups at both ends of the EGS with AB-NTA (AB-NTA/EGS/AB-NTA), namely, "unreacted EGS EGS/AB-NTA:AB-NTA/EGS/AB-NTA"=10:40:50 (molar ratio). From this result, it was known that the obtained EGS/AB-NTA solution had 17 mM of EGS/AB-NTA compound.

Further, the chip for biomaterial structure QCM was immersed in the HEPES buffer (10 mM, pH7.4) 8 mL, to which 50 μL of EGS/AB-NTA solution was added, and the immersion was conducted for 30 minutes.

After the chip for biomaterial structure QCM was taken out from the HEPES buffer, 3 μL of a EGS/AB-NTA solution 10 fold diluted with HEPES buffer was spotted to the chip for biomaterial structure QCM, in order to surely introduce the EGS/AB-NTA into the biomaterial, or the surface of albumin.

After that, the chip for biomaterial structure QCM was washed with desalted water, and unreacted succinimide of EGS was blocked with a 1M aqueous ethanol amine solution (pH 8.5) 8 mL for 15 minutes, and then the chip was washed with desalted water again.

These operations were performed for binding EGS/AB-NTA to the chip for biomaterial structure QCM. That is, succinimide group at one end of EGS/AB-NTA and amino group on the albumin in the biomaterial structure were bound.

(2-4) Introduction of Nickel Ion

The chip for biomaterial structure QCM was immersed in a 2 nM aqueous solution of nickel (II) sulfate hexahydrate (made by Wako Pure Chemical Industries, Ltd.) 8 mL for 1 hour to introduce $Ni^{2+}$ into the biomaterial structure. At this time, the specific material, or a nickel chelate was formed from AB-NTA, which was previously introduced into the biomaterial structure and $Ni^{2+}$. Further, the chip for biomaterial structure QCM was immersed in desalted water 8 mL for 30 minutes to wash out the non-bound $Ni^{2+}$. The chip obtained by this operation, which was the biomaterial-complex-carrying object, was used as the chip 3D for QCM.

(3) QCM Measurement

As the interacting substance (target material), polyhistidine was used. This utilized a characteristic that histidine adsorbs specifically to $Ni^{2+}$ of the chip 3D for QCM to which $Ni^{2+}$ was introduced.

The QCM used in the measurement was AFFINIX Q (made by Initium Inc.).

Specifically, first, the chip 3D for QCM was immersed in 8 mL of HEPES buffer (10 mM, pH 7.4), and the measurement by QCM was started. At the time when the frequency was sufficiently stable, 80 μL of an aqueous solution of 5 mg/ml polyhistidine (POLY-L-HISTIDINE made by SIGMA) (pH 1.7 glycine-HCl buffer) was injected.

The measurement results are shown in FIG. 26(a), and FIG. 26(b). FIG. 26(b) is an enlarged view of the main section of FIG. 26(a).

Comparative Example 3-1

To the sensor chip for QCM formed from gold was introduced succinimide group in the same manner as in "(2-1) Surface treatment of QCM sensor chip" of Example 3-1.

Next, the sensor chip for QCM was immersed in HEPES buffer (10 mM, pH 7.4) 8 mL, to which 50 μL of a DMSO solution of 17 mM AB-NTA was added, and the immersion was conducted for 30 minutes.

After the sensor chip for QCM was taken out from the HEPES buffer, 3 μL of a DMSO solution of AB-NTA solution 10 fold diluted with HEPES buffer was spotted to the chip, in order to surely bind the AB-NTA to the gold surface, and the mixture was allowed to stand for 15 minutes. This operation was performed for binding amino group contained in AB-NTA to the succinimide group on the gold surface.

After that, $Ni^{2+}$ was introduced into the surface of the sensor chip for QCM in the same manner as in "(2-4) Introduction of nickel ion" of Example 3-1. The chip obtained in this operation was used as the chip 2D for QCM.

Using this chip 2D for QCM, the polyhistidine (target material) and the nickel chelate (specific material) were interacted and the QCM measurement was performed in the same manner as in "(3) QCM measurement" of Example 3-1. The results are shown in FIG. 26(a) and FIG. 26(b).

Comparative Example 3-2

To the sensor chip for QCM formed from gold was introduced succinimide group in the same manner as in "(2-1) Surface treatment of QCM sensor chip" of Example 3-1.

Next, 34 µL of a 10 mg/ml aqueous albumin solution (phosphate buffer, 10 mM, pH 9.0) was spotted to the surface of this sensor chip for QCM.

After that, $Ni^{2+}$ was introduced into the surface of the sensor chip for QCM in the same manner as in "(2-3) Chelate surface treatment to biomaterial structure" and "(2-4) Introduction of nickel ion" of Example 3-1. The chip obtained in this operation was used as a chip albumin 2D for QCM.

Using this chip albumin 2D for QCM, polyhistidine (target material) and a nickel chelate (specific material) were interacted, and the QCM measurement was performed in the same manner as in "(3) QCM measurement" of Example 3-1. The results are shown in FIG. 26(a) and FIG. 26(b).

Consideration about Example 3-1 and Comparative Examples 3-1 and 3-2

As shown in FIGS. 26(a) and (b), in the results of Example of the invention, or Example 3-1, in which the chip 3D for QCM was used, remarkably bigger change in frequency occurred than in Comparative Examples 3-1 and 3-2. The reason for this can be considered as follows:

First, in the chip 2D for QCM used in Comparative Example 3-1, the nickel chelate, which was the specific material, was immobilized on the chip having exposed gold. Consequently, the non-specific interaction occurred between the gold of the chip surface and the target material, or the polyhistidine, whereby the change in frequency was lowered.

Further, chip albumin 2D for QCM used in Comparative Example 3-2 was one obtained by two-dimensionally covering the chip surface with albumin and then immobilizing the specific material, or the nickel chelate, on the chip. It can be considered that by binding the albumin to the surface of the chip for QCM as a single surface, a larger amount of the specific material, or the nickel chelate could be bound. Further, it can also be considered that by the introduction of EGS, the polyhistidine could be bound more easily. However, according to Comparative Example 3-2, the satisfactory frequency change could not be obtained.

On the contrary, in Example 3-1, since the biomaterial complex having the three-dimensional structure was formed, the chip surface could be covered with a larger amount of the albumin than in Comparative Example 3-2. As a result, according to the biomaterial complex, the specific material, or $Ni^{2+}$ was bound to the amino groups of three-dimensionally arranged albumin (usually, one molecule of albumin has about 60 amino groups), and accordingly, a larger amount of $Ni^{2+}$ could be immobilized than in conventional technique. Further, since the biomaterial complex had a porous structure, the polyhistidine could enter into the deep inside of the biomaterial complex, whereby an amount of the interaction to be detected can be remarkably increased. As a result, the frequency change was large, as shown in FIG. 26(a).

Example 3-2

Biomaterial Complex Using Biotin

As a sensor chip for SPR, a polycarbonate flat basal plate having a size of length 2.5 cm×width 2.5 cm×thickness 1.2 mm, having a diffraction grating with a groove pitch of about 870 nm and a groove depth of about 40 nm on its surface, and having gold deposited on its surface in a thickness of about 80 nm was prepared.

The sensor chip for SPR was surface-treated in the same manner as in "(2-1) Surface treatment for sensor chip for QCM" of Example 3-1 to introduce succinimide group into the surface of the sensor chip for SPR.

Next, the biomaterial structure was formed on the sensor chip for SPR in the same manner as in "2-2. Formation of biomaterial structure" of Example 3-1 except that the dropped amount in spotting was changed to 1 µL.

In order to bind biotin to the surface of the biomaterial structure as the specific material, 2 µL of a 100 mg/mL aqueous solution of EZ-Link NHS-$PEO_4$-Biotin (made by PIERCE) was spotted to the sensor chip for SPR, which was allowed to stand for 30 minutes under a saturated vapor pressure, and then dried at room temperature. This operation was performed for supporting biotin on the biomaterial structure by reacting the amino group of albumin contained in the biomaterial structure with the succinimide group contained in the EZ-Link NHS-$PEO_4$-Biotin and causing the binding. The spot obtained by this operation was used as SPR 3D.

Using as the measuring apparatus a grating type SPR measuring apparatus FLEX CHIPS™ Kinetic Analysis System (made by HTS Biosystems), the SPR measurement was performed, while liquid contacting with the spot SPR 3D was sent as follows: that is, HEPES buffer (10 mM, pH 7.4) was sent for 2 minutes from the start of the measurement; then, a 10 µg/ml aqueous solution of streptavidin (ImmunoPure Streptavidin made by PIERCE) (HEPES buffer, 10 mM, pH 7.4) was sent as the interacting substance; and finally HEPES buffer (10 mM, pH 7.4) was sent for 15 minutes. The sending speeds were all 500 µL/min.

The SPR measurement results are shown in FIG. 27.

Comparative Example 3-3

1 µL of a 10 mg/mL aqueous solution of albumin (phosphate buffer, pH 9) was spotted on the sensor chip for SPR in the same manner as in Example 3-2, and then, biotin was bound to the albumin of the spot in the same manner as in Example 3-2. The spot obtained in this operation was used as SPR 2D.

With respect to this spot SPR 2D, the SPR measurement was performed in the same manner as in Example 3-2. The results of the SPR measurement are shown in FIG. 27.

Consideration about Example 3-2 and Comparative Example 3-3

As shown in FIG. 27, a resonance angle shift amount of the spot SPR 3D produced in Example 3-2 was larger than that of the spot SPR 2D produced in Comparative Example 3-3, and the reactivity of the spot SPR 3D was higher than that of the spot SPR 2D. The reason for this can be considered as follows:

That is, the spot SPR 3D produced in Example 3-2 had a biomaterial complex, and therefore had a large amount biotin three-dimensionally; whereas, the spot SPR 2D produced in Comparative Example 3-3 had biotin two-dimensionally, and therefore the amount thereof is smaller than that of the spot SPR 3D. It can be considered that since the shift amount in the SPR measurement is caused by interacting biotin in each of the spots SPR 3D and SPR 2D with the interacting substance, or streptavidin, and, as mentioned above, the amount of biotin in the spot SPR 3D was larger than that in the spot SPR 2D, the interaction caused in the spot SPR 3D was bigger than that caused in the spot SPR 2D, and accordingly the resonance angle shift amount in the spot SPR 3D was larger than that in the spot SPR 2D. Further, it can be considered that the structure of the biomaterial complex, that is, the porous structure in which the particulate lumps were assembled is one of the causes that the high reactivity was generated.

Reference Example 3-1

A spot SPR ref 3D was produced in the same manner as in Example 3-2 except that the aqueous solution of EZ-Link NHS-PEO$_4$-Biotin (made by PIERCE) was not spotted on the same sensor chip for SPR as that in Example 3-2.

With respect to the spot SPR ref 3D, the SPR measurement was performed in the same manner as in Example 3-2. The results of the SPR measurement are shown in FIG. 28.

Reference Example 3-2

A spot SPR ref 2D was produced in the same manner as in Comparative Example 3-3 except that the aqueous solution of EZ-Link NHS-PEO$_4$-Biotin (made by PIERCE) was not spotted on the same sensor chip for SPR as that in Example 3-2.

With respect to the spot SPR ref 2D, the SPR measurement was performed in the same manner as in Example 3-2. The results of the SPR measurement are shown in FIG. 28.

In FIG. 28, SPR measurement results of a sensor chip for SPR, which was not treated with albumin are also shown. (In FIG. 28, it is shown as "gold-surface (treated with ethanol amine.)" When the treatment with albumin was not performed, the succinimide on the gold surface was treated with ethanol amine.

Consideration about Reference Examples 3-1 and 3-2

As shown in FIG. 28, the shift amount of the spot SPR ref 3D was the smallest, followed by the shift amount of the spot SPR ref 2D, and the shift amount of the no treated moiety was the largest. It can be considered that this difference is caused by the difference in amount of the albumin which inhibits the non-specific interaction at each measuring moiety (spot).

That is, since there was no albumin and gold exposed at the moiety where no treatment was conducted, the non-specific interaction was caused, and the resonance angle was greatly shifted due to the non-specific interaction.

In the spot SPR ref 2D, the albumin was present two-dimensionally on the surface of the sensor chip for SPR, whereby the chip surface was coated with albumin, thus resulting in inhibition of the non-specific interaction and the small shift amount of the resonance angle.

On the other hand, in the spot SPR ref 3D, a large amount of albumin was present three-dimensionally on the surface of the sensor chip for SPR because of the biomaterial structure, whereby the chip surface was covered with a large amount of albumin. Consequently, it can be considered that the non-specific interaction was more surely inhibited compared to the spot SPR ref 2D, and the shift amount of the resonance angle was smaller.

Example 3-3

Structure of Biomaterial Structure

A biomaterial complex was formed in the same manner as in Example 3-2, using the same sensor chip for SPR as used in Example 3-2 except that the chip has no grating.

The surface of the chip was observed with AFM. A photograph, instead of a drawing, showing the observation result is shown in FIG. 29. As shown in FIG. 29, particulate lumps with sub-micron orders were confirmed on the chip surface.

4. Examples Concerning Bio-Related Material Immobilized Carrier

Now, Examples in which the bio-related material immobilized carriers were studied will be shown.

[Synthesis of Polymer (Support Compound for Immobilization)]

First, two kinds of polymers, polymers A4 and B4 were synthesized as a compound capable of binding the bio-related material, for producing the bio-related material immobilized carrier of the present invention.

Production Example 4-1

Synthesis of Polymer A4

N-acryloylmorpholine (NAM made by KOHJIN CO., LTD.) 0.564 parts by weight and N-acryloyloxysuccinimide (NAS made by ACROS ORGANICS) 0.169 parts by weight, which were monomer, and dehydrated dioxane (made by Wako Pure Chemical Industries, Ltd.), which was the solvent, 8.75 parts by weight were thoroughly mixed, and the mixture was poured into a 50 mL-four necked flask, which was degassed at room temperature for 30 minutes under nitrogen to give a monomer solution. The temperature of this monomer solution was elevated to 60° C. in an oil bath, to which a solution in which a polymerization initiator azobisisobutyronitrile (AIBN made by Kishida Chemical Co., Ltd.) 0.008 parts by weight was dissolved in dehydrated dioxane 0.5 g was added to start the polymerization. The polymerization was performed for 8 hours under a nitrogen atmosphere.

After the polymerization, the solution containing the produced polymer was added dropwise to 0.5 L of diethyl ether (made by Kokusan Chemical Co, Ltd.) to precipitate the polymer again, and then the solvent was removed to give a compound for binding polymer A4 as a powder.

As to the obtained polymer A4, SEC measurement which was corrected by standard polystyrene was performed. As a result, it was estimated that the polymer A1 had a weight average molecular weight (Mw) of about 86,000.

The molar ratio (NAS/NAM) of NAS and NAM contained in the obtained polymer A4 was estimated to be NAS/NAM=30/70 according to the NMR measurement.

Production Example 4-2

Synthesis of Polymer B4

A polymer B4 was obtained in the same manner as in Production Example 4-1 (synthesis of polymer A4) except that as the monomer, dimethyl acrylamide (DMAA made by KOHJIN CO., LTD.) 0.793 parts by weight and NAS 0.338 parts by weight were used instead of NAM and NAS; the amount of dehydrated dioxane, which was the solvent, was changed to 18.37 parts by weight; and the amount of AIBN, which was the polymerization initiator, was changed to 0.00164 parts by weight.

As to the obtained polymer B4, SEC measurement which was corrected by standard polystyrene was performed. As a result, it was estimated that the polymer B4 had a weight average molecular weight (Mw) of about 26,000.

The molar ratio (NAS/DMAA) of NAS and DMAA contained in the obtained polymer B4 was estimated to be NAS/DMAA=43/57 according to the NMR measurement.

[Surface Treatment of Sensor Chip]

Next, the solid-state carrier, which was the basal plate of the bio-related material immobilized carrier of the invention was prepared.

Production Example 4-3

Sensor Chip A

As the sensor chip for measurement, a sensor chip coated with gold in which gold was deposited on a flat plastic basal plate having a size of length 2.5 cm×width 2.5 cm×thickness 1.2 mm in a thickness of about 80 nm, was used.

A surface treatment was conducted by immersing this sensor chip coated with gold in an ethanol solution of 10 mM 16-mercaptohexadecanoic acid (made by ALDRICH), and conducting the reaction at 60° C. for 2 hours. After finishing the reaction, the sensor chip coated with gold was washed with ethanol and desalted water. By the surface treatment, carboxyl group was introduced to the surface of the sensor chip coated with gold through gold-thiol binding.

Next, a 0.1M aqueous solution of N-hydroxysuccinimide (NHS made by Wako Pure Chemical Industries, Ltd.) 1 mL and a 0.4 M aqueous solution of 1-ethyl-3-(3-dimethylaminopropyl)carbodiimide hydrochloride (EDC made by Dojindo Laboratories) 1 mL were mixed, which was diluted with desalted water 18 g. In the resulting solution was immersed a sensor chip coated with gold to which carboxyl group was introduced, and the reaction was conducted for 15 minutes. The thus obtained sensor chip coated with gold to which succinimide group was introduced was used as the sensor chip A.

[Production of Supporting Material]

A supporting material used for producing the bio-related material immobilized carrier of the invention was produced as follows:

Production Example 4-4

Bovine Serum Albumin-Immobilized Latex

A 10% aqueous solution of polystyrene latex (made by Japan Synthetic Rubber Co., Ltd., particle diameter: 0.101 μm) 200 μL, 0.1% bovine serum albumin (made by SIGMA), and 0.15 M sodium chloride-containing 0.1M phosphate buffer (pH 7.4: hereinafter referred to as "buffer diluted with phosphoric acid") 800 μL were mixed, and the mixture was stirred at room temperature for 30 minutes, and then the supernatant was removed through centrifugation. To the precipitate were added 0.1% bovine serum albumin (made by SIGMA) and 0.15 M sodium chloride-containing 0.1 M phosphate buffer (pH 7.4) 200 μL to give a 10% bovine serum albumin-immobilized latex solution (supporting material).

[Production of Sensor Chip for Measurement]

Biosensor chips 1 to 6, which were the bio-related material immobilized carriers of the invention, and comparative biosensor chips 1 to 4 were produced as follows:

Production Example 4-5

Biosensor Chip 1

A biosensor chip 1 was produced by adding a mixture of the polymer A4 (the compound capable of binding to the bio-related material), 1% mouse IgG (bio-related material), and the latex (supporting material) to the above-mentioned sensor chip A to conduct the immobilization.

First, with the above-mentioned 10% bovine serum albumin-immobilized latex solution (particle diameter: 0.101 μm, the supporting material) 10 μL were mixed the 1% aqueous solution of the polymer A4 (the support compound for immobilization) in 0.1 M phosphate buffer (pH 7.2) 10 μL, and a 1% aqueous solution of mouse IgG (made by LAMPIRE BIOLOGICAL LABORATORIES; bio-related material) 100 μL, and then the obtained mixed liquid 0.5 μL was added dropwise to the above-mentioned sensor chip A, and the immobilization was conducted at 37° C. for 30 minutes under a saturated vapor pressure. After that, the solvent was dried by air-drying at room temperature for 15 hours. After the predetermined matrix was formed, it was immersed in a 0.5 M ethanol solution of ethanol amine hydrochloric acid salt (made by SIGMA, pH 8.5) containing 3% bovine serum albumin (made by SIGMA) for 30 minutes, while shaking, whereby the unreacted succinimide group was blocked. Further, the basal plate was washed with desalted water and dried to give the biomaterial-immobilized carrier, or a biosensor chip 1.

Production Example 4-6

Biosensor Chip 2

Biosensor chips 2 were produced in the same manner as in the production of the biosensor chip 1 to give four kinds of biosensor chips 2(a) to (d), by adjusting the latex concentration at four levels.

First, 10 μL of an aqueous solution obtained by diluting the bovine serum albumin-immobilized latex solution (particle diameter: 0.101 μm, supporting material) with the buffer diluted with phosphoric acid to concentrations of 0%, 2%, 10% or 40%; and 10 μL of an aqueous solution obtained by diluting the polymer A4 (support compound for immobilization) with the above-mentioned phosphate buffer in a concentration of 1% were mixed with 100 μL of an aqueous solution of the mouse IgG diluted with the above-mentioned phosphate buffer in a concentration of 1%, respectively, and the resulting mixed liquid 0.5 μL was added dropwise to the sensor chip A, and the immobilization was performed at 37° C. for 30 minutes under a saturated vapor pressure. After that, the air-drying, blocking and washing were performed in the same manner as in Production Example 4-5 (production of biosensor chip 1) to produce biosensor chips. The thus produced biosensor chip, which was the biomaterial-immobilized carrier of the invention, was used as a biosensor chip 2.

Production Example 4-7

Biosensor Chip 3

A biosensor chip 3 was obtained by immobilizing the polymer A4, the mouse antibody F(ab') 2 (bio-related material), and the latex on the sensor chip A. Two kinds of concentrations were set for the polymer A4 and the latex, and four kinds of biosensor chips 3(a) to (d) were produced.

First, 10 μL of an aqueous solution obtained by diluting the bovine serum albumin-immobilized latex solution (particle diameter: 0.101 μm, supporting material) with the above-mentioned buffer diluted with phosphoric acid to concentrations of 0% or 10%; and 10 μL of an aqueous solution obtained by diluting the polymer A4 (support compound for immobilization) with the above-mentioned phosphate buffer to concentrations of 1% or 3.8% were mixed with 100 μL of an aqueous solution obtained by diluting mouse antibody F(ab') 2 (made by our company, bio-related material) with the above-mentioned phosphate buffer to a concentration of 1%, respectively, and the resulting mixed liquid 0.5 μL was added dropwise to the sensor chip A, and the immobilization was performed 37° C. for 30 minutes under a saturated vapor pressure. After that, the air-drying, blocking and washing were performed in the same manner as in Production Example 4-5 (production of biosensor chip 1) to produce biosensor chips. The thus produced biosensor chip, which was the biomaterial-immobilized carrier of the invention, was used as a biosensor chip 3.

Production Example 4-8

Biosensor Chip 4

A biosensor chip 4 was produced in the same manner as in the production of the biochip 1 in Production Example 4-5 except that two kinds of latex with different particle diameters were mixed and used as the latex which was used as the supporting material.

As an aqueous polystyrene latex solution, a mixed latex solution of 20% bovine serum albumin-immobilized latex solution (made by Japan Synthetic Rubber Co., Ltd., particle diameter: 0.101 μm) 7.5 μL and 40% bovine serum albumin-immobilized latex solution (made by Japan Synthetic Rubber Co., Ltd., particle diameter: 3.26 μm) 2.5 μL was used. A 40% bovine serum albumin-immobilized latex solution (particle diameter: 3.26 μm) was produced in the same manner as in the production of 20% bovine serum albumin-immobilized latex solution (made by Japan Synthetic Rubber Co., Ltd., particle diameter: 0.101 μm) in Production Example 4-4.

Other conditions were the same as in Production Example 4-5 (production of biosensor chip 1) to produce the biosensor chip 4.

Production Example 4-9

Biosensor Chip 5

A biosensor chip 5 was produced in the same manner as in the production of biochip 4 in Production Example 4-8 except that as the compound, the polymer B4 was used.

The biosensor chip 5 was produced in the same manner as in Production Example 4-8 (production of biosensor chip 4) except that as the support compound for immobilization, the polymer B4 was used instead of the polymer A4.

Production Example 4-10

Biosensor Chip 6

A biosensor chip 6 was produced with the sensor chip A containing a mixture of the polymer A4, anti-HBs antigen mouse monoclonal antibody F(ab') 2 (bio-related material) and the latex.

As the bio-related material, 100 μL of a 1% aqueous solution of anti-HBs antigen mouse monoclonal antibody F(ab') 2 (made by our company) diluted with the above-mentioned phosphate buffer was used instead of the aqueous mouse IgG solution. Also, the concentration of the aqueous solution of the polymer A4 was changed to 1%. Other conditions were the same as in Production Example 4-5 (production of biosensor chip 1) to give the biosensor chip 6.

Comparative Production Example 4-1

Comparative Biosensor Chip 1

A comparative biosensor chip 1 was one in which only 1% mouse IgG (bio-related material) was directly immobilized on the sensor chip A without using the compound and the supporting material.

A biosensor chip was produced in the same manner as in Production Example 4-5 (production of biosensor chip 1) except that only the 1% aqueous mouse IgG solution (the aqueous solution of bio-related material) 0.5 μL was used, instead of the mixed liquid of the bovine serum albumin-immobilized latex solution, the aqueous solution of the polymer A4 and the aqueous mouse IgG solution. The thus produced biosensor chip was used as the comparative biosensor chip 1.

Comparative Production Example 4-2

Comparative Biosensor Chip 2

A comparative biosensor chip 2 was produced by mixing 1% mouse IgG (bio-related material) and the polymer A4 without using the supporting material, and immobilizing the mixture on the sensor chip A.

A biosensor chip was produced in the same manner as in Production Example 4-5 (production of biosensor chip 1), using 0.5 μL of a mixed liquid of the 1% aqueous solution of the polymer A4 10 μL and the 1% aqueous mouse IgG solution 100 μL, instead of the mixed liquid of the bovine serum albumin-immobilized latex solution, the aqueous polymer A4 solution and the aqueous mouse IgG solution. The thus produced biosensor chip was used as the comparative biosensor chip 2.

Comparative Production Example 4-3

Comparative Biosensor Chip 3

A comparative biosensor chip 3 was produced by mixing the 1% mouse IgG (bio-related material) and the latex solution (supporting material) without the compound, and immobilizing the mixture on the sensor chip A.

A 10% aqueous polystyrene latex solution (made by Japan Synthetic Rubber Co., Ltd., particle diameter: 0.101 μm) 200 μL, 0.1% mouse IgG (made by LAMPIREBIOLOGICAL LABORATORIES; bio-related material) and a 0.15 M sodium chloride-containing 0.1M phosphate buffer (pH 7.4: hereinafter referred to as "buffer diluted with phosphoric acid") 800 μL were mixed, and the mixture was stirred at room temperature for 30 minutes, after which the supernatant was removed through centrifugation. To the precipitate were added 0.1% bovine serum albumin (made by SIGMA), 0.15 M sodium chloride-containing 0.1M phosphate buffer (pH 7.4) 200 μL to give a 10% mouse IgG-immobilized latex solution.

A biosensor chip was produced in the same manner as in Production Example 4-5 (production of biosensor chip 1) except that the 10% mouse IgG-immobilized latex solution 10 μL and 0.1M phosphate buffer (pH 7.2) 100 μL were mixed, and 0.5 μL of the mixed liquid was used, instead of the mixed liquid of the bovine serum albumin-immobilized latex solution, the aqueous polymer A4 solution and the aqueous mouse IgG solution. The thus produced biosensor chip was used as the comparative biosensor chip 3.

Comparative Production Example 4-4

Comparative Biosensor Chip 4

A comparative biosensor chip 4 was produced by mixing anti-HBs antigen mouse monoclonal antibody F(ab') 2 (bio-related material) and the polymer A4 without using the supporting material, and immobilizing the mixture on the sensor chip A.

A biosensor chip was produced in the same manner as in the production of the biochip 6 of Production Example 4-10 except that 1% aqueous polymer A4 solution 10 μL and 1% aqueous solution of anti-HBs antigen mouse monoclonal antibody F(ab') 2 100 μL were mixed and 0.5 μL of the mixed liquid was used, instead of the mixed liquid of the bovine serum albumin-immobilized latex solution, the aqueous polymer A4 solution and the anti-HBs antigen mouse monoclonal antibody F(ab') 2. The thus produced biosensor chip was used as the comparative biosensor chip 4.

Example 4-1

Measurement of Mouse IgG According to Chemiluminescence Method

Using the biosensor chips produced in Production Examples 4-5 (biosensor chip 1) to 8 (biosensor chip 4), and in Comparative Production Examples 4-1 (comparative biosensor chip 1) to 3 (comparative biosensor chip 3), chemiluminescence measurement for detecting antigen-antibody reaction between the mouse IgG and antimouse IgG was performed.

As a sample (analyte, interacting substance), a rabbit anti-mouse IgG (made by Immuno Probe, Inc.) which was labeled with biotin was used. The biotinylation of the rabbit anti-mouse IgG was performed as follows: First, to 100 μL of an aqueous biotin solution obtained by diluting EZ-Link™ Sulfo-NHS-LC-Biotin (made by PIERCE) with aqueous MilliQ in a concentration of 1 mg/mL was added 1 mL of rabbit anti-mouse IgG diluted with 0.05 M carbonate buffer (pH 8.5) in a concentration of 1 mg/mL, the reaction was conducted in ice-water for 2 hours. After finishing the reaction, to the obtained solution was added 100 μL of 1M glycine buffer (pH 8.0), and the reaction was performed in ice-water for 2 hours. Dialysis was performed at 4° C. overnight to 0.1 M phosphate buffer (pH 7.4) to remove the unreacted labeling reagent, thus resulting a biotinylated rabbit anti-mouse IgG.

Each biosensor chip was immersed in 4 mL of the biotinylated anti-mouse IgG which was diluted with the buffer diluted with phosphoric acid in a pre-determined concentration, and the reaction was conducted at normal temperature for 30 minutes while shaking, and then the biosensor chip was washed with 0.01% Tween 20-containing 0.01M phosphate buffer (pH7.4, hereinafter referred to as "washing buffer") and with aqueous MilliQ. This chip was immersed in 4 mL of 50 ng/mL aqueous Neutra-Avidin-HRP (made by PIERCE) solution, which was diluted with buffer diluted with phosphoric acid, and the reaction was conducted at normal temperature for 30 minutes while shaking, and then the biosensor chip was washed with the washing buffer and aqueous MilliQ, and dried. To this chip was added 1 mL of SuperSignal ELISA Femto Maximum Sensitivity Substrate (made by PIERCE), and a chemiluminescence amount was measured by imaging with a CCD camera (ORCAII-ER made by Hamamatsu Photonics K. K.) for an elapsed time of 60 seconds.

Example 4-2

Measurement of HBs Antigen According to Chemiluminescence Method

Using the biosensor chips produced in Production Example 4-10 and Comparative Production Example 4-4, chemiluminescence measurement for detecting antigen-antibody reaction between the HBs antigen and anti-HBs antibody was performed.

As a sample (analyte, interacting substance), a recombinant HBs antigen (subtype adw: and made by our company) was used; and as a labeled one for HBs antigen measurement, rabbit anti-HBs antigen F(ab') 2 (made by Immuno Probe, Inc.) which was labeled with biotin was used. The biotinylation of the rabbit anti-HBs antigen F(ab') 2 was performed in the same manner as in Example 4-1 except that rabbit anti-HBs antigen F(ab) 2 was used instead of the rabbit anti-mouse IgG.

The recombinant HBs antigen was diluted with the buffer diluted with phosphoric acid in a pre-determined concentration, and in 4 mL of each of the thus obtained solutions was immersed the biosensor chip, and the reaction was performed at normal temperature for 60 minutes while shaking, after which the biosensor was washed with the washing buffer and aqueous MilliQ. This chip was immersed in 4 mL of an aqueous solution in which the biotinylated rabbit anti-HBs antigen F(ab') 2 was diluted with the buffer diluted with phosphoric acid in a concentration of 2 μg/mL, and the reaction was performed at normal temperature for 30 minutes while shaking, and then the biosensor chip was washed with the washing buffer and aqueous MilliQ. Then, the biosensor chip was immersed in 4 mL of an aqueous solution in which Neutra-Avidin-HRP (made by PIERCE) was diluted with the buffer diluted with phosphoric acid in a concentration of 50 ng/mL, and the reaction was performed at normal temperature for 30 minutes while shaking, and the biosensor chip was washed with the washing buffer and aqueous MilliQ, and dried. To this chip was added 1 mL of SuperSignal ELISA Femto Maximum Sensitivity Substrate (made by PIERCE), and a chemiluminescence amount was measured by imaging with a CCD camera (ORCAII-ER made by Hamamatsu Photonics K. K.) for an elapsed time of 60 seconds.

[Chemiluminescence Measurement Results 1: Mouse IgG Measurement According to Chemiluminescence Method: Analysis of Biosensor Chip of the Present Invention]

The chemiluminescence measurement results obtained by using the biosensor chip 1 and the comparative biosensor chips 1 to 3, are shown in Table 4-1. From these results, it was confirmed that the biosensor chip 1 had higher emission intensity and higher reproducibility (smaller CV value) than those of comparative biosensor chips 1, 2 and 3.

Each of the emission intensities is an average value of eight spots obtained from eight different places, where the mixed liquid was spotted, in each chip, and CV is a CV of eight spots.

TABLE 4-1

| | Biosensor chip 1 | | Comparative biosensor chip 1 | | Comparative biosensor chip 2 | | Comparative biosensor chip 3 | |
|---|---|---|---|---|---|---|---|---|
| Biotinylated anti-mouse IgG concentration (ng/mL) | 0 | 1 | 0 | 1 | 0 | 1 | 0 | 1 |
| Emission intensity | <1000 | 1156000 | <1000 | 196000 | <1000 | 451000 | 2000 | 81000 |
| S.D. | | 115000 | | 47000 | | 111000 | | 47000 |
| CV (%) | | 9.95 | | 23.98 | | 24.61 | | 58.02 |

FIG. 30(a) and FIG. 30(b) show images of CCD camera on the chemiluminescence measurement in a biotinylated anti-mouse IgG concentration of 1 ng/mL. FIG. 30(a) is the image of the biosensor chip 1 upon the chemiluminescence measurement; and FIG. 30(b) is the image of the comparative biosensor chip 2 upon the chemiluminescence measurement. In FIG. 30(a) and FIG. 30(b), white parts are parts where the chemiluminescence was emitted. As shown in the figures, in the chemiluminescence measurement, the comparative biosensor chip 2 showed ring-shaped emission of light and uneven emission, whereas the biosensor chip 1 did not show ring-shaped emission of light nor uneven emission. From this result, it can be also known that the biochip produced according to the present invention showed a high degree of precision.

[Chemiluminescence Measurement Results 2: Mouse IgG Measurement According to Chemiluminescence Method: Analysis of the Supporting Material Concentration-Dependency in the Biosensor Chip of the Present Invention]

Using the biosensor chips 2(a) to (d), which have different supporting material concentrations, produced in Production Example 4-6, the influence caused by variation in supporting material concentration was studied. The chemiluminescence measurement results are shown in Table 4-2.

From these results, it was confirmed that the higher the concentration of the supporting material, the higher the emission intensity and the higher the reproducibility (CV). When the concentration was too high, however, a blank value (the emission intensity at a biotinylated anti-mouse IgG concentration of 0 ng/mL) was also elevated, and therefore, it was known that there is an optimal supporting material concentration.

Each of the emission intensities is an average value of eight spots obtained from eight different places, where the mixed liquid was spotted, in each chip, and CV is a CV of eight spots.

TABLE 4-2

| | Biosensor chip 2(a) | | Biosensor chip 2(b) | | Biosensor chip 2(c) | | Biosensor chip 2(d) | |
|---|---|---|---|---|---|---|---|---|
| Supporting material concentration (%) | Supporting material 0% | | Supporting material 2% | | Supporting material 10% | | Supporting material 40% | |
| Biotinylated anti-mouse IgG concentration (ng/mL) | 0 | 1 | 0 | 1 | 0 | 1 | 0 | 1 |
| Emission intensity | <1000 | 451000 | <1000 | 952000 | <1000 | 1156000 | 50000 | 2245000 |
| S.D. | | 111000 | | 132000 | | 115000 | | 193000 |
| CV (%) | | 24.61 | | 13.87 | | 9.95 | | 8.60 |

[Chemiluminescence Measurement Results 3: Measurement of Mouse F(ab')2 According to Chemiluminescence Method: Analysis of Compound Concentration-Dependency in Biosensor Chip of the Present Invention]

Using the biosensor chips 3(a) to (d) produced in Production Example 4-7, the influence caused by the presence of the supporting material and the concentration variation of the support compound for immobilization were studied. The results of the chemiluminescence measurement are shown in Table 4-3.

It was confirmed that when there was no supporting material, the higher the concentration of the support compound for immobilization, the higher the emission intensity, but the lower the reproducibility (CV). It was also confirmed that when there was the supporting material, the higher the concentration of the support compound for immobilization, the higher the emission intensity slightly and the better the reproducibility (CV). From these results, it was known that there are optimal concentrations of the supporting material and the immobilized compound.

Each of the emission intensities is an average value of eight spots obtained from eight different places, where the mixed liquid was spotted, in each chip, and CV is a CV of eight spots.

TABLE 4-3

|  | Biosensor chip 3(a) | | Biosensor chip 3(b) | | Biosensor chip 3(c) | | Biosensor chip 3(d) | |
| --- | --- | --- | --- | --- | --- | --- | --- | --- |
|  | Supporting material 10% Compound for immobilization 10% | | Supporting material 10% Compound for immobilization 3.8% | | Supporting material 40% Compound for immobilization 1% | | Supporting material 40% Compound for immobilization 3.8% | |
| Biotinylated anti-mouse IgG concentration (ng/mL) | 0 | 1 | 0 | 1 | 0 | 1 | 0 | 1 |
| Emission intensity | 3000 | 302000 | 4000 | 343000 | <1000 | 78000 | <1000 | 329000 |
| S.D. | | 43000 | | 40000 | | 28000 | | 119000 |
| CV (%) | | 14.24 | | 11.66 | | 35.90 | | 36.17 |

[Chemiluminescence Measurement Results 4: Measurement of Mouse IgG According to Chemiluminescence Method: Analysis of Influence Caused by Particle Diameter of Supporting Material]

Using the biosensor chip 4 using the latex particles with different particle diameters, produced in Production Example 4-8, chemiluminescence measurement was preformed and the results are shown in Table 4-4. From these results, it was confirmed that the biosensor chip 4 had a higher emission intensity and reproducibility (CV) than the comparative biosensor chip 1.

Each of the emission intensities is an average value of eight spots obtained from eight different places, where the mixed liquid was spotted, in each chip, and CV is a CV of eight spots.

TABLE 4-4

|  | Comparative biosensor chip 1 | | Comparative biosensor chip 2 | |
| --- | --- | --- | --- | --- |
|  | Biotinylated anti-mouse IgG concentration (ng/mL) | | | |
|  | 0 | 1 | 0 | 1 |
| Emission intensity | <1000 | 196000 | 43000 | 923000 |
| S.D. | | 47000 | | 13600 |
| CV (%) | | 23.98 | | 14.73 |

[Chemiluminescence Measurement Results 5: Measurement of Mouse IgG According to Chemiluminescence Method: Analysis of Biochip Produced from Different Polymer]

Using the biosensor chip 4 produced in Production Example 4-8 and the biosensor chip 5 produced in Production Example 4-9, the influence on the blank value (emission intensity at a biotinylated anti-mouse IgG concentration of 0 ng/mL) caused by the support compound for immobilization was examined. The biosensor chip 4 was produced using the polymer A4, and the biosensor chip 5 was produced by using the polymer B4. The chemiluminescence measurement results are shown in Table 4-5.

It was known that the polymer B4 had a lower blank value than the polymer A4, and as a result, an S/N ratio (=emission intensity/blank value at a biotinylated anti-mouse IgG concentration of 1 ng/mL) was high. From these results, it was known that by suitably selecting a compound according to the purpose, the blank value could be inhibited or the S/N ratio could be increased.

Each of the emission intensities is an average value of eight spots obtained from eight different places, where the mixed liquid was spotted, in each chip, and CV is a CV of eight spots.

TABLE 4-5

|  | Polymer A | | Polymer B | |
| --- | --- | --- | --- | --- |
|  | Biotinylated anti-mouse IgG concentration (ng/mL) | | | |
|  | 0 | 1 | 0 | 1 |
| Emission intensity | 43000 | 923000 | 6000 | 774000 |
| S/N ratio | | 21 | | 129 |
| S.D. | | 136000 | | 94000 |
| CV (%) | | 14.73 | | 12.14 |

[Chemiluminescence Measurement Results 6: Measurement of HBs Antigen According to Chemiluminescence Method]

Using the biosensor chip 6 produced in Production Example 4-10 and the comparative biosensor chip 4 produced in Comparative Production Example 4-4, the chemiluminescence measurement of the antigen-antibody reaction (interaction) to the HBs antigen was performed. The chemiluminescence measurement results are shown in Table 4-6.

From these results, it was confirmed that the biosensor chip 6 had a higher emission intensity and reproducibility (CV) than the comparative biosensor chip 4. From this, it was confirmed that even if the bio-related material or measuring system was different, the method of the present invention was effective.

Each of the emission intensities is an average value of eight spots obtained from eight different places, where the mixed liquid was spotted, in each chip, and CV is a CV of eight spots.

TABLE 4-6

|  | Comparative biosensor chip 4 | | Biosensor chip 6 | |
| --- | --- | --- | --- | --- |
|  | HBs antigen concentration (IU/mL) | | | |
|  | 0 | 1 | 0 | 1 |
| Emission intensity | 118000 | 305000 | 138000 | 609000 |
| S/N ratio | | 3 | | 4 |
| S.D. | | 106000 | | 150000 |
| CV (%) | | 34.75 | | 24.63 |

Example 4-3

Observation with SEM

Matrix structures of the biosensor chip 1 produced in Production Example 4-5, the biosensor chip 3 (*b*) produced in Production Example 4-7, and the biosensor chip 4 produced in Production Example 4-8 were observed with SEM after the evaluations in the above-mentioned Examples. Also, using the obtained electron microscope photograph, a film thickness and a void ratio of the biosensor chip 1 were calculated.

Photographs (scale: ×4000 and ×60000) showing the surface of the biosensor chip 1 observed with SEM are shown in FIG. 31; and photographs (scale: ×50000 and ×5000) showing the cross-sections are shown in FIG. 32 and FIG. 33. Also, a cross-sectional photograph (scale: ×5000) of the biosensor chip 4 is shown in FIG. 34; and a cross-sectional photograph (scale: ×50000) of the biosensor chip 3(*b*) is shown in FIG. 35.

In these photographs, white parts are the matrix skeletons.

(1) Calculation of Film Thickness

From the cross-section of FIG. 33, a film thickness of the dry biosensor chip 1 was calculated. As a result, the biosensor chip 1 had a film thickness of about 3 μm. Also, as to the biosensor chip 4 whose film thickness was changed by using a mixture of two kinds of latexes with different particle diameters, it was found that from the cross-section in FIG. 34, the biosensor chip 4 had a film thickness of about 9 μm.

From this fact, it was known that by using the particles having different particle diameters as the supporting material, biosensor chips having different film thickness could be produced, and that a biosensor chip having any film thickness could be produced.

(2) Calculation of Void Ratio

Using the cross-sectional view of the biosensor chip 1 in FIG. 32, and the cross-sectional view of the biosensor chip 3(*b*) (in case of 10% of the supporting material and 3.8% of the support compound for immobilization) in FIG. 35, an image analysis was performed, using an image programmer (made by MEDIA CYBERNETICS, Image-Pro-Plus ver. 4.0). A void ratio of each biosensor chip was measured in dry state, based on image shading information.

(2-1) Image Input

The above-mentioned SEM photograph was input through a scanner at 240 DPI. The size of the image was 1019×764 pixel, and a calibration value was 2.17 nm/pixel.

(2-2) Image Processing

Deionizing was performed by using a median filter 3×3, 5 times. A background image was made (background image generation condition: "bright" "object width: 20"), and shading correction (division correction) was conducted.

(2-3) Measurement of Area Ratio

A particle region was set, the image was changed into a binary phase with fixed threshold values (concentration: 30%) and the shape of a hole was corrected with a morphology treatment (connection 5×5 once, fill-in-the-blank), and an area ratio was calculated. The results are shown in Table 4-7.

TABLE 4-7

|  | The number of holes measured | Area ratio |
|---|---|---|
| Biosensor chip 1 | 93 | 23.2% |
| Biosensor chip 3 (b) | 236 | 16.3% |

From the analysis results, the void ratio of the biosensor chip 1 was 23.2%. Also the biosensor chip 3(*b*), which was 3.8 times in concentration of the support compound for immobilization, (the case of 10% of the supporting material and 3.8% of the support compound for immobilization), had a void ratio of about 16.3%.

The results of the above-mentioned (1) and (2) showed that by suitably changing the concentrations of the supporting material, the support compound for immobilization, and the bio-related material, the film thickness and the void ratio could be appropriately changed, and biosensor chips having different properties could be suitably produced.

INDUSTRIAL APPLICABILITY

The biomaterial structure, the method of producing the biomaterial structure, the biomaterial-carrying object, the method of purifying the target material, the container for affinity chromatography, the method of analyzing the target material, the biomaterial-immobilized carrier, the method of producing the biomaterial-immobilized carrier, the biomaterial complex, the biomaterial-complex-carrying object, the method of purifying the target material, the container for affinity chromatography, the chip for the separation, the method of analyzing the target material, the separation apparatus for analysis of the target material, the sensor chip, the array, the biosensor, the device or method for diagnosis of the present invention can be used in any industrial fields. Among them, they are suitably used in, for example sensor chips for analyzing the interaction between the biomaterials, surface treatments of medical materials for which the biocompatibility is required, biosensors, and diagnostic devices, and the like. Further, they can be suitably used in the fields of medical care, diagnosis, food analysis, and bioanalysis. Specifically, they can be used in affinity purification in which the non-specific adsorption is inhibited with a small amount of the sample, or analysis tools for medical effects. Further, for example, automated affinity purification apparatuses or analysis apparatuses for medical effects can be easily produced by using as the biomaterial-carrying object or the biomaterial-complex-carrying object, a product in which the biomaterial structure or the biomaterial complex is formed on the surface of a channel, and flowing a mixed solution to be separated/purified to the channel.

Although the present invention has been described in detail by means of the specific embodiments, it is apparent to those skilled in the art that various modifications can be made without departing from the spirit and the scope of the present invention.

The present application is based on Japanese Patent Application No. 2004-267272 filed on Sep. 14, 2004, Japanese Patent Application No. 2005-201134 filed on Jul. 11, 2005 and Japanese Patent Application No. 2005-217572 filed on Jul. 27, 2005, the entire contents of which are incorporated herein by reference.

The invention claimed is:

1. A biomaterial-immobilized solid-state carrier, comprising:
 a solid-state carrier; and
 a matrix formed on a surface of the carrier, the matrix including a support material, a bio-related material, and a compound capable of binding to the bio-related material and/or the support material;
 wherein
 the compound is a polymer compound;
 the compound has two or more binding functional groups capable of binding to the biorelated material and/or the support material through covalent binding as reactive group in each molecule;
 the matrix comprises a structure having a core of the support material and having a principal chain comprising the bio-related material and the compound, and a cross-linked structure between the compound and the biorelated material and/or the compound and the support material through the binding functional group; and the matrix at least partially contains a cross-linked structure in which the biorelated material is positioned between the compounds by binding the bio-related material to the compounds through the two or more binding functional groups.

2. A biomaterial-immobilized solid-state carrier as defined in claim 1, wherein the matrix has voids.

3. A biomaterial-immobilized solid-state carrier as defined in claim 2, wherein the matrix has a void ratio of 5% or higher.

4. A biomaterial-immobilized solid-state carrier as defined in claim 1, wherein the matrix is formed by supplying a mixture containing a support material, a bio-related material, and a compound capable of binding to the bio-related material and/or the support material, onto an surface of the solid-state carrier in the presence of a solvent, and then removing the solvent.

5. A biomaterial-immobilized solid-state carrier as defined in claim 4, wherein the solvent is water.

6. A biomaterial-immobilized solid-state carrier as defined in claim 1, wherein the matrix has a film thickness of 20 nm or larger in a dry state.

7. A biomaterial-immobilized solid-state carrier as defined in claim 1, wherein the compound can be mixed with water and also can be mixed with at least one organic solvent.

8. A biomaterial-immobilized solid-state carrier as defined in claim 1, wherein the support material is in the form of particles having an average diameter of about 10 nm-100 μm.

9. A method of producing a biomaterial-immobilized solid-state carrier as defined in claim 1, comprising the steps of:

supplying a mixture containing the support material, the bio-related material, and the compound capable of binding to the bio-related material and/or the support material, onto the surface of the solid-state carrier in the presence of a solvent; and removing the solvent to form the matrix.

10. A bio-related-material immobilization kit for producing a biomaterial-immobilized solid-state carrier as defined in claim 1, comprising at least:

the support material; and the compound capable of binding to the bio-related material and/or the support material.

11. An array of a bio-related material, comprising:

a solid-state carrier; and at least two matrices arranged in different areas on the solid-state carrier;

each of the matrices including the bio-related material, a support material, and a compound capable of binding to the bio-related material and/or the support material;

wherein the compound is a polymer compound;

the compound has two or more binding functional groups capable of binding to the biorelated material and/or the support material through covalent binding as reactive group in each molecule;

the matrix comprises a structure having a core of the support material and having a principal chain comprising the bio-related material and the compound, and a cross-linked structure between the compound and the bio-related material and/or the compound and the support material through the binding functional group; and the matrix at least partially contains a cross-linked structure in which the biorelated material is positioned between the compounds by binding the bio-related material to the compounds through the two or more binding functional groups.

12. A biosensor comprising a biomaterial-immobilized solid-state carrier as defined in claim 1.

13. A diagnostic device comprising a biomaterial-immobilized solid-state carrier as defined in claim 1.

14. A method of assaying at least one assay target in a sample, comprising the steps of:

(a) delivering the sample to a biomaterial-immobilized solid-state carrier as defined in claim 1 the carrier including at least one bio-related material that can react with the assay target; and (b) detecting an interaction between the bio-related material and the assay target or a reaction caused by adding a labeling material capable of reacting with the assay target, to thereby detect the presence or the amount of the assay target.

15. A method as defined in claim 14, wherein at least the sample is fluid, and the delivery of the sample is carried out by means of flow.

16. A method as defined in claim 14, further comprising the step of detecting a reaction in a reference area defined on the biomaterial-immobilized solid-state carrier as defined in claim 1, to determine whether or not the assay is successful or to correct the detection results of the presence of, or the amount of, the assay target.

17. A method as defined in claim 14, further comprising the step of (c) associating the presences or the amounts of two or more assay targets with specific symptoms in order to assay the two or more assay targets simultaneously.

18. A biomaterial-immobilized solid-state carrier as defined in claim 11, wherein the compound has two or more binding functional groups capable of binding to the bio-related material or to the bio-related material and the support material through covalent binding as reactive group in each molecule.

19. A biomaterial-immobilized solid-state carrier as defined in claim 1, wherein the compound has two or more binding functional groups capable of binding to the bio-related material or to the bio-related material and the support material through covalent binding as reactive group in each molecule.

20. A biomaterial-immobilized solid-state carrier as defined in claim 1, wherein the compound is a synthetic polymer compound.

21. A biomaterial-immobilized solid-state carrier as defined in claim 11, wherein the compound is a synthetic polymer compound.

22. A biomaterial-immobilized solid-state carrier as defined in claim 1, wherein two covalent linkages are present between the bio-related material, the support material and the compound.

23. A biomaterial-immobilized solid-state carrier as defined in claim 11, wherein two covalent linkages are present between the bio-related material, the support material and the compound.

* * * * *